US009938236B2

(12) United States Patent
Xu et al.

(10) Patent No.: US 9,938,236 B2
(45) Date of Patent: Apr. 10, 2018

(54) ANTIVIRAL AGENTS AGAINST HBV INFECTION

(71) Applicants: DREXEL UNIVERSITY, Philadelphia, PA (US); BARUCH S. BLUMBERG INSTITUTE, Doylestown, PA (US); ARBUTUS BIOPHARMA, INC., Doylestown, PA (US)

(72) Inventors: Xiaodong Xu, Doylestown, PA (US); Ju-Tao Guo, Lansdale, PA (US); Tong Xiao, Edison, NJ (US); Yanming Du, Cheshire, CT (US); Timothy Block, Doylestown, PA (US); Simon David Peter Baugh, Ringoes, NJ (US); Hong Ye, Lansdale, PA (US)

(73) Assignees: Drexel University, Philadelphia, PA (US); Baruch S. Blumberg Institute, Doylestown, PA (US); Arbutus Biopharma, Inc., Warminster, PA (US)

( * ) Notice: Subject to any disclaimer, the term of this patent is extended or adjusted under 35 U.S.C. 154(b) by 0 days.

(21) Appl. No.: 14/759,385

(22) PCT Filed: Dec. 27, 2013

(86) PCT No.: PCT/US2013/077940
§ 371 (c)(1),
(2) Date: Jul. 6, 2015

(87) PCT Pub. No.: WO2014/106019
PCT Pub. Date: Jul. 3, 2014

(65) Prior Publication Data
US 2016/0024004 A1      Jan. 28, 2016

Related U.S. Application Data

(60) Provisional application No. 61/746,552, filed on Dec. 27, 2012.

(51) Int. Cl.
| | | |
|---|---|---|
| C07C 311/16 | (2006.01) |
| C07D 213/75 | (2006.01) |
| C07D 213/76 | (2006.01) |
| C07D 309/04 | (2006.01) |
| C07D 215/38 | (2006.01) |
| C07D 215/42 | (2006.01) |
| C07D 217/24 | (2006.01) |
| C07D 319/18 | (2006.01) |

(Continued)

(52) U.S. Cl.
CPC .......... *C07C 311/16* (2013.01); *C07C 233/66* (2013.01); *C07C 309/89* (2013.01); *C07C 311/17* (2013.01); *C07C 311/18* (2013.01); *C07C 311/19* (2013.01); *C07C 311/20* (2013.01); *C07C 311/48* (2013.01); *C07C 317/14* (2013.01); *C07D 203/26* (2013.01); *C07D 205/04* (2013.01); *C07D 211/96* (2013.01); *C07D 213/40* (2013.01); *C07D 213/75* (2013.01); *C07D 213/76* (2013.01); *C07D 215/38* (2013.01); *C07D 215/42* (2013.01); *C07D 217/24* (2013.01); *C07D 231/40* (2013.01); *C07D 231/42* (2013.01); *C07D 239/26* (2013.01); *C07D 261/14* (2013.01); *C07D 263/48* (2013.01); *C07D 263/50* (2013.01); *C07D 263/58* (2013.01); *C07D 277/46* (2013.01); *C07D 277/52* (2013.01); *C07D 295/26* (2013.01); *C07D 295/30* (2013.01); *C07D 295/32* (2013.01); *C07D 305/08* (2013.01); *C07D 309/04* (2013.01); *C07D 319/16* (2013.01); *C07D 319/18* (2013.01); *C07B 2200/07* (2013.01); *C07C 2101/02* (2013.01); *C07C 2101/04* (2013.01); *C07C 2101/08* (2013.01); *C07C 2101/14* (2013.01)

(58) Field of Classification Search
None
See application file for complete search history.

(56) References Cited

U.S. PATENT DOCUMENTS 2,891,938 A     6/1959 Schetty et al.
3,557,111 A  *  1/1971 Shetty .................. C07D 265/26
                                                       514/869

(Continued)

FOREIGN PATENT DOCUMENTS

DE      102007041116 A1      3/2009
EP         2236505       * 10/2010

(Continued)

OTHER PUBLICATIONS

Database Caplus Chemical Abstracts Service, Columbus, Ohio, US; Database Accession No. 2009:846112, Abstract of US 20090163545 Goldfrab, University of Rochester, USA, Jun. 25, 2009.*
Petrow et al., Journal of Pharmacy and Pharmacology (1963), 15(2), 138-48.*
Database Caplus Chemical Abstracts Service, Columbus, Ohio, US; Database Accession No. 1963:441424, Abstract of Petrow et al., Journal of Pharmacy and Pharmacology (1963), 15(2), 138-48.*
Kato et al., Chemical & Pharmaceutical Bulletin (1995), 43(4), 582-7.*
Supplementary Partial European Search Report dated Jul. 14, 2016 for corresponding European Application No. 13868405.5.
Van Molle, W. et al., "Tumor Necrosis Factor-Induced Lethal Hepatitis: Pharmacological Intervention with Verapamil, Tannic Acid, Picotamide and K76COOH," FEBS Letters, 2000, vol. 467, No. 2-3, pp. 201-205.

(Continued)

*Primary Examiner* — Karl J Puttlitz
(74) *Attorney, Agent, or Firm* — Saul Ewing Arnstein & Lehr LLP; Kathryn Doyle; Domingos J. Silva

(57) ABSTRACT

The present invention provides novel compounds of formula (I) and methods of use thereof. In certain embodiments, the compounds of the invention are useful as nucleocapsid assembly inhibitors. In other embodiments, the compounds of the invention are useful as pregenomic RNA encapsidation inhibitors of Hepatitis B virus (HBV). In yet other embodiments, the compounds of the invention are useful for the treatment of viral infection, including HBV and related viral infections.

19 Claims, No Drawings

(51) Int. Cl.
| | |
|---|---|
| *C07D 231/40* | (2006.01) |
| *C07D 231/42* | (2006.01) |
| *C07D 239/26* | (2006.01) |
| *C07D 261/14* | (2006.01) |
| *C07D 263/48* | (2006.01) |
| *C07D 263/50* | (2006.01) |
| *C07D 203/26* | (2006.01) |
| *C07D 263/58* | (2006.01) |
| *C07D 205/04* | (2006.01) |
| *C07D 277/46* | (2006.01) |
| *C07D 277/52* | (2006.01) |
| *C07D 211/96* | (2006.01) |
| *C07D 295/26* | (2006.01) |
| *C07D 295/30* | (2006.01) |
| *C07D 213/40* | (2006.01) |
| *C07D 305/08* | (2006.01) |
| *C07C 309/89* | (2006.01) |
| *C07C 311/17* | (2006.01) |
| *C07C 311/18* | (2006.01) |
| *C07C 311/19* | (2006.01) |
| *C07C 311/20* | (2006.01) |
| *C07C 311/48* | (2006.01) |
| *C07C 233/66* | (2006.01) |
| *C07C 317/14* | (2006.01) |
| *C07D 295/32* | (2006.01) |
| *C07D 319/16* | (2006.01) |

(56) References Cited

U.S. PATENT DOCUMENTS

| | | | |
|---|---|---|---|
| 3,567,746 A * | 3/1971 | Shetty | C07D 265/26 544/288 |
| 2003/0092748 A1 | 5/2003 | Barrett et al. | |
| 2008/0280875 A1 | 11/2008 | Bai et al. | |
| 2009/0036420 A1 | 2/2009 | Galley et al. | |
| 2009/0118268 A1 | 5/2009 | Riedl et al. | |
| 2009/0163545 A1* | 6/2009 | Goldfarb | A61K 31/122 514/312 |
| 2009/0197787 A1 | 8/2009 | Venet et al. | |
| 2009/0197871 A1 | 8/2009 | Callahan et al. | |
| 2010/0004324 A1 | 1/2010 | Skaar et al. | |
| 2015/0266890 A1 | 9/2015 | Vandyck et al. | |
| 2015/0274653 A1 | 10/2015 | Vandyck et al. | |

FOREIGN PATENT DOCUMENTS

| | | | |
|---|---|---|---|
| JP | 62022761 A | | 1/1987 |
| WO | 2007056016 A2 | | 5/2007 |
| WO | 2007067836 A2 | | 6/2007 |
| WO | 2008070707 | * | 6/2008 |
| WO | 2008070707 A1 | | 6/2008 |
| WO | 2008093614 A1 | | 8/2008 |
| WO | 2008137794 A1 | | 11/2008 |
| WO | 2008147962 A1 | | 12/2008 |
| WO | 2010132404 A1 | | 11/2010 |
| WO | 2011088561 A1 | | 7/2011 |
| WO | 2012018668 A1 | | 2/2012 |
| WO | 2012117000 A1 | | 9/2012 |
| WO | 2012122391 A1 | | 9/2012 |
| WO | 2013006394 | * | 1/2013 |
| WO | 2013006394 A1 | | 1/2013 |
| WO | 2013096744 A1 | | 6/2013 |
| WO | 2013096744 | * | 7/2013 |
| WO | 2013130703 A2 | | 9/2013 |
| WO | 2014033170 A1 | | 3/2014 |
| WO | 2014033176 A1 | | 3/2014 |
| WO | 2014089296 A2 | | 6/2014 |

OTHER PUBLICATIONS

PCT International Search Report dated Jul. 8, 2014 for International Application No. PCT/US2013/077940.

Aoyama, et al., "Development of Tubulin-Polymerization Inhibitors Based on the Thalidomide Skeleton", Chem Pharm Bull, vol. 55, No. 6, 2007, pp. 944-949.

* cited by examiner

ANTIVIRAL AGENTS AGAINST HBV INFECTION

CROSS-REFERENCE TO RELATED APPLICATIONS

The present application is a 35 U.S.C. § 371 national phase application of, and claims priority to, PCT Application No. PCT/US2013/077940, filed Dec. 27, 2013, which claims priority under 35 U.S.C. § 119(e) to U.S. Provisional Patent Application No. 61/746,552, filed Dec. 27, 2012, all of which applications are incorporated herein by reference in their entireties.

GOVERNMENT RIGHTS

This invention was made with government support under Grant Nos. R43AI098200 R43AI104066 awarded by the NIH's National Institute of Allergy and Infectious Diseases (NIAID). The government has certain rights in the invention.

FIELD OF INVENTION

The present invention describes compounds and methods useful as pregenomic RNA encapsidation inhibitors, useful for the treatment of Hepatitis B virus (HBV) infection and related conditions.

BACKGROUND OF THE INVENTION

Hepatitis B virus (HBV) infection remains a major public health problem. Currently, an estimated 350 million people worldwide and 1.4 million in the US are chronically infected with HBV (McMahon, 2005). Approximately one-third of these individuals will die from serious liver diseases, such as cirrhosis and hepatocellular carcinoma, if left untreated (Lee, 1997; Lok, 2004).

Seven drugs are currently available for the management of chronic hepatitis B, which include two formulations of alpha-interferon (standard and pegylated) and five nucleos(t)ide analogues (lamivudine, adefovir, entecavir, telbivudine, and tenofovir) that inhibit HBV DNA polymerase (Keeffe et al., 2008). At present, the preferred first-line treatment choices are entecavir, tenofovir or peg-interferon alfa-2a. However, even with the first-line treatment options, peg-interferon alfa-2a is effective in achieving certain serological milestones in only one-third of treated patients and frequently associated with severe side effects (Janssen et al., 2005; Lau et al., 2005; Perrillo, 2009). Entecavir and tenofovir are highly potent HBV inhibitors, but a long-term or possibly life-time treatment is required to continuously suppress HBV replication, which may eventually fail due to emergence of drug resistant viruses (Dienstag, 2009). Hence, there is a pressing need for the introduction of novel, safe and effective therapies for chronic hepatitis B, which is listed by National Institute of Allergy and Infectious Diseases (NIAID) as a High Priority Area of Interest.

HBV is a noncytopathic, liver tropic DNA virus belonging to Hepadnaviridae family. Pregenomic (pg) RNA is the template for reverse transcriptional replication of HBV DNA and its encapsidation, together with viral DNA polymerase, into nucleocapsid is essential for the subsequent viral DNA synthesis Inhibition of pregenomic RNA (pg) encapsidation would block HBV replication and provide a new therapeutic approach to the treatment of HBV. A similar approach would also lead to new therapeutic approaches to other viruses.

Clinically, inhibition of pregenomic RNA (pg) encapsidation, or more generally of inhibition of nucleocapsid assembly, offers the following therapeutic advantages: First, inhibition of pregenomic RNA (pg) encapsidation will complement the current medications by providing an additional option for a subpopulation of patients that do not tolerate or benefit from the current medications (Akbar et al., 2009; Liaw, 2009; Peters, 2009; Wiegand, van Bommel, and Berg). Second, based on their distinct antiviral mechanism, inhibition of pregenomic RNA (pg) encapsidation will be effective against HBV variants that are resistant to the currently available DNA polymerase inhibitors (Zoulim and Locarnini, 2009). Third, like the Highly Active Antiretroviral Therapy (HAART) for human immunodeficiency virus (HIV) infection (Este and Cihlar), combination therapy of the inhibitors of pregenomic RNA (pg) encapsidation with DNA polymerase inhibitors should synergistically suppress HBV replication and prevent the emergence of drug resistance and thus offers a safer and more effective treatment for chronic hepatitis B infection.

There is a long-felt need for new antiviral drugs that are both disease-modifying and effective in treating patients that are infected with hepatitis B virus, and other viruses, or preventing the onset thereof in patients at risk of getting the associated disease(s). There is also a clear and present need for new antiviral drugs that are both disease modifying and effective in treating patients that are infected with drug resistant hepatitis B virus, and other viruses. The present invention addresses the need for new antiviral drugs that are both disease-modifying and effective in treating patients that are infected with hepatitis B virus, and other viruses. Administration of these therapeutic agents to an infected patient, either as monotherapy or in combination with other treatments or ancillary treatments, will lead to significantly improved prognosis, diminished progression of the disease, and enhanced seroconversion rates.

BRIEF SUMMARY OF THE INVENTION

The present invention is directed toward novel compounds and novel methods of use of said compounds of the formula (I), useful as nucleocapsid assembly inhibitors for the treatment of viruses, especially but not exclusively, including pregenomic RNA encapsidation inhibitors of HBV for the treatment of Hepatitis B virus (HBV) infection and related conditions.

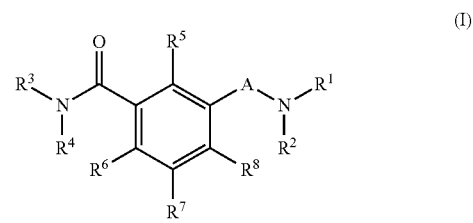

including hydrates, solvates, pharmaceutically acceptable salts, prodrugs and complexes thereof, wherein:

A is selected from a group consisting of $SO_2$ and CO;

$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted $C_{1-6}$ haloalkyl, optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;

$R^2$ is selected from a group consisting of hydrogen and optionally substituted $C_{1-6}$ linear alkyl; $R^2$ may also alternatively or additionally optionally include optionally substituted $C_{3-7}$cycloalkyl or optionally substituted heterocyclic; or $R^1$ and $R^2$ are taken together with the atoms to which they are bound to form an optionally substituted heterocycle (including bicyclic or adamantyl structures) with 3 to 10 atoms; and $R^3$ is selected from a group consisting of optionally substituted aryl, optionally substituted benzyl, optionally substituted alkylaryl, optionally substituted heteroaryl, and optionally substituted alkylheteroaryl; in some embodiments, $R^3$ may also comprise an optionally substituted $C_{1-6}$ linear alkyl;

$R^4$ is selected from a group consisting of hydrogen and optionally substituted $C_{1-6}$ linear alkyl;

$R^5$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; $R^6$ may also alternatively or additionally optionally include cyano or $N(R^9)_2$; or $R^4$ and $R^6$ are taken together with the atoms to which they are bound to form an optionally substituted carbocyclic or heterocyclic ring with 5 to 6 atoms, optionally containing a carbonyl, optionally containing two carbonyls; and $R^7$ is selected from a group consisting of hydrogen, halogen, optionally substituted $C_{1-6}$ linear alkyl, optionally substituted $C_{1-6}$branched alkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$branched alkyl, and $OR^9$; $R^8$ may also alternatively or additionally optionally include cyano or $N(R^9)_2$; or $R^2$ and $R^8$ are taken together with the atoms to which they are bound to form an optionally substituted carbocyclic or heterocyclic ring with 5 to 6 atoms; and $R^9$ is independently at each occurrence selected from a group consisting of hydrogen, optionally substituted $C_{1-6}$ linear alkyl, optionally substituted $C_{1-6}$branched alkyl, and optionally substituted $C_{3-7}$cycloalkyl; $R^9$ may also alternatively or additionally optionally include independently at each occurrence optionally substituted aryl, optionally substituted benzyl, optionally substituted heterocyclyl, or optionally substituted heteroaryl;

provided that when A is $SO_2$; $R^4$ and $R^6$ taken together with the atoms to which they are bound do not to form an optionally substituted ring; and $R^2$ and $R^8$ taken together with the atoms to which they are bound do not to form an optionally substituted ring, then none of the following (a) through (d) apply:

(a) $R^3$ is an optionally substituted phenyl and $R^1$ or $R^2$, either individually or when taken together, contain a hydroxyl group, or (b) $R^3$ is an optionally substituted alkyl or phenyl, and $N(R^1)(R^2)$ is an optionally substituted piperazine or

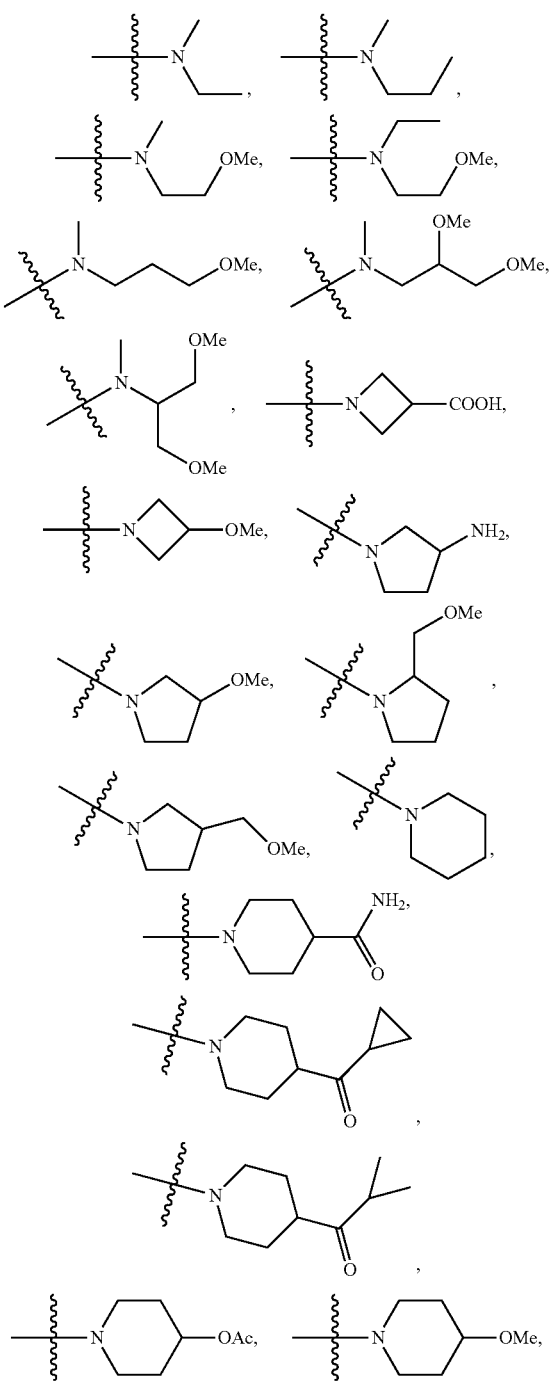

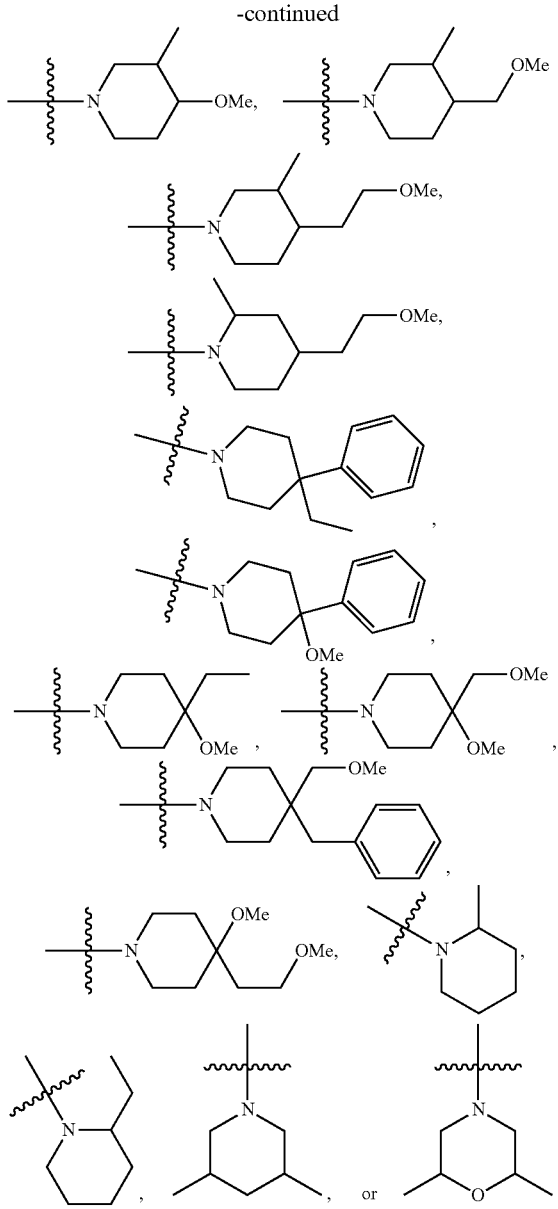
(c) R³ is optionally substituted alkyl, aryl, or alkaryl and N(R¹)(R²) is
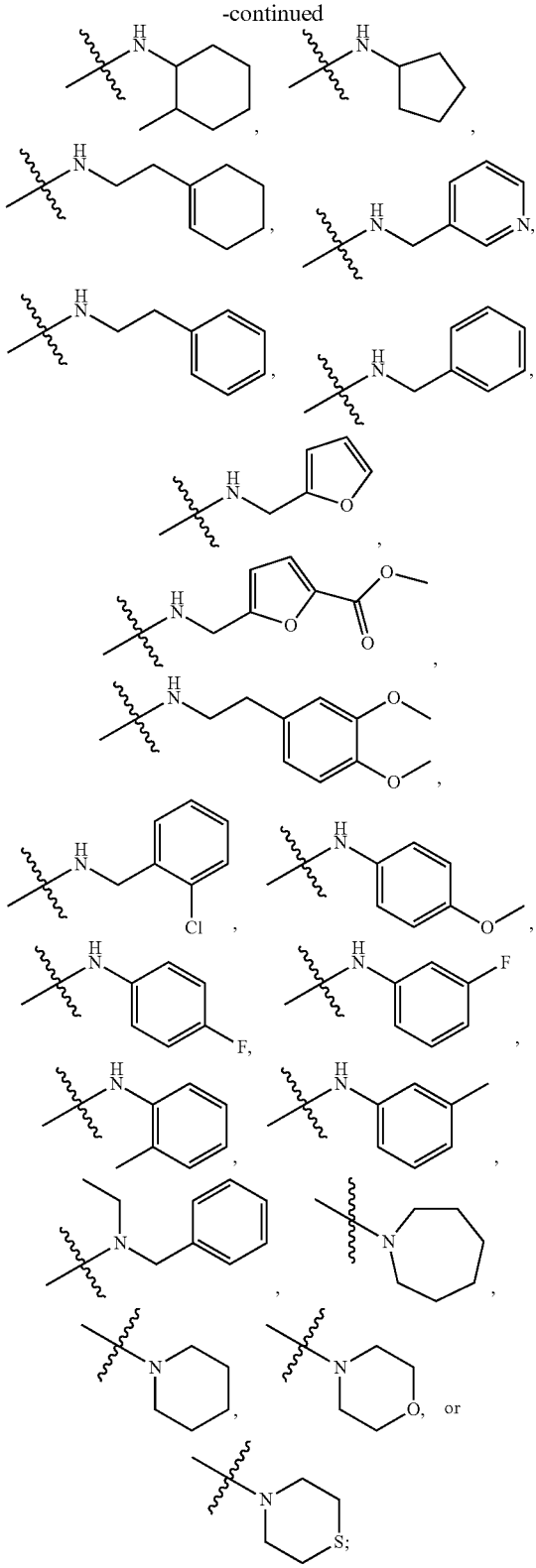
or
(d) either R³ or R⁴ is an unsubstituted or monosubstituted aryl, or an unsubstituted or monosubstituted aralkyl, or unsubstituted or monosubstituted heteroaryl and R¹ and R² are taken together with the atoms to which they are bound to form an optionally substituted heterocyclic ring structure with 6 to 12 atoms; or provided that the compound is not 3-{[(dicyclopropylmethyl)amino]sulfonyl}-N-(4-isopropoxyphenyl)benzamide; or 3-({[2-(1H-benzimidazol-2-yl)propyl]amino}sulfonyl)-N-(4-isopropoxyphenyl)benzamide; or 3-[(cyclohexylamino)sulfonyl]-N-(4-isopropylphenyl)benzamide; or 3-(anilinosulfonyl)-N-(4-isopropylphenyl)benzamide; or 5-{[(3-{[(4-methoxyphenyl)amino]carbonyl}phenyl)sulfonyl]amino}pentanoic acid; or 3-[(tert-butylamino)sulfonyl]-N-(4-methoxyphenyl)benzamide; or (3S)-1-[(3-{[(5-isopropoxypyridin-2-yl)amino]carbonyl}phenyl)sulfonyl]piperidine-3-carboxamide; or (3R)-1-[(3-{[(5-isopropoxypyridin-2-yl)amino]carbonyl}phenyl)sulfonyl]piperidine-3-carboxamide; or 3-(piperidin-1-ylsulfonyl)-N-[(1S)-1,2,3,4-tetrahydronaphthalen-1-yl]benzamide; or N-(5-bromo-3-methoxypyridin-2-yl)-3-(piperidin-1-ylsulfonyl)benzamide; or N-(3-methoxy-5-phenylpyridin-2-yl)-3-(pyrrolidin-1-ylsulfonyl)benzamide; or N-(3-methoxy-5-phenoxypyridin-2-yl)-3-(pyrrolidin-1-ylsulfonyl)benzamide; or N-[3-methoxy-5-(phenylthio)pyridin-2-yl]-3-(pyrrolidin-1-ylsulfonyl)benzamide; or N-(5-ethyl-3-methoxypyridin-2-yl)-3-(piperidin-1-ylsulfonyl)benzamide; or N-(3-methoxy-5-vinylpyridin-2-yl)-3-(piperidin-1-ylsulfonyl)benzamide; or

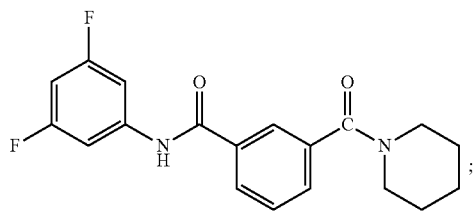

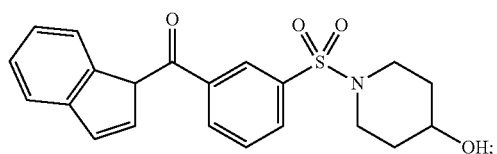

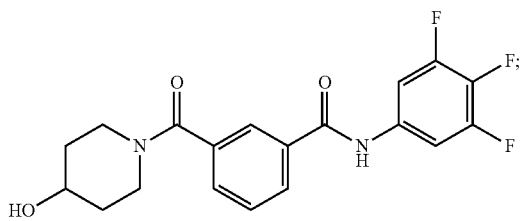

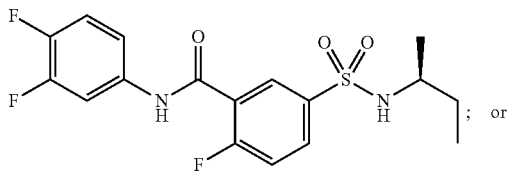

(XXVII)

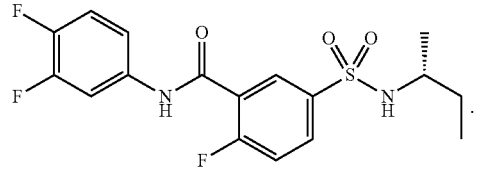

(XXVIII)

Some embodiments of the compounds of formula (I) also exclude those compounds when A is $SO_2$; $R^4$ and $R^6$ taken together with the atoms to which they are bound do not to form an optionally substituted ring; and $R^2$ and $R^8$ taken together with the atoms to which they are bound do not to form an optionally substituted ring, $R^3$ is optionally substituted alkyl, aryl, or alkaryl and $N(R^1)(R^2)$ is an optionally substituted piperidine.

The embodiments of the present invention include compounds of formula (I) where

A is $SO_2$;

$R^4$ and $R^6$ taken together with the atoms to which they are bound do not to form an optionally substituted ring; and $R^2$ and $R^8$ taken together with the atoms to which they are bound do not to form an optionally substituted ring;

thereby providing compounds having formula (II),

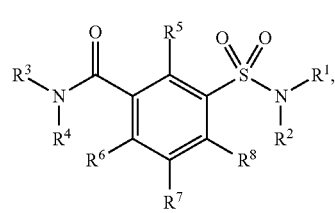

including hydrates, solvates, pharmaceutically acceptable salts, prodrugs and complexes thereof.

In some embodiments, $R^1$ through $R^8$ are as defined for the compound of formula (I). In other independent embodiments, $R^1$ through $R^8$ are as defined below.

The embodiments of the present invention include compounds of formula (I) where A is $SO_2$, thereby providing compounds having formula (III),

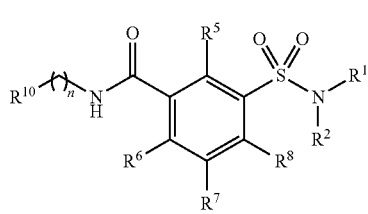

including hydrates, solvates, pharmaceutically acceptable salts, prodrugs and complexes thereof, wherein:

$R^{10}$ is selected from a group consisting of optionally substituted aryl and optionally substituted heteroaryl; and n is 0 or 1.

In some embodiments, $R^1$, $R^2$, and $R^5$ through $R^8$ are as defined for the compound of formula (I). In other independent embodiments, $R^1$, $R^2$, and $R^5$ through $R^8$ are as defined below. In some embodiments, $R^2$ and $R^8$ taken together with the atoms to which they are bound do not to form an optionally substituted carbocyclic or heterocyclic ring.

The embodiments of the present invention include compounds of formula (I) specifically having formula (IV),

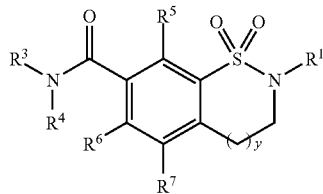

(IV)

including hydrates, solvates, pharmaceutically acceptable salts, prodrugs and complexes thereof, wherein: y is 0 or 1. In some embodiments, y is 2.

In some embodiments, $R^1$ and $R^3$ through $R^8$ are as defined for the compound of formula (I). In other independent embodiments, $R^1$ and $R^3$ through $R^8$ are as defined below. In some embodiments, $R^4$ and $R^6$ taken together with the atoms to which they are bound do not to form an optionally substituted carbocyclic or heterocyclic ring.

The embodiments of the present invention include compounds of formula (I) where A is $SO_2$, having formula (V),

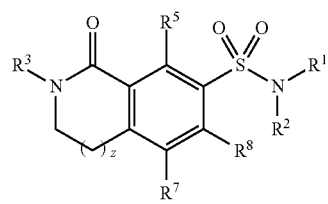

(V)

including hydrates, solvates, pharmaceutically acceptable salts, prodrugs and complexes thereof, wherein: z is 0 or 1.

In some embodiments, $R^1$ through $R^3$, $R^5$, and $R^7$ through $R^8$ are as defined for the compound of formula (I). In other independent embodiments, $R^1$ through $R^3$, $R^5$, and $R^7$ through $R^8$ are as defined below. In some embodiments, $R^2$ and $R^8$ taken together with the atoms to which they are bound do not to form an optionally substituted carbocyclic or heterocyclic ring.

The embodiments of the present invention include compounds of formula (I) where A is $SO_2$, having formula (VI),

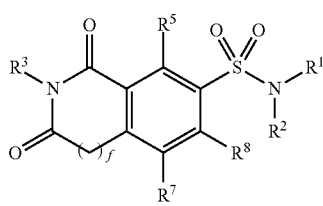

(VI)

including hydrates, solvates, pharmaceutically acceptable salts, prodrugs and complexes thereof, wherein: f is 0 or 1.

In some embodiments, $R^1$ through $R^3$, $R^5$, and $R^7$ through $R^8$ are as defined for the compound of formula (I). In other independent embodiments, $R^1$ through $R^3$, $R^5$, and $R^7$ through $R^8$ are as defined below. In some embodiments, $R^2$ and $R^8$ taken together with the atoms to which they are bound do not to form an optionally substituted carbocyclic or heterocyclic ring.

The embodiments of the present invention include compounds of formula (I) where A is CO, having formula (VII),

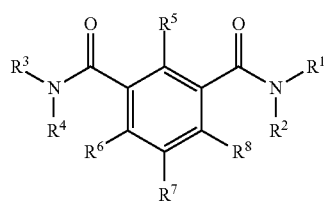

(VII)

including hydrates, solvates, pharmaceutically acceptable salts, prodrugs and complexes thereof.

In some embodiments, $R^1$ through $R^8$ are as defined for the compound of formula (I). In other independent embodiments, $R^1$ through $R^8$ are as defined below.

In some embodiments of the compounds of Formula (VII), $R^4$ and $R^6$ taken together with the atoms to which they are bound do not to form an optionally substituted carbocyclic or heterocyclic ring; and $R^2$ and $R^8$ taken together with the atoms to which they are bound do not to form an optionally substituted carbocyclic or heterocyclic ring;

The embodiments of the present invention include compounds of formula (I) where A is CO, thereby providing compounds having formula (VIII),

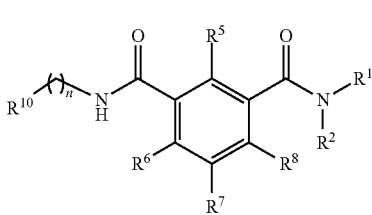

(VIII)

including hydrates, solvates, pharmaceutically acceptable salts, prodrugs and complexes thereof, wherein:

$R^{10}$ is selected from a group consisting of optionally substituted aryl and optionally substituted heteroaryl; and n is 0 or 1.

In some embodiments, $R^1$ through $R^2$ and $R^5$ through $R^8$ are as defined for the compound of formula (I). In other independent embodiments, $R^1$ through $R^2$ and $R^5$ through $R^8$ are as defined below.

The embodiments of the present invention include compounds of formula (I) where A is CO, having formula (IX):

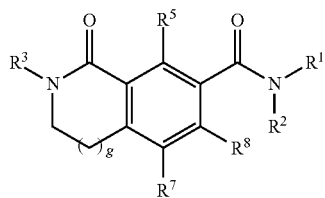

including hydrates, solvates, pharmaceutically acceptable salts, prodrugs and complexes thereof, wherein: g is 0 or 1.

In some embodiments, $R^1$ through $R^3$, $R^5$, and $R^7$ through $R^8$ are as defined for the compound of formula (I). In other embodiments, $R^1$ through $R^3$, $R^5$, and $R^7$ through $R^8$ are as defined below. In some embodiments, $R^2$ and $R^8$ taken together with the atoms to which they are bound do not to form an optionally substituted carbocyclic or heterocyclic ring; and The embodiments of the present invention include compounds of formula (I) where A is CO, having formula (X),

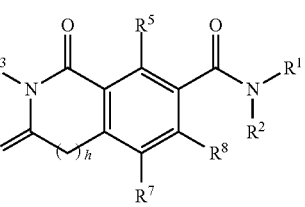

including hydrates, solvates, pharmaceutically acceptable salts, prodrugs and complexes thereof, wherein: h is 0 or 1.

In some embodiments, $R^1$ through $R^3$, $R^5$, and $R^7$ through $R^8$ are as defined for the compound of formula (I). In other independent embodiments, $R^1$ through $R^3$, $R^5$, and $R^7$ through $R^8$ are as defined below.

The embodiments of the present invention include compounds having formula (XI), useful as nucleocapsid assembly inhibitors for the treatment of viruses, especially but not exclusively, including pregenomic RNA encapsidation inhibitors of HBV for the treatment of Hepatitis B virus (HBV) infection and related conditions

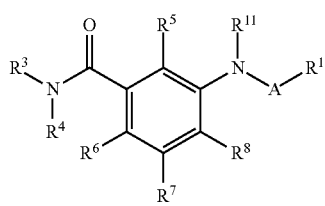

including hydrates, solvates, pharmaceutically acceptable salts, prodrugs and complexes thereof, wherein:

A is selected from a group consisting of $SO_2$ and CO;

$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted $C_{1-6}$ haloalkyl, optionally substituted 3-7 membered cyclo-heteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;

$R^3$ is selected from a group consisting of optionally substituted aryl, optionally substituted benzyl, optionally substituted alkylaryl, optionally substituted heteroaryl, and optionally substituted alkylheteroaryl; in some embodiments, $R^3$ may also comprise an optionally substituted $C_{1-6}$ linear alkyl;

$R^4$ is selected from a group consisting of hydrogen and optionally substituted $C_{1-6}$ linear alkyl;

$R^5$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^6$ may also alternatively or additionally optionally include cyano or $N(R^9)_2$; or $R^4$ and $R^6$ are taken together with the atoms to which they are bound to form an optionally substituted carbocyclic or heterocyclic ring with 5 to 6 atoms, optionally containing a carbonyl, optionally containing two carbonyls; and $R^7$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^8$ may also alternatively or additionally optionally include cyano or $N(R^9)_2$;

$R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$ cycloalkyl; $R^9$ may also alternatively or additionally optionally include independently at each occurrence optionally substituted aryl, optionally substituted benzyl, optionally substituted heterocyclyl, or optionally substituted heteroaryl; and $R^{11}$ is selected from a group consisting of hydrogen, optionally substituted $C_{1-6}$ linear alkyl, optionally substituted $C_{1-6}$ branched alkyl, and optionally substituted $C_{3-7}$ cycloalkyl.

The embodiments of the present invention also include compounds having formula (XII),

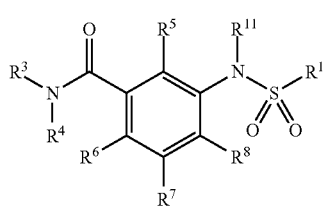

(XII)

including hydrates, solvates, pharmaceutically acceptable salts, prodrugs and complexes thereof.

In some embodiments, $R^1$, $R^3$ through $R^8$ and $R^{11}$ are as defined for the compound of formula (XI). In other embodiments, $R^1$, $R^3$ through $R^8$ and $R^{11}$ are as defined below.

The embodiments of the present invention include compounds having formula (XIII),

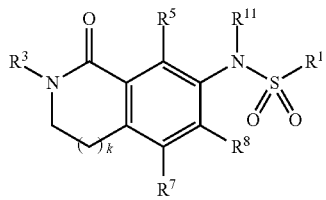

(XIII)

including hydrates, solvates, pharmaceutically acceptable salts, prodrugs and complexes thereof wherein: k is 0 or 1.

In some embodiments, $R^1$, $R^3$, $R^5$, $R^7$, $R^8$ and $R^{11}$ are as defined for the compound of formula (XI). In other independent embodiments, $R^1$, $R^3$, $R^5$, $R^7$, $R^8$ and $R^{11}$ are as defined below.

The embodiments of the present invention include compounds having formula (XIV),

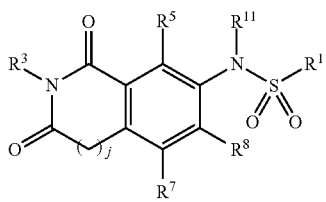

(XIV)

including hydrates, solvates, pharmaceutically acceptable salts, prodrugs and complexes thereof wherein: j is 0 or 1.

In some embodiments, $R^1$, $R^3$, $R^5$, $R^7$, $R^8$ and $R^{11}$ are as defined for the compound of formula (XI). In other embodiments, $R^1$, $R^3$, $R^5$, $R^7$, $R^8$ and $R^{11}$ are as defined below.

The embodiments of the present invention include compounds having formula (XV),

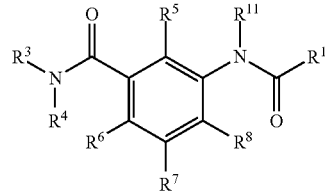

(XV)

including hydrates, solvates, pharmaceutically acceptable salts, prodrugs and complexes thereof.

In some embodiments, $R^1$, $R^3$ through $R^8$ and $R^{11}$ are as defined for the compound of formula (XI). In other embodiments, $R^1$, $R^3$ through $R^8$ and $R^{11}$ are as defined below.

The embodiments of the present invention include compounds having formula (XVI),

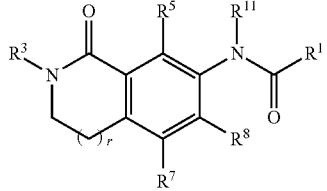

(XVI)

including hydrates, solvates, pharmaceutically acceptable salts, prodrugs and complexes thereof wherein: r is 0 or 1.

In some embodiments, $R^1$, $R^3$, $R^5$, $R^7$, $R^8$ and $R^{11}$ are as defined for the compound of formula (XI). In other embodiments, $R^1$, $R^3$, $R^5$, $R^7$, $R^8$ and $R^{11}$ are as defined below.

The embodiments of the present invention include compounds having formula (XVII),

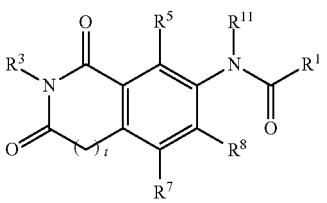

(XVII)

including hydrates, solvates, pharmaceutically acceptable salts, prodrugs and complexes thereof wherein: t is 0 or 1.

In some embodiments, $R^1$, $R^3$, $R^5$, $R^7$, $R^8$ and $R^{11}$ are as defined for the compound of formula (XI). In other embodiments, $R^1$, $R^3$, $R^5$, $R^7$, $R^8$ and $R^{11}$ are as defined below.

The embodiments of the present invention include compounds having formula (XVIII), useful as nucleocapsid assembly inhibitors for the treatment of viruses, especially but not exclusively, including pregenomic RNA encapsidation inhibitors of HBV for the treatment of Hepatitis B virus (HBV) infection and related conditions

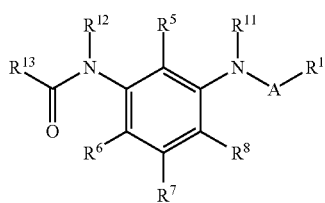

(XVIII)

including hydrates, solvates, pharmaceutically acceptable salts, prodrugs and complexes thereof wherein:

A is selected from a group consisting of $SO_2$ and CO;

$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;

$R^5$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$ branched alkyl, and $OR^9$; $R^6$ may also alternatively or additionally optionally cyano or $N(R^9)_2$;

$R^7$ is selected from a group consisting of hydrogen, halogen, optionally substituted $C_{1-6}$ linear alkyl, optionally substituted $C_{1-6}$ branched alkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$ branched alkyl, and $OR^9$; $R^8$ may also alternatively or additionally optionally include cyano or $N(R^9)_2$;

$R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$; $R^9$ may also alternatively or additionally optionally include independently at each occurrence optionally substituted aryl, optionally substituted benzyl, optionally substituted heterocyclyl, or optionally substituted heteroaryl;

$R^{11}$ is selected from a group consisting of hydrogen, optionally substituted $C_{1-6}$ linear alkyl, optionally substituted $C_{1-6}$ branched alkyl, and optionally substituted $C_{3-7}$ cycloalkyl;

$R^{12}$ is selected from a group consisting of hydrogen, optionally substituted $C_{1-6}$ linear alkyl, optionally substituted $C_{1-6}$ branched alkyl, and optionally substituted $C_{3-7}$ cycloalkyl; and $R^{13}$ is selected from a group consisting of optionally substituted aryl, optionally substituted benzyl, optionally substituted alkylaryl, optionally substituted heteroaryl, and optionally substituted alkylheteroaryl.

The embodiments of the present invention include compounds having formula (XIX),

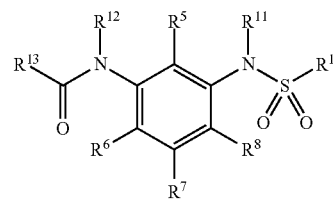

(XIX)

including hydrates, solvates, pharmaceutically acceptable salts, prodrugs and complexes thereof.

In some embodiments, $R^1$, $R^5$ through $R^8$ and $R^{11}$ through $R^{13}$ are as defined for the compound of formula (XVIII). In other embodiments, $R^1$, $R^5$ through $R^8$ and $R^{11}$ through $R^{13}$ are as defined below.

The embodiments of the present invention include compounds having formula (XX),

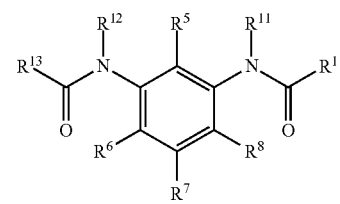

(XX)

including hydrates, solvates, pharmaceutically acceptable salts, prodrugs and complexes thereof.

In some embodiments, $R^1$, $R^5$ through $R^8$ and $R^{11}$ through $R^{13}$ are as defined for the compound of formula (XVIII). In other embodiments, $R^1$, $R^5$ through $R^8$ and $R^{11}$ through $R^{13}$ are as defined below.

The embodiments of the present invention include compounds having formula (XU), useful as nucleocapsid assembly inhibitors for the treatment of viruses, especially but not exclusively, including pregenomic RNA encapsidation inhibitors of HBV for the treatment of Hepatitis B virus (HBV) infection and related conditions

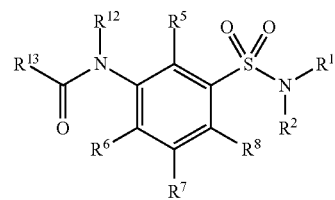

(XXI)

including hydrates, solvates, pharmaceutically acceptable salts, prodrugs and complexes thereof, wherein:

$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;

$R^2$ is selected from a group consisting of hydrogen and optionally substituted $C_{1-6}$ linear alkyl; $R^2$ may also alternatively or additionally optionally include optionally substituted $C_{3-7}$ cycloalkyl or optionally substituted heterocyclic; or $R^1$ and $R^2$ are taken together with the atoms to which they are bound to form an optionally substituted heterocycle (including bicyclic or adamantyl structures) with 3 to 10 atoms;

$R^5$ is selected from a group consisting of hydrogen, halogen, optionally substituted $C_{1-6}$ linear alkyl, optionally substituted $C_{1-6}$ branched alkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$ branched alkyl, and $OR^9$; $R^6$ may also alternatively or additionally optionally include cyano or $N(R^9)_2$;

$R^7$ is selected from a group consisting of hydrogen, halogen, optionally substituted $C_{1-6}$ linear alkyl, optionally substituted $C_{1-6}$ branched alkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$ branched alkyl, and $OR^9$; $R^8$ may also alternatively or additionally optionally include cyano or $N(R^9)_2$;

$R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$ cycloalkyl, and optionally substituted $C_{1-6}$ haloalkyl; $R^9$ may also alternatively or additionally optionally include independently at each occurrence optionally substituted aryl, optionally substituted benzyl, optionally substituted heterocyclyl, or optionally substituted heteroaryl;

$R^{12}$ is selected from a group consisting of hydrogen, optionally substituted $C_{1-6}$ linear alkyl, optionally substituted $C_{1-6}$ branched alkyl, and optionally substituted $C_{3-7}$ cycloalkyl; and $R^{13}$ is selected from a group consisting of optionally substituted aryl, optionally substituted benzyl, optionally substituted alkylaryl, optionally substituted heteroaryl, and optionally substituted alkylheteroaryl.

The present invention further relates to compositions comprising:
an effective amount of one or more compounds according to the present invention and an excipient.

The present invention also relates to a method for treating or preventing diseases that involve nucleocapsid assembly, especially but not exclusively, including pregenomic RNA encapsidation, including, for example, HBV infection, said method comprising administering to a subject an effective amount of a compound or composition according to the present invention.

The present invention yet further relates to a method for treating or preventing diseases that involve nucleocapsid assembly, especially but not exclusively, including pregenomic RNA encapsidation, including, for example, HBV infection, wherein said method comprises administering to a subject a composition comprising an effective amount of one or more compounds according to the present invention and an excipient.

The present invention also relates to a method for treating or preventing disease or conditions associated with HBV infection, and diseases that involve nucleocapsid assembly, especially but not exclusively, including pregenomic RNA encapsidation. Said methods comprise administering to a subject an effective amount of a compound or composition according to the present invention.

The present invention yet further relates to a method for treating or preventing disease or conditions associated with HBV infection, and diseases that involve nucleocapsid assembly, especially but not exclusively, including pregenomic RNA encapsidation, wherein said method comprises administering to a subject a composition comprising an effective amount of one or more compounds according to the present invention and an excipient.

These, and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

Without intending to be bound by the correctness or incorrectness of any particular theory, the compounds of the present invention are believed to operate by the inhibition of nucleocapsid assembly, generally, and by inhibiting the formation of viral genomic RNA/DNA-containing capsids (i.e., pregenomic RNA encapsidation inhibitors of HBV), specifically. The term "pregenomic RNA encapsidation inhibitors of HBV" refer to a class of compounds that interfere with the association of a viral nucleic acid and its capsid proteins specifically related to that virus. By interfering with capsid formation, this mechanism provides an effective strategy to suppress viral replication, generally, and with HBV specifically. While the language used in this application is largely directed to the treatment of HBV, possibly by inhibiting the association of hepdnaviral pregenomic RNA and capsid, the same strategy of interfering with the association of the essential RNA or DNA of other viruses and their capsids would also be effective antiviral strategies using the compounds described herein, e.g., HIV. That is, in each case where the compound or treatment refers specifically to the treatment of HBV, additional embodiments provide that other viruses may also be treated by the application of the compounds described herein, for example by repressing viral replication and morphogenesis by interfering with capsid formation; by interfering with the association of nucleic acids with capsid; by interfering with association of RNA with capsid protein; interfering with pregenomic RNA association and capsid; and by interfering with nucleic acid capsid association, particularly by interfering with formation of the hepadna and HBV capsid formation.

The pregenomic RNA encapsidation inhibitors of the present invention are capable of treating and preventing diseases associated with pregenomic RNA encapsidation, for example HBV infection. Pregenomic (pg) RNA is the template for reverse transcriptional replication of HBV DNA and its encapsidation, together with viral DNA polymerase, into nucleocapsid is essential for the subsequent viral DNA synthesis. Without wishing to be limited by theory, it is believed that inhibition of pregenomic RNA encapsidation can ameliorate, abate, or otherwise cause to be controlled, diseases associated with pregenomic RNA encapsidation, for example HBV infection. Pregenomic RNA encapsidation inhibitors of the present invention address the clear and unmet need to identify novel and safe antiviral agents for the treatment of HBV infection that are chemically and mechanistically distinct from HBV antiviral drugs in current clinical use.

Clinically, the pregenomic RNA encapsidation inhibitors of the present invention complement the current medications by providing an additional option for a subpopulation of patients that do not tolerate or benefit from the current medications (Akbar et al., 2009; Liaw, 2009; Peters, 2009; Wiegand, van Bommel, and Berg). In addition, the pregenomic RNA encapsidation inhibitors of the present invention may be effective on HBV variants that are resistant to the currently available DNA polymerase inhibitors (Zoulim and Locarnini, 2009). Further, combination therapies of the pregenomic RNA encapsidation inhibitors of the present invention with DNA polymerase inhibitors may synergistically suppress HBV replication and prevent the emergence of drug resistance, offering a safer and more effective treatment for chronic hepatitis B (Billioud et al., 2011).

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the compounds and compositions, as well as the methods of making, formulating, and treating using the compounds and compositions themselves, and vice versa.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods (or the systems used in such methods or the compositions derived therefrom) in treating the conditions described herein.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, a subscript description for carbons or ring structures, such as $C_{1-6}$ alkyl, is understood to include each individual element of that list, and every combination of that list, as a separate embodiment, for example $C_1$-alkyl, $C_2$-alkyl, $C_3$-alkyl, $C_4$-alkyl, $C_5$-alkyl, $C_6$-alkyl, $C_{1-2}$-alkyl, $C_{1-3}$-alkyl, $C_{1-4}$-alkyl, $C_{1-5}$-alkyl, $C_{1-6}$-alkyl, $C_{2-3}$-alkyl, $C_{2-4}$-alkyl, $C_{2-5}$-alkyl, $C_{2-6}$-alkyl, $C_{3-4}$-alkyl, $C_{3-5}$-alkyl, $C_{3-6}$-alkyl, $C_{4-5}$-alkyl, $C_{4-6}$-alkyl, and $C_{5-6}$-alkyl, Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

As used herein, the terms "treating" or "treatment" of a disease or disorder refers to the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose of controlling the progression (i.e., arresting or reducing the development of the disease or at least one of the clinical symptoms thereof) of the disease, or ameliorating the effects of the disease. In another embodiment, the terms refer to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

The terms "preventing" or "prevention" are intended to connote the ability of the treatment or compound to reduce the risk of a disease or condition described herein. In other embodiments, these terms may also refer to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to both straight and branched carbon chains having 1 to 20 carbon atoms or any number within this range, for example, 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$amino, the alkyl groups may be the same or different. Optionally substituted alkyls include, as specific individual embodiments, haloalkyls and particularly partially fluorinated or perfluorinated alkyls, for example, —$CH_2F$, —$CHF_2$, and —$CF_3$.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

The terms "carboxyamine" and "carboxy-alkoxide" refers to structures —$C(O)N(R^{15})_2$ and —$C(O)$—$OR^{15}$, respectively. Preferred carboxyamine" and carboxy-alkoxide moeties of the present invention include those where $R^{15}$ is, independently at each occurrence, H, $C_{1-6}$ alkyl, $C_{2-8}$ alkenyl, $C_{2-8}$ alkynyl, cycloalkyl (e.g., $C_{3-6}$ cycloalkyl), aryl, heterocyclyl, or heteroaryl. In but one example, —$C(O)N(R^{15})_2$ may be —$C(O)N(CH_3)_2$ As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

Non-limiting examples of alkyl, alkenyl, alkynyl, cycloalkyl, and cycloheteroalkyl include at least the following: methyl, methyl amine (or protected analog thereof), methoxy, ethyl, ethyl amine (or protected analog thereof), ethoxy, n-propyl, propyl amine (or protected analog thereof), n-propoxy, isopropyl, isopropyl amine (or protected analog thereof), isopropoxy, n-butyl, n-butyl amine (or protected analog thereof), n-butoxy, sec-butyl, sec-butyl amine (or protected analog thereof), sec-butoxy, tert-butyl, tert-butyl amine (or protected analog thereof), tert-butoxy, vinyl,

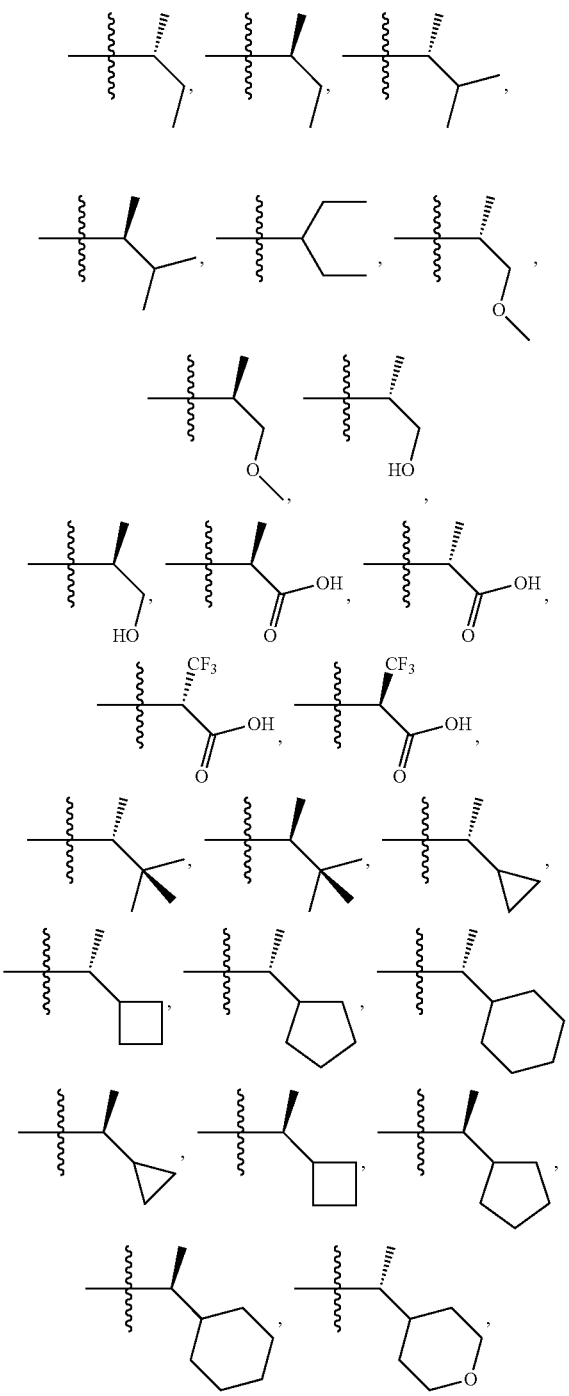

-continued

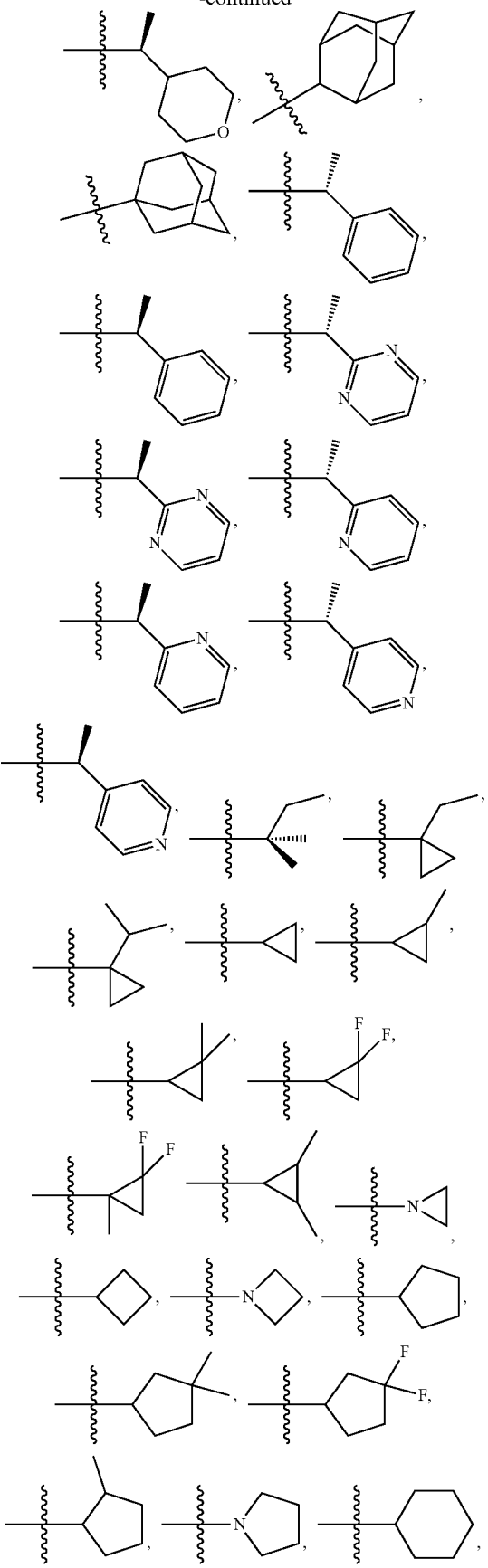

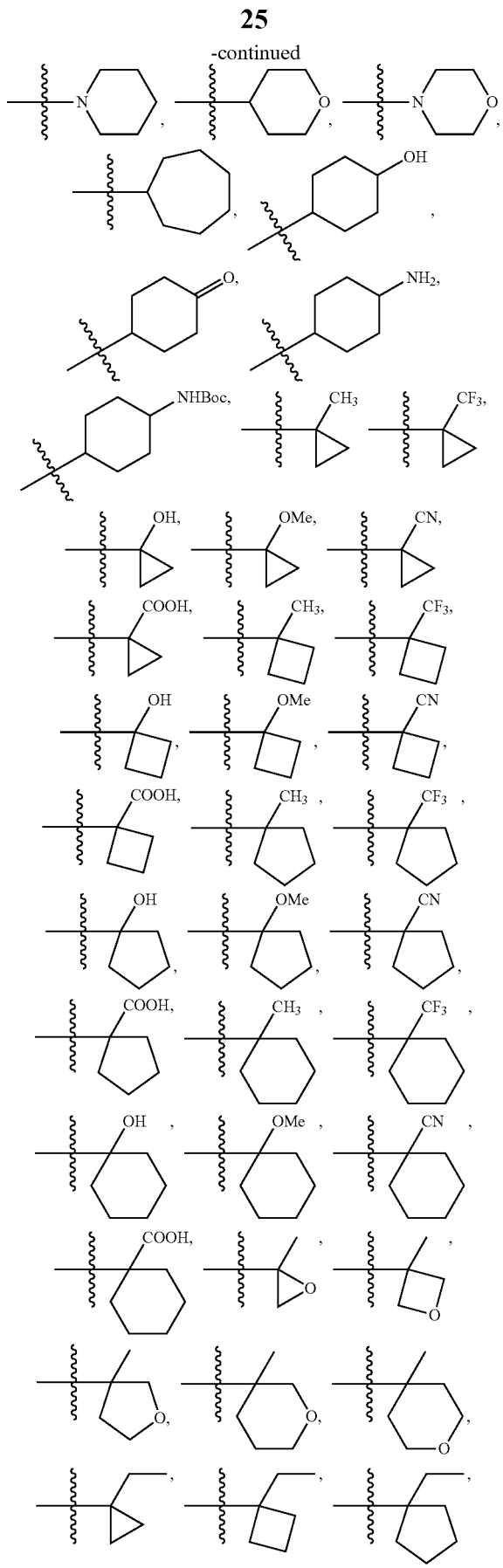

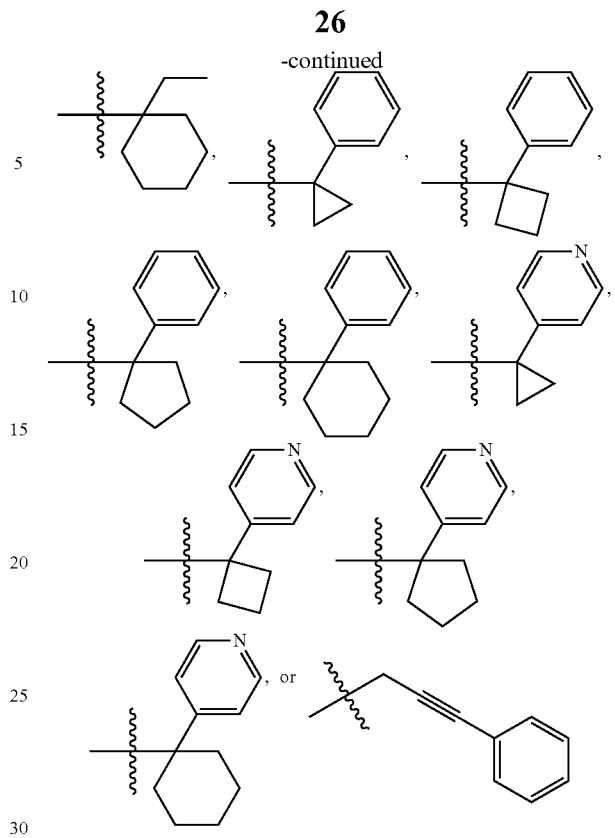

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "amidine" refers to a structure of formula —C(NR$^{15}$)(R$^{15}$)$_2$, where R$^{15}$ is defined below. Preferred amidine moeties of the present invention include those where R$^{15}$ is, independently at each occurrence, H, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocyclyl, or heteroaryl.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, benzo[1,3]dioxolyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, thiazolidinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydroquinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a carbocyclic or heterocyclic ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The carbocyclic or heterocyclic ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

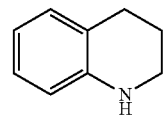

is, for the purposes of the present invention, considered a heterocyclic unit. 6,7-Dihydro-5H-cyclopentapyrimidine having the formula:

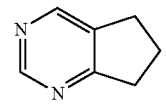

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

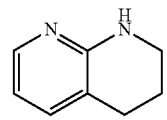

is, for the purposes of the present invention, considered a heteroaryl unit.

Non-limiting examples of aryls, heteraryls, alkaryls, and alkylheteroaryls (or heteroalkaryls) include at least the following structures:

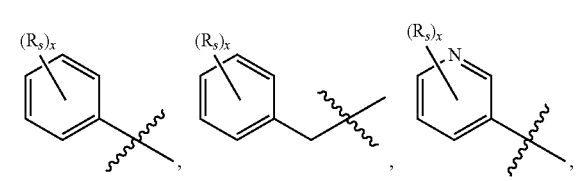

-continued

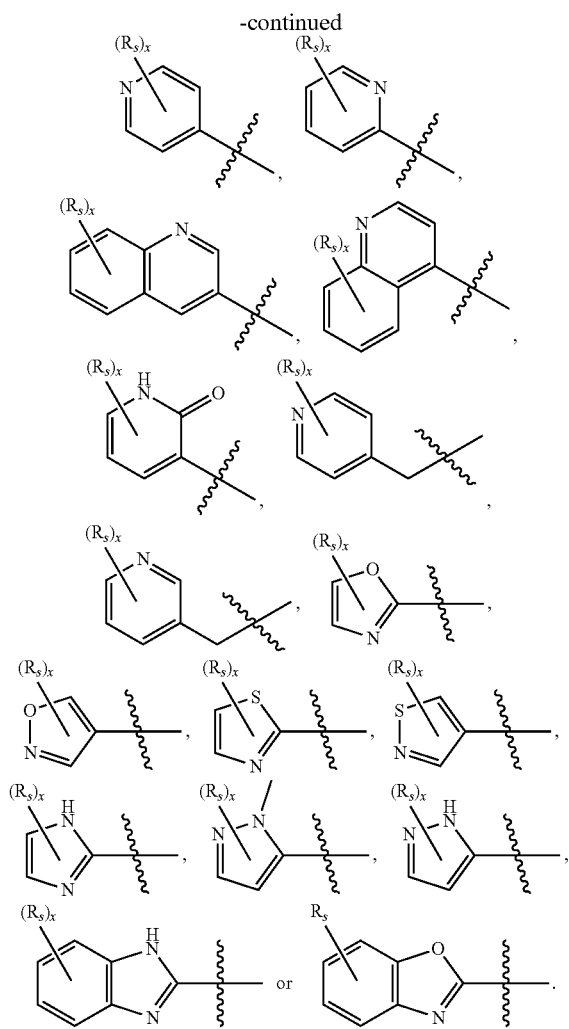

wherein $R_S$ is independently at each occurrence bromo, chloro, fluoro, cyano, hydroxyl, optionally fluorinated $C_{1-6}$ alkyl (e.g., —$CH_3$, —$CH_2F$, —$CF_2H$, —$CF_3$), —O—($C_{1-6}$ alkyl), or when two are taken form a fused cyclic or heterocyclic moiety; and x is 0, 1, 2, or 3.

It is appreciated that, where used, the designator

indicates that the substituent(s) may be present on any available ring member, as valence allows (including alkyl substitution on nitrogen). For fused bicyclic systems, the same designator connote that the substituent(s) may be present on a ring member of either ring, as valence allows. Similarly, while the points of attachments shown above are to specific carbon atoms, it should be appreciated that the aryl or heteroaryl rings may be attached to any carbon or heteroatom that valence allows.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated. The terms "optional" and "optionally," in the context of substituents connotes that the indicated substituent may or may not be present and each of these conditions represents a separate embodiment of the invention.

The following are non-limiting examples of substituents which can substitute for hydrogen atoms on a moiety: halogen (chlorine (Cl), bromine (Br), fluorine (F) and iodine (I)), —CN, —$NO_2$, oxo (=O), —$OR^{14}$, —$SR^{14}$, —$N(R^{14})_2$, —$NR^{14}C(O)R^{14}$, —$SO_2R^{14}$, $SO_2OR^{14}$, —$SO_2N(R^{14})_2$, —$C(O)R^{14}$, —$C(O)OR^{14}$, —$C(O)N(R^{14})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^{14}$; wherein $R^{14}$, at each occurrence, independently is hydrogen, —$OR^{15}$, —$SR^{15}$, —$C(O)R^{15}$, —$C(O)OR^{15}$, —$C(O)N(R^{15})_2$, —$SO_2R^{15}$, —$S(O)_2OR^{15}$, —$N(R^{15})_2$, —$NR^{15}C(O)R^{15}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{14}$ units taken together with the atom(s) to which they are bound form an optionally substituted carbocycle or heterocycle wherein said carbocycle or heterocycle has 3 to 7 ring atoms; wherein $R^{15}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{15}$ units taken together with the atom(s) to which they are bound form an optionally substituted carbocycle or heterocycle wherein said carbocycle or heterocycle preferably has 3 to 7 ring atoms. Depending on the number of substitutable hydrogen atoms, there may be 0, 1, 2, 3, 4, 5, or 6 substituents independently substituted for hydrogen atoms on the moiety.

In some embodiments, the substituents are selected from
i) —$OR^{16}$; for example, —OH, —$OCH_3$, —$OCH_2CH_3$, —$OCH_2CH_2CH_3$;
ii) —$C(O)R^{16}$; for example, —$COCH_3$, —$COCH_2CH_3$, —$COCH_2CH_2CH_3$;
iii) —$C(O)OR^{16}$; for example, —$CO_2CH_3$, —$CO_2CH_2CH_3$, —$CO_2CH_2CH_2CH_3$;
iv) —$C(O)N(R^{16})_2$; for example, —$CONH_2$, —$CONHCH_3$, —$CON(CH_3)_2$;
v) —$N(R^{16})_2$; for example, —$NH_2$, —$NHCH_3$, —$N(CH_3)_2$, —$NH(CH_2CH_3)$;
vi) halogen: —F, —Cl, —Br, and —I;
vii) —$CH_eX_g$; wherein X is halogen, m is from 0 to 2, e+g=3; for example, —$CH_2F$, —$CHF_2$, —$CF_3$, —$CCl_3$, or —$CBr_3$;
viii) —$SO_2R^{16}$; for example, —$SO_2H$; —$SO_2CH_3$; —$SO_2C_6H_5$;
ix) $C_1$-$C_6$ linear, branched, or cyclic alkyl;
x) Cyano
xi) Nitro;
xii) $N(R^{16})C(O)R^{16}$;
xiii) Oxo (=O);
xiv) Heterocycle; and
xv) Heteroaryl.
wherein each $R^{16}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{16}$ units can be taken together to form a ring comprising 3-7 ring atoms. In certain aspects, each $R^{16}$ is independently hydrogen, $C_1$-$C_6$ linear or branched alkyl optionally substituted with halogen or $C_3$-$C_6$cycloalkyl or $C_{0-6}[C_3$-$C_6$cycloalkyl].

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for nucleocapsid assembly inhibitors, especially but not exclusively, including the pregenomic RNA encapsidation inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography. For those compounds that are described as, or may comprise, optical isomers, vrious embodiments embrace at least the individual isomer or an enriched or racemic mixture thereof.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine) Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect. "Therapeutically effective amount" refers to the amount of a compound that, when administered to a subject for treating a disease or a condition, is sufficient to effect such treatment for the disease or condition. The "therapeutically effective amount" can vary depending on the compound, the disease or condition and its severity, and the age, weight, etc., of the subject to be treated.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

Compounds and Compositions

The compounds and compositions of the present invention useful for the treatment of viruses including Hepatitis B virus (HBV) infection and related conditions include all enantiomeric and diastereomeric forms and pharmaceutically accepted salts thereof having the formula (I):

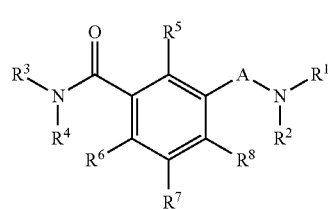

including hydrates, solvates, pharmaceutically acceptable salts, prodrugs and complexes thereof, wherein:

A is selected from a group consisting of $SO_2$ and CO;

$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted $C_{1-6}$ haloalkyl, optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;

$R^2$ is selected from a group consisting of hydrogen and optionally substituted $C_{1-6}$ linear alkyl; $R^2$ may also alternatively or additionally optionally include optionally substituted $C_{3-7}$cycloalkyl or optionally substituted heterocyclic; or $R^1$ and $R^2$ are taken together with the atoms to which they are bound to form an optionally substituted heterocycle (including bicyclic or adamantyl structures) with 3 to 10 atoms; and $R^3$ is selected from a group consisting of optionally substituted aryl, optionally substituted benzyl, optionally substituted alkylaryl, optionally substituted heteroaryl, and optionally substituted alkylheteroaryl; $R^3$ may also optionally comprise an optionally substituted $C_{1-6}$ linear alkyl;

$R^4$ is selected from a group consisting of hydrogen and optionally substituted $C_{1-6}$ linear alkyl;

$R^5$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; in some embodiments, $R^6$ may also alternatively or additionally optionally include cyano or $N(R^9)_2$; $R^6$ may also alternatively or additionally optionally include cyano or $N(R^9)_2$; or $R^4$ and $R^6$ are taken together with the atoms to which they are bound to form an optionally substituted carbocyclic or heterocyclic ring with 5 to 6 atoms, optionally containing a carbonyl, optionally containing two carbonyls; and $R^7$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^8$ may also alternatively or additionally optionally include cyano or $N(R^9)_2$; or $R^2$ and $R^8$ are taken together with the atoms to which they are bound to form an optionally substituted carbocyclic or heterocyclic ring with 5 to 6 atoms; and $R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$ cycloalkyl; $R^9$ may also alternatively or additionally optionally include independently at each occurrence optionally substituted aryl, optionally substituted benzyl, optionally substituted heterocyclyl, or optionally substituted heteroaryl;

provided that when A is $SO_2$; $R^4$ and $R^6$ taken together with the atoms to which they are bound do not to form an optionally substituted ring; and $R^2$ and $R^8$ taken together with the atoms to which they are bound do not to form an optionally substituted ring, then none of the following (a) through (d) apply:

(a) $R^3$ is an optionally substituted phenyl and $R^1$ or $R^2$, either individually or when taken together, contain a hydroxyl group, or (b) $R^3$ is an optionally substituted alkyl or phenyl, and $N(R^1)(R^2)$ is an optionally substituted piperazine or

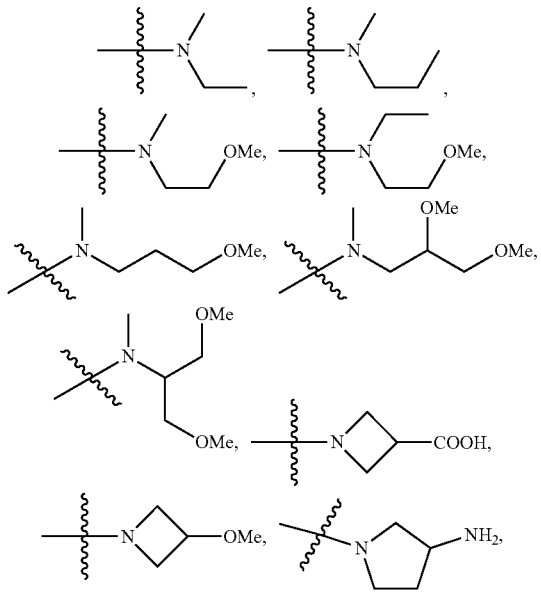

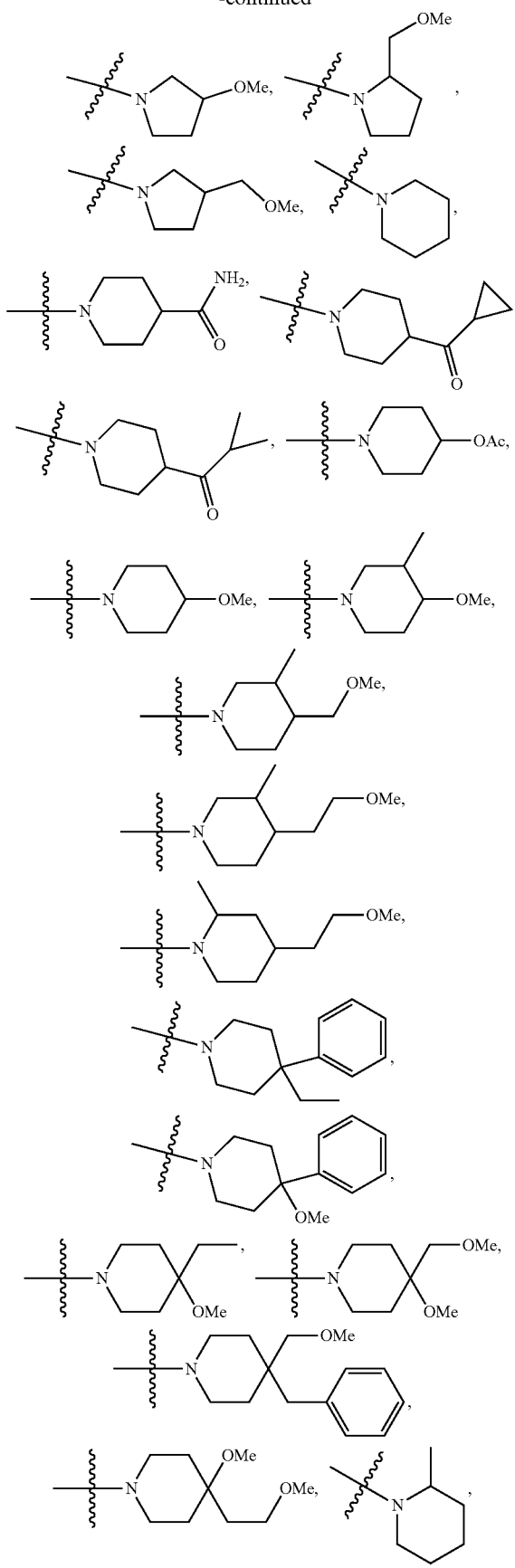
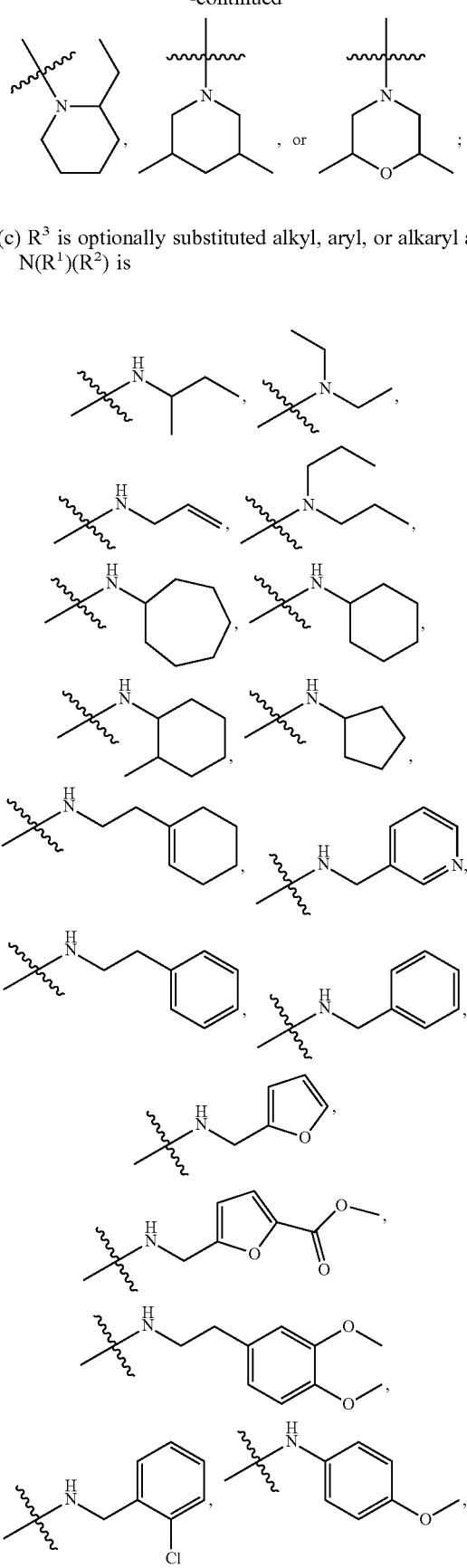
(c) $R^3$ is optionally substituted alkyl, aryl, or alkaryl and $N(R^1)(R^2)$ is

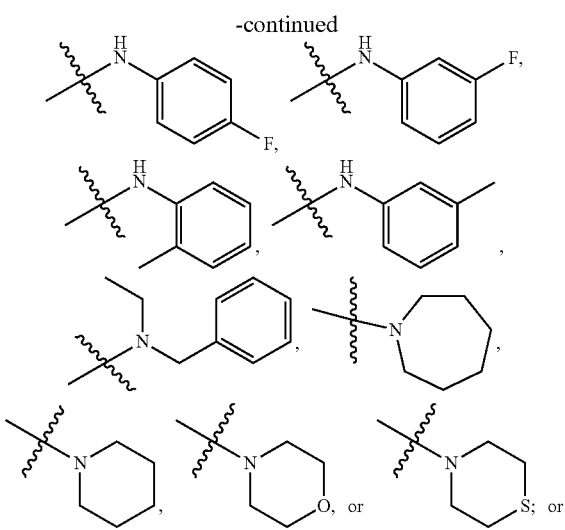

(d) either $R^3$ or $R^4$ is an unsubstituted or monosubstituted aryl, or an unsubstituted or monosubstituted aralkyl, or unsubstituted or monosubstituted heteroaryl and $R^1$ and $R^2$ are taken together with the atoms to which they are bound to form an optionally substituted heterocyclic ring structure with 6 to 12 atoms; or provided that the compound is not 3-{[(dicyclopropylmethyl)amino]sulfonyl}-N-(4-isopropoxyphenyl)benzamide; or 3-({[2-(1H-benzimidazol-2-yl)propyl]amino}sulfonyl)-N-(4-isopropoxyphenyl)benzamide; or 3-[(cyclohexylamino)sulfonyl]-N-(4-isopropylphenyl)benzamide; or 3-(anilinosulfonyl)-N-(4-isopropylphenyl)benzamide; or 5-{[(3-{[(4-methoxyphenyl)amino]carbonyl}phenyl)sulfonyl]amino}pentanoic acid; or 3-[(tert-butylamino)sulfonyl]-N-(4-methoxyphenyl)benzamide; or (3S)-1-[(3-{[(5-isopropoxypyridin-2-yl)amino]carbonyl}phenyl)sulfonyl]piperidine-3-carboxamide; or (3R)-1-[(3-{[(5-isopropoxypyridin-2-yl)amino]carbonyl}phenyl)sulfonyl]piperidine-3-carboxamide; or 3-(piperidin-1-ylsulfonyl)-N-[(1S)-1,2,3,4-tetrahydronaphthalen-1-yl]benzamide; or N-(5-bromo-3-methoxypyridin-2-yl)-3-(piperidin-1-ylsulfonyl)benzamide; or N-(3-methoxy-5-phenylpyridin-2-yl)-3-(pyrrolidin-1-ylsulfonyl)benzamide; or N-(3-methoxy-5-phenoxypyridin-2-yl)-3-(pyrrolidin-1-ylsulfonyl)benzamide; or N-[3-methoxy-5-(phenylthio)pyridin-2-yl]-3-(pyrrolidin-1-ylsulfonyl)benzamide; or N-(5-ethyl-3-methoxypyridin-2-yl)-3-(piperidin-1-ylsulfonyl)benzamide; or N-(3-methoxy-5-vinylpyridin-2-yl)-3-(piperidin-1-ylsulfonyl)benzamide; or Some embodiments of the compounds of formula (I) also exclude those compounds when A is $SO_2$; $R^4$ and $R^6$ taken together with the atoms to which they are bound do not to form an optionally substituted ring; and $R^2$ and $R^8$ taken together with the atoms to which they are bound do not to form an optionally substituted ring, $R^3$ is optionally substituted alkyl, aryl, or alkaryl and $N(R^1)(R^2)$ is an optionally substituted piperidine.

The embodiments of the present invention include compounds of formula (I) where

A is $SO_2$;

$R^4$ and $R^6$ taken together with the atoms to which they are bound do not to form an optionally substituted carbocyclic or heterocyclic ring; and $R^2$ and $R^8$ taken together with the atoms to which they are bound do not to form an optionally substituted carbocyclic or heterocyclic ring;

thereby providing compounds having formula (II), including hydrates, solvates, pharmaceutically acceptable salts, prodrugs and complexes thereof and considering the exclusions described above. In some embodiments, $R^1$ through $R^8$ are as defined for the compound of formula (I). In other independent embodiments, $R^1$ through $R^8$ are as defined below.

The embodiments of the present invention include compounds of formula (I) where A is $SO_2$, thereby providing compounds having formula (III),

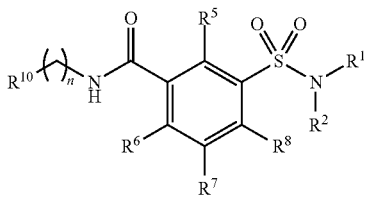

(III)

including hydrates, solvates, pharmaceutically acceptable salts, prodrugs and complexes thereof, wherein:

$R^{10}$ is selected from a group consisting of optionally substituted aryl and optionally substituted heteroaryl; and n is 0 or 1.

In some embodiments, $R^1$, $R^2$, and $R^5$ through $R^8$ are as defined for the compound of formula (I). In other independent embodiments, $R^1$, $R^2$, and $R^5$ through $R^8$ are as defined below.

The embodiments of the present invention include compounds of formula (I) where A is $SO_2$, thereby providing compounds having formula (IV),

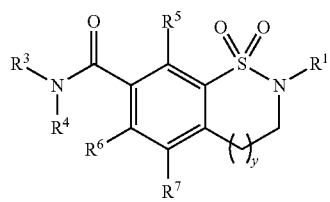

(IV)

including hydrates, solvates, pharmaceutically acceptable salts, prodrugs and complexes thereof, wherein: y is 0 or 1. In some embodiments, y is 2.

In some embodiments, $R^1$ and $R^3$ through $R^8$ are as defined for the compound of formula (I). In other independent embodiments, $R^1$ and $R^3$ through $R^8$ are as defined below.

The embodiments of the present invention include compounds of formula (I) where A is $SO_2$, thereby providing compounds having formula (V),

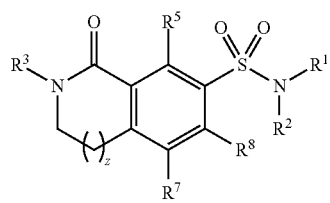

(V)

including hydrates, solvates, pharmaceutically acceptable salts, prodrugs and complexes thereof, wherein:

z is 0 or 1.

In some embodiments, $R^1$ through $R^3$, $R^5$, and $R^7$ through $R^8$ are as defined for the compound of formula (I). In other independent embodiments, $R^1$ through $R^3$, $R^5$, and $R^7$ through $R^8$ are as defined below.

The embodiments of the present invention include compounds having formula (VI),

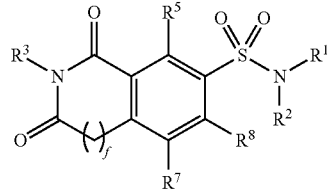

(VI)

including hydrates, solvates, pharmaceutically acceptable salts, prodrugs and complexes thereof, wherein: f is 0 or 1.

In some embodiments, $R^1$ through $R^3$, $R^5$, and $R^7$ through $R^8$ are as defined for the compound of formula (I). In other independent embodiments, $R^1$ through $R^3$, $R^5$, and $R^7$ through $R^8$ are as defined below.

The embodiments of the present invention include compounds of formula (I) where A is CO, thereby providing compounds having formula (VII),

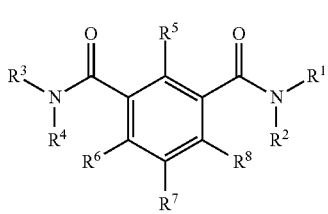

(VII)

including hydrates, solvates, pharmaceutically acceptable salts, prodrugs and complexes thereof.

In some embodiments, $R^1$ through $R^8$ are as defined for the compound of formula (I). In other independent embodiments, $R^1$ through $R^8$ are as defined below.

The embodiments of the present invention include compounds of formula (I) where A is CO, thereby providing compounds having formula (VIII),

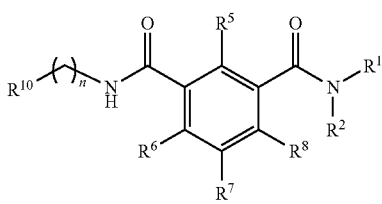

(VIII)

including hydrates, solvates, pharmaceutically acceptable salts, prodrugs and complexes thereof, wherein:

$R^{10}$ is selected from a group consisting of optionally substituted aryl and optionally substituted heteroaryl; and n is 0 or 1.

In some embodiments, $R^1$ through $R^2$ and $R^5$ through $R^8$ are as defined for the compound of formula (I). In other independent embodiments, $R^1$ through $R^2$ and $R^5$ through $R^8$ are as defined below.

The embodiments of the present invention include compounds having formula (IX),

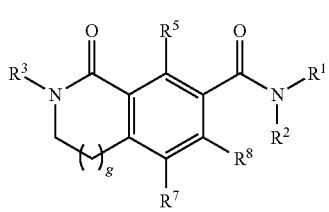

(IX)

including hydrates, solvates, pharmaceutically acceptable salts, prodrugs and complexes thereof, wherein: g is 0 or 1.

In some embodiments, $R^1$ through $R^3$, $R^5$, and $R^7$ through $R^8$ are as defined for the compound of formula (I). In other embodiments, $R^1$ through $R^3$, $R^5$, and $R^7$ through $R^8$ are as defined below.

The embodiments of the present invention include compounds of formula (I) where A is CO, thereby providing compounds having formula (X),

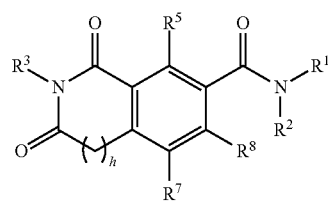

(X)

including hydrates, solvates, pharmaceutically acceptable salts, prodrugs and complexes thereof, wherein: h is 0 or 1.

In some embodiments, $R^1$ through $R^3$, $R^5$, and $R^7$ through $R^8$ are as defined for the compound of formula (I). In other independent embodiments, $R^1$ through $R^3$, $R^5$, and $R^7$ through $R^8$ are as defined below.

The embodiments of the present invention include compounds having formula (XI), useful as nucleocapsid assembly inhibitors, especially but not exclusively, including pregenomic RNA encapsidation inhibitors of HBV for the treatment of Hepatitis B virus (HBV) infection and related conditions

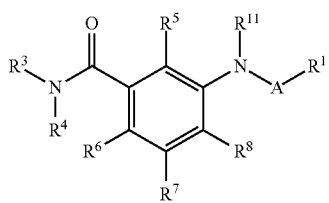

(XI)

including all enantiomeric forms, diastereomeric forms, hydrates, solvates, pharmaceutically acceptable salts, prodrugs and complexes thereof,
wherein:
A is selected from a group consisting of $SO_2$ and CO;
$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl;

$R^3$ is selected from a group consisting of optionally substituted aryl, optionally substituted benzyl, optionally substituted alkylaryl, optionally substituted heteroaryl, and optionally substituted alkylheteroaryl; in some embodiments, $R^3$ may also comprise an optionally substituted $C_{1-6}$ linear alkyl;

$R^4$ is selected from a group consisting of hydrogen and optionally substituted $C_{1-6}$ linear alkyl;

$R^5$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^6$ may also alternatively or additionally optionally include cyano or $N(R^9)_2$; or $R^4$ and $R^6$ are taken together with the atoms to which they are bound to form an optionally substituted carbocyclic or heterocyclic ring with 5 to 6 atoms, optionally containing a carbonyl, optionally containing two carbonyls; and $R^7$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^8$ may also alternatively or additionally optionally include cyano or $N(R^9)_2$;

$R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$ cycloalkyl, and optionally substituted $C_{1-6}$ haloalkyl; $R^9$ may also alternatively or additionally optionally include independently at each occurrence optionally substituted aryl, optionally substituted benzyl, optionally substituted heterocyclyl, or optionally substituted heteroaryl; and $R^{11}$ is selected from a group consisting of hydrogen, optionally substituted $C_{1-6}$ linear alkyl, optionally substituted $C_{1-6}$ branched alkyl, and optionally substituted $C_{3-7}$ cycloalkyl.

The embodiments of the present invention include compounds having formula (XII),

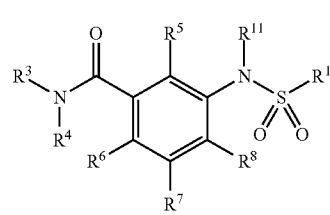

(XII)

including hydrates, solvates, pharmaceutically acceptable salts, prodrugs and complexes thereof.

In some embodiments, $R^1$, $R^3$ through $R^8$ and $R^{11}$ are as defined for the compound of formula (XI). In other embodiments, $R^1$, $R^3$ through $R^8$ and $R^{11}$ are as defined below.

The embodiments of the present invention include compounds having formula (XIII),

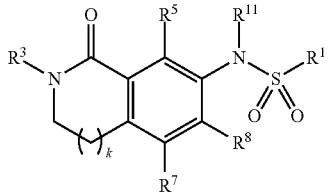

(XIII)

including hydrates, solvates, pharmaceutically acceptable salts, prodrugs and complexes thereof wherein: k is 0 or 1.

In some embodiments, $R^1$, $R^3$, $R^5$, $R^7$, $R^8$ and $R^{11}$ are as defined for the compound of formula (XI). In other independent embodiments, $R^1$, $R^3$, $R^5$, $R^7$, $R^8$ and $R^{11}$ are as defined below.

The embodiments of the present invention include compounds having formula (XIV),

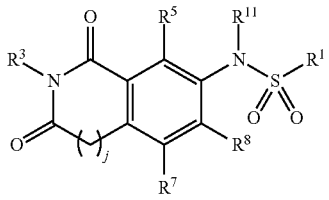

(XIV)

including hydrates, solvates, pharmaceutically acceptable salts, prodrugs and complexes thereof wherein: j is 0 or 1.

In some embodiments, $R^1$, $R^3$, $R^5$, $R^7$, $R^8$ and $R^{11}$ are as defined for the compound of formula (XI). In other embodiments, $R^1$, $R^3$, $R^5$, $R^7$, $R^8$ and $R^{11}$ are as defined below.

The embodiments of the present invention include compounds having formula (XV),

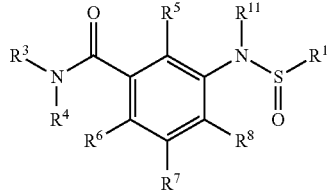

(XV)

including hydrates, solvates, pharmaceutically acceptable salts, prodrugs and complexes thereof.

In some embodiments, $R^1$, $R^3$ through $R^8$ and $R^{11}$ are as defined for the compound of formula (XI). In other embodiments, $R^1$, $R^3$ through $R^8$ and $R^{11}$ are as defined below.

The embodiments of the present invention include compounds having formula (XVI),

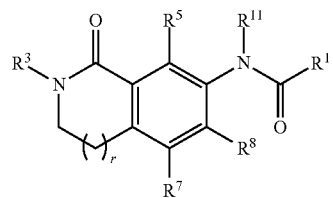

(XVI)

including hydrates, solvates, pharmaceutically acceptable salts, prodrugs and complexes thereof wherein: r is 0 or 1.

In some embodiments, $R^1$, $R^3$, $R^5$, $R^7$, $R^8$ and $R^{11}$ are as defined for the compound of formula (XI). In other embodiments, $R^1$, $R^3$, $R^5$, $R^7$, $R^8$ and $R^{11}$ are as defined below.

The embodiments of the present invention include compounds having formula (XVII),

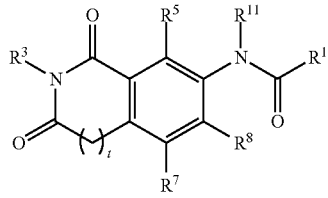

(XVII)

including hydrates, solvates, pharmaceutically acceptable salts, prodrugs and complexes thereof wherein: t is 0 or 1.

In some embodiments, $R^1$, $R^3$, $R^5$, $R^7$, $R^8$ and $R^{11}$ are as defined for the compound of formula (XI). In other embodiments, $R^1$, $R^3$, $R^5$, $R^7$, $R^8$ and $R^{11}$ are as defined below.

The embodiments of the present invention include compounds having formula (XVIII), useful as nucleocapsid assembly inhibitors, especially but not exclusively, including pregenomic RNA encapsidation inhibitors of HBV for the treatment of Hepatitis B virus (HBV) infection and related conditions

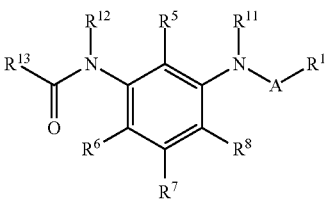

(XVIII)

including all enantiomeric forms, diastereomeric forms, hydrates, solvates, pharmaceutically acceptable salts, prodrugs and complexes thereof wherein:
A is selected from a group consisting of $SO_2$ and CO;
$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl;
$R^5$ is selected from a group consisting of hydrogen, halogen, optionally substituted $C_{1-6}$ linear alkyl, optionally substituted $C_{1-6}$ branched alkyl, optionally substituted C$_{1-6}$haloalkyl, and OR$^9$; R$^5$ may also alternatively or additionally optionally include cyano or N(R$^9$)$_2$;

R$^6$ is selected from a group consisting of hydrogen, halogen, optionally substituted C$_{1-6}$ linear alkyl, optionally substituted C$_{1-6}$ branched alkyl, optionally substituted C$_{1-6}$haloalkyl, and OR$^9$; R$^6$ may also alternatively or additionally optionally include cyano or N(R$^9$)$_2$;

R$^7$ is selected from a group consisting of hydrogen, halogen, optionally substituted C$_{1-6}$ linear alkyl, optionally substituted C$_{1-6}$ branched alkyl, optionally substituted C$_{1-6}$haloalkyl, and OR$^9$; R$^7$ may also alternatively or additionally optionally include cyano or N(R$^9$)$_2$;

R$^8$ is selected from a group consisting of hydrogen, halogen, optionally substituted C$_{1-6}$ linear alkyl, optionally substituted C$_{1-6}$ branched alkyl, optionally substituted C$_{1-6}$haloalkyl, and OR$^9$; R$^8$ may also alternatively or additionally optionally include cyano or N(R$^9$)$_2$;

R$^9$ is independently at each occurrence selected from a group consisting of hydrogen, optionally substituted C$_{1-6}$ linear alkyl, optionally substituted C$_{1-6}$ branched alkyl, and optionally substituted C$_{3-7}$ cycloalkyl; R$^9$ may also alternatively or additionally optionally include independently at each occurrence optionally substituted aryl, optionally substituted benzyl, optionally substituted heterocyclyl, or optionally substituted heteroaryl;

R$^{11}$ is selected from a group consisting of hydrogen, optionally substituted C$_{1-6}$ linear alkyl, optionally substituted C$_{1-6}$ branched alkyl, and optionally substituted C$_{3-7}$ cycloalkyl;

R$^{12}$ is selected from a group consisting of hydrogen, optionally substituted C$_{1-6}$ linear alkyl, optionally substituted C$_{1-6}$ branched alkyl, and optionally substituted C$_{3-7}$ cycloalkyl; and R$^{13}$ is selected from a group consisting of optionally substituted aryl, optionally substituted benzyl, optionally substituted alkylaryl, optionally substituted heteroaryl, and optionally substituted alkylheteroaryl.

The embodiments of the present invention include compounds having formula (XIX),

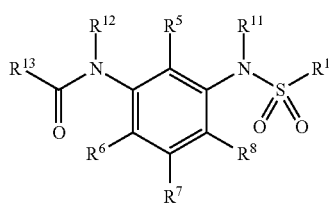

(XIX)

including hydrates, solvates, pharmaceutically acceptable salts, prodrugs and complexes thereof.

In some embodiments, R$^1$, R$^5$ through R$^8$ and R$^{11}$ through R$^{13}$ are as defined for the compound of formula (XVIII). In other embodiments, R$^1$, R$^5$ through R$^8$ and R$^{11}$ through R$^{13}$ are as defined below.

The embodiments of the present invention include compounds having formula (XX),

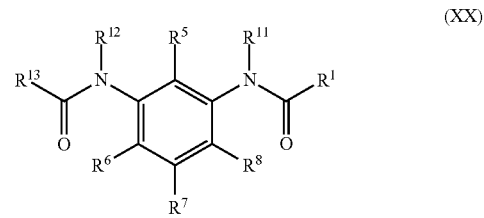

(XX)

including hydrates, solvates, pharmaceutically acceptable salts, prodrugs and complexes thereof.

In some embodiments, R$^1$, R$^5$ through R$^8$ and R$^{11}$ through R$^{13}$ are as defined for the compound of formula (XVIII). In other embodiments, R$^1$, R$^5$ through R$^8$ and R$^{11}$ through R$^{13}$ are as defined below.

The embodiments of the present invention include compounds having formula (XXI), useful as nucleocapsid assembly inhibitors, especially but not exclusively, including pregenomic RNA encapsidation inhibitors of HBV for the treatment of Hepatitis B virus (HBV) infection and related conditions

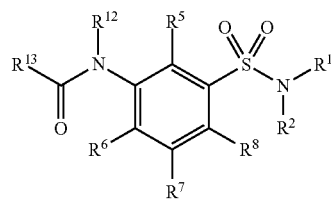

(XXI)

including all enantiomeric forms, diastereomeric forms, hydrates, solvates, pharmaceutically acceptable salts, prodrugs and complexes thereof, wherein:

R$^1$ is selected from a group consisting of optionally substituted C$_{1-6}$ linear alkyl, optionally substituted C$_{1-6}$branched alkyl, optionally substituted C$_{3-7}$ cycloalkyl, optionally substituted aryl, and optionally substituted benzyl; R$^1$ may also alternatively or additionally optionally include optionally substituted C$_{1-6}$ haloalkyl, optionally substituted 3-7 membered cycloheteroalkyl, optionally substituted C$_{2-8}$ alkenyl, optionally substituted C$_{2-8}$ alkynyl, optionally substituted C$_{1-6}$ alkoxy, optionally substituted amine, optionally substituted amidine, optionally substituted carboxyamine, optionally substituted carboxy-C$_{1-6}$-alkoxide, —SO$_2$—C$_{1-6}$alkyl, optionally substituted heterocyclic, or optionally substituted heteroaryl;

R$^2$ is selected from a group consisting of hydrogen and optionally substituted C$_{1-6}$ linear alkyl; R$^2$ may also alternatively or additionally optionally include optionally substituted C$_{3-7}$ cycloalkyl or optionally substituted heterocyclic; or R$^1$ and R$^2$ are taken together with the atoms to which they are bound to form an optionally substituted heterocycle (including cyclic and heterocyclic structures) with 3 to 10 atoms;

R$^5$ is selected from a group consisting of hydrogen, halogen, optionally substituted C$_{1-6}$ linear alkyl, optionally substituted C$_{1-6}$branched alkyl, optionally substituted $C_{1-6}$haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; $R^6$ may also alternatively or additionally optionally include cyano or $N(R^9)_2$;

$R^7$ is selected from a group consisting of hydrogen, halogen, optionally substituted $C_{1-6}$ linear alkyl, optionally substituted $C_{1-6}$branched alkyl, optionally substituted $C_{1-6}$haloalkyl, $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; $R^8$ may also alternatively or additionally optionally include cyano or $N(R^9)_2$;

$R^9$ is independently at each occurrence selected from a group consisting of hydrogen, optionally substituted $C_{1-6}$ linear alkyl, optionally substituted $C_{1-6}$branched alkyl, and optionally substituted $C_{3-7}$ cycloalkyl, and optionally substituted $C_{1-6}$haloalkyl; $R^9$ may also alternatively or additionally optionally include, independently at each occurrence, optionally substituted aryl, optionally substituted benzyl, optionally substituted heterocyclyl, or optionally substituted heteroaryl;

$R^{12}$ is selected from a group consisting of hydrogen, optionally substituted $C_{1-6}$ linear alkyl, optionally substituted $C_{1-6}$ branched alkyl, and optionally substituted $C_{3-7}$ cycloalkyl; and $R^{13}$ is selected from a group consisting of optionally substituted aryl, optionally substituted benzyl, optionally substituted alkylaryl, optionally substituted heteroaryl, and optionally substituted alkylheteroaryl.

For the purposes of demonstrating the manner in which the compounds of the present invention are named and referred to herein, the compound having the formula (XXII):

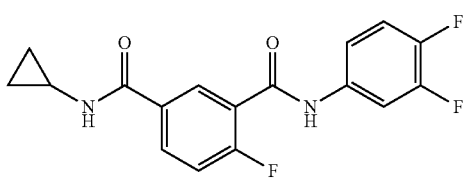

(XXII)

has the chemical name $N^1$-cyclopropyl-$N^3$-(3,4-difluorophenyl)-4-fluoroisophthalamide.

For the purposes of demonstrating the manner in which the compounds of the present invention are named and referred to herein, the compound having the formula (XXIII):

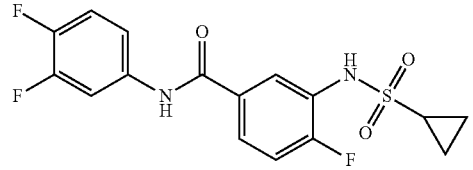

(XXIII)

has the chemical name 3-(cyclopropanesulfonamido)-N-(3,4-difluorophenyl)-4-fluorobenzamide.

For the purposes of demonstrating the manner in which the compounds of the present invention are named and referred to herein, the compound having the formula (XXIV):

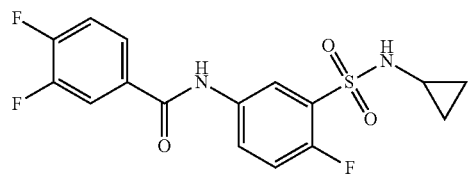

(XXIV)

has the chemical name N-(3-(N-cyclopropylsulfamoyl)-4-fluorophenyl)-3,4-difluorobenzamide.

For the purposes of demonstrating the manner in which the compounds of the present invention are named and referred to herein, the compound having the formula (XXV):

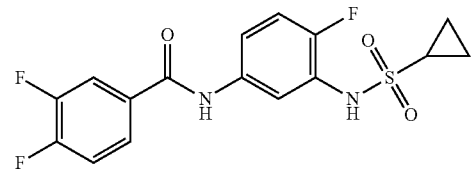

(XXV)

has the chemical name N-(3-(cyclopropanesulfonamido)-4-fluorophenyl)-3,4-difluorobenzamide.

For the purposes of the present invention, a compound depicted by the racemic formula (XXVI), for example:

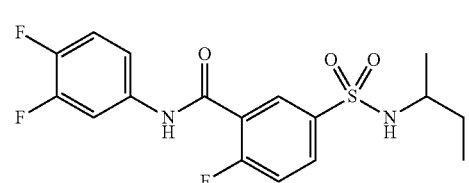

(XXVI)

will stand equally well for either of the two enantiomers having the formula (XXVII):

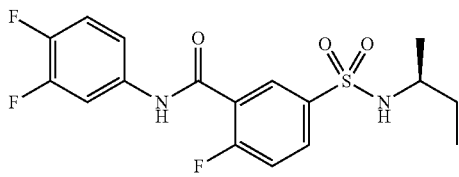

(XXVII)

or the formula (XXVIII):

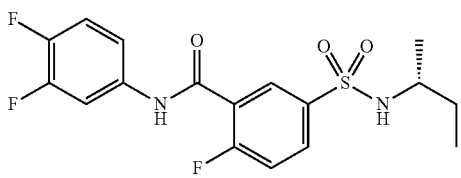

(XXVIII)

or mixtures thereof, or in the case where a second chiral center is present, all diastereomers.

In some embodiments of the preceding compounds, A is $SO_2$.

In some embodiments of the preceding compounds, A is CO.

In some embodiments of the preceding compounds, $R^1$ is optionally substituted $C_{1-6}$ linear alkyl.

In some embodiments of the preceding compounds, $R^1$ is optionally substituted $C_{1-6}$ branched alkyl.

In some embodiments of the preceding compounds, $R^1$ is optionally substituted $C_{3-7}$ cycloalkyl In some embodiments of the preceding compounds, $R^1$ is optionally substituted aryl.

In some embodiments of the preceding compounds, $R^1$ is optionally substituted benzyl. The alkyl or benzyl substituents may be chiral or achiral, and if chiral may be S- or R-configured. Particularly attractive embodiments appear to comprise those where $R^1$ has predominantly an R-configured branched alkyl group, such as

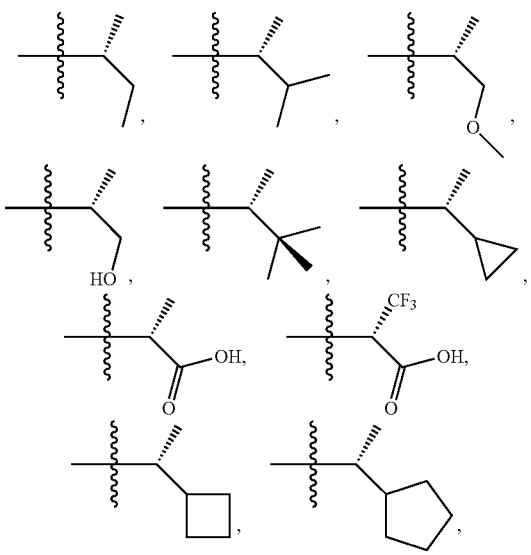

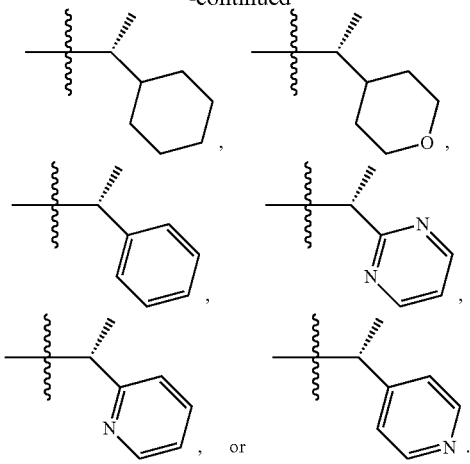

As used herein, the term "predominantly R-configured" includes those compounds where the carbon is pure or enriched in R-isomer at the respective position. In other embodiments, useful enbodiments include those where $R^1$ has predominantly an S-configured branched alkyl group.

In some embodiments of the preceding compounds, $R^2$ is hydrogen.

In some embodiments of the preceding compounds, $R^2$ is optionally substituted $C_{1-6}$ linear alkyl.

In some embodiments of the preceding compounds, Wand $R^2$ are taken together with the atoms to which they are bound to form an optionally substituted ring with 3 atoms.

In some embodiments of the preceding compounds, Wand $R^2$ are taken together with the atoms to which they are bound to form an optionally substituted ring with 4 atoms.

In some embodiments of the preceding compounds, Wand $R^2$ are taken together with the atoms to which they are bound to form an optionally substituted ring with 5 atoms.

In some embodiments of the preceding compounds, Wand $R^2$ are taken together with the atoms to which they are bound to form an optionally substituted ring with 6 atoms.

In some embodiments of the preceding compounds, Wand $R^2$ are taken together with the atoms to which they are bound to form an optionally substituted ring with 7 atoms.

In some embodiments of the preceding compounds, $R^1$ and $R^2$ are taken together with the atoms to which they are bound to form an optionally substituted heterocycle with 6 atoms.

In some embodiments of the preceding compounds, $R^1$ and $R^2$ are taken together with the atoms to which they are bound to form an optionally substituted heterocycle with 7 atoms.

In some embodiments of the preceding compounds, $R^1$ and $R^2$ are taken together with the atoms to which they are bound to form an optionally substituted heterocycle with 8 atoms.

In some embodiments of the preceding compounds, $R^1$ and $R^2$ are taken together with the atoms to which they are bound to form an optionally substituted heterocycle with 9 atoms.

In some embodiments of the preceding compounds, $R^1$ and $R^2$ are taken together with the atoms to which they are bound to form an optionally substituted heterocycle with 10 atoms.

In some embodiments of the preceding compounds, $R^3$ is optionally substituted aryl.

In some embodiments of the preceding compounds, $R^3$ is optionally substituted benzyl In some embodiments of the preceding compounds, $R^3$ is optionally substituted alkylaryl In some embodiments of the preceding compounds, $R^3$ is optionally substituted heteroaryl In some embodiments of the preceding compounds, $R^3$ is optionally substituted alkylheteroaryl In some embodiments of the preceding compounds, $R^4$ is hydrogen.

In some embodiments of the preceding compounds, $R^4$ is optionally substituted $C_{1-6}$ linear alkyl.

In some embodiments of the preceding compounds, $R^5$ is hydrogen.

In some embodiments of the preceding compounds, $R^5$ is halogen.

In some embodiments of the preceding compounds, $R^5$ is optionally substituted $C_{1-6}$ linear alkyl.

In some embodiments of the preceding compounds, $R^5$ is optionally substituted $C_{1-6}$ branched alkyl.

In some embodiments of the preceding compounds, $R^5$ is optionally substituted $C_{1-6}$ haloalkyl.

In some embodiments of the preceding compounds, $R^5$ is $OR^9$.

In some embodiments of the preceding compounds, $R^6$ is hydrogen.

In some embodiments of the preceding compounds, $R^6$ is halogen.

In some embodiments of the preceding compounds, $R^6$ is optionally substituted $C_{1-6}$ linear alkyl.

In some embodiments of the preceding compounds, $R^6$ is optionally substituted $C_{1-6}$ branched alkyl.

In some embodiments of the preceding compounds, $R^6$ is optionally substituted $C_{1-6}$ haloalkyl.

In some embodiments of the preceding compounds, $R^6$ is $OR^9$.

In some embodiments of the preceding compounds, $R^4$ and $R^6$ are taken together with the atoms to which they are bound to form an optionally substituted carbocyclic or heterocyclic ring with 5 atoms.

In some embodiments of the preceding compounds, $R^4$ and $R^6$ are taken together with the atoms to which they are bound to form an optionally substituted carbocyclic or heterocyclic ring with 6 atoms.

In some embodiments of the preceding compounds, $R^4$ and $R^6$ are taken together with the atoms to which they are bound to form an optionally substituted carbocyclic or heterocyclic ring with 5 atoms containing a carbonyl.

In some embodiments of the preceding compounds, $R^4$ and $R^6$ are taken together with the atoms to which they are bound to form an optionally substituted carbocyclic or heterocyclic ring with 6 atoms containing a carbonyl.

In some embodiments of the preceding compounds, $R^4$ and $R^6$ are taken together with the atoms to which they are bound to form an optionally substituted carbocyclic or heterocyclic ring with 5 atoms containing two carbonyls.

In some embodiments of the preceding compounds, $R^4$ and $R^6$ are taken together with the atoms to which they are bound to form an optionally substituted carbocyclic or heterocyclic ring with 6 atoms containing two carbonyls.

In some embodiments of the preceding compounds, $R^7$ is hydrogen.

In some embodiments of the preceding compounds, $R^7$ is halogen.

In some embodiments of the preceding compounds, $R^7$ is optionally substituted $C_{1-6}$ linear alkyl.

In some embodiments of the preceding compounds, $R^7$ is optionally substituted $C_{1-6}$ branched alkyl.

In some embodiments of the preceding compounds, $R^7$ is optionally substituted $C_{1-6}$ haloalkyl.

In some embodiments of the preceding compounds, $R^7$ is $OR^9$.

In some embodiments of the preceding compounds, $R^8$ is hydrogen.

In some embodiments of the preceding compounds, $R^8$ is halogen.

In some embodiments of the preceding compounds, $R^8$ is optionally substituted $C_{1-6}$ linear alkyl.

In some embodiments of the preceding compounds, $R^8$ is optionally substituted $C_{1-6}$ branched alkyl.

In some embodiments of the preceding compounds, $R^8$ is optionally substituted $C_{1-6}$ haloalkyl.

In some embodiments of the preceding compounds, $R^8$ is $OR^9$.

In some embodiments of the preceding compounds, $R^2$ and $R^8$ are taken together with the atoms to which they are bound to form an optionally substituted carbocyclic or heterocyclic ring with 5 atoms.

In some embodiments of the preceding compounds, $R^2$ and $R^8$ are taken together with the atoms to which they are bound to form an optionally substituted carbocyclic or heterocyclic ring with 6 atoms.

In some embodiments of the preceding compounds, $R^9$ is hydrogen.

In some embodiments of the preceding compounds, $R^9$ is optionally substituted $C_{1-6}$ linear alkyl.

In some embodiments of the preceding compounds, $R^9$ is optionally substituted $C_{1-6}$ branched alkyl.

In some embodiments of the preceding compounds, $R^9$ is optionally substituted $C_{3-7}$ cycloalkyl.

In some embodiments of the preceding compounds, $R^9$ is optionally substituted $C_{1-6}$ haloalkyl.

In some embodiments of the preceding compounds, $R^9$ is optionally substituted aryl.

In some embodiments of the preceding compounds, $R^9$ is optionally substituted heteroaryl.

In some embodiments of the preceding compounds, $R^9$ is optionally substituted benzyl.

In some embodiments of the preceding compounds, $R^9$ is optionally substituted heterocyclyl.

In some embodiments of the preceding compounds, $R^{10}$ is optionally substituted aryl.

In some embodiments of the preceding compounds, $R^{10}$ is optionally substituted heteroaryl.

In some embodiments of the preceding compounds, n is 0.

In some embodiments of the preceding compounds, n is 1.

In some embodiments of the preceding compounds, y is 0.

In some embodiments of the preceding compounds, y is 1.

In some embodiments of the preceding compounds, y is 2

In some embodiments of the preceding compounds, z is 0.

In some embodiments of the preceding compounds, z is 1.

In some embodiments of the preceding compounds, f is 0.

In some embodiments, f is 1.

In some embodiments of the preceding compounds, g is 0.

In some embodiments of the preceding compounds, g is 1.

In some embodiments of the preceding compounds, h is 0.

In some embodiments of the preceding compounds, h is 1.

In some embodiments of the preceding compounds, $R^{11}$ is hydrogen.

In some embodiments of the preceding compounds, $R^{11}$ is optionally substituted $C_{1-6}$ linear alkyl.

In some embodiments of the preceding compounds, $R^{11}$ is optionally substituted $C_{1-6}$ branched alkyl.

In some embodiments of the preceding compounds, $R^{11}$ is optionally substituted $C_{3-7}$ cycloalkyl.

In some embodiments of the preceding compounds, k is 0.

In some embodiments of the preceding compounds, k is 1.

In some embodiments of the preceding compounds, j is 0.
In some embodiments of the preceding compounds, j is 1.
In some embodiments of the preceding compounds, r is 0.
In some embodiments of the preceding compounds, r is 1.
In some embodiments of the preceding compounds, t is 0.
In some embodiments of the preceding compounds, t is 1.
In some embodiments, $R^{12}$ is hydrogen.
In some embodiments of the preceding compounds, $R^{12}$ is optionally substituted $C_{1-6}$ linear alkyl.
In some embodiments of the preceding compounds, $R^{12}$ is optionally substituted $C_{1-6}$ branched alkyl.
In some embodiments of the preceding compounds, $R^{12}$ is optionally substituted $C_{3-7}$ cycloalkyl.
In some embodiments of the preceding compounds, $R^{13}$ is optionally substituted aryl.
In some embodiments of the preceding compounds, $R^{13}$ is optionally substituted benzyl.
In some embodiments of the preceding compounds, $R^{13}$ is optionally substituted alkylaryl.
In some embodiments of the preceding compounds, $R^{13}$ is optionally substituted heteroaryl.
In some embodiments of the preceding compounds, $R^{13}$ is optionally substituted alkylheteroaryl.

Exemplary embodiments include compounds having the formula (XXIX) or a pharmaceutically acceptable salt form thereof:

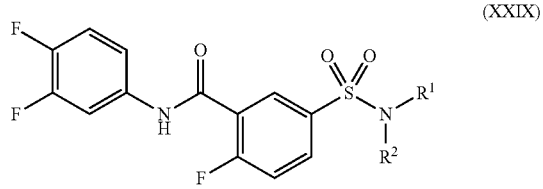

(XXIX)

wherein non-limiting examples of $R^1$ and $R^2$ are defined herein below in Table 1.

TABLE 1

Exemplary embodiments of compounds of the formula (XXIX):

TABLE 1-continued

Exemplary embodiments of compounds of the formula (XXIX):

| R¹ | R² | R¹ | R² |
|---|---|---|---|
| isopropyl | H | 2,2-dimethylcyclopropyl | H |
| tert-butyl | H | 1-methylcyclopropyl | H |
| sec-butyl | H | 1-cyanocyclopropyl | H |
| 3-methylbutan-2-yl | H | benzyl | —CH₂CH₃ |
| cyclohexylmethyl | H | | —CH₂CH₂— |
| 3-hydroxy-2-methylpropyl | H | | —CH₂CH₂CH₂— |
| 3-hydroxy-2-methylpropyl | H | | —CH₂(CH₂)₂CH₂— |
| 3-methylbutan-2-yl | H | | —CH₂(CH₂)₃CH₂— |
| 1-phenylethyl | H | | —CH₂(CH₂)₄CH₂— |
| neopentyl | H | cyclopentylmethyl | |

Exemplary embodiments include compounds having the formula (XXX) or a pharmaceutically acceptable salt form thereof:

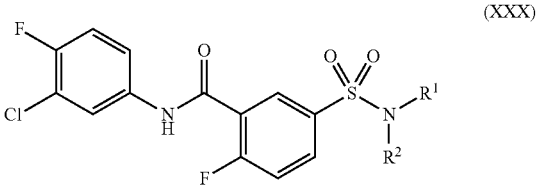

(XXX)

wherein non-limiting examples of R¹ and R² are defined herein below in Table 2.

TABLE 2

Exemplary embodiments of compounds of the formula (XXX):

| R¹ | R² | R¹ | R² |
|---|---|---|---|
| cycloheptyl | H | 3-methylbutan-2-yl | H |
| cyclohexyl | H | methoxymethyl-methyl | H |
| 2-chlorobenzyl | H | methoxymethyl-methyl | H |
| cyclopentyl | H | 1-phenylethyl | H |
| sec-butyl | H | 1-phenylethyl | H |
| cyclopropyl | H | 2-methylcyclopropylmethyl | H |

TABLE 2-continued

Exemplary embodiments of compounds of the formula (XXX):

| R¹ | R² | R¹ | R² |
|---|---|---|---|
| 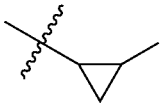 [SMILES: *C1CC1C] | H |  | H |
|  | H | 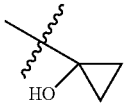 [SMILES: *C1(O)CC1] | H |
| —CH₃ | H |  | H |
| —CH₂CH₃ | H | 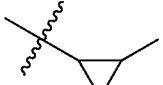 | H |
|  | H | 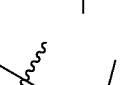 | H |
|  | H |  | H |
|  | H |  | H |
|  | H | 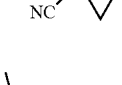 | —CH₂CH₃ |
| 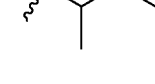 | H | —CH₂CH₂— | |
| 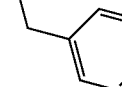 | H | —CH₂CH₂CH₂— | |
| 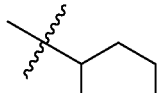 | H | —CH₂(CH₂)₂CH₂— | |
| 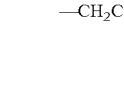 | H | —CH₂(CH₂)₃CH₂— | |
| 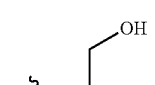 | H | —CH₂(CH₂)₄CH₂— | |
| 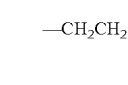 | H | | |
| 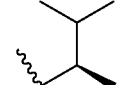 | H | 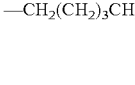 | |

Exemplary embodiments include compounds having the formula (XXXI) or a pharmaceutically acceptable salt form thereof:

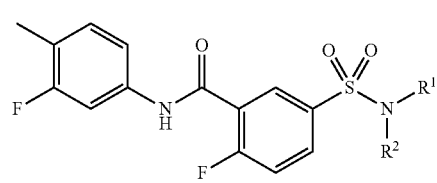

(XXXI)

wherein non-limiting examples of R¹ and R² are defined herein below in Table 3.

TABLE 3

Exemplary embodiments of compounds of the formula (XXXI):

| R¹ | R² | R¹ | R² |
|---|---|---|---|
| 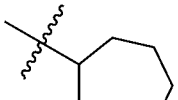 | H | 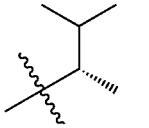 [SMILES: *[C@@H](C)C(C)C] | H |
| 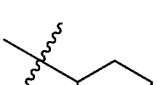 | H | 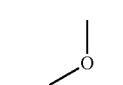 | H |

TABLE 3-continued
Exemplary embodiments of compounds of the formula (XXXI):
| R¹ | R² | R¹ | R² |
|---|---|---|---|
| 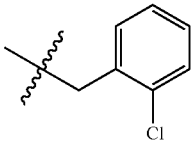 [SMILES: *Cc1ccccc1Cl] | H | 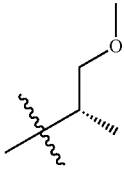 [SMILES: *[C@@H](C)COC] | H |
| 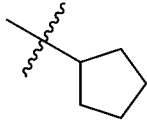 [SMILES: *C1CCCC1] | H | 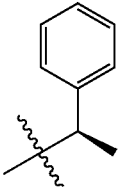 [SMILES: *[C@H](C)c1ccccc1] | H |
| 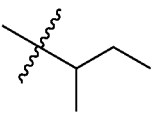 [SMILES: *C(C)CC] | H | 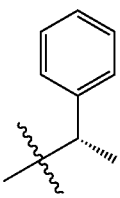 | H |
| 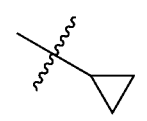 | H | 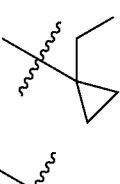 | H |
| 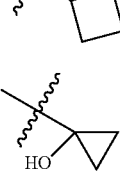 | H | 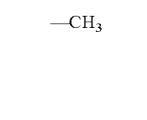 | H |
| 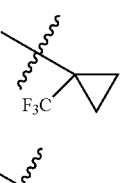 | H |  | H |
| —CH₃ | H | 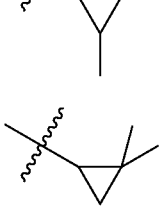 | H |
| —CH₂CH₃ | H | 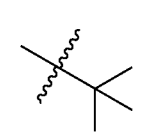 [SMILES: *C(C)(C)C] | H |
| 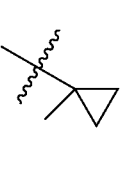 [SMILES: *C1(C)CC1] | H |  | H |
|  | H | 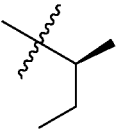 [SMILES: *[C@@H](C)CC] | H |
| 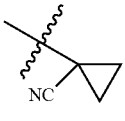 [SMILES: *C1(C#N)CC1] | H | 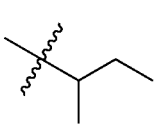 [SMILES: *C(C)CC] | H |
| 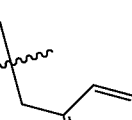 | H | 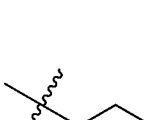 | —CH₂CH₃ |
| 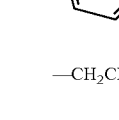 | H | —CH₂CH₂— | |
| 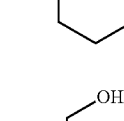 | H | —CH₂CH₂CH₂— | |
| 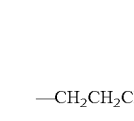 | H | —CH₂(CH₂)₂CH₂— | |
| 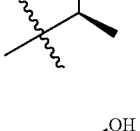 | H | —CH₂(CH₂)₃CH₂— | |
|  | H | —CH₂(CH₂)₄CH₂— | |
| 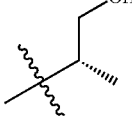 | H | | |
|  | H | 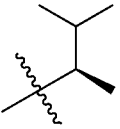 [SMILES: *[C@H](C)C(C)C] | |
Exemplary embodiments include compounds having the formula (XXXII) or a pharmaceutically acceptable salt form thereof:

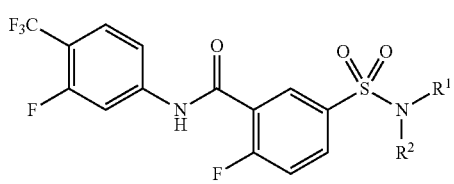
(XXXII)
wherein non-limiting examples of R¹ and R² are defined herein below in Table 4.

TABLE 4-continued

Exemplary embodiments of compounds of the formula (XXXII):

| R¹ | R² | R¹ | R² |
|---|---|---|---|
| (isopropyl-methyl-CH) | H | —CH₂(CH₂)₃CH₂— | |
| (phenyl-CH(CH₃)) | H | —CH₂(CH₂)₄CH₂— | |
| (neopentyl-like) | H | (cyclopentyl-CH) | |

Exemplary embodiments include compounds having the formula (XXXIII) or a pharmaceutically acceptable salt form thereof:

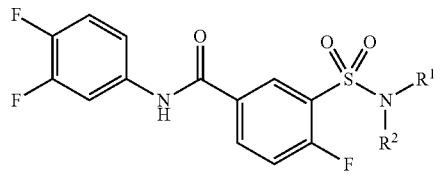

(XXXIII)

wherein non-limiting examples of R¹ and R² are defined herein below in Table 5.

TABLE 5

Exemplary embodiments of compounds of the formula (XXXIII):

| R¹ | R² | R¹ | R² |
|---|---|---|---|
| cycloheptyl | H | isopropyl-CH(CH₃) | H |
| cyclohexyl | H | CH₃-O-CH₂-CH(CH₃) | H |

TABLE 5-continued

Exemplary embodiments of compounds of the formula (XXXIII):

| R¹ | R² | R¹ | R² |
|---|---|---|---|
| 3-Cl-phenyl | H | CH₃-O-CH₂-CH(CH₃) | H |
| cyclopentyl | H | phenyl-CH(CH₃) | H |
| sec-butyl | H | phenyl-CH(CH₃) | H |
| cyclopropyl | H | 1-ethyl-cyclopropyl | H |
| methylcyclopropyl | H | cyclobutyl | H |
| sec-butyl (stereo) | H | HO-cyclopropyl | H |
| —CH₃ | H | F₃C-cyclopropyl | H |
| —CH₂CH₃ | H | methylcyclopropyl | H |
| isopropyl | H | dimethylcyclopropyl | H |
| tert-butyl | H | cyclopropyl | H |

TABLE 5-continued

Exemplary embodiments of compounds of the formula (XXXIII):

| R¹ | R² | R¹ | R² |
|---|---|---|---|
| (sec-butyl) | H | (1-cyanocyclopropyl) | H |
| (3-methylbutan-2-yl) | H | (benzyl) | —CH₂CH₃ |
| (cyclohexylmethyl) | H | | —CH₂CH₂— |
| (2-hydroxy-1-methylethyl, R) | H | | —CH₂CH₂CH₂— |
| (2-hydroxy-1-methylethyl, S) | H | | —CH₂(CH₂)₂CH₂— |
| (3-methylbutan-2-yl) | H | | —CH₂(CH₂)₃CH₂— |
| (1-phenylethyl) | H | | —CH₂(CH₂)₄CH₂— |
| (2,2-dimethylpropyl) | H | (cyclopentyl) | |

Exemplary embodiments include compounds having the formula (XXXIV) or a pharmaceutically acceptable salt form thereof:

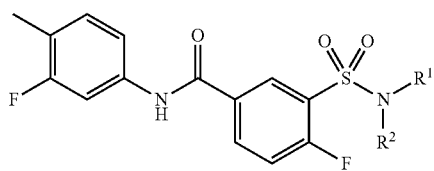

(XXXIV)

wherein non-limiting examples of R¹ and R² are defined herein below in Table 6.

TABLE 6

Exemplary embodiments of compounds of the formula (XXXIV):

| R¹ | R² |
|---|---|
| (cycloheptyl) | H |
| (3-methylbutan-2-yl) | H |
| (cyclohexyl) | H |
| (methoxymethyl-substituted) | H |
| (2-chlorobenzyl) | H |
| (methoxymethyl-substituted) | H |
| (cyclopentyl) | H |

TABLE 6-continued

Exemplary embodiments of compounds of the formula (XXXIV):

| R¹ | R² |
|---|---|
| (S)-1-phenylethyl | H |
| sec-butyl | H |
| (R)-1-phenylethyl | H |
| cyclopropyl | H |
| 1-ethylcyclopropyl | H |
| 2-methylcyclopropyl | H |
| cyclobutyl | H |
| (S)-sec-butyl | H |
| 1-hydroxycyclopropyl | H |
| —CH₃ | H |
| 1-(trifluoromethyl)cyclopropyl | H |
| —CH₂CH₃ | H |
| 2,2-dimethylcyclopropyl | H |
| isopropyl | H |
| 2,2-dimethylcyclopropyl | H |
| tert-butyl | H |
| 1-methylcyclopropyl | H |
| (R)-sec-butyl | H |
| 1-cyanocyclopropyl | H |
| 3-methylpentan-3-yl | H |
| benzyl | —CH₂CH₃ |
| cyclohexyl | H |
| | —CH₂CH₂— |
| (S)-1-hydroxy-2-methylpropan-2-yl | H |

TABLE 6-continued

Exemplary embodiments of compounds of the formula (XXXIV):

| R¹ | R² |
|---|---|
| —CH₂CH₂CH₂— | |
| (2-hydroxy-2-methylpropyl, R-config) | H |
| —CH₂(CH₂)₂CH₂— | |
| (3-methylbutan-2-yl) | H |
| —CH₂(CH₂)₃CH₂— | |
| (1-phenylethyl, R-config) | H |
| —CH₂(CH₂)₄CH₂— | |
| (3,3-dimethylbutan-2-yl) | H |
| (cyclopentylmethyl-bridged) | |

Exemplary embodiments include compounds having the formula (XXXV) or a pharmaceutically acceptable salt form thereof:

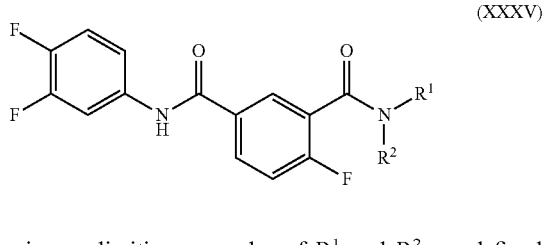

(XXXV)

wherein non-limiting examples of R¹ and R² are defined herein below in Table 7.

TABLE 7

Exemplary embodiments of compounds of the formula (XXXV):

| R¹ | R² |
|---|---|
| cycloheptyl | H |
| isopropylmethyl (sec-butyl variant) | H |
| cyclohexylmethyl | H |
| 2-methoxy-1-methylethyl | H |
| 2-chlorobenzyl | H |
| 2-methoxy-1-methylethyl | H |
| cyclopentylmethyl | H |
| 1-phenylethyl | H |
| 2-methylbutyl | H |

TABLE 7-continued
Exemplary embodiments of compounds of the formula (XXXV):
| R¹ | R² |
|---|---|
| 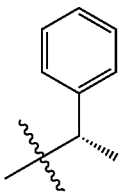 [SMILES: *[C@@H](C)c1ccccc1] | H |
|  | H |
|  | H |
|  | H |
|  | H |
|  | H |
| 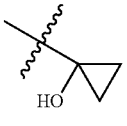 [SMILES: *C1(O)CC1] | H |
| —CH₃ | H |
|  | H |
| —CH₂CH₃ | H |
| 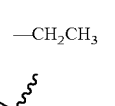 | H |
|  | H |
TABLE 7-continued
Exemplary embodiments of compounds of the formula (XXXV):
| R¹ | R² |
|---|---|
| 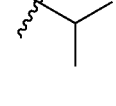 | H |
|  | H |
| 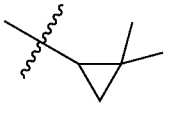 [SMILES: *C1CC1(C)C] | H |
| 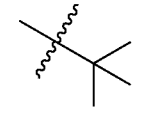 [SMILES: *C(C)(C)C] | H |
| 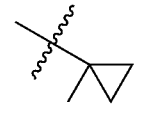 [SMILES: *C1(C)CC1] | H |
| 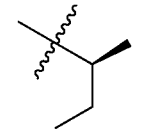 [SMILES: *[C@@H](C)CC] | H |
| 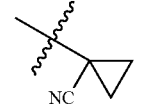 [SMILES: *C1(C#N)CC1] | H |
| 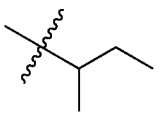 [SMILES: *C(C)CC] | —CH₂CH₃ |
|  | H |
| —CH₂CH₂— | |
|  | H |

TABLE 7-continued

Exemplary embodiments of compounds of the formula (XXXV):

| R¹ | R² |
|---|---|
| —CH₂CH₂CH₂— | |
| (CH with OH, methyl) | H |
| —CH₂(CH₂)₂CH₂— | |
| (isopropyl-methyl branched) | H |
| —CH₂(CH₂)₃CH₂— | |
| (phenyl-methyl) | H |
| —CH₂(CH₂)₄CH₂— | |
| (neopentyl) | H |
| (bicyclic) | |

Exemplary embodiments include compounds having the formula (XXXVI) or a pharmaceutically acceptable salt form thereof:

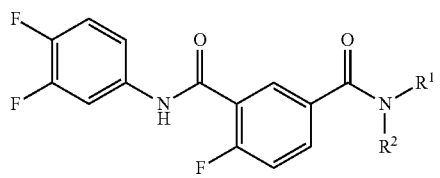

(XXXVI)

wherein non-limiting examples of R¹ and R² are defined herein below in Table 8.

TABLE 8

Exemplary embodiments of compounds of the formula (XXXVI):

| R¹ | R² |
|---|---|
| cycloheptyl | H |
| isopropyl-methyl | H |
| cyclohexyl | H |
| CH₂OCH₃ branched | H |
| 2-chlorobenzyl | H |
| CH₂OCH₃ branched | H |
| cyclopentyl-methyl | H |
| phenyl-methyl | H |
| sec-butyl/isobutyl | H |

TABLE 8-continued

Exemplary embodiments of compounds of the formula (XXXVI):

| R¹ | R² |
|---|---|
| (S)-1-phenylethyl | H |
| cyclopropylmethyl | H |
| 1-ethylcyclopropyl | H |
| 2-methylcyclopropyl | H |
| cyclobutyl | H |
| (S)-sec-butyl | H |
| 1-hydroxycyclopropyl | H |
| —CH₃ | H |
| 1-(trifluoromethyl)cyclopropyl | H |
| —CH₂CH₃ | H |
| 2,2-dimethylcyclopropyl | H |
| isobutyl | H |
| 2,2-dimethylcyclopropyl | H |
| neopentyl | H |
| 1-methylcyclopropyl | H |
| (S)-sec-butyl | H |
| 1-cyanocyclopropyl | H |
| 3-pentyl | H |
| benzyl | —CH₂CH₃ |
| cyclohexylmethyl | H |
| —CH₂CH₂— | |
| (S)-2-methyl-3-hydroxypropyl | H |

TABLE 8-continued

Exemplary embodiments of compounds of the formula (XXXVI):

| R¹ | R² |
|---|---|
| —CH₂CH₂CH₂— | |
| (2-hydroxymethyl-1-methylethyl group) | H |
| —CH₂(CH₂)₂CH₂— | |
| (isopropyl-methyl-methylene group) | H |
| —CH₂(CH₂)₃CH₂— | |
| (1-phenylethyl group) | H |
| —CH₂(CH₂)₄CH₂— | |
| (neopentyl group) | H |
| (cyclopentylmethylene group) | |

Exemplary embodiments include compounds having the formula (XXXVII) or a pharmaceutically acceptable salt form thereof:

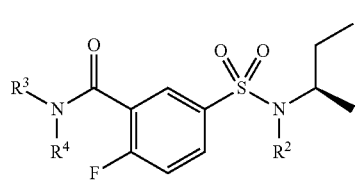

(XXXVII)

wherein non-limiting examples of R², R³, and R⁴ are defined herein below in Table 9.

TABLE 9

Exemplary embodiments of compounds of the formula (XXXVII):

| R² | R³ | R⁴ |
|---|---|---|
| H | 4-Cl-3-F-phenyl | H |
| H | 3-Cl-4-F-phenyl | H |
| H | 3,4-diCl-phenyl | H |
| H | 3,4-diF-phenyl | CH₃ |
| H | 3,4-diF-benzyl | H |
| Me | 3,4-diF-phenyl | H |
| H | 2,4,5-triF-phenyl | H |
| H | 2,4-diF-phenyl | H |
| H | 2,5-diF-phenyl | H |
| H | 3-Cl-4-F-benzyl | H |

TABLE 9-continued

Exemplary embodiments of compounds of the formula (XXXVII):

| R² | R³ | R⁴ |
|---|---|---|
| H | (3-pyridyl) | H |
| H | (2-fluoro-5-pyridyl) | H |
| H | (5-fluoro-3-pyridyl) | H |
| H | (2,3-dichloro-5-pyridyl) | H |
| H | (quinolin-3-yl) | H |
| H | (2-oxo-1,2-dihydropyridin-3-yl) | H |
| H | (2-pyridyl) | H |
| H | (2-fluoro-4-pyridyl) | H |
| H | (isoquinolin-4-yl) | H |
| H | (pyridin-3-ylmethyl) | H |
| H | (pyridin-4-ylmethyl) | H |
| H | (thiazol-2-yl) | H |
| H | (oxazol-2-yl) | H |
| H | (1-methyl-1H-pyrazol-5-yl) | H |
| H | (isoxazol-4-yl) | H |
| H | (6-chlorobenzo[d]oxazol-2-yl) | H |

Exemplary embodiments include compounds having the formula (XXXVIII) or a pharmaceutically acceptable salt form thereof:

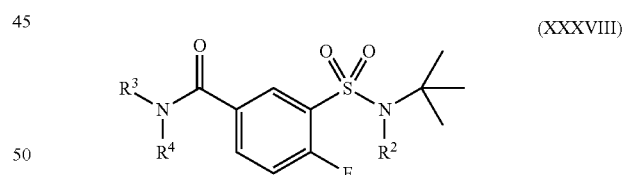

(XXXVIII)

wherein non-limiting examples of R², R³, and R⁴ are defined herein below in Table 10.

TABLE 10

Exemplary embodiments of compounds of the formula (XXXVIII):

| R² | R³ | R⁴ |
|---|---|---|
| H | (4-fluoro-3-chlorophenyl) | H |

TABLE 10-continued

Exemplary embodiments of compounds of the formula (XXXVIII):

| R² | R³ | R⁴ |
|---|---|---|
| H | 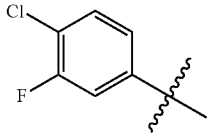 4-Cl, 3-F phenyl | H |
| H | 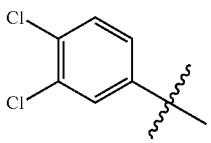 3,4-diCl phenyl | H |
| H | 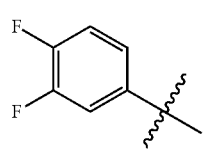 [SMILES: *c1ccc(F)c(F)c1] 3,4-diF phenyl | CH₃ |
| H | 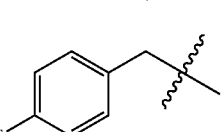 3,4-diF benzyl | H |
| Me | 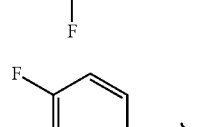 3,4-diF phenyl | H |
| H | 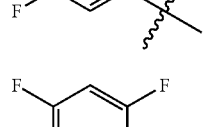 2,4,5-triF phenyl | H |
| H | 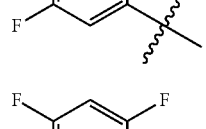 2,4-diF phenyl | H |
| H | 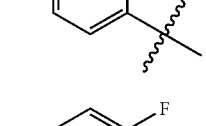 2,5-diF phenyl | H |
| H | 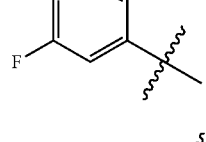 3-Cl, 4-F benzyl | H |
| H | 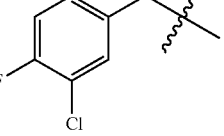 pyridin-3-yl | H |
| H | 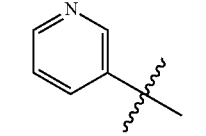 [SMILES: *c1cccnc1] 6-F pyridin-3-yl | H |
| H | 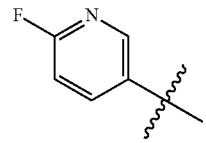 [SMILES: *c1ccc(F)nc1] 5-F pyridin-3-yl | H |
| H | 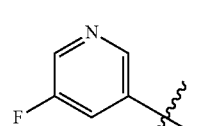 2,3-diCl pyridin-5-yl | H |
| H | 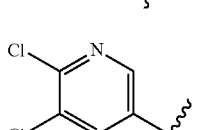 quinolin-3-yl | H |
| H | 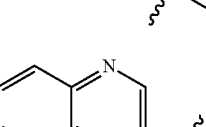 2-oxo-pyridin-3-yl | H |
| H | 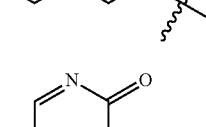 pyridin-2-yl | H |
| H | 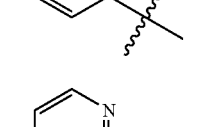 2-F pyridin-4-yl | H |
| H | 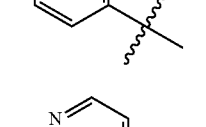 quinolin-4-yl | H |
| H | 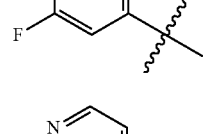 pyridin-3-ylmethyl | H |
| H | 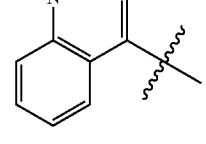 pyridin-4-ylmethyl | H |

TABLE 10-continued

Exemplary embodiments of compounds of the formula (XXXVIII):

| R² | R³ | R⁴ |
|---|---|---|
| H | 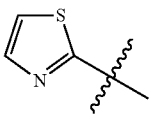 [SMILES: *c1nccs1] (thiazol-2-yl) | H |
| H | 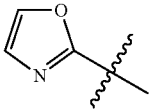 (oxazol-2-yl) | H |
| H | 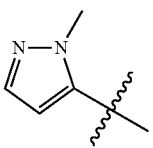 [SMILES: *c1ccnn1C] (1-methylpyrazol-5-yl) | H |
| H | 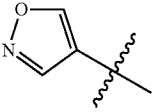 (isoxazol-4-yl) | H |
| H | 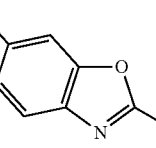 (6-chlorobenzoxazol-2-yl) | H |

Exemplary embodiments include compounds having the formula (XXXIX) or a pharmaceutically acceptable salt form thereof:

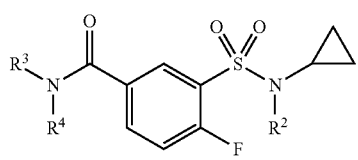

(XXXIX)

wherein non-limiting examples of R², R³, and R⁴ are defined herein below in Table 11.

TABLE 11

Exemplary embodiments of compounds of the formula (XXXIX):

| R² | R³ | R⁴ |
|---|---|---|
| H | 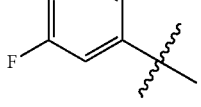 (4-F, 3-Cl-phenyl) | H |
| H | 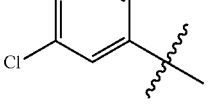 (4-Cl, 3-F-phenyl) | H |
| H | 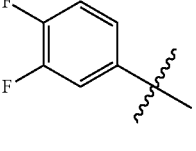 (3,4-diCl-phenyl) | H |
| H | 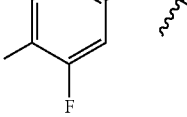 (3,4-diF-phenyl) | CH₃ |
| H | 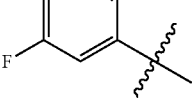 (3,4-diF-benzyl) | H |
| Me | 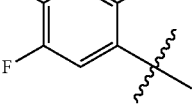 (3,4-diF-phenyl) | H |
| H | 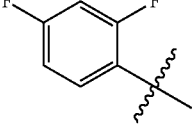 (3,4,5-triF-phenyl) | H |
| H | 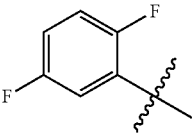 (2,4-diF-phenyl) | H |
| H | 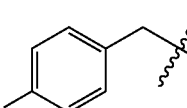 (2,4-diF-phenyl) | H |
| H | 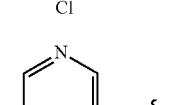 (3-Cl, 4-F-benzyl) | H |
| H | 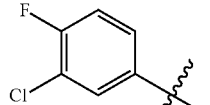 (pyridin-3-yl) | H |

TABLE 11-continued

Exemplary embodiments of compounds of the formula (XXXIX):

| R² | R³ | R⁴ |
|---|---|---|
| H | 2-fluoropyridin-5-yl | H |
| H | 5-fluoropyridin-3-yl | H |
| H | 2,3-dichloropyridin-5-yl | H |
| H | quinolin-3-yl | H |
| H | 2-oxo-pyridin-3-yl | H |
| H | pyridin-2-yl | H |
| H | 2-fluoropyridin-4-yl | H |
| H | quinolin-4-yl | H |
| H | (pyridin-3-yl)methyl | H |
| H | (pyridin-4-yl)methyl | H |
| H | thiazol-2-yl | H |
| H | oxazol-2-yl | H |
| H | 1-methylpyrazol-5-yl | H |
| H | isoxazol-4-yl | H |
| H | 6-chlorobenzoxazol-2-yl | H |

Exemplary embodiments include compounds having the formula (XXXX) or a pharmaceutically acceptable salt form thereof:

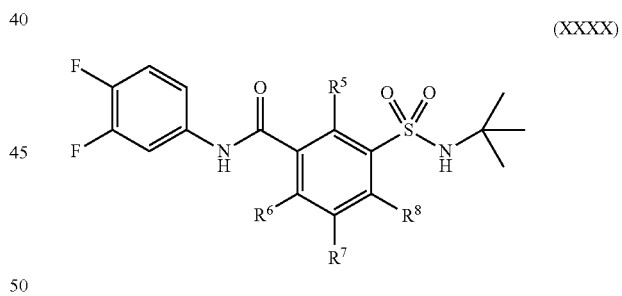

(XXXX)

wherein non-limiting examples of R⁵, R⁶, R⁷, and W are defined herein below in Table 12.

TABLE 12

Exemplary embodiments of compounds of the formula (XXXX):

| R⁵ | R⁶ | R⁷ | R⁸ |
|---|---|---|---|
| H | H | H | Me |
| H | H | H | OMe |
| H | H | H | Cl |
| H | F | H | F |
| H | H | F | F |

Exemplary embodiments include compounds having the formula (XXXXI-A or XXXI-B) or a pharmaceutically acceptable salt form thereof:

(XXXXI-A)

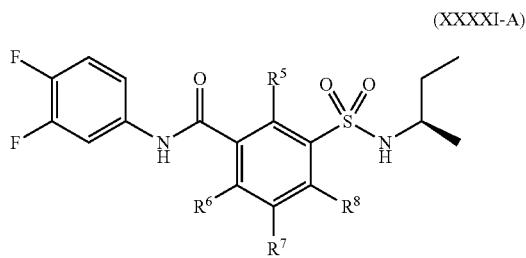

(XXXXI-B)

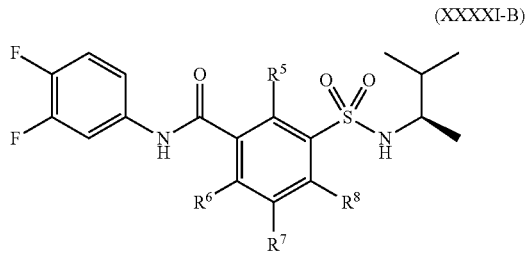

wherein non-limiting examples of $R^5$, $R^6$, $R^7$, and $R^8$ are defined herein below in Table 13.

TABLE 13

Exemplary embodiments of compounds of the formula (XXXXI-A or XXXXI-B):

| $R^5$ | $R^6$ | $R^7$ | $R^8$ |
|---|---|---|---|
| H | Me | H | H |
| H | OMe | H | H |
| H | Cl | H | H |
| F | F | H | H |
| H | F | F | H |
| H | F | H | F |

Exemplary embodiments include compounds having the formula (XXXXII) or a pharmaceutically acceptable salt form thereof:

(XXXXII)

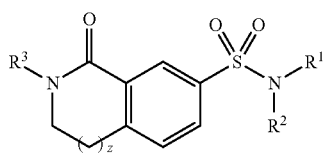

wherein non-limiting examples of $R^1$, $R^2$, $R^3$, and z are defined herein below in Table 14.

TABLE 14

Exemplary embodiments of compounds of the formula (XXXXII):

| z | $R^1$ | $R^2$ | $R^3$ |
|---|---|---|---|
| 0 | | H | 3,4-diF-phenyl |
| 1 | | H | 3,4-diF-phenyl |
| 0 | | H | 3,4-diF-phenyl |
| 1 | | H | 3,4-diF-phenyl |

Exemplary embodiments include compounds having the formula (XXXXIII) or a pharmaceutically acceptable salt form thereof:

(XXXXIII)

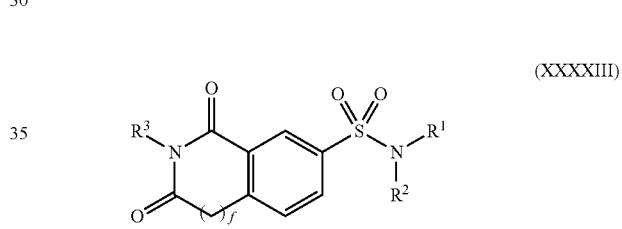

wherein non-limiting examples of $R^1$, $R^2$, $R^3$, and f are defined herein below in Table 15.

TABLE 15

Exemplary embodiments of compounds of the formula (XXXXIII):

| f | R | $R^2$ | $R^3$ |
|---|---|---|---|
| 0 | sec-butyl | H | 3,4-diF-phenyl |
| 1 | sec-butyl | H | 3,4-diF-phenyl |
| 0 | cyclopropyl | H | 3,4-diF-phenyl |

TABLE 15-continued

Exemplary embodiments of compounds of the formula (XXXXIII):

| f | R | R² | R³ |
|---|---|----|----|
| 1 | cyclopropyl | H | 3,4-difluorophenyl |

Exemplary embodiments include compounds having the formula (XXXXIV) or a pharmaceutically acceptable salt form thereof:

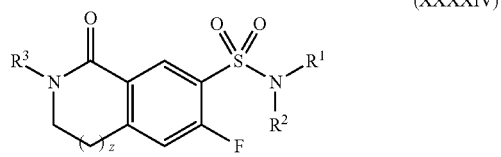

(XXXXIV)

wherein non-limiting examples of $R^1$, $R^2$, $R^3$, and z are defined herein below in Table 16.

TABLE 16

Exemplary embodiments of compounds of the formula (XXXXIV):

| z | R¹ | R² | R³ |
|---|----|----|----|
| 0 | cyclopropyl | H | 3,4-difluorophenyl |
| 1 | cyclopropyl | H | 3,4-difluorophenyl |
| 0 | isobutyl (sec-butyl) | H | 3,4-difluorophenyl |
| 1 | isobutyl (sec-butyl) | H | 3,4-difluorophenyl |

Exemplary embodiments include compounds having the formula (XXXXV) or a pharmaceutically acceptable salt form thereof:

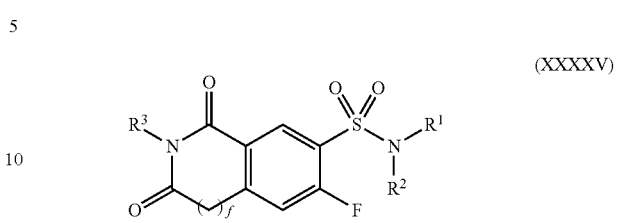

(XXXXV)

wherein non-limiting examples of $R^1$, $R^2$, $R^3$, and f are defined herein below in Table 17.

TABLE 17

Exemplary embodiments of compounds of the formula (XXXXV):

| f | R¹ | R² | R³ |
|---|----|----|----|
| 0 | cyclopropyl | H | 3,4-difluorophenyl |
| 1 | cyclopropyl | H | 3,4-difluorophenyl |
| 0 | isobutyl (sec-butyl) | H | 3,4-difluorophenyl |
| 1 | isobutyl (sec-butyl) | H | 3,4-difluorophenyl |

Exemplary embodiments include compounds having the formula (XXXXVI) or a pharmaceutically acceptable salt form thereof:

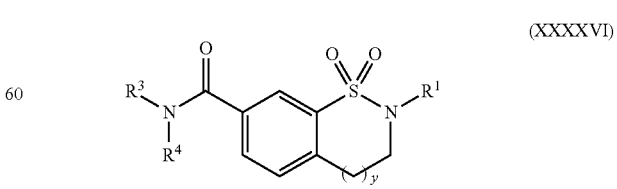

(XXXXVI)

wherein non-limiting examples of $R^1$, $R^3$, $R^4$, and y are defined herein below in Table 18.

TABLE 18

Exemplary embodiments of compounds of the formula (XXXXVI):

| y | R$^1$ | R$^3$ | R$^4$ |
|---|---|---|---|
| 0 | cyclopropyl | 3,4-difluorophenyl | H |
| 1 | cyclopropylmethyl | 3,4-difluorophenyl | H |
| 2 | cyclopropylethyl | 3,4-difluorophenyl | H |

Exemplary embodiments include compounds having the formula (XXXXVII) or a pharmaceutically acceptable salt form thereof:

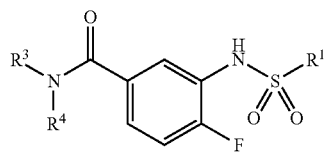

(XXXXVII)

wherein non-limiting examples of R$^1$, R$^3$ and R$^4$ are defined herein below in Table 19.

TABLE 19

Exemplary embodiments of compounds of the formula (XXXXVII):

| R$^1$ | R$^3$ | R$^4$ |
|---|---|---|
| cyclopropyl | 3,4-difluorophenyl | H |

Exemplary embodiments include compounds having the formula (XXXXVIII) or a pharmaceutically acceptable salt form thereof:

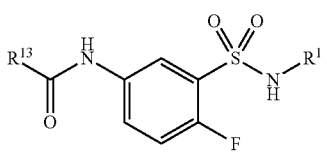

(XXXXVIII)

wherein non-limiting examples of R$^1$ and R$^{13}$ defined herein below in Table 19.

TABLE 20

Exemplary embodiments of compounds of the formula (XXXXVIII):

| R$^1$ | R$^{13}$ |
|---|---|
| cyclopropyl | 3,4-difluorophenyl |

In all of the embodiments provided herein, examples of suitable optional substituents are not intended to limit the scope of the claimed invention. The compounds of the invention may contain any of the substituents, or combinations of substituents, provided herein.

Each compound enumerated herein by name, structure, or both name and structure is considered an individual embodiment as a composition of matter. Additional embodiments include each compound enumerated herein by name, structure, or both name and structure is considered an individual embodiment as part of a pharmaceutical composition when combined with a pharmaceutically acceptable excipient. Additional embodiments include the use of each compound enumerated herein by name, structure, or both name and structure, either by itself or as part of a pharmaceutical composition or an enumerated treatment regimen for the treatment of at least one of the conditions described herein. Additional embodiments include methods of treating a patient for at least one of the conditions described herein by the administration to a patient in need thereof of a phamaceutically effective amount of at least one of the compounds enumerated herein by name, structure, or both name and structure, either by itself or as part of a pharmaceutical composition or an enumerated treatment regimen.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds.

The reagents used in the preparation of the compounds of this invention can be either commercially obtained or can be prepared by standard procedures described in the literature. In accordance with this invention, compounds in the genus may be produced by one of the following reaction schemes.

Compounds of the formula (6) may be prepared according to the process outlined in Schemes 1-2.

Scheme 1

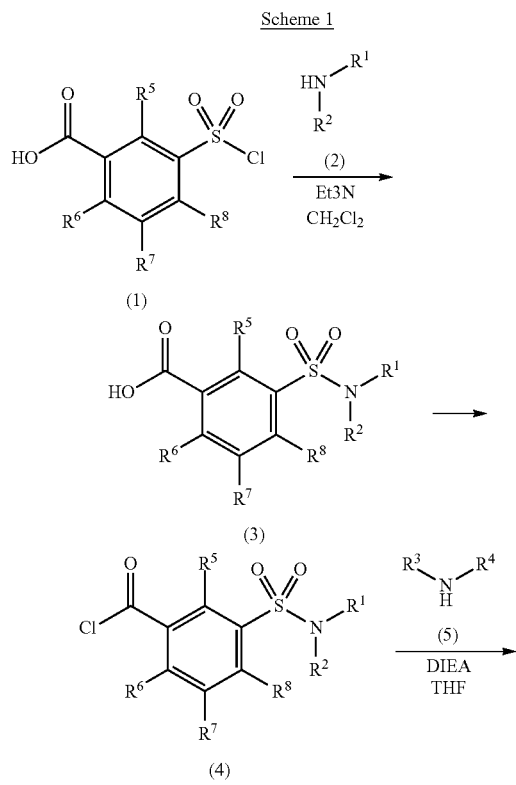

Accordingly, a compound of the formula (1), a known compound or compound prepared by known methods, is reacted with a compound of the formula (2), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (3). A compound of the formula (3) is reacted with thionyl chloride, optionally in the presence an organic solvent such as methylene chloride, dichloroethane, tetrahydrofuran, 1,4-dioxane, dimethyl formamide, and the like to provide a compound of the formula (4). Alternatively, A compound of the formula (3) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (4). A compound of the formula (4) is then reacted with a compound of the formula (5), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (6).

Scheme 2

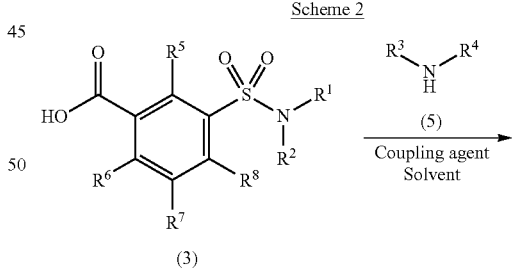

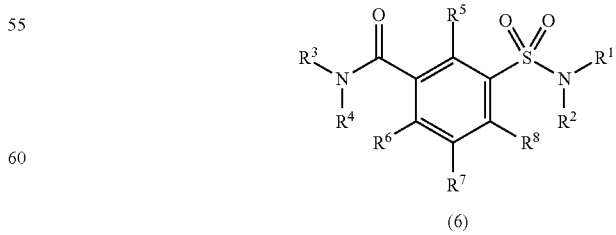

Alternatively, a compound of the formula (3) is reacted with a compound of the formula (5), a known compound or compound prepared by known methods, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyl-uronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (6).

Compounds of formula (10) may be prepared according to the process outlined in Schemes 3-5.

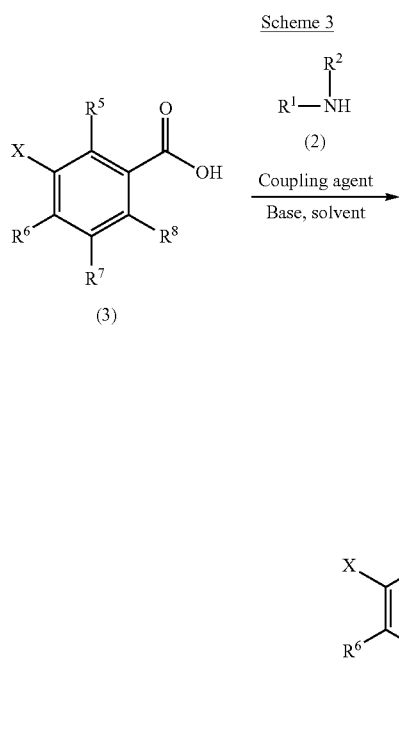

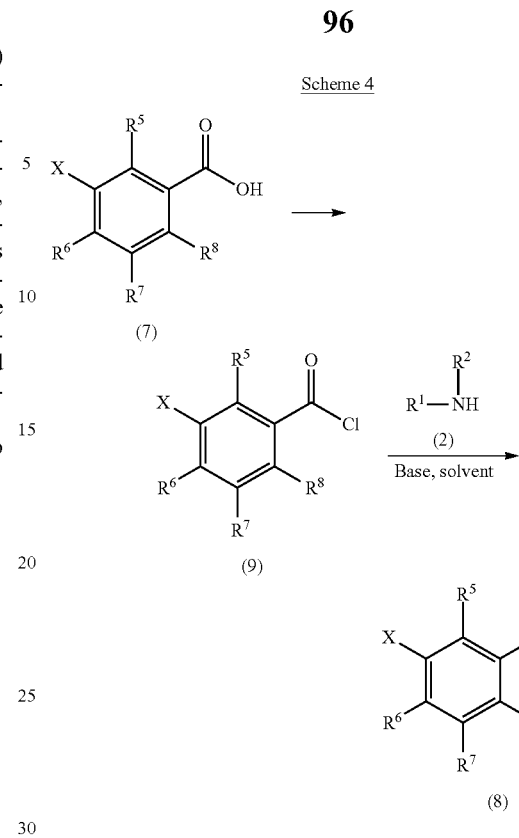

A suitably substituted compound of the formula (7), a known compound or compound prepared by known methods, where X is a halogen, is reacted with a compound of the formula (2), a known compound or compound prepared by known methods, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (8).

Alternatively, a suitably substituted compound of the formula (7), a known compound or compound prepared by known methods where X is a halogen, is reacted with thionyl chloride, optionally in the presence an organic solvent such as methylene chloride, dichloroethane, tetrahydrofuran, 1,4-dioxane, dimethyl formamide, and the like to provide a compound of the formula (9). Alternatively, A compound of the formula (7) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (9). A compound of the formula (9) is then reacted with a compound of the formula (2), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (8).

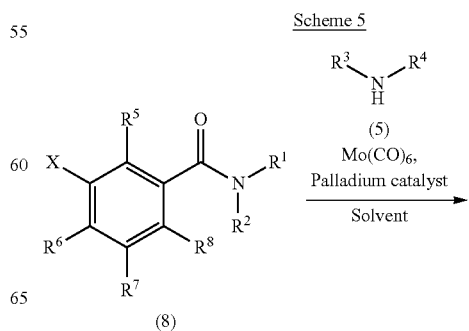

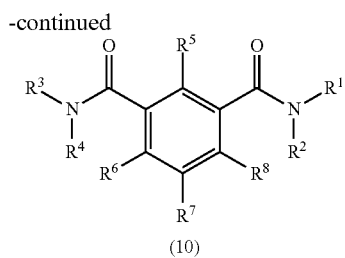

(10)

A compound of the formula (8) is reacted with a compound of the formula (5) in the presence of Molybdenum hexacarbonyl, in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, in the presence of 4,5-bis(diphenylphosphino)-9,9-dimethylxanthene (Xantphos), in an solvent such as water, dimethyl formamide, dimethyl acetamide, methanol, ethanol, methylene chloride, dichloroethane, tetrahydrofuran, 1,4-dioxane, and the like, optionally with heating, optionally with microwave irradiation, optionally in an inert atmosphere such as nitrogen or argon, to provide a compound of the formula (10)

Compounds of formula (17) may be prepared according to the process outlined in Schemes 6-7.

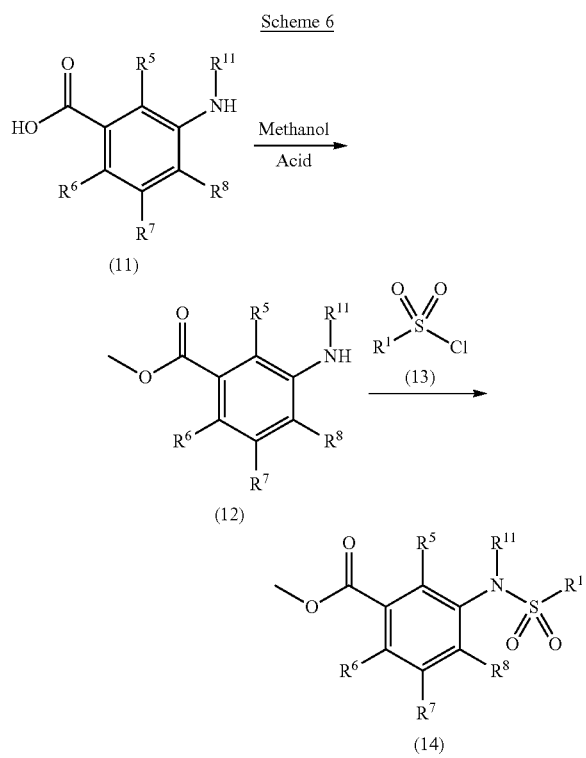

A compound of the formula (11), a known compound or compound prepared by known methods, is reacted with an methanol in the presence of an acid such as hydrochloric acid, sulfuric acid, optionally with heating to provide a compound of the formula (12). A compound of the formula (12) is reacted with a compound of the formula (13), a known compound or compound prepared by known methods, in the presence of a base such as pyridine, 2,6-lutidine, and the like, optionally in the presence of dimethylaminopyridine (DMAP), optionally in the presence of a solvent such as dimethyl formamide, dimethyl acetamide, methylene chloride, dichloroethane, tetrahydrofuran, 1,4-dioxane, and the like, optionally with heating, to provide a compound of the formula (14)

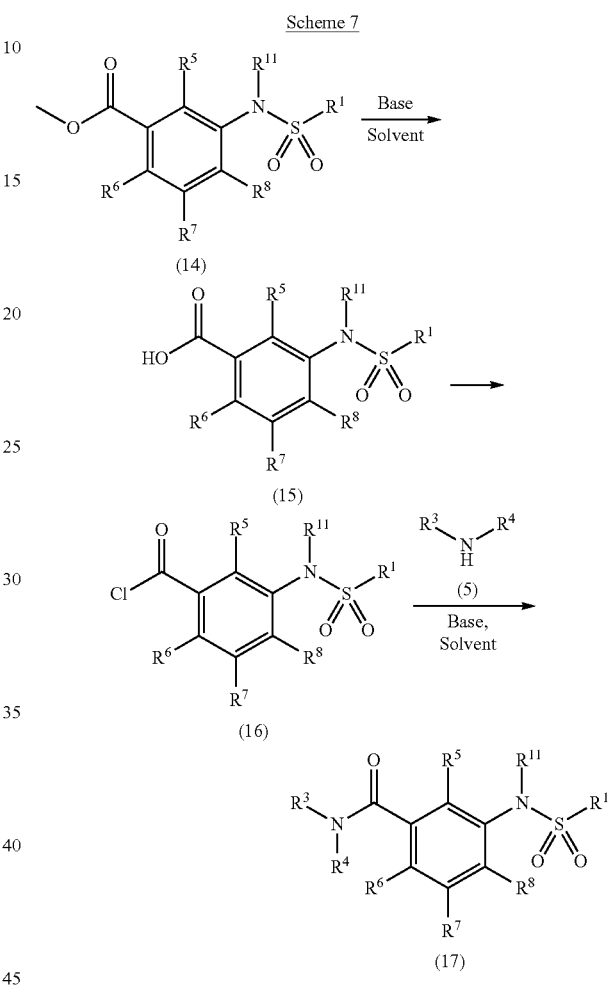

A compound of the formula (14) is reacted with a base such as lithium hydroxide, sodium hydroxide, potassium hydroxide, cesium hydroxide, potassium carbonate, sodium carbonate, and the like, in an solvent such as ethanol, methanol, water, dimethyl formamide, dimethyl acetamide, tetrahydrofuran, 1,4-dioxane, and the like, to provide a compound of the formula (15). A compound of the formula (15) is then reacted with thionyl chloride, optionally in the presence an organic solvent such as methylene chloride, dichloroethane, tetrahydrofuran, 1,4-dioxane, dimethyl formamide, and the like to provide a compound of the formula (16). Alternatively, A compound of the formula (15) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (16). A compound of the formula (16) is then reacted with a compound of the formula (5), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (17).

Compounds of formula (23) may be prepared according to the process outlined in Schemes 8-9.

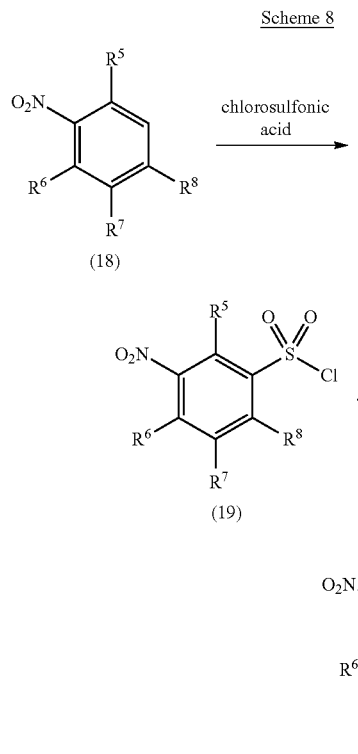

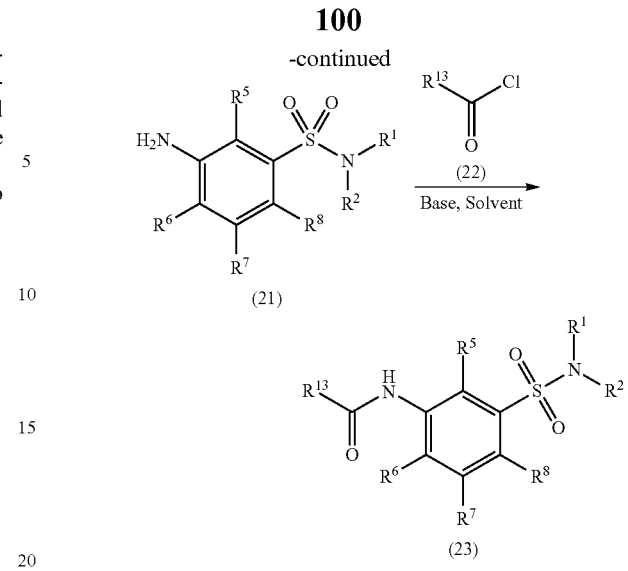

A compound of the formula (18), a known compound or compound prepared by known methods, is reacted with chlorosulfonic acid, optionally in the presence of an organic solvent such as methylene chloride, dichloroethane, tetrahydrofuran, 1,4-dioxane, dimethyl formamide, and the like to provide a compound of the formula to provide a compound of the formula (19). A compound of the formula (19) is reacted with a compound of the formula (2) a known compound or compound prepared by known methods, in the presence of a base such as triethylamine, diisopropylethylamine, pyridine, 2,6-lutidine, and the like, in the presence of an organic solvent such as methylene chloride, dichloroethane, tetrahydrofuran, 1,4-dioxane, dimethyl formamide, and the like to provide a compound of the formula (20).

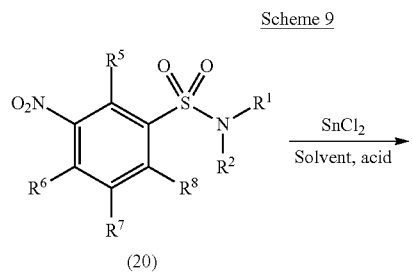

A compound of the formula (20) is then reacted with tin chloride in the presence of an acid such as hydrochloric acid, sulfuric acid, and the like, in an organic solvent such as tetrahydrofuran, 1,4-dioxane, dimethyl formamide, and the like to provide a compound of the formula to provide a compound of the formula (21). A compound of the formula (21) is then reacted with a compound of the formula (22), a known compound or compound prepared by known methods, in the presence of a base such as triethylamine, diisopropylethylamine, pyridine, 2,6-lutidine, and the like, in an organic solvent such as methylene chloride, dichloroethane, tetrahydrofuran, 1,4-dioxane, dimethyl formamide, and the like to provide a compound of the formula to provide a compound of the formula (23).

Compounds of formula (30) may be prepared according to the process outlined in Schemes 10-11.

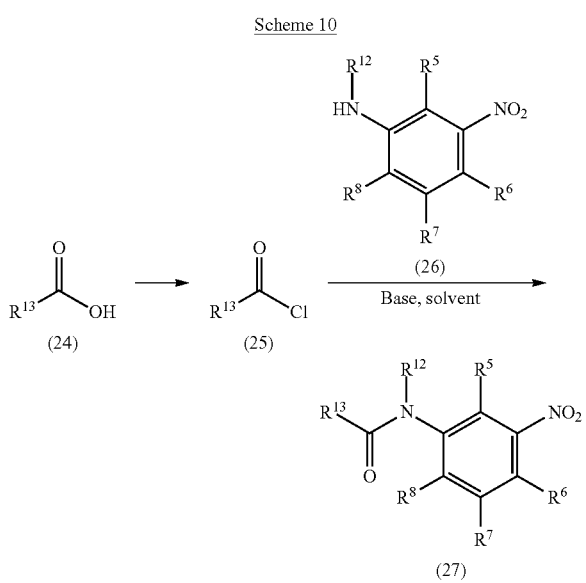

A compound of the formula (24), a known compound or compound prepared by known methods, is reacted with thionyl chloride, optionally in the presence an organic solvent such as methylene chloride, dichloroethane, tetrahydrofuran, 1,4-dioxane, dimethyl formamide, and the like to provide a compound of the formula (25). Alternatively, a compound of the formula (24) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (25). A compound of the formula (25) is then reacted with a compound of the formula (26), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (27).

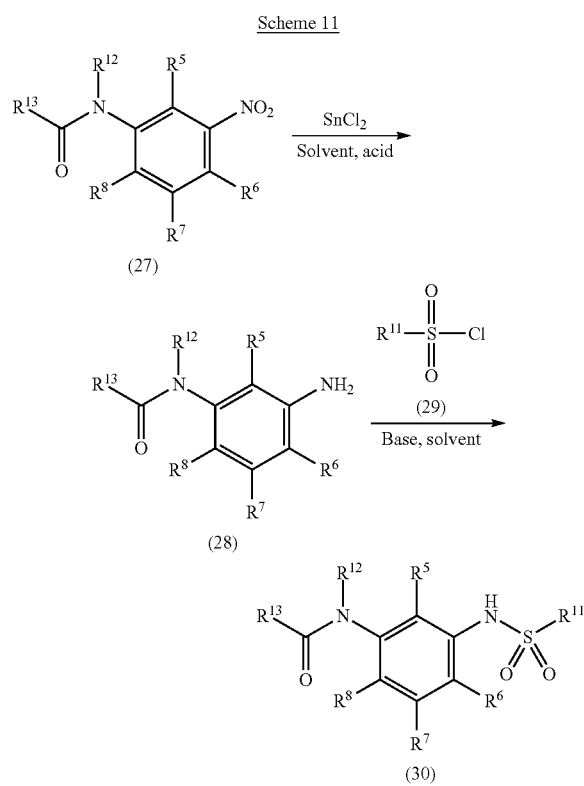

A compound of the formula (27) is then reacted with tin chloride in the presence of an acid such as hydrochloric acid, sulfuric acid, and the like, in an organic solvent such as tetrahydrofuran, 1,4-dioxane, dimethyl formamide, and the like to provide a compound of the formula to provide a compound of the formula (28). A compound of the formula (28) is then reacted with a compound of the formula (29), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (30).

Compounds of formula (36) may be prepared according to the process outlined in Schemes 12-14.

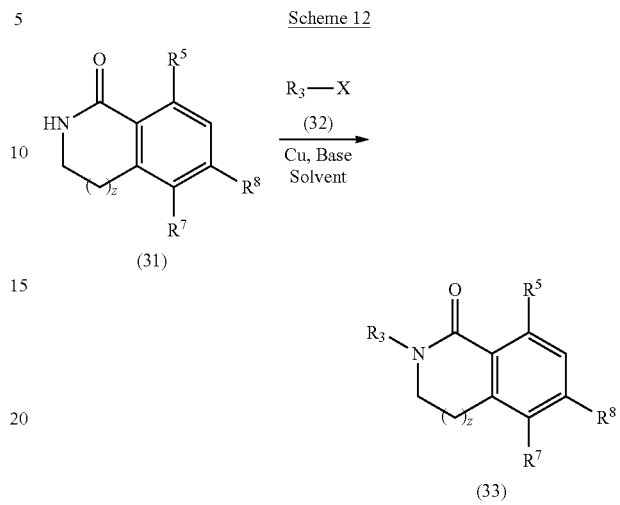

A compound of the formula (31), a known compound or compound prepared by known methods, is reacted with a compound of the formula (32), a known compound or compound prepared by known methods wherein X is a halogen, in the presence of a copper salt such as copper sulfate, copper iodide, copper chloride, copper acetate and the like, optionally in the presence of a palladium catalyst such as palladium (II) acetate, tetrakis(triphenylphosphine) palladium(0), dichlorobis(triphenylphosphine)palladium (II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (33).

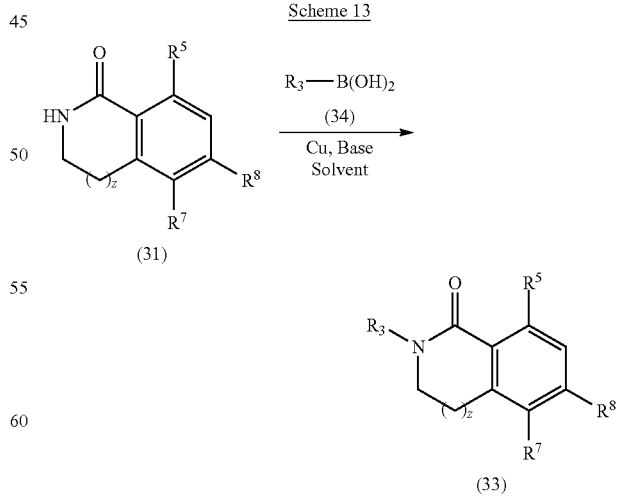

Alternatively, a compound of the formula (31), a known compound or compound prepared by known methods, is reacted with a compound of the formula (34), a known compound or compound prepared by known methods, in the presence of a copper salt such as copper sulfate, copper iodide, copper chloride, copper acetate, and the like optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (33).

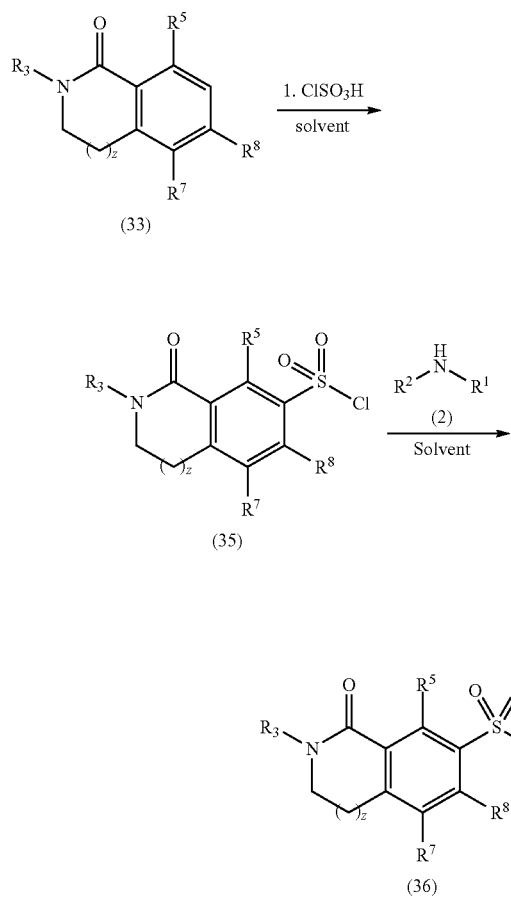

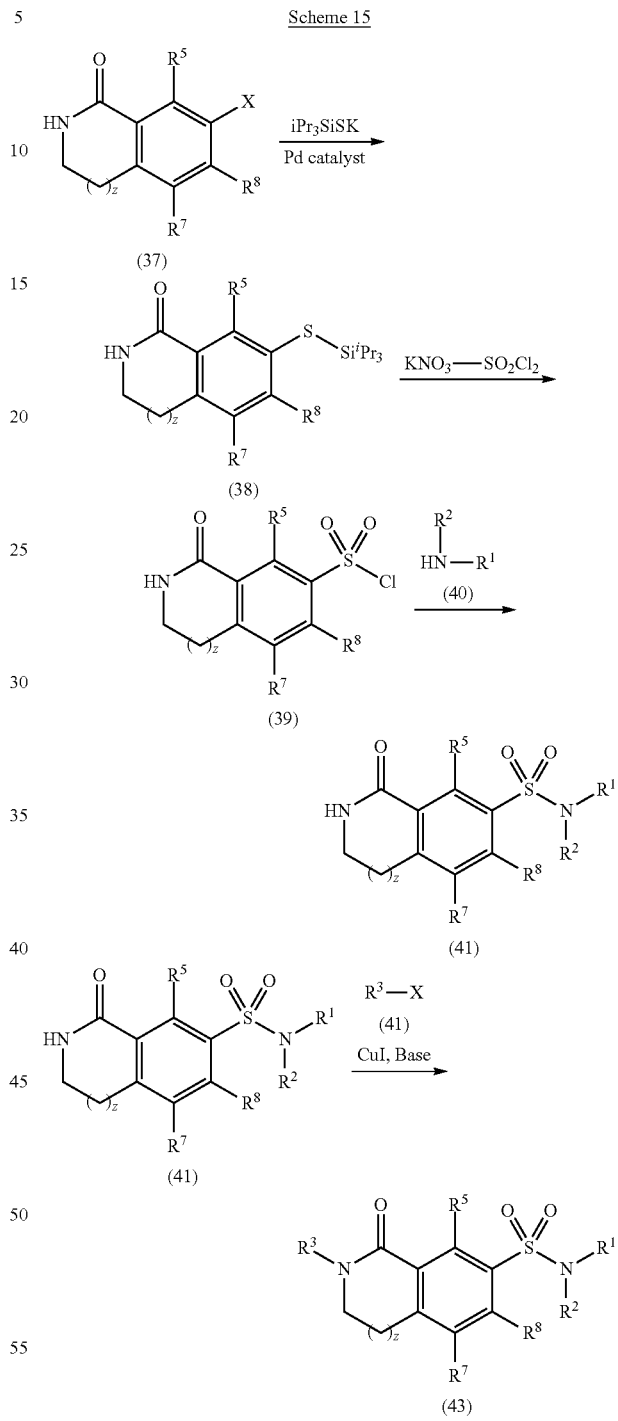

A compound of the formula (33) is reacted with chlorosulfonic acid, optionally in the presence of an organic solvent such as methylene chloride, dichloroethane, tetrahydrofuran, 1,4-dioxane, dimethyl formamide, and the like to provide a compound of the formula to provide a compound of the formula (35). A compound of the formula (35) is reacted with a compound of the formula (2) a known compound or compound prepared by known methods, in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (36).

Compounds of formula (43) may be prepared according to the process outlined in Scheme 15.

A compound of the formula (37), a known compound or compound prepared by known methods wherein X is a halogen, is reacted with triisopropyl-silanethiol potassium salt in the presence of a palladium catalyst such as palladium (II)acetate, tetrakis(triphenylphosphine)palladium(0), dichlorobis(triphenylphosphine)palladium(II), palladium on carbon, bis(acetonitrile)dichloropalladium(II), and the like, in an solvent such as dimethyl formamide, dimethyl acetamide, methylene chloride, dichloroethane, tetrahydrofuran, 1,4-dioxane, and the like, optionally with heating, optionally with microwave irradiation, optionally in an inert atmosphere such as nitrogen or argon, to provide a compound of the formula (38). A compound of the formula (38) is then reacted with KNO₃-5O₂Cl₂ in a solvent such as dimethyl formamide, dimethyl acetamide, methylene chloride, dichloroethane, tetrahydrofuran, 1,4-dioxane, methanol, ethanol, and the like, to provide a compound of the formula (39). A compound of the formula (39) is reacted with a compound of the formula (40) a known compound or compound prepared by known methods, in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (41). A compound of the formula (41) is then reacted with a compound of the formula (42), a known compound or compound prepared by known methods wherein X is a halogen, in the presence of a copper salt such as copper sulfate, copper iodide, copper chloride, copper acetate, and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (43).

Compounds of formula (51) may be prepared according to the process outlined in Schemes 16-18.

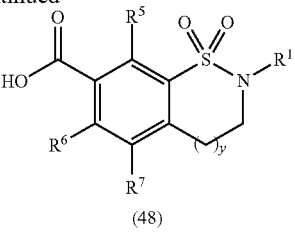

(48)

A compound of the formula (44), a known compound or compound prepared by known methods, is reacted with chlorosulfonic acid, optionally in a solvent such as methylene chloride, dichloroethane, tetrahydrofuran, 1,4-dioxane, dimethyl formamide, and the like, optionally with heating, optionally with microwave irradiation to provide a compound of the formula (45). A compound of the formula (45) is then reacted with a compound of the formula (46), a known compound or compound prepared by known methods, in a solvent such as methylene chloride, dichloroethane, tetrahydrofuran, 1,4-dioxane, dimethyl formamide, and the like, optionally with heating, optionally with microwave irradiation to provide a compound of the formula (47). A compound of the formula (47) is then reacted with a base such as sodium hydroxide, lithium hydroxide, potassium hydroxide, sodium carbonate, potassium carbonate, lithium carbonate, and the like, in a solvent such as methylene chloride, dichloroethane, tetrahydrofuran, 1,4-dioxane, dimethyl formamide, methanol, ethanol, and the like, optionally with heating, optionally with microwave irradiation to provide a compound of the formula (48).

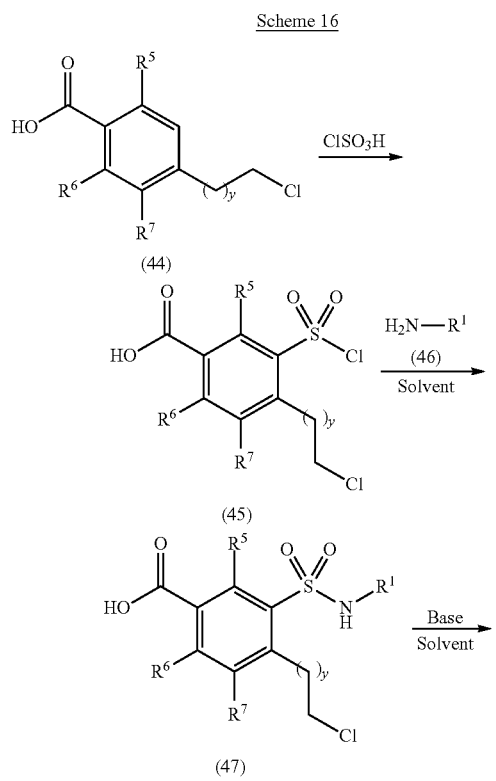

Scheme 16

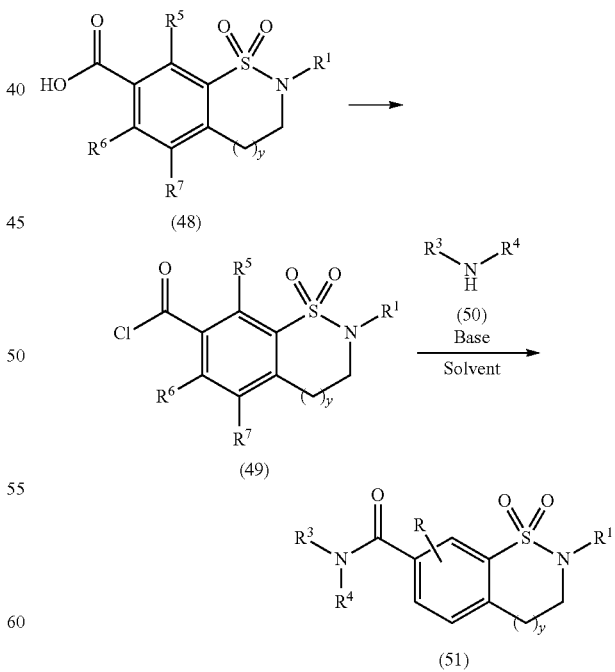

Scheme 17

A compound of the formula (48) is reacted with thionyl chloride, optionally in the presence an organic solvent such as methylene chloride, dichloroethane, tetrahydrofuran, 1,4-dioxane, dimethyl formamide, and the like to provide a compound of the formula (49). Alternatively, a compound of the formula (48) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (49). A compound of the formula (49) is then reacted with a compound of the formula (50), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like, optionally with heating, optionally with microwave irradiation to provide a compound of the formula (51).

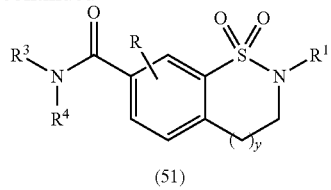

Alternatively, a compound of the formula (48) is reacted with a compound of the formula (50), a known compound or compound prepared by known methods, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (51).

Compounds of formula (58) may be prepared according to the process outlined in Schemes 19-20.

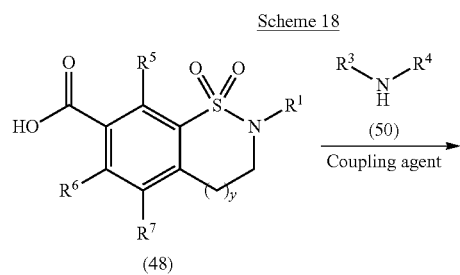

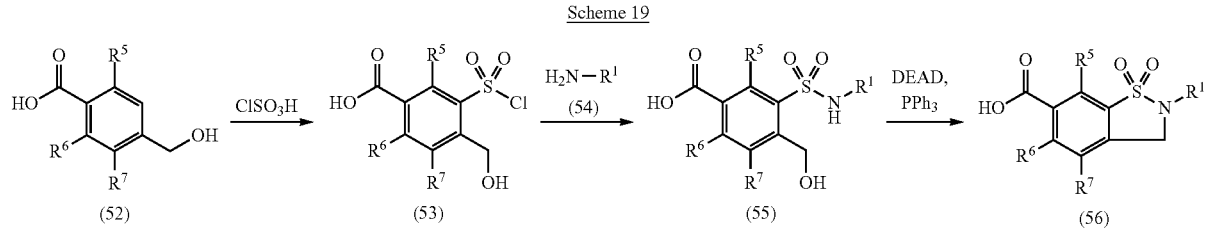

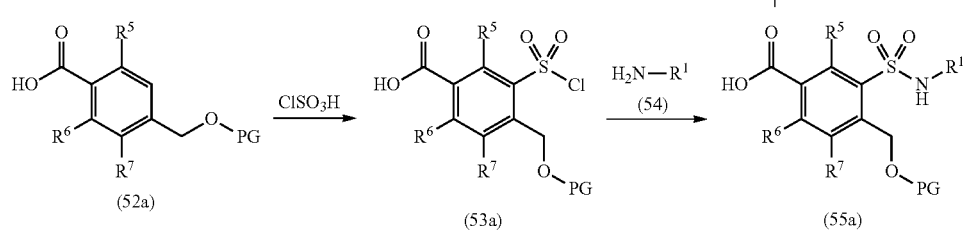

A compound of the formula (52), a known compound or compound prepared by known methods, is reacted with chlorosulfonic acid, optionally in a solvent such as methylene chloride, dichloroethane, tetrahydrofuran, 1,4-dioxane, dimethyl formamide, and the like, optionally with heating, optionally with microwave irradiation to provide a compound of the formula (53). A compound of the formula (53) is then reacted with a compound of the formula (54), a known compound or compound prepared by known methods, in a solvent such as methylene chloride, dichloroethane, tetrahydrofuran, 1,4-dioxane, dimethyl formamide, and the like, optionally with heating, optionally with microwave irradiation to provide a compound of the formula (55). A compound of the formula (55) is then reacted with diethyl azodicarboxylate (DEAD) in the presence of triphenylphosphine, in a solvent such as methylene chloride, dichloroethane, tetrahydrofuran, 1,4-dioxane, dimethyl formamide, and the like, optionally with heating, optionally with microwave irradiation to provide a compound of the formula (56).

Alternatively, a compound of the formula (52a), a known compound or compound prepared by known methods wherein PG is a protecting group such as tert-butyldimethylsilyl ether, methyl ether, tert-butyl ether, benzyl ether, β-methoxyethoxymethyl ether, acetyl, benzoyl, carbobenzyloxy, tert-butyloxycarbonyl, 9-fluorenylmethyloxycarbonyl, and the like, is reacted with chlorosulfonic acid, optionally in a solvent such as methylene chloride, dichloroethane, tetrahydrofuran, 1,4-dioxane, dimethyl formamide, and the like, optionally with heating, optionally with microwave irradiation to provide a compound of the formula (53a). A compound of the formula (53a) is then reacted with a compound of the formula (54), a known compound or compound prepared by known methods, in a solvent such as methylene chloride, dichloroethane, tetrahydrofuran, 1,4-dioxane, dimethyl formamide, and the like, optionally with heating, optionally with microwave irradiation to provide a compound of the formula (55a). A compound of the formula (55a) is then deprotected by reaction with an acid such as trifluoroacetic acid, hydrochloric acid, and the like in a solvent such methylene chloride, dichloroethane, tetrahydrofuran, methanol, ethanol, 1,4-dioxane, dimethyl formamide, and the like to provide a compound of the formula (55). Alternatively, a compound of the formula (55a) is then deprotected by reaction with hydrogen in the presence of a catalyst such as palladium on carbon, platinum oxide and the like in a suitable solvent such as methanol, ethanol, tetrahydrofuran and the like to provide a compound of formula (55). Alrenatively, a compound of the formula (55a) is then deprotected by reaction with a base such as sodium hydroxide, potassium hydroxide, lithium hydroxide, and the like, in a solvent such as methanol, ethanol, tetrahydrofuran 1,4-dioxane, dimethyl formamide, and the like to provide a compound of the formula (55). Alternatively, a compound of the formula (55a) is then deprotected by reaction with a base such piperidine in a solvent such as methanol, ethanol, tetrahydrofuran 1,4-dioxane, dimethyl formamide, and the like to provide a compound of the formula (55). A compound of the formula (55) is then reacted with diethyl azodicarboxylate (DEAD) in the presence of triphenylphosphine, in a solvent such as methylene chloride, dichloroethane, tetrahydrofuran, 1,4-dioxane, dimethyl formamide, and the like, optionally with heating, optionally with microwave irradiation to provide a compound of the formula (56).

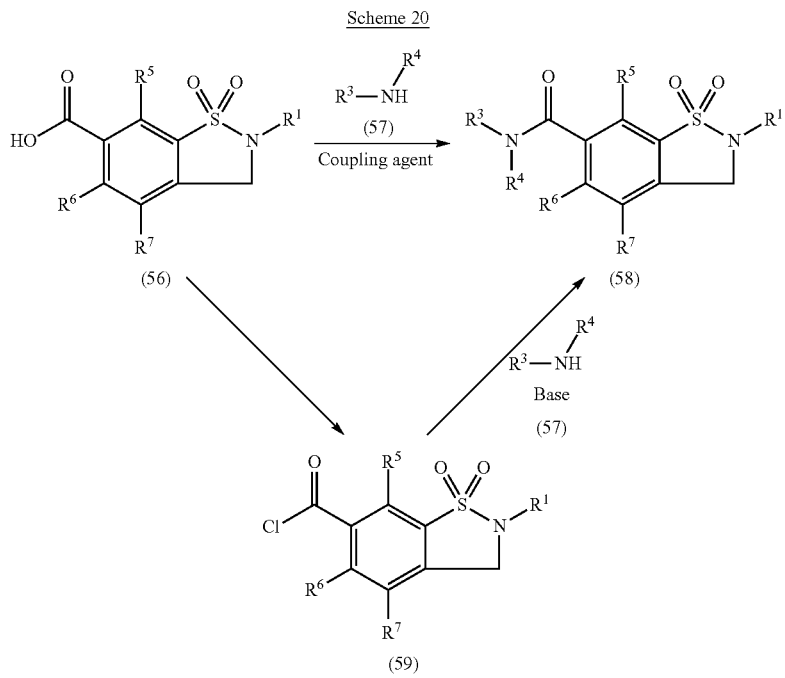

Scheme 20

A compound of the formula (56) is reacted with a compound of the formula (57), a known compound or compound prepared by known methods, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (58).

Alternatively, a compound of the formula (56) is reacted with thionyl chloride, optionally in the presence an organic solvent such as methylene chloride, dichloroethane, tetrahydrofuran, 1,4-dioxane, dimethyl formamide, and the like to provide a compound of the formula (59). Alternatively, a compound of the formula (56) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (59). A compound of the formula (59) is then reacted with a compound of the formula (57), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, dimethyl formamide, and the like, optionally with heating, optionally with microwave irradiation to provide a compound of the formula (58).

Compounds of formula (66) may be prepared according to the process outlined in Schemes 21-22.

Scheme 21

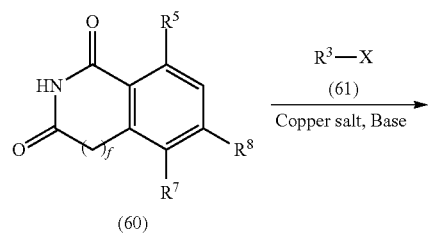

(60)

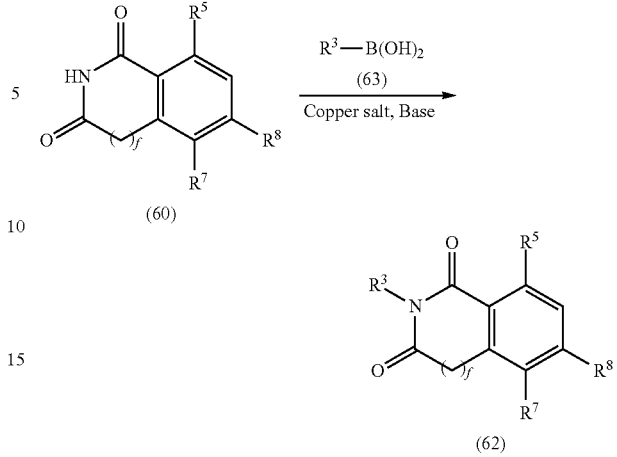

A compound of the formula (60), a known compound or compound prepared by known methods, is reacted with a compound of the formula (61), a known compound or compound prepared by known methods wherein X is a halogen, in the presence of a copper salt such as copper sulfate, copper iodide, copper chloride, copper acetate and the like, optionally in the presence of a palladium catalyst such as palladium (II) acetate, tetrakis(triphenylphosphine)palladium(0), dichlorobis(triphenylphosphine)palladium (II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (62). Alternatively, a compound of the formula (30), a known compound or compound prepared by known methods, is reacted with a compound of the formula (63), a known compound or compound prepared by known methods, in the presence of a copper salt such as copper sulfate, copper iodide, copper chloride, copper acetate and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (62).

Scheme 22

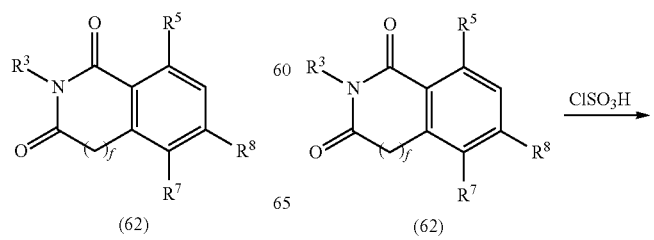

113

-continued

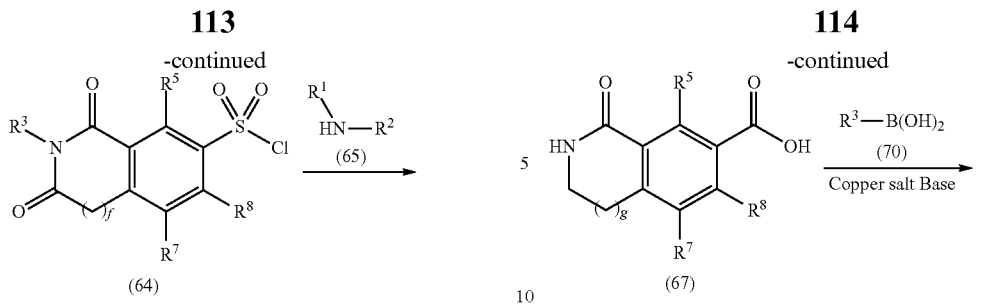

(64)            (67)

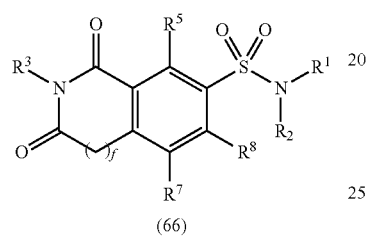

(66)

A compound of the formula (62), a known compound or compound prepared by known methods, is reacted with chlorosulfonic acid, optionally in the presence of an organic solvent such as methylene chloride, dichloroethane, tetrahydrofuran, 1,4-dioxane, dimethyl formamide, and the like to provide a compound of the formula to provide a compound of the formula (64). A compound of the formula (64) is reacted with a compound of the formula (65) a known compound or compound prepared by known methods, in the presence of a base such as triethylamine, diisopropylethylamine, pyridine, 2,6-lutidine, and the like, in the presence of an organic solvent such as methylene chloride, dichloroethane, tetrahydrofuran, 1,4-dioxane, dimethyl formamide, and the like to provide a compound of the formula (66).

Compounds of formula (71) may be prepared according to the process outlined in Schemes 23-24.

Scheme 23

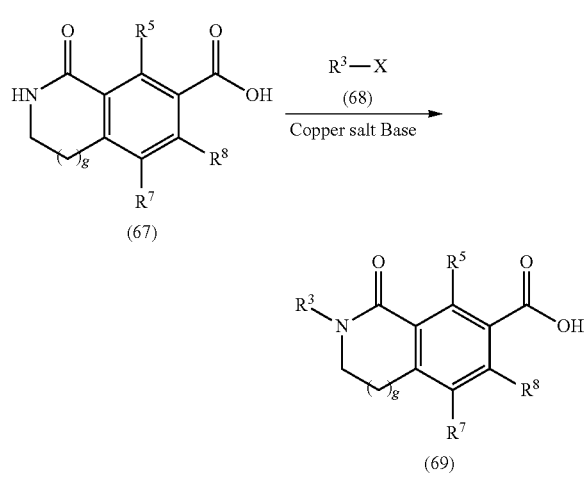

114

-continued

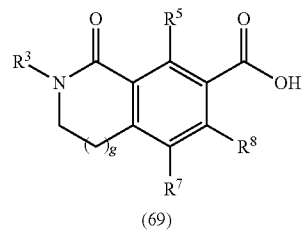

(69)

A compound of the formula (67), a known compound or compound prepared by known methods, is reacted with a compound of the formula (68), a known compound or compound prepared by known methods wherein X is a halogen, in the presence of a copper salt such as copper sulfate, copper iodide, copper chloride, copper acetate, and the like, optionally in the presence of a palladium catalyst such as palladium (II) acetate, tetrakis(triphenylphosphine) palladium(0), dichlorobis(triphenylphosphine)palladium (II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (69). Alternatively, a compound of the formula (67), a known compound or compound prepared by known methods, is reacted with a compound of the formula (70), a known compound or compound prepared by known methods, in the presence of a copper salt such as copper sulfate, copper iodide, copper chloride, copper acetate, and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (69).

Scheme 24

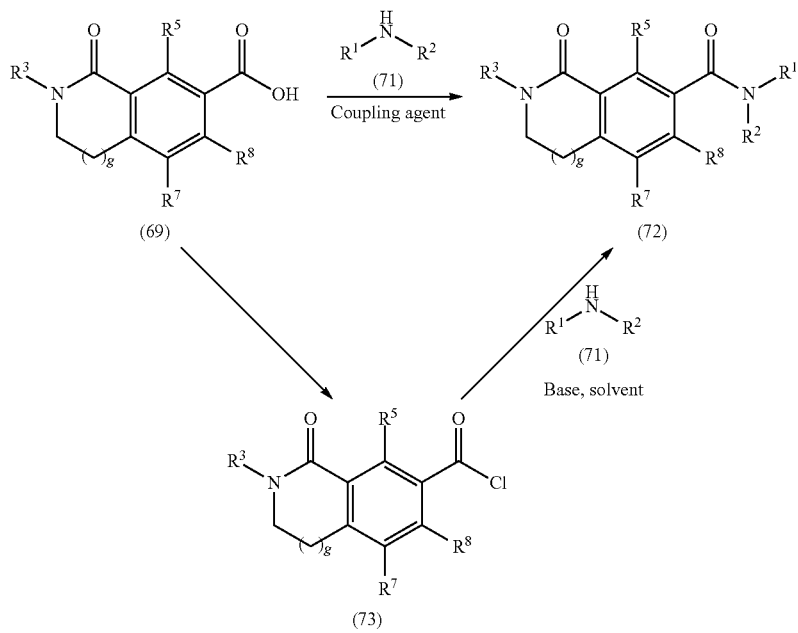

A compound of the formula (69) is reacted with a compound of the formula (71), a known compound or compound prepared by known methods, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (72). Alternatively, a compound of the formula (69) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (73). Alternatively, a compound of the formula (69) is reacted with thionyl chloride, optionally in the presence an organic solvent such as methylene chloride, dichloroethane, tetrahydrofuran, 1,4-dioxane, dimethyl formamide, and the like to provide a compound of the formula (73). A compound of the formula (73) is then reacted with a compound of the formula (71), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (72).

Compounds of formula (78) may be prepared according to the process outlined in Scheme 25.

Scheme 25

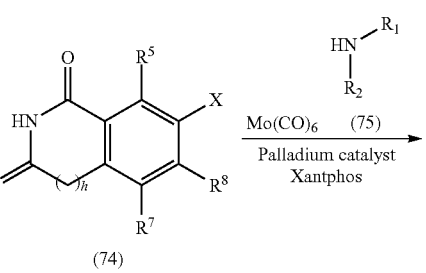

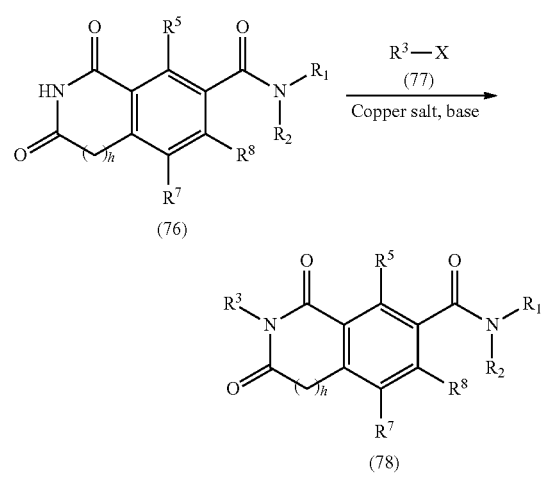

-continued

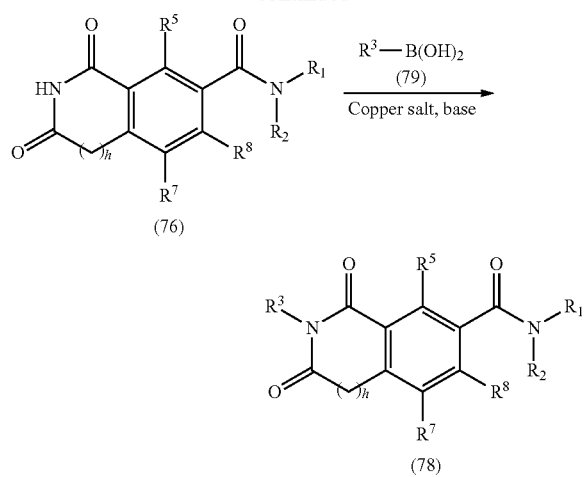

A compound of the formula (74) is reacted with a compound of the formula (75) in the presence of Molybdenum hexacarbonyl, in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, in the presence of 4,5-bis(diphenylphosphino)-9,9-dimethylxanthene (Xantphos), in an solvent such as water, dimethyl formamide, dimethyl acetamide, methanol, ethanol, methylene chloride, dichloroethane, tetrahydrofuran, 1,4-dioxane, and the like, optionally with heating, optionally with microwave irradiation, optionally in an inert atmosphere such as nitrogen or argon, to provide a compound of the formula (76). A compound of the formula (76) is reacted with a compound of the formula (77), a known compound or compound prepared by known methods wherein X is a halogen, in the presence of a copper salt such as copper sulfate, copper iodide, copper chloride, copper acetate and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (78). Alternatively, a compound of the formula (76) is reacted with a compound of the formula (79), a known compound or compound prepared by known methods, in the presence of a copper salt such as copper sulfate, copper iodide, copper chloride, copper acetate, and the like, optionally in the presence of a palladium catalyst such palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (78).

Compounds of formula (86) may be prepared according to the process outlined in Schemes 26-27.

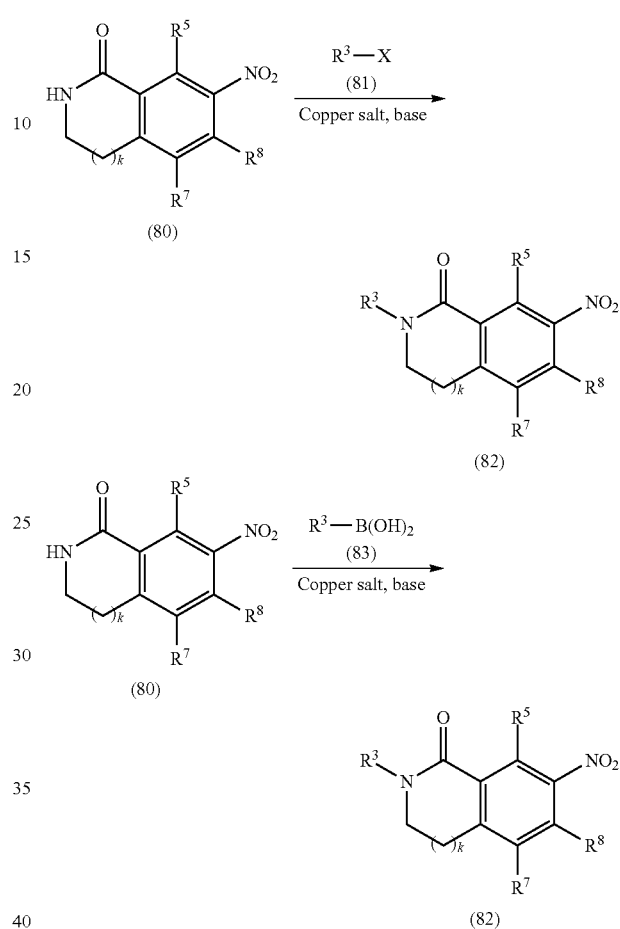

A compound of the formula (80) is reacted with a compound of the formula (81), a known compound or compound prepared by known methods wherein X is a halogen, in the presence of a copper salt such as copper sulfate, copper iodide, copper chloride, copper acetate and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (82). Alternatively, a compound of the formula (80) is reacted with a compound of the formula (83), a known compound or compound prepared by known methods, in the presence of a copper salt such as copper sulfate, copper iodide, copper chloride, copper acetate, and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (82).

Compounds of formula (93) may be prepared according to the process outlined in Schemes 28-29.

Scheme 27

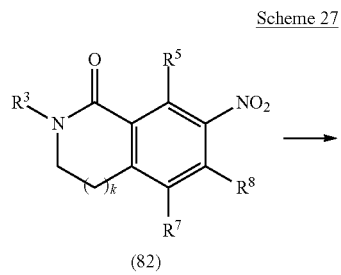

(82)

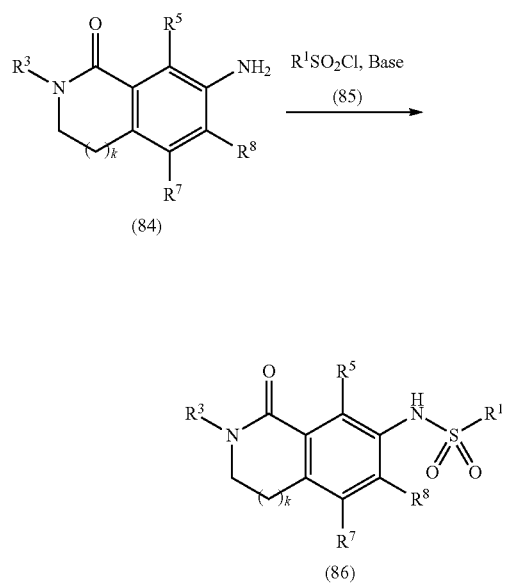

(84)

(86)

A compound of the formula (82) is then reacted with tin chloride in the presence of an acid such as hydrochloric acid, sulfuric acid, and the like, in an organic solvent such as tetrahydrofuran, 1,4-dioxane, dimethyl formamide, and the like to provide a compound of the formula to provide a compound of the formula (84). Alternatively, a compound of the formula (82) is reacted with hydrogen in the presence of a palladium catalyst such as palladium on carbon, palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of acetic acid, optionally in a solvent such as methanol, ethanol, tetrahydrofuran, 1,4-dioxane, and the like to provide a compound of the formula to provide a compound of the formula (84). A compound of the formula (84) is then reacted with a compound of the formula (85), a known compound or compound prepared by known methods, in the presence of a base such as triethylamine, diisopropylethylamine, pyridine, 2,6-lutidine, and the like, in an organic solvent such as methylene chloride, dichloroethane, tetrahydrofuran, 1,4-dioxane, dimethyl formamide, and the like to provide a compound of the formula to provide a compound of the formula (86).

Schem 28

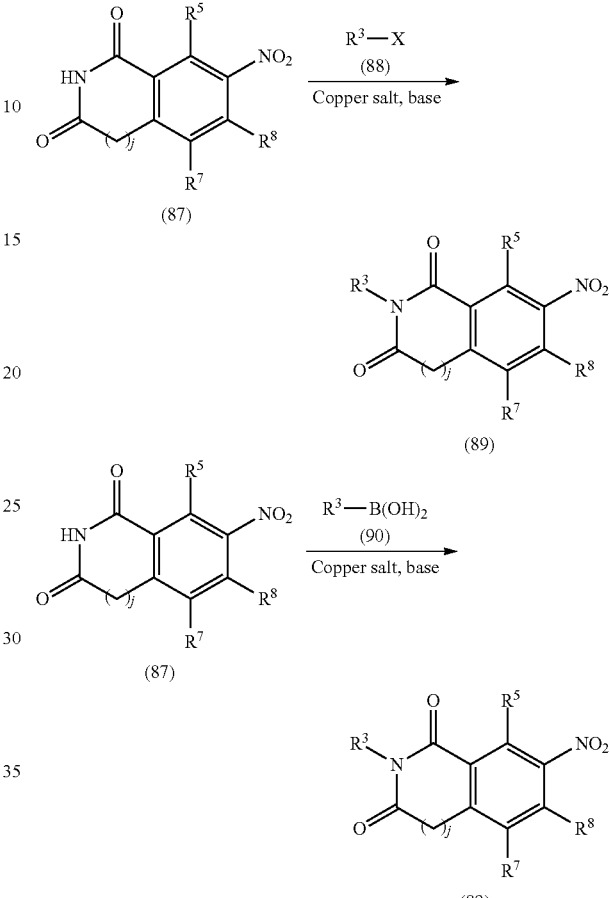

A compound of the formula (87) is reacted with a compound of the formula (88), a known compound or compound prepared by known methods wherein X is a halogen, in the presence of a copper salt such as copper sulfate, copper iodide, copper chloride, copper acetate and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (89). Alternatively, a compound of the formula (87) is reacted with a compound of the formula (90), a known compound or compound prepared by known methods, in the presence of a copper salt such as copper sulfate, copper iodide, copper chloride, copper acetate and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (89).

Scheme 29

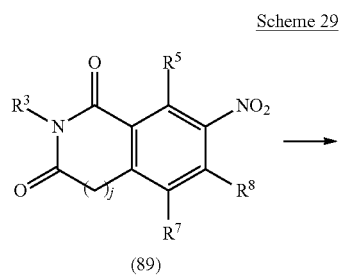

(89)

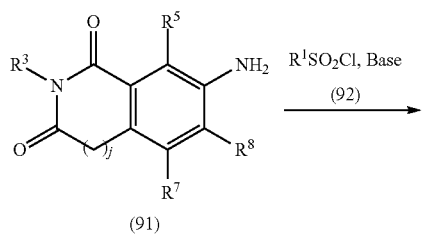

(91)

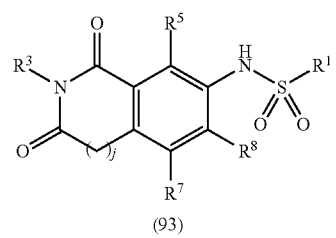

(93)

A compound of the formula (89) is then reacted with tin chloride in the presence of an acid such as hydrochloric acid, sulfuric acid, and the like, in an organic solvent such as tetrahydrofuran, 1,4-dioxane, dimethyl formamide, and the like to provide a compound of the formula to provide a compound of the formula (91). Alternatively, a compound of the formula (89) is reacted with hydrogen in the presence of a palladium catalyst such as palladium on carbon, palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of acetic acid, optionally in a solvent such as methanol, ethanol, tetrahydrofuran, 1,4-dioxane, and the like to provide a compound of the formula to provide a compound of the formula (91). A compound of the formula (91) is then reacted with a compound of the formula (92), a known compound or compound prepared by known methods, in the presence of a base such as triethylamine, diisopropylethylamine, pyridine, 2,6-lutidine, and the like, in an organic solvent such as methylene chloride, dichloroethane, tetrahydrofuran, 1,4-dioxane, dimethyl formamide, and the like to provide a compound of the formula to provide a compound of the formula (93).

Compounds of formula (100) may be prepared according to the process outlined in Schemes 30-31.

Scheme 30

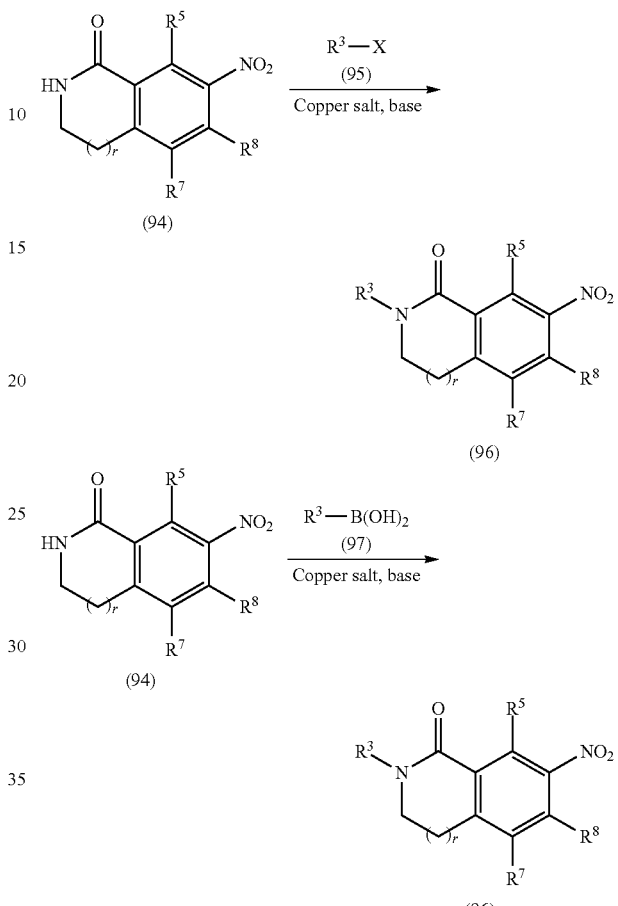

A compound of the formula (94) is reacted with a compound of the formula (95), a known compound or compound prepared by known methods wherein X is a halogen, in the presence of a copper salt such as copper sulfate, copper iodide, copper chloride, copper acetaete and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (96). Alternatively, a compound of the formula (94) is reacted with a compound of the formula (97), a known compound or compound prepared by known methods, in the presence of a copper salt such as copper sulfate, copper iodide, copper chloride, copper acetate and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (96).

Compounds of formula (107) may be prepared according to the process outlined in Schemes 32-33.

Scheme 31

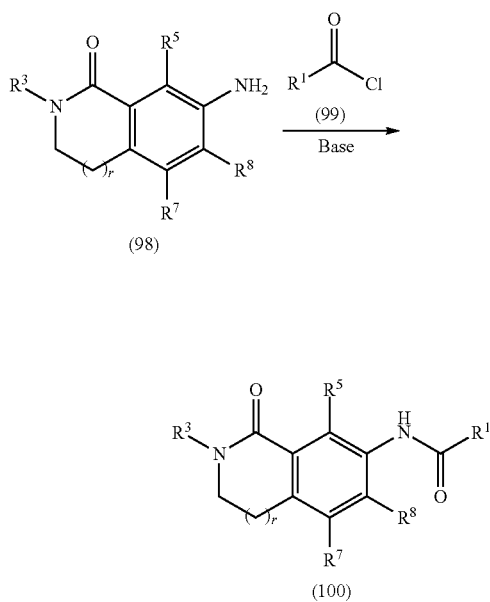

Scheme 32

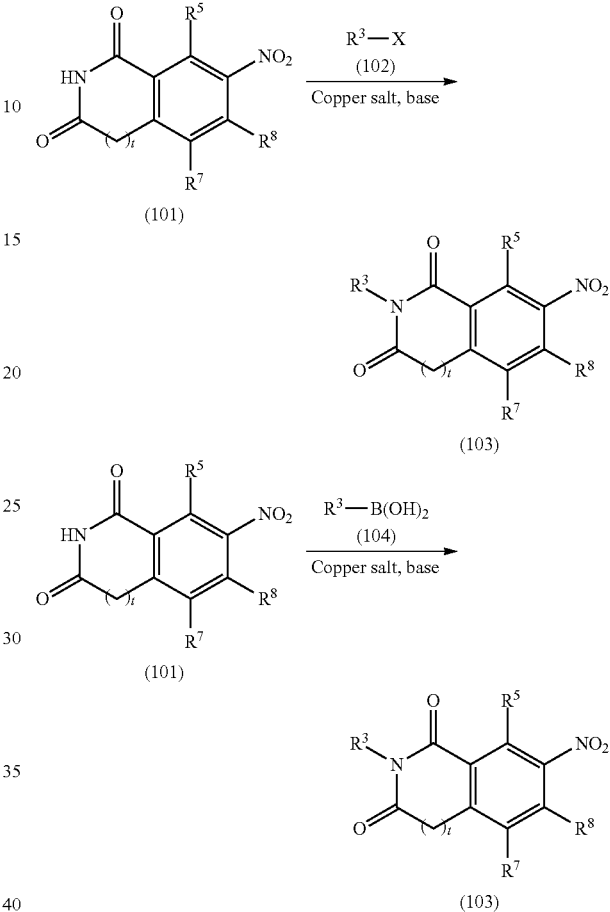

A compound of the formula (96) is then reacted with tin chloride in the presence of an acid such as hydrochloric acid, sulfuric acid, and the like, in an organic solvent such as tetrahydrofuran, 1,4-dioxane, dimethyl formamide, and the like to provide a compound of the formula to provide a compound of the formula (98). Alternatively, a compound of the formula (96) is reacted with hydrogen in the presence of a palladium catalyst such as palladium on carbon, palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of acetic acid, optionally in a solvent such as methanol, ethanol, tetrahydrofuran, 1,4-dioxane, and the like to provide a compound of the formula to provide a compound of the formula (98). A compound of the formula (98) is then reacted with a compound of the formula (99), a known compound or compound prepared by known methods, in the presence of a base such as triethylamine, diisopropylethylamine, pyridine, 2,6-lutidine, and the like, in an organic solvent such as methylene chloride, dichloroethane, tetrahydrofuran, 1,4-dioxane, dimethyl formamide, and the like to provide a compound of the formula to provide a compound of the formula (100).

A compound of the formula (101) is reacted with a compound of the formula (102), a known compound or compound prepared by known methods wherein X is a halogen, in the presence of a copper salt such as copper sulfate, copper iodide, copper chloride copper acetate and the like, optionally in the presence of a palladium catalyst such as palladium (II) acetate, tetrakis(triphenylphosphine) palladium(0), dichlorobis(triphenylphosphine)palladium (II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (103). Alternatively, a compound of the formula (101) is reacted with a compound of the formula (104), a known compound or compound prepared by known methods, in the presence of a copper salt such as copper sulfate, copper iodide, copper chloride, copper acetate and the like, optionally in the presence of a palladium catalyst such as palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of a base such as triethylamine, diisopropylethylamine, pyridine, 2,6-lutidine, and the like, in a solvent such as methylene chloride, dichloroethane, tetrahydrofuran, 1,4-dioxane, dimethyl formamide, and the like, optionally with heating, optionally with microwave irradiation to provide a compound of the formula (103).

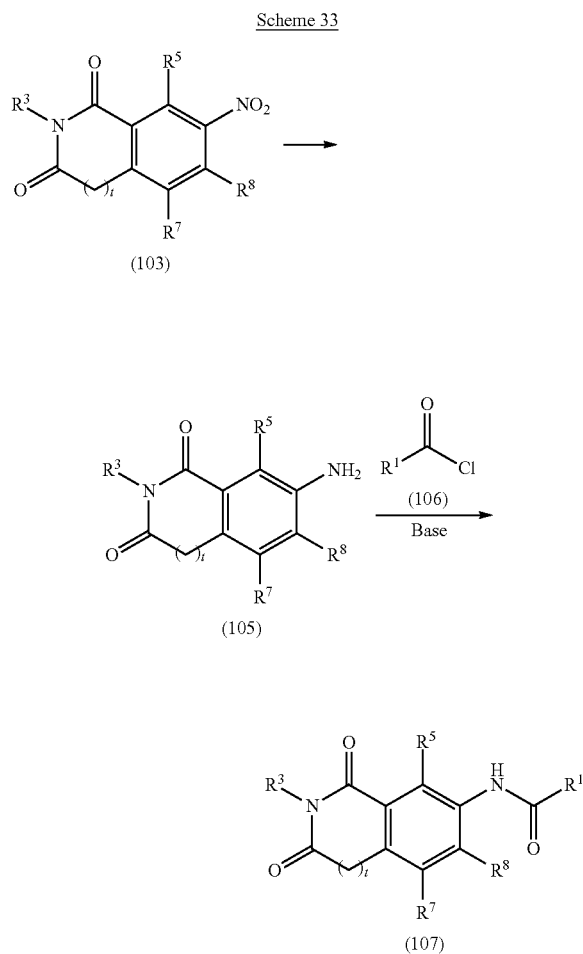

A compound of the formula (103) is then reacted with tin chloride in the presence of an acid such as hydrochloric acid, sulfuric acid, and the like, in an organic solvent such as tetrahydrofuran, 1,4-dioxane, dimethyl formamide, and the like to provide a compound of the formula to provide a compound of the formula (105). Alternatively, a compound of the formula (103) is reacted with hydrogen in the presence of a palladium catalyst such as palladium on carbon, palladium (II) acetate, tetrakis(triphenylphosphine)palladium(0), dichlorobis(triphenylphosphine)palladium(II), palladium on carbon, bis(acetonitrile)dichloropalladium(II), and the like, optionally in the presence of acetic acid, optionally in a solvent such as methanol, ethanol, tetrahydrofuran, 1,4-dioxane, and the like to provide a compound of the formula to provide a compound of the formula (105). A compound of the formula (105) is then reacted with a compound of the formula (106), a known compound or compound prepared by known methods, in the presence of a base such as triethylamine, diisopropylethylamine, pyridine, 2,6-lutidine, and the like, in an organic solvent such as methylene chloride, dichloroethane, tetrahydrofuran, 1,4-dioxane, dimethyl formamide, and the like to provide a compound of the formula to provide a compound of the formula (107).

Compounds of formula (115) may be prepared according to the process outlined in Schemes 34-35.

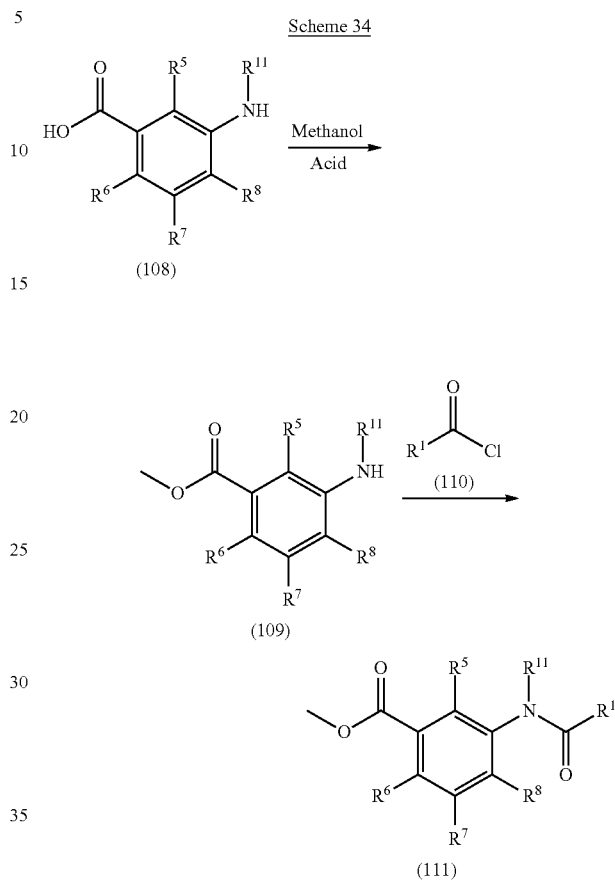

A compound of the formula (108), a known compound or compound prepared by known methods, is reacted with methanol in the presence of an acid such as hydrochloric acid, sulfuric acid, optionally with heating to provide a compound of the formula (109). A compound of the formula (109) is reacted with a compound of the formula (110), a known compound or compound prepared by known methods, in the presence of a base such as pyridine, 2,6-lutidine, and the like, optionally in the presence of dimethylaminopyridine (DMAP), optionally in the presence of a solvent such as dimethyl formamide, dimethyl acetamide, methylene chloride, dichloroethane, tetrahydrofuran, 1,4-dioxane, and the like, optionally with heating, to provide a compound of the formula (111).

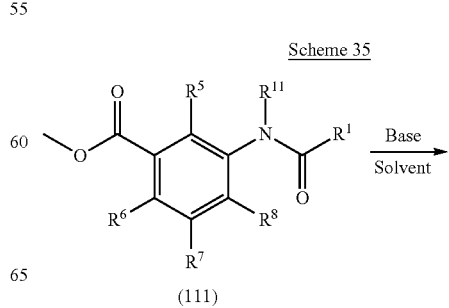

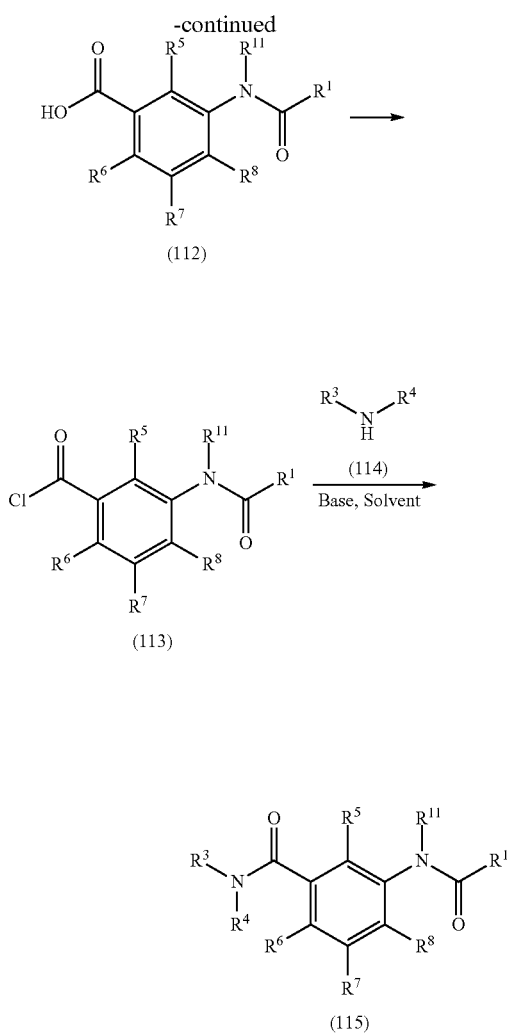

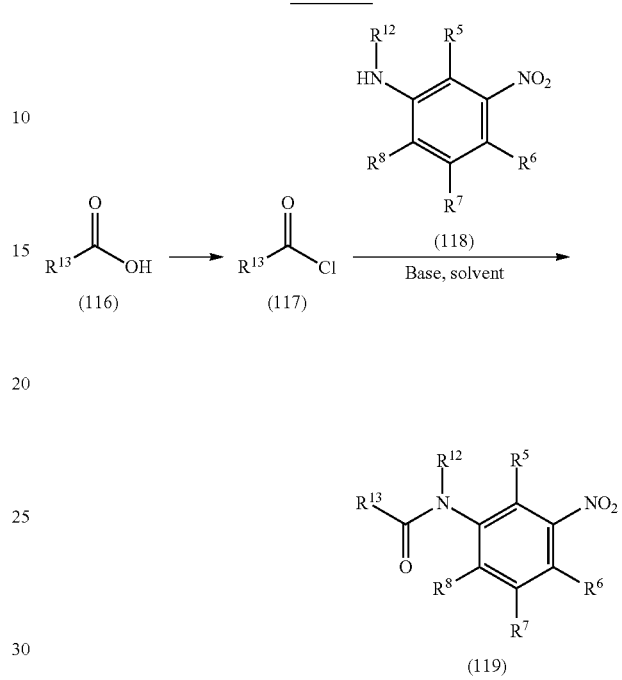

Compounds of formula (122) may be prepared according to the process outlined in Schemes 36-37.

Scheme 36

A compound of the formula (111) is reacted with a base such as lithium hydroxide, sodium hydroxide, potassium hydroxide, cesium hydroxide, potassium carbonate, sodium carbonate, and the like, in an solvent such as ethanol, methanol, water, dimethyl formamide, dimethyl acetamide, tetrahydrofuran, 1,4-dioxane, and the like, to provide a compound of the formula (112). A compound of the formula (112) is then reacted with thionyl chloride, optionally in the presence an organic solvent such as methylene chloride, dichloroethane, tetrahydrofuran, 1,4-dioxane, dimethyl formamide, and the like to provide a compound of the formula (113). Alternatively, a compound of the formula (112) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (113). A compound of the formula (113) is then reacted with a compound of the formula (114), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (115).

A compound of the formula (116), a known compound or compound prepared by known methods, is reacted with thionyl chloride, optionally in the presence an organic solvent such as methylene chloride, dichloroethane, tetrahydrofuran, 1,4-dioxane, dimethyl formamide, and the like to provide a compound of the formula (117). Alternatively, a compound of the formula (116) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (117). A compound of the formula (117) is then reacted with a compound of the formula (118), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (119).

Scheme 37

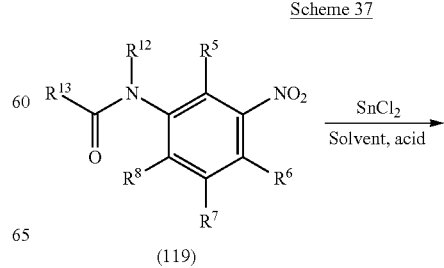

129

-continued

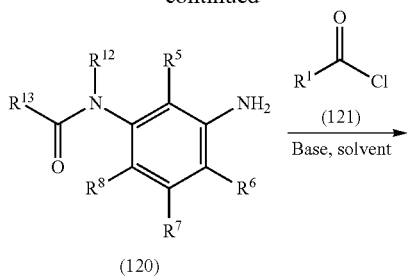

(120)

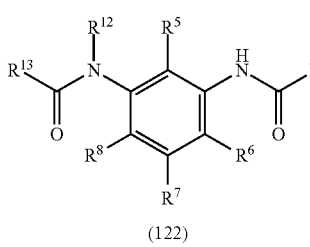

(122)

A compound of the formula (119) is then reacted with tin chloride in the presence of an acid such as hydrochloric acid, sulfuric acid, and the like, in an organic solvent such as tetrahydrofuran, 1,4-dioxane, dimethyl formamide, and the like to provide a compound of the formula to provide a compound of the formula (120). A compound of the formula (120) is then reacted with a compound of the formula (121), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (122).

Scheme 38

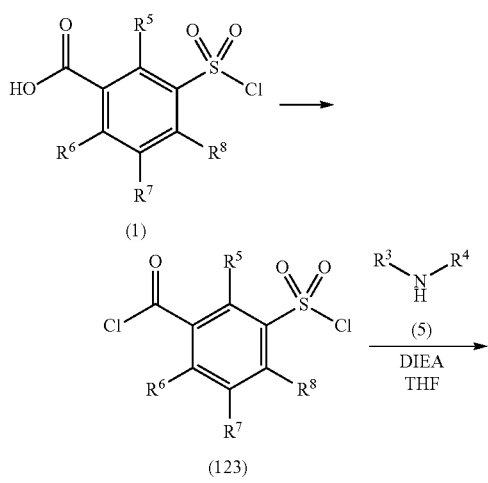

130

-continued

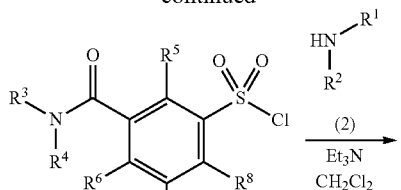

(124)

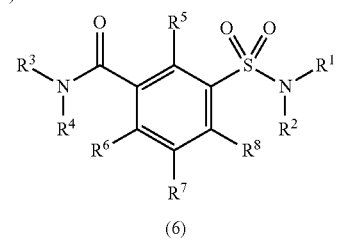

(6)

Alternatively, a compound of the formula (1), a known compound or compound prepared by known methods, is reacted with thionyl chloride, optionally in the presence an organic solvent such as methylene chloride, dichloroethane, tetrahydrofuran, 1,4-dioxane, dimethyl formamide, and the like to provide a compound of the formula (123). Alternatively, a compound of the formula (1) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like to provide a compound of the formula (123). A compound of the formula (123) is then reacted with a compound of the formula (5), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (124). A compound of formula (124) is then reacted with a compound of the formula (2), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like to provide a compound of the formula (6).

Formulations and Methods of Treatment

The present invention also relates to compositions or formulations which comprise the compounds of the present invention. In general, the compositions of the present invention comprise an effective amount of one or more of the compounds of the disclosure and salts thereof according to the present invention which are effective for useful for the treatment of viral infection, especially Hepatitis B virus (HBV) infection and related conditions; and one or more pharmaceutically acceptable excipient.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known antiviral agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, *acacia* gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal (including a human patient) a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more of the compounds of the present invention and one or more excipient; from about 0.01 mg to about 100 mg of one or more of the compounds according to the present invention and one or more excipients; and from about 0.1 mg to about 10 mg of one or more of the compounds according to the present invention; and one or more excipients.

In any above methods, the compound, or pharmaceutically acceptable salt of the present invention, can be administered either in monotherapy or in combination with one or more additional therapeutic agents. In certain embodiments the additional therapeutic agent may include an HBV polymerase inhibitor, interferon, viral entry inhibitor, viral maturation inhibitor, literature-described capsid assembly modulator, 5 reverse transcriptase inhibitor, a TLR-agonist, or an agents of distinct or unknown mechanism, or a combination thereof.

The additional therapeutic agent selected from immune modulator or immune stimulator therapies, which includes biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HB V replication or persistence.

The reverse transcriptase inhibitor may include at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

The combination therapy, the TLR-7 agonist may be SM360320 (9-benzyl-8-hydroxy-2-(2-methoxyethoxy)adenine) or AZD 8848 (methyl[3-({[3-(6-amino-2-butoxy-8-oxo-7,8-dihydro-9H-purin-9-yl)propyl][3-(4-morpholinyl)propyl]amino}methyl)phenyl]acetate).

In some embodiments of these combination therapies, the compound, or pharmaceutically acceptable salt of the present invention, and the additional therapeutic agent are co-formulated. In other embodiments, the compound and the additional therapeutic agent are co-administered. In other embodiments the compound, or pharmaceutically acceptable salt, of the present invention, and the additional therapeutic agent are separately formulated or administered.

In still other embodiments of the combination therapy, administering the compound, or pharmaceutically acceptable salt of the present invention allows for administering of the additional therapeutic agent at a lower dose or frequency as compared to the administering of the at least one additional therapeutic agent alone that is required to achieve similar results in prophylactically treating an HBV infection in an individual in need thereof.

In other embodiments of the combination therapy, before administering the therapeutically effective amount of the compound, or pharmaceutically acceptable salt of the present invention, the individual is known to be refractory to a compound selected from the group consisting of a HBV polymerase inhibitor, interferon, viral entry inhibitor, viral maturation inhibitor, distinct capsid assembly modulator, an antiviral compound of distinct or unknown mechanism, or a combination thereof.

In still other embodiments of the methods, administering a compound, or pharmaceutically acceptable salt of the present invention reduces viral load in the individual to a greater extent compared to the administering of a a HBV polymerase inhibitor, interferon, viral entry inhibitor, viral maturation inhibitor, distinct capsid assembly modulator, an antiviral compound of distinct or unknown mechanism, or a combination thereof.

In further embodiments, administering a compound, or pharmaceutically acceptable salt of the present invention causes a lower incidence of viral mutation and/or viral resistance than the administering of a HBV polymerase inhibitor, interferon, viral entry inhibitor, viral maturation inhibitor, distinct capsid assembly modulator, an antiviral compound of distinct or unknown mechanism, or a combination thereof.

The following listing of Embodiments is intended to complement, rather than displace or supersede, the previous descriptions.

Embodiment 1. A compound comprising a structure of Formula (I), or an enantiomer, diastereomer or pharmaceutically accepted salt, hydrate, or solvate thereof:

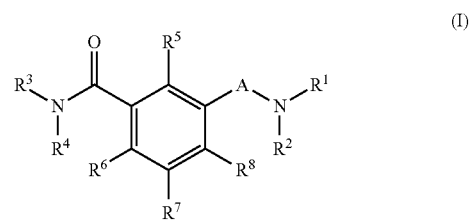

including hydrates, solvates, pharmaceutically acceptable salts, prodrugs and complexes thereof, wherein:

A is selected from a group consisting of $SO_2$ and CO;

$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted $C_{1-6}$ haloalkyl, optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;

$R^2$ is selected from a group consisting of hydrogen and optionally substituted $C_{1-6}$ linear alkyl; $R^2$ may also alternatively or additionally optionally include optionally substituted $C_{3-7}$ cycloalkyl or optionally substituted heterocyclic; or $R^1$ and $R^2$ are taken together with the atoms to which they are bound to form an optionally substituted heterocycle (including bicyclic or adamantyl structures) with 3 to 10 atoms; and $R^3$ is selected from a group consisting of optionally substituted aryl, optionally substituted benzyl, optionally substituted alkylaryl, optionally substituted heteroaryl, and optionally substituted alkylheteroaryl; in some embodiments, $R^3$ may also comprise an optionally substituted $C_{1-6}$ linear alkyl;

$R^4$ is selected from a group consisting of hydrogen and optionally substituted $C_{1-6}$ linear alkyl;

$R^5$ is selected from a group consisting of hydrogen, halogen, optionally substituted $C_{1-6}$ linear alkyl, optionally substituted $C_{1-6}$ branched alkyl, optionally substituted $C_{1-6}$haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; $R^6$ may also alternatively or additionally optionally include cyano or $N(R^9)_2$; or $R^4$ and $R^6$ are taken together with the atoms to which they are bound to form an optionally substituted carbocyclic or heterocyclic ring with 5 to 6 atoms, optionally containing a carbonyl, optionally containing two carbonyls; and $R^7$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$branched alkyl, optionally substituted $C_{1-6}$haloalkyl, and $OR^9$; $R^8$ may also alternatively or additionally optionally include cyano or $N(R^9)_2$; or $R^2$ and $R^8$ are taken together with the atoms to which they are bound to form an optionally substituted carbocyclic or heterocyclic ring with 5 to 6 atoms; and $R^9$ is independently at each occurrence selected from a group consisting of hydrogen, optionally substituted $C_{1-6}$ linear alkyl, optionally substituted $C_{1-6}$branched alkyl, and optionally substituted $C_{3-7}$cycloalkyl; $R^9$ may also alternatively or additionally optionally include, independently at each occurrence, optionally substituted aryl, optionally substituted benzyl, optionally substituted heterocyclyl, or optionally substituted heteroaryl;

provided that when A is $SO_2$; $R^4$ and $R^6$ taken together with the atoms to which they are bound do not to form an optionally substituted ring; and $R^2$ and $R^8$ taken together with the atoms to which they are bound do not to form an optionally substituted ring, then none of the following (a) through (d) apply:

(a) $R^3$ is an optionally substituted phenyl and $R^1$ or $R^2$, either individually or when taken together, contain a hydroxyl group, or (b) $R^3$ is an optionally substituted alkyl or phenyl, and $N(R^1)(R^2)$ is an optionally substituted piperazine or

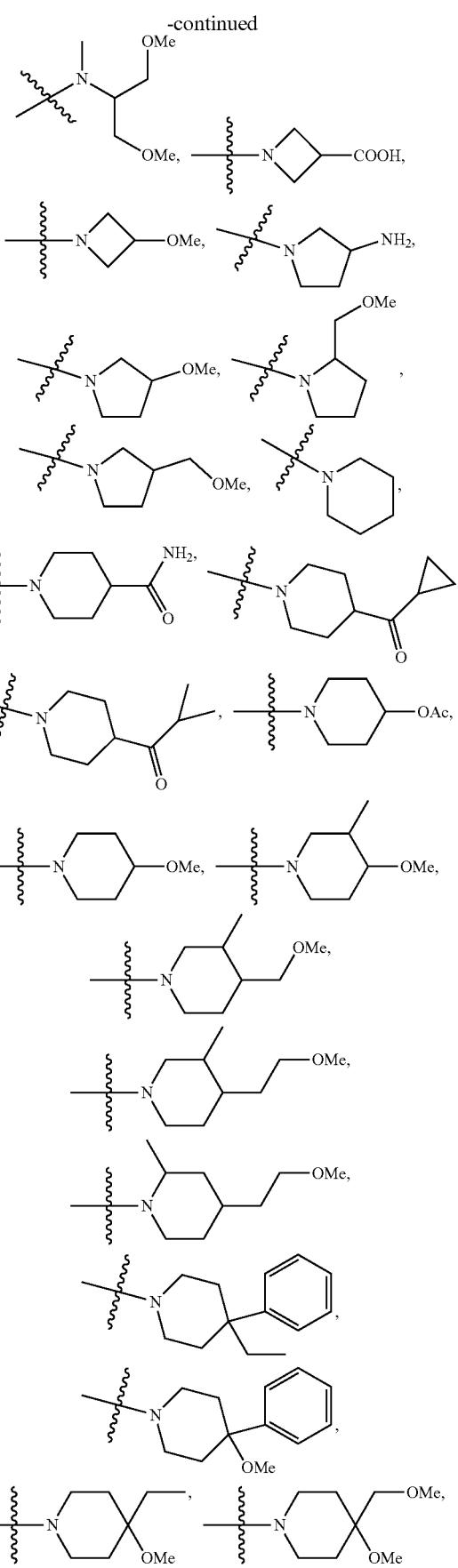

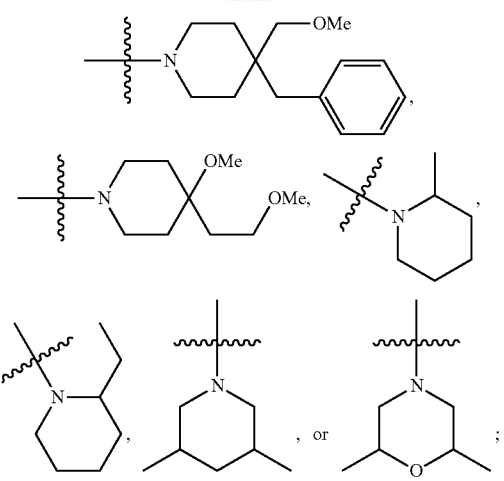

(c) $R^3$ is optionally substituted alkyl, aryl, or alkaryl and $N(R^1)(R^2)$ is

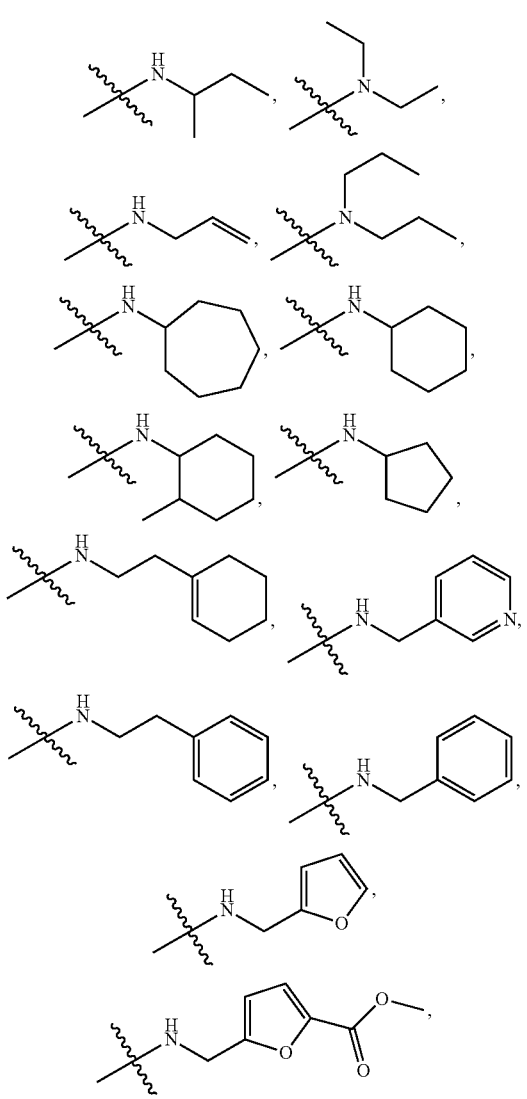

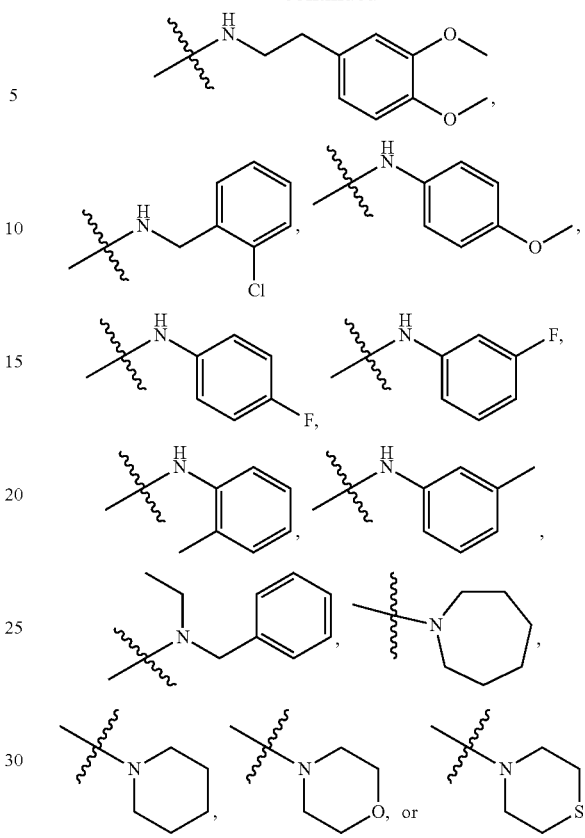

or (d) either $R^3$ or $R^4$ is an unsubstituted or monosubstituted aryl, or an unsubstituted or monosubstituted aralkyl, or unsubstituted or monosubstituted heteroaryl and $R^1$ and $R^2$ are taken together with the atoms to which they are bound to form an optionally substituted heterocyclic ring structure with 6 to 12 atoms; or provided that the compound is not 3-{[(dicyclopropylmethyl)amino]sulfonyl}-N-(4-isopropoxyphenyl)benzamide; or 3-({[2-(1H-benzimidazol-2-yl)propyl]amino}sulfonyl)-N-(4-isopropoxyphenyl)benzamide; or 3-[(cyclohexylamino)sulfonyl]-N-(4-isopropylphenyl)benzamide; or 3-(anilinosulfonyl)-N-(4-isopropylphenyl)benzamide; or 5-{[(3-{[(4-methoxyphenyl)amino]carbonyl}phenyl)sulfonyl]amino}pentanoic acid; or 3-[(tert-butylamino)sulfonyl]-N-(4-methoxyphenyl)benzamide; or (3S)-1-[(3-{[(5-isopropoxypyridin-2-yl)amino]carbonyl}phenyl)sulfonyl]piperidine-3-carboxamide; or (3R)-1-[(3-{[(5-isopropoxypyridin-2-yl)amino]carbonyl}phenyl)sulfonyl]piperidine-3-carboxamide; or 3-(piperidin-1-ylsulfonyl)-N-[(1S)-1,2,3,4-tetrahydronaphthalen-1-yl]benzamide; or N-(5-bromo-3-methoxypyridin-2-yl)-3-(piperidin-1-ylsulfonyl)benzamide; or N-(3-methoxy-5-phenylpyridin-2-yl)-3-(pyrrolidin-1-ylsulfonyl)benzamide; or N-(3-methoxy-5-phenoxypyridin-2-yl)-3-(pyrrolidin-1-ylsulfonyl)benzamide; or N-[3-methoxy-5-(phenylthio)pyridin-2-yl]-3-(pyrrolidin-1-ylsulfonyl)benzamide; or N-(5-ethyl-3-methoxypyridin-2-yl)-3-(piperidin-1-ylsulfonyl)benzamide; or N-(3-methoxy-5-vinylpyridin-2-yl)-3-(piperidin-1-ylsulfonyl)benzamide; or

141

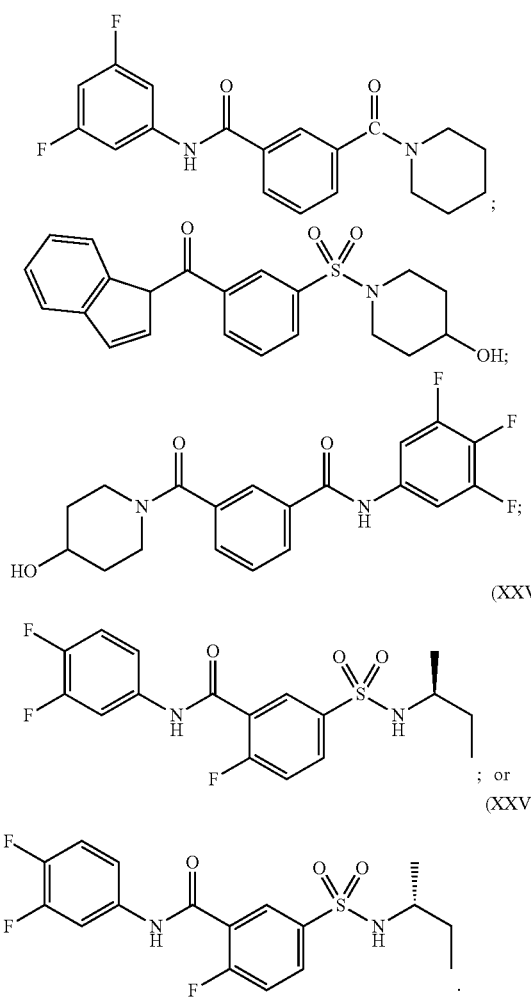

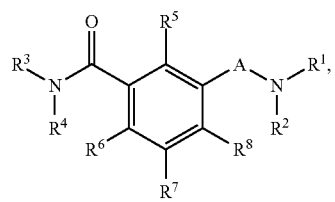

Some embodiments of the compounds of formula (I) also exclude those compounds when A is SO$_2$; R$^4$ and R$^6$ taken together with the atoms to which they are bound do not to form an optionally substituted ring; and R$^2$ and R$^8$ taken together with the atoms to which they are bound do not to form an optionally substituted ring, R$^3$ is optionally substituted alkyl, aryl, or alkaryl and N(R$^1$)(R$^2$) is an optionally substituted piperidine.

Embodiment 2. The compound of formula (I) wherein:

R$^4$ and R$^6$ taken together with the atoms to which they are bound do not to form an optionally substituted ring; and R$^2$ and R$^8$ taken together with the atoms to which they are bound do not to form an optionally substituted ring;

thereby providing a compound having a formula:

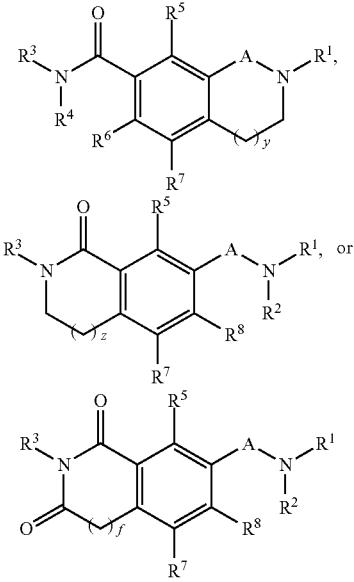

142

Embodiment 3. The compound, enantiomer, diastereomer or pharmaceutically accepted salt, hydrate, or solvate of Embodiment 1, the compound comprising one of the following structures:

wherein, as appropriate:

R$^4$ and R$^6$ taken together with the atoms to which they are bound do not to form an optionally substituted ring; and R$^2$ and R$^8$ taken together with the atoms to which they are bound do not to form an optionally substituted ring; and wherein z and f are independently is 0 or 1, and y is independently 0, 1, or 2.

Embodiment 4. The compound, enantiomer, diastereomer or pharmaceutically accepted salt, hydrate, or solvate of any one of Embodiments 1 to 3, wherein A is SO$_2$.

Embodiment 5. The compound, enantiomer, diastereomer or pharmaceutically accepted salt, hydrate, or solvate of any one of Embodiments 1 to 3, wherein A is CO.

Embodiment 6. The compound, enantiomer, diastereomer or pharmaceutically accepted salt, hydrate, or solvate of any one of Embodiments 1 to 5, wherein R$^3$ is selected from a group consisting of optionally substituted aryl, optionally substituted benzyl, optionally substituted alkylaryl, optionally substituted heteroaryl, optionally substituted alkylheteroaryl, and optionally substituted C$_{1-6}$ linear alkyl; and where present, R$^4$ is hydrogen.

Embodiment 7. The compound, enantiomer, diastereomer or pharmaceutically accepted salt, hydrate, or solvate of Embodiment 6, wherein R$^3$ is selected from a group consisting of optionally substituted phenyl, optionally substituted benzyl, optionally substituted benzoisoxazolyl, optionally substituted benzooxazolyl, optionally substituted furyl, optionally substituted imidazolyl, optionally substituted indoyl, optionally substituted isoxazolyl, optionally substituted isothiazolyl, optionally substituted oxazolyl, optionally substituted pyrazolyl, optionally substituted pyridin-2-on-yl, optionally substituted pyridyl, optionally substituted pyrrolyl, optionally substituted quinolinyl, optionally substituted thiazolyl optionally substituted thienyl, and optionally substituted methylpyridyl.

Embodiment 8. The compound, enantiomer, diastereomer or pharmaceutically accepted salt, hydrate, or solvate of Embodiment 7, wherein $R^3$ is

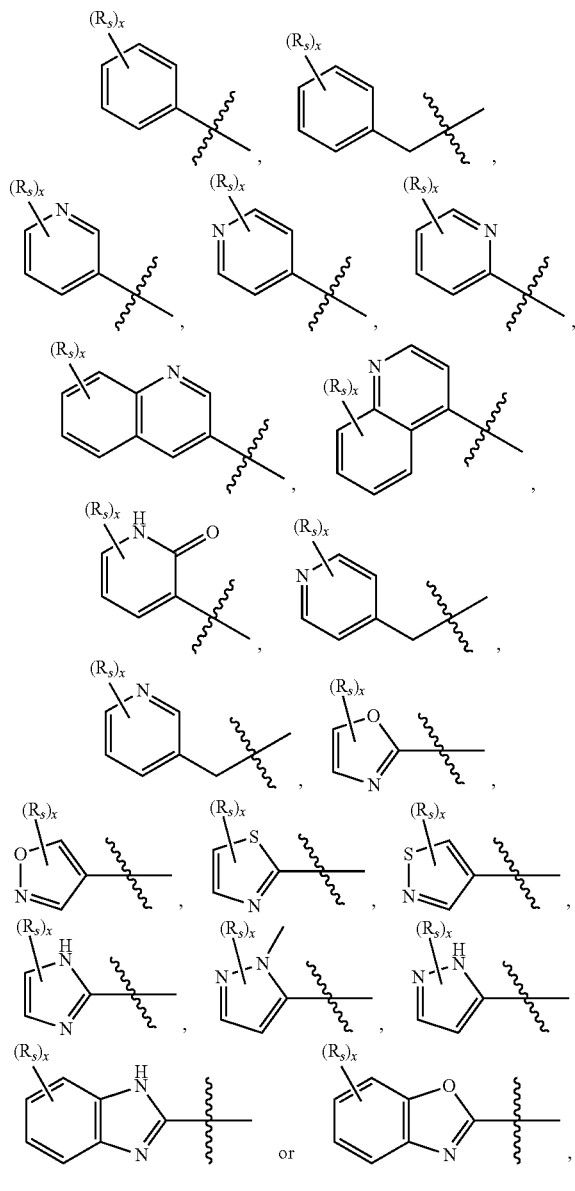

wherein
$R_S$ is independently at each occurrence bromo, chloro, fluoro, cyano, hydroxyl, optionally fluorinated $C_{1-6}$ alkyl (e.g., —$CH_3$, —$CH_2F$, —$CF_2H$, —$CF_3$), —O—($C_{1-6}$ alkyl), or when two are taken form a fused cyclic or heterocyclic moiety; and
x is 0, 1, 2, or 3; and
where present, $R^4$ is hydrogen.
It is appreciated that the designator $(R_s)_x$
\ indicates that the substituent(s) may be present on any available ring member, as valence allows (including alkyl substitution on nitrogen). For fused bicyclic systems, the same designator connote that the substituent(s) may be present on a ring member of either ring, as valence allows.

Embodiment 9. The compound, enantiomer, diastereomer or pharmaceutically accepted salt, hydrate, or solvate of any one of Embodiments 1 to 7, wherein the optional substitution of $R^3$ comprises at least one halo or $C_{1-6}$ alkyl.

Embodiment 10 The compound, enantiomer, diastereomer or pharmaceutically accepted salt, hydrate, or solvate of Embodiment 8, wherein the optional substitution of $R^3$ comprises at least one halo.

Embodiment 11 The compound, enantiomer, diastereomer or pharmaceutically accepted salt of any one of Embodiments 1 to 9, wherein $R^3$ is

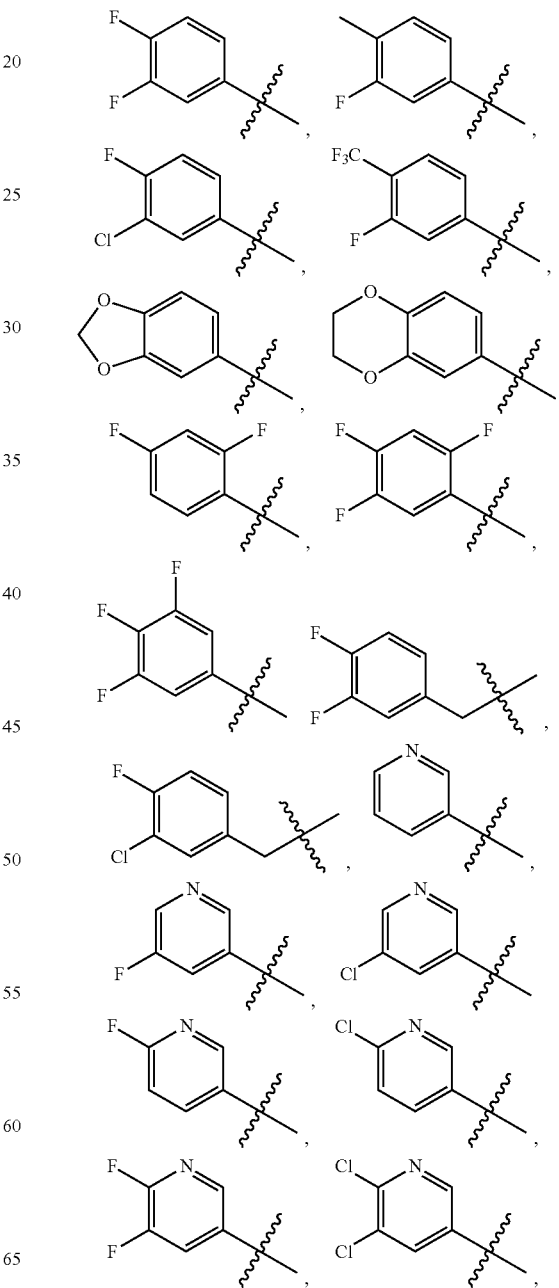

-continued

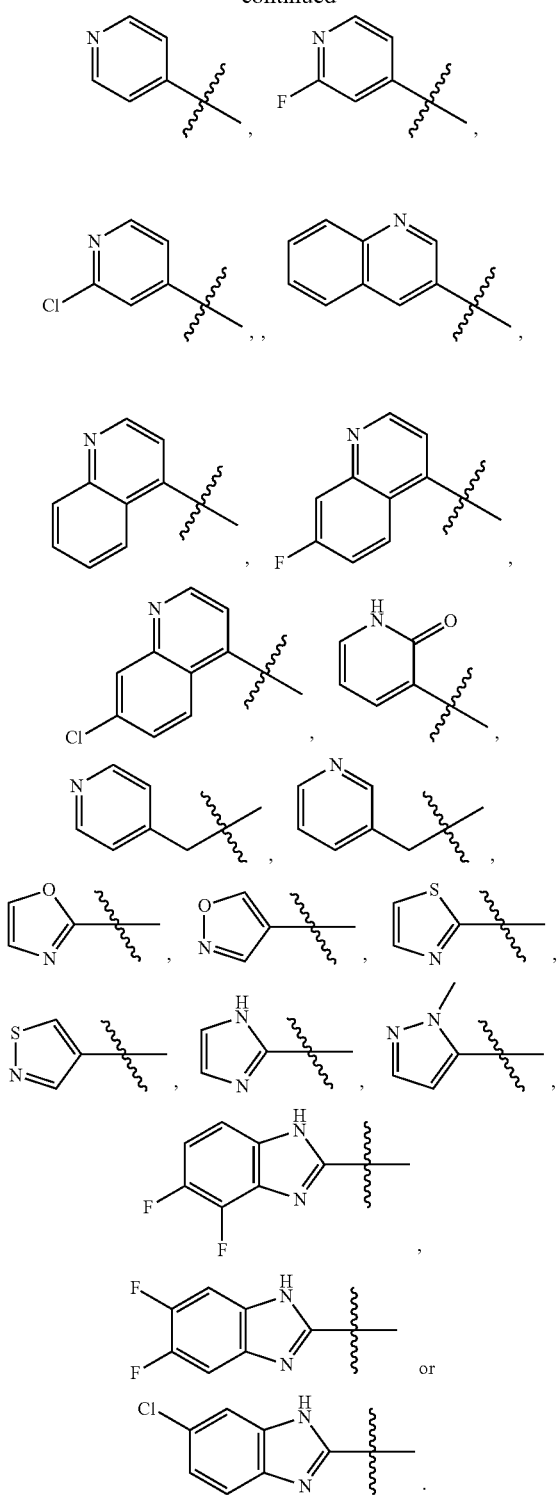

Embodiment 12. The compound, enantiomer, diastereomer or pharmaceutically accepted salt, hydrate, or solvate of any of the Embodiments 1 to 10, wherein $R^5$ and $R^7$ are each independently at each occurrence H or F; and $R^6$ and $R^8$ are each independently at each occurrence hydrogen, chloro, fluoro, or $C_{1-3}$ alkyl, or $C_{1-3}$ alkoxy.

Embodiment 13. The compound, enantiomer, diastereomer or pharmaceutically accepted salt of any one of Embodiments 1 to 11, wherein
$R^3$ is

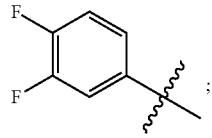

and
where present, $R^4$ is hydrogen.

Embodiment 14. The compound, enantiomer, diastereomer or pharmaceutically accepted salt, hydrate, or solvate of any one of Embodiments 1 to 12, wherein
$R^5$, $R^7$, and $R^8$ are each H; and
$R^6$ is hydrogen, chloro, fluoro, or methoxy.

Embodiment 15. The compound, enantiomer, diastereomer or pharmaceutically accepted salt, hydrate, or solvate of any one of Embodiments 1 to 13, wherein,
$R^1$ is methyl, methyl amine (or protected analog thereof), methoxy, ethyl, ethyl amine (or protected analog thereof), ethoxy, n-propyl, propyl amine (or protected analog thereof), n-propoxy, isopropyl, isopropyl amine (or protected analog thereof), isopropoxy, n-butyl, n-butyl amine (or protected analog thereof), n-butoxy, sec-butyl, sec-butyl amine (or protected analog thereof), sec-butoxy, tert-butyl tert-butyl amine (or protected analog thereof), tert-butoxy, vinyl, optionally substituted phenyl, optionally substituted benzyl, optionally substituted benzoisoxazolyl, optionally substituted benzooxazolyl, optionally substituted furyl, optionally substituted imidazolyl, optionally substituted indoyl, optionally substituted isoxazolyl, optionally substituted isothiazolyl, optionally substituted oxazolyl, optionally substituted pyrazolyl, optionally substituted pyridin-2-on-yl, optionally substituted pyridyl, optionally substituted pyrrolyl, optionally substituted quinolinyl, optionally substituted thiazolyl optionally substituted thienyl, and optionally substituted methylpyridyl,

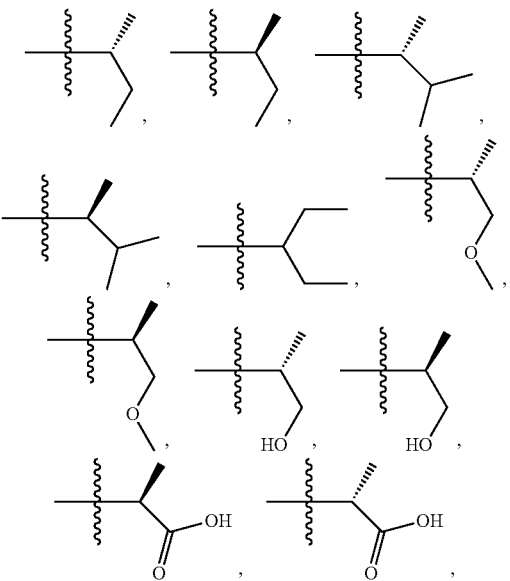

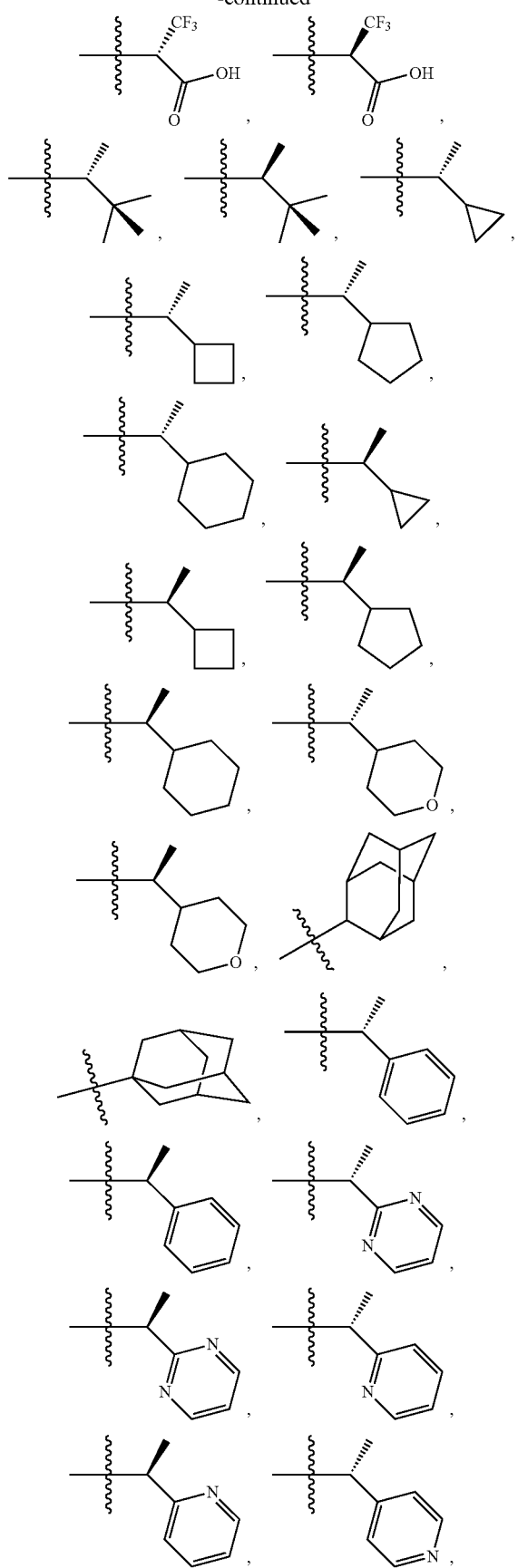
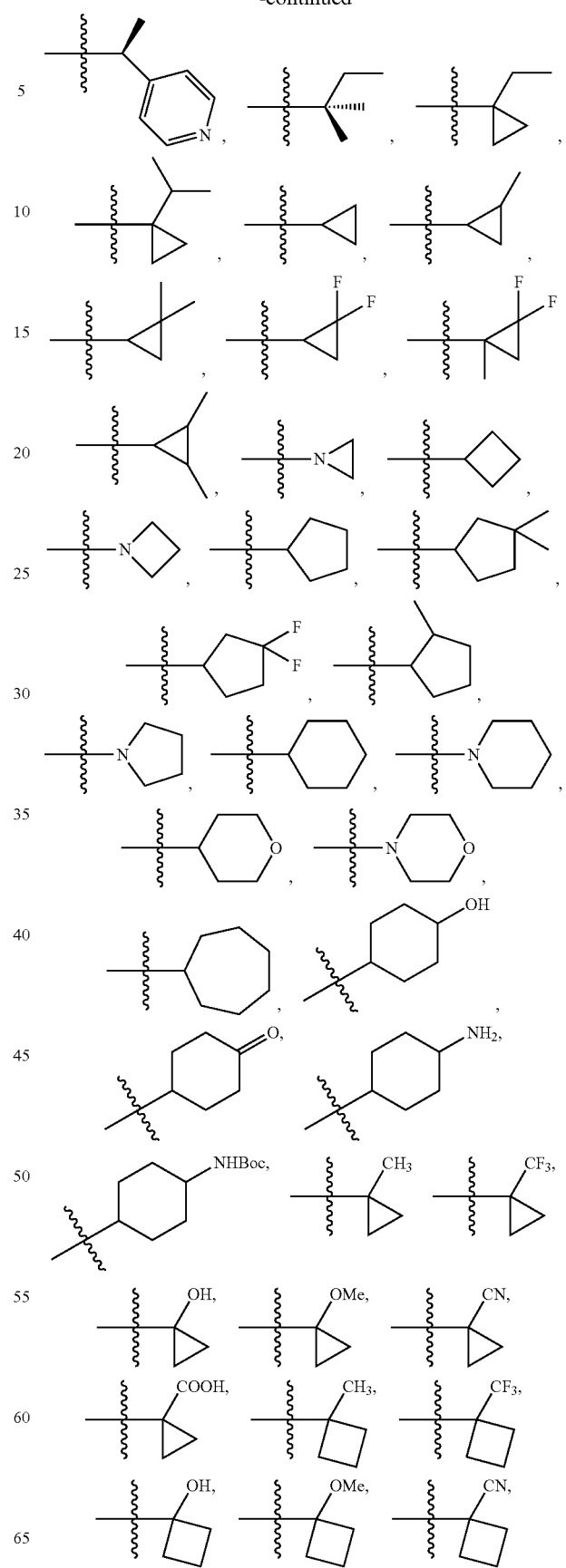

-continued

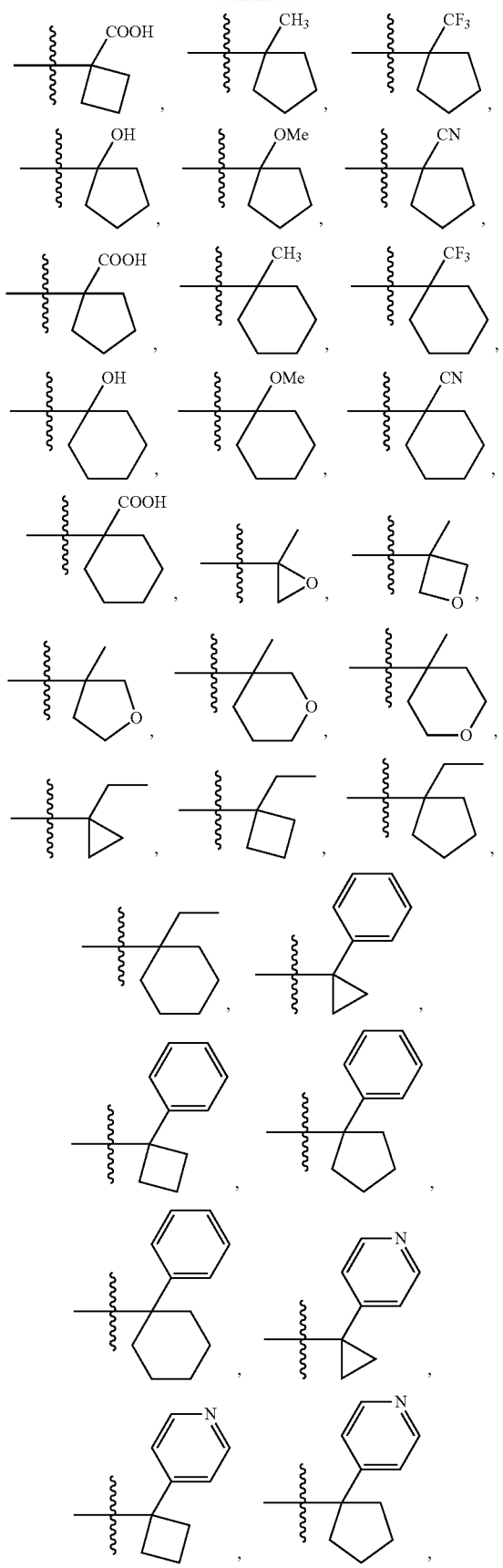

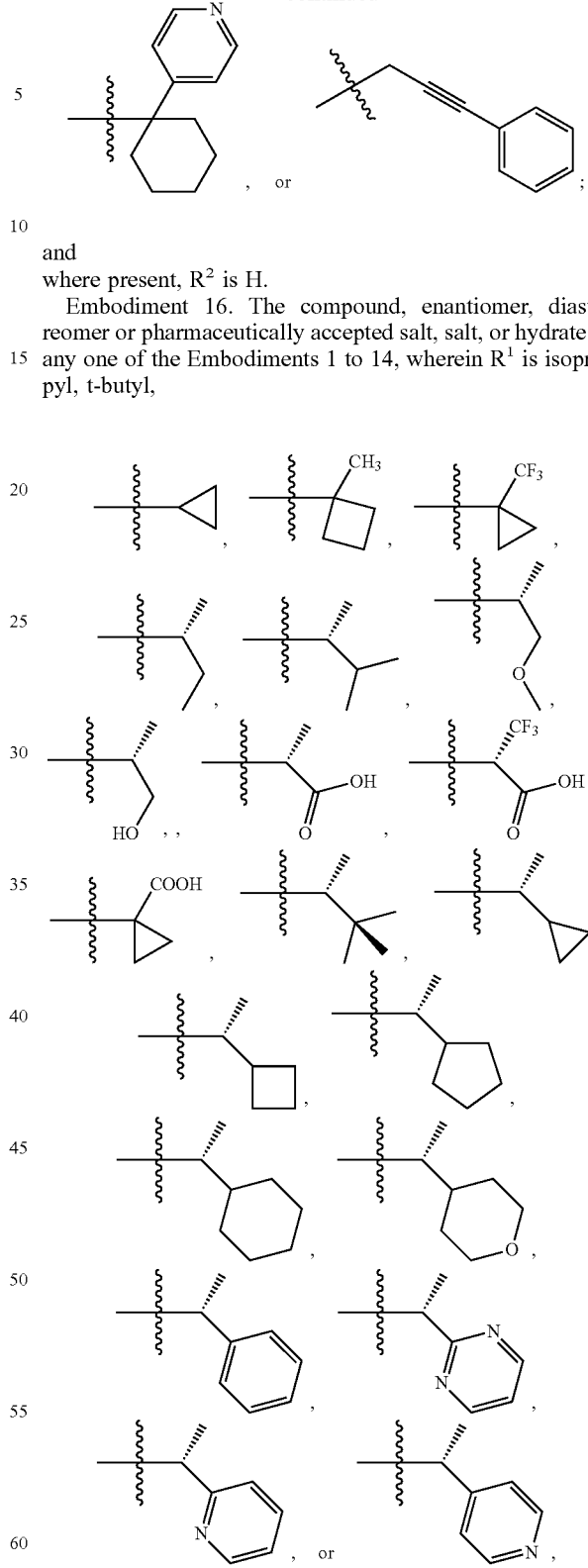

and
where present, R² is H.

Embodiment 16. The compound, enantiomer, diastereomer or pharmaceutically accepted salt, salt, or hydrate of any one of the Embodiments 1 to 14, wherein R¹ is isopropyl, t-butyl,

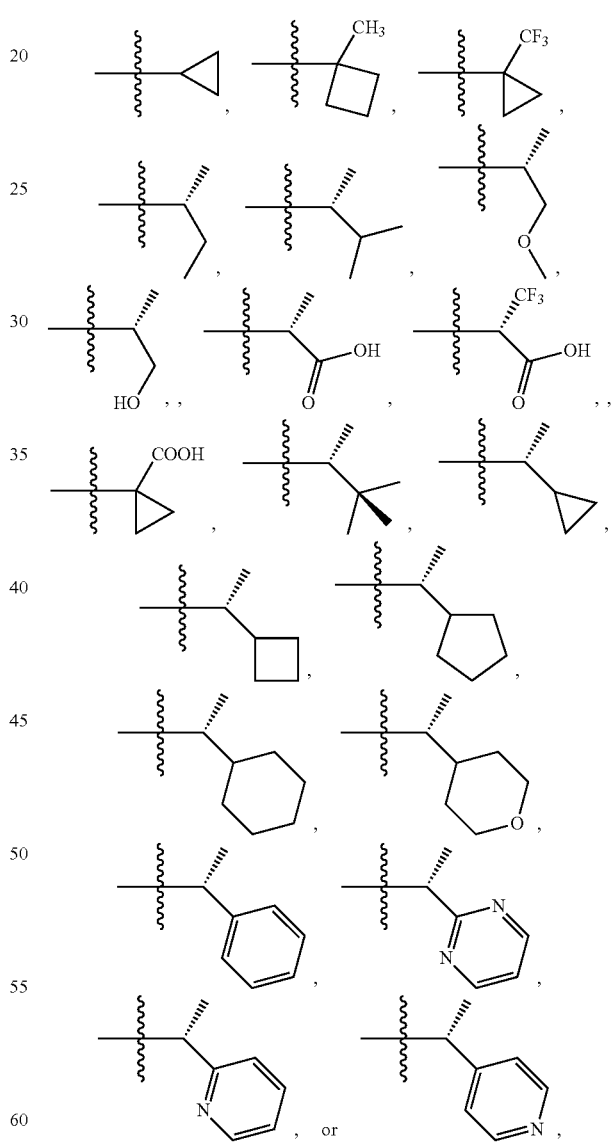

and where present, R² is H.

Embodiment 17. The compound, enantiomer, diastereomer or pharmaceutically accepted salt, hydrate, or solvate of any one of Embodiments 1 to 15, with the proviso that the —N(R¹)(R²) moiety does not contain hydroxyl.

Embodiment 18. The compound, enantiomer, diastereomer or pharmaceutically accepted salt, hydrate, or solvate of any one of Embodiments 1 to 15, with the proviso that $R^1$ is not cyclopentane Embodiment 19. The compound, enantiomer, diastereomer or pharmaceutically accepted salt, hydrate, or solvate of any one of the Embodiments 1 to 15, wherein

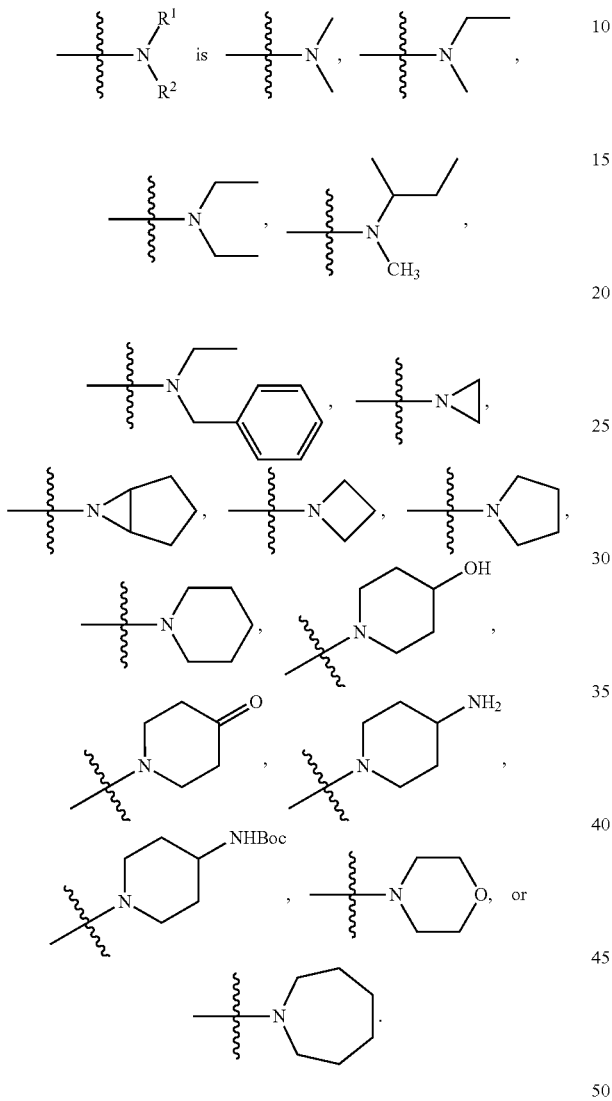

wherein $R^1$ is

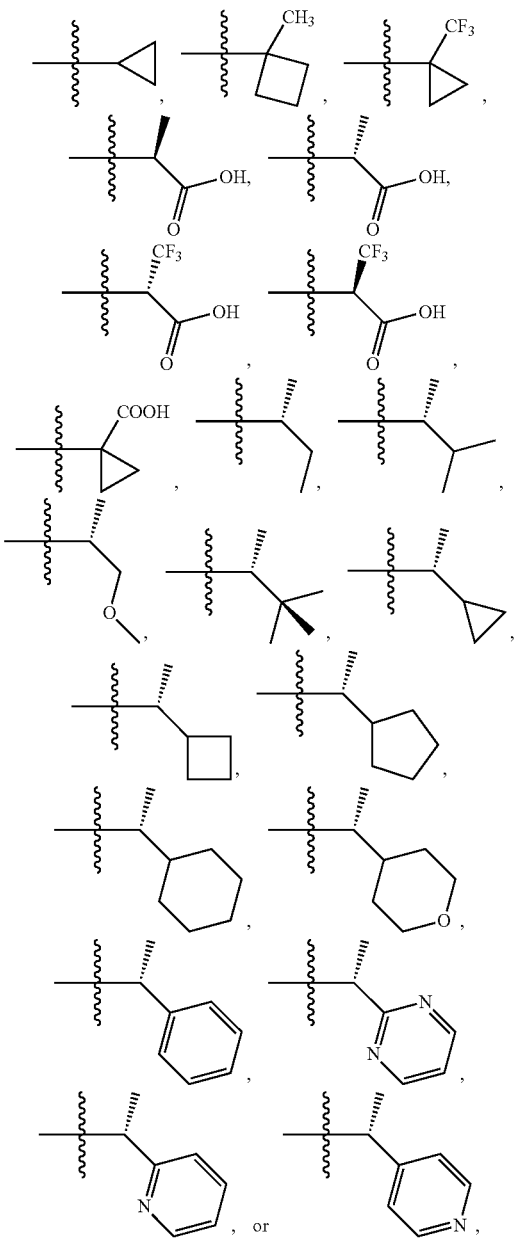

and $R^3$ is

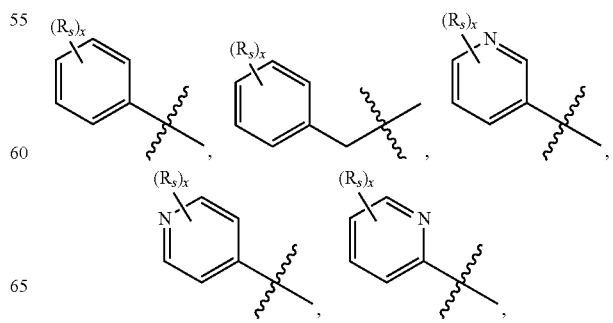

Embodiment 20. The compound, enantiomer, diastereomer or pharmaceutically accepted salt, hydrate, or solvate of Embodiment 1, comprising a structure

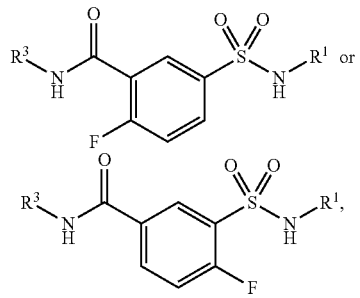

-continued

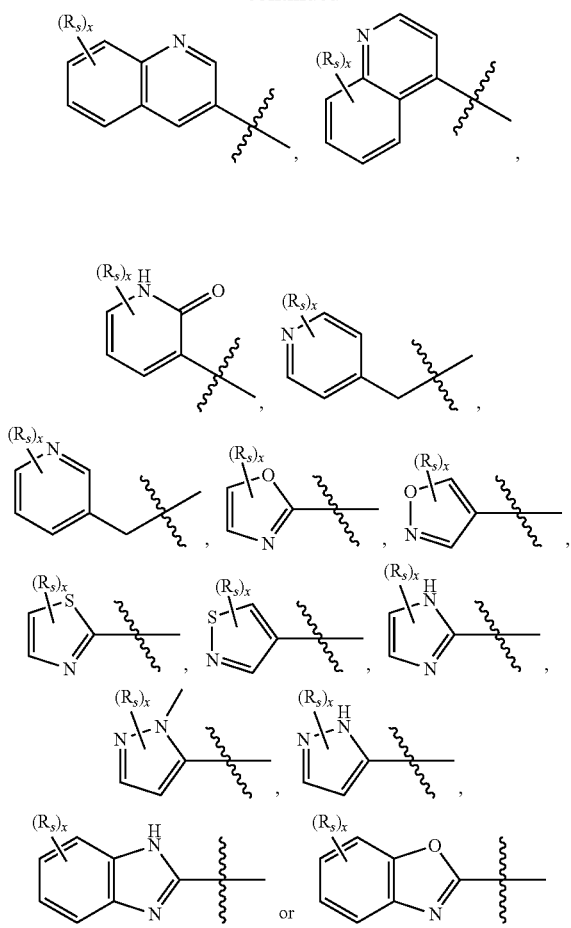

wherein
R_S is independently at each occurrence bromo, chloro, fluoro, cyano, hydroxyl, optionally fluorinated $C_{1-6}$alkyl (e.g., —$CH_3$, —$CH_2F$, —$CF_2H$, —$CF_3$), —O—($C_{1-6}$alkyl), or when two are taken form a fused cyclic or heterocyclic moiety; and x is 0, 1, 2, or 3 with the proviso that when $R^1$ is

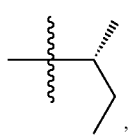

then $R^3$ is not

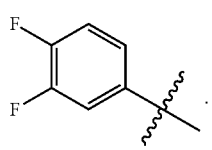 [SMILES: *c1ccc(F)c(F)c1]

Embodiment 21. The compound, enantiomer, diastereomer or pharmaceutically accepted salt, hydrate, or solvate of Embodiment 20, comprising a structure

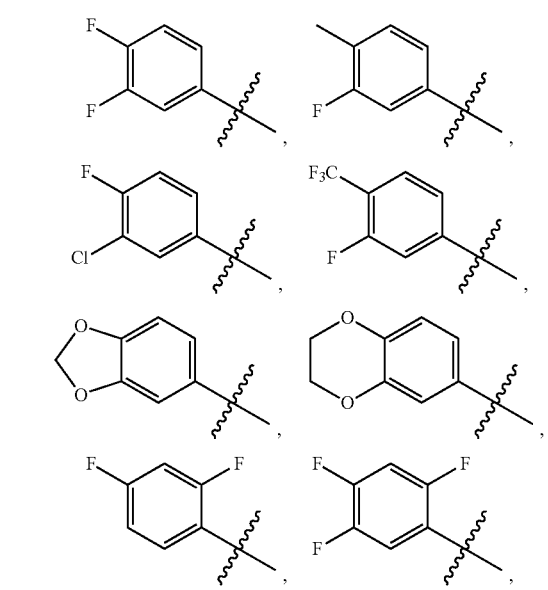

wherein $R^1$ is isopropyl, tert-butyl, and $R^3$ is

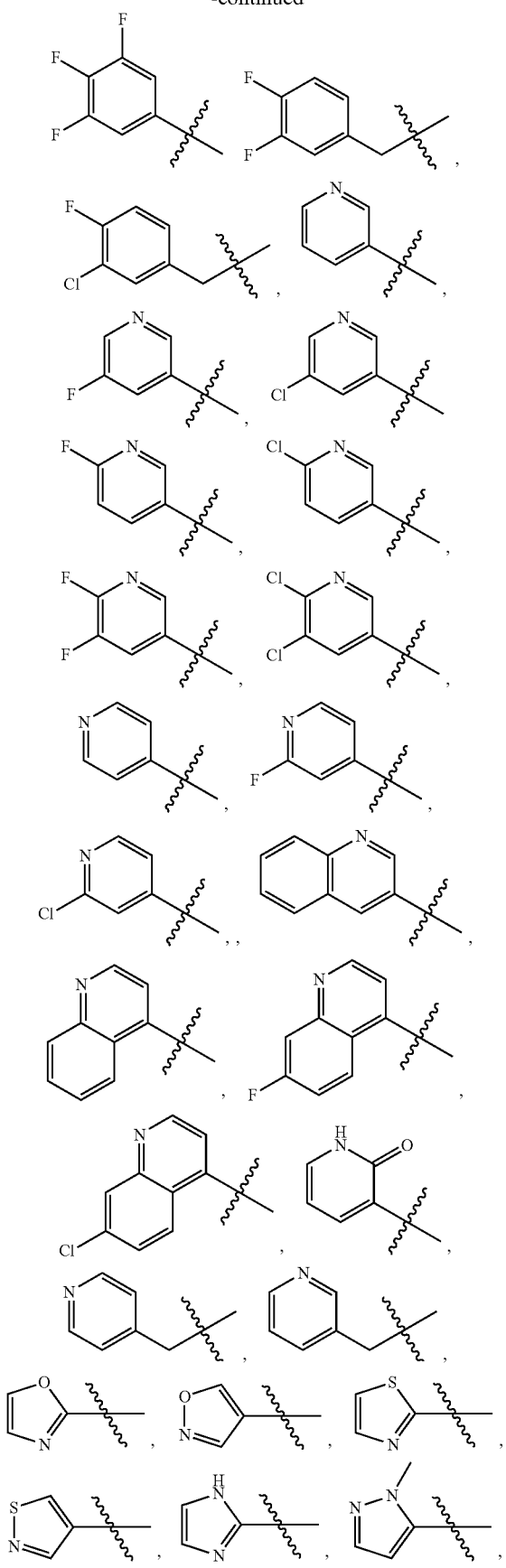
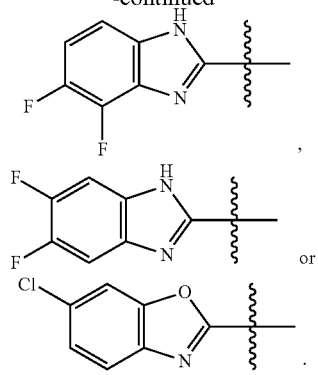
Embodiment 22. The compound, enantiomer, diastereomer or pharmaceutically accepted salt, hydrate, or solvate of Embodiment 1, comprising a structure
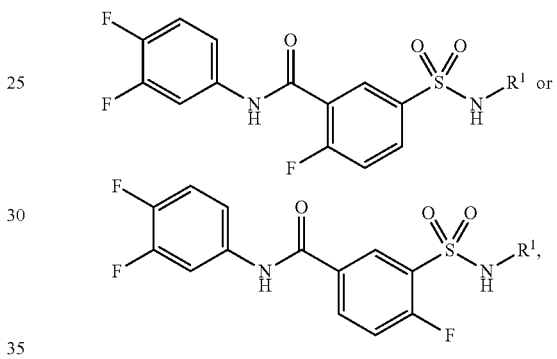
wherein $R^1$ is isopropyl, t-butyl,
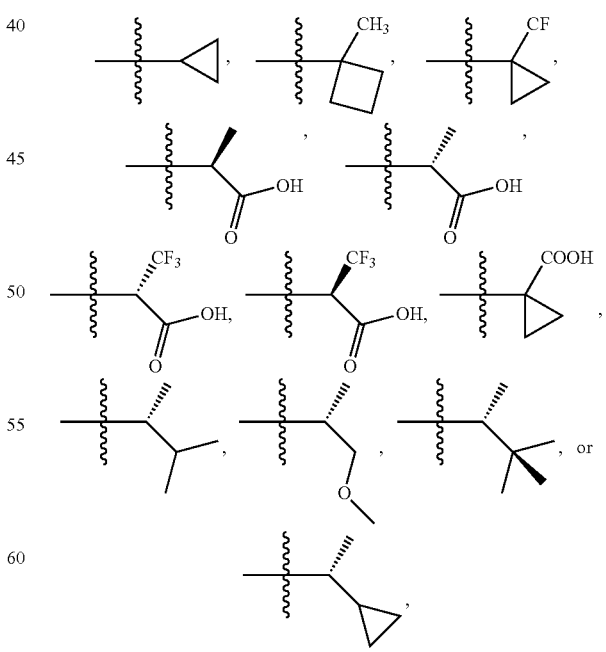
Embodiment 23. The compound, enantiomer, diastereomer or pharmaceutically accepted salt, hydrate, or solvate of Embodiment 2, or any one of Embodiments 5 to 18, the compound comprising a structure:

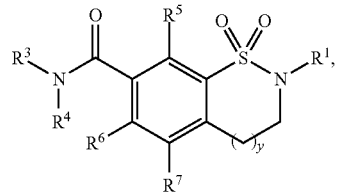

wherein y is 0, 1, or 2.

Embodiment 24. The compound, enantiomer, diastereomer or pharmaceutically accepted salt, hydrate, or solvate of Embodiment 22, wherein $R^1$ is isopropyl, tert-butyl,

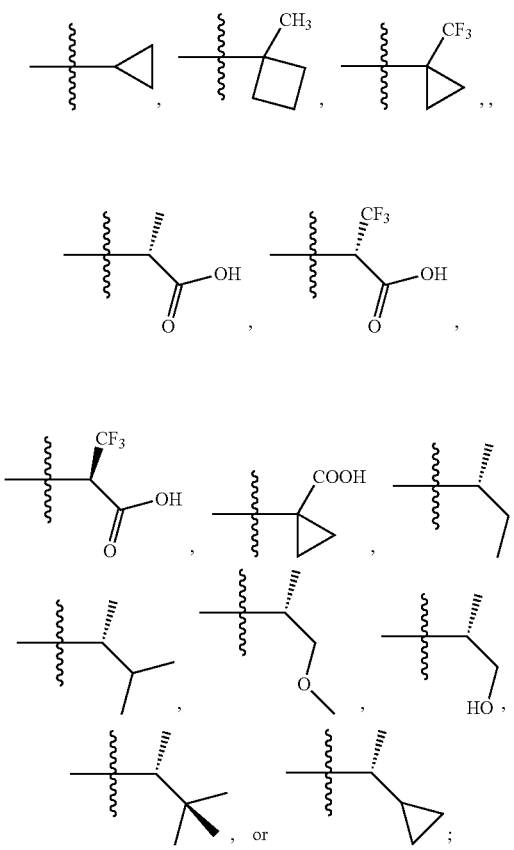

$R^3$ is

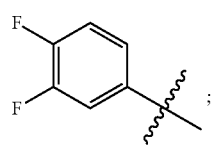

$R^4$, $R^5$, and $R^7$ are H; and
$R^6$ is H or F.

Embodiment 25. The compound, enantiomer, diastereomer or pharmaceutically accepted salt, hydrate, or solvate of Embodiment 2, or any one of Embodiments 5 to 18, the compound comprising a structure:

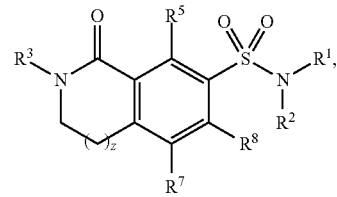

wherein z is 0 or 1.

Embodiment 26. The compound, enantiomer, diastereomer or pharmaceutically accepted salt, hydrate, or solvate of Embodiment 24, wherein $R^1$ is isopropyl, tert-butyl,

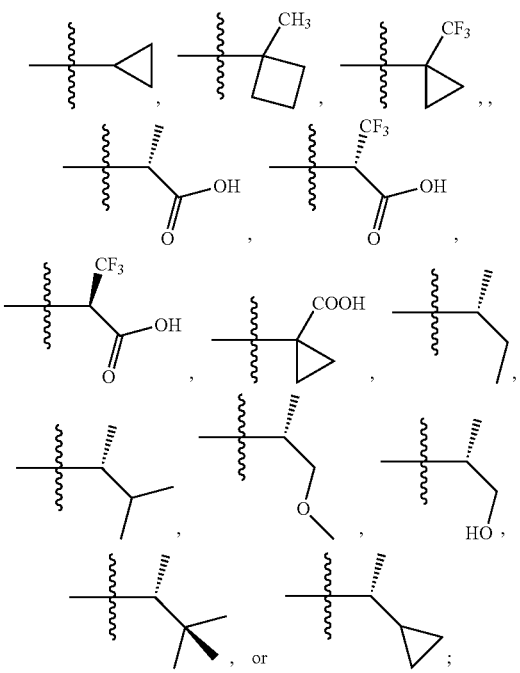

$R^3$ is

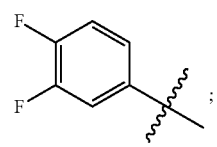

$R^5$, and $R^7$ are H; and
$R^8$ is H or F.

Embodiment 27. The compound, enantiomer, diastereomer or pharmaceutically accepted salt, hydrate, or solvate of Embodiment 2, and any one of Embodiments 5 to 18, the compound comprising a structure:

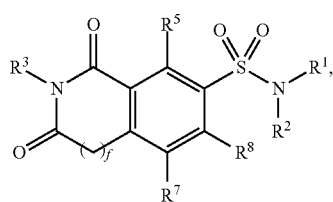

wherein f is 0 or 1.

Embodiment 28. The compound, enantiomer, diastereomer or pharmaceutically accepted salt, hydrate, or solvate of Embodiment 26, wherein $R^1$ is isopropyl, tert-butyl,

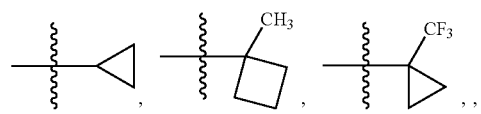

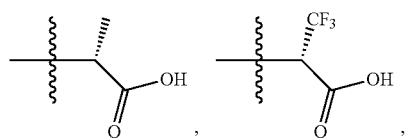

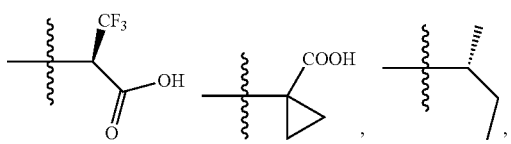

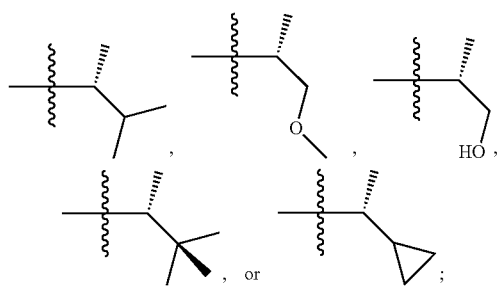

$R^2$ is H;
$R^3$ is

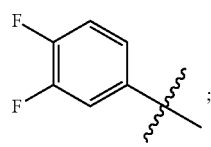 [SMILES: *c1ccc(F)c(F)c1]

$R^5$, and $R^7$ are H; and
$R^8$ is H or F.

Embodiment 29. The compound, enantiomer, diastereomer or pharmaceutically accepted salt, hydrate, or solvate of Embodiment 3, or any one of Embodiments 6 to 19, the compound comprising a structure:

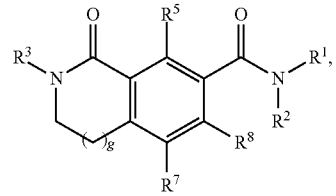

wherein g is 0 or 1.

Embodiment 30. The compound, enantiomer, diastereomer or pharmaceutically accepted salt, hydrate, or solvate of Embodiment 29, wherein $R^1$ is isopropyl, tert-butyl,

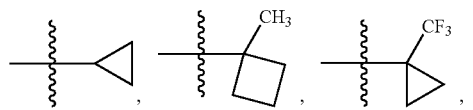

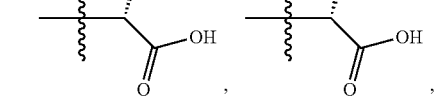

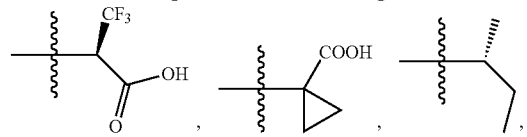

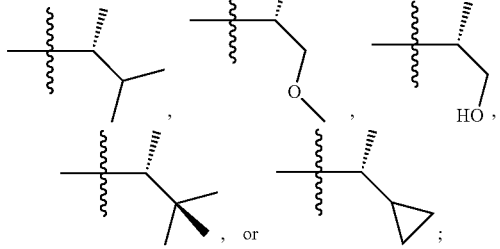

$R^2$ is H;
$R^3$ is

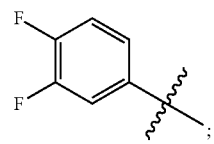 [SMILES: *c1ccc(F)c(F)c1]

$R^5$, and $R^7$ are H; and
$R^8$ is H or F.

Embodiment 31. The compound, enantiomer, diastereomer or pharmaceutically accepted salt, hydrate, or solvate of Embodiment 3, or any one of Embodiments 6 to 19, the compound comprising a structure:

161

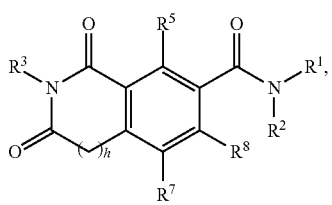

wherein h is 0 or 1.

Embodiment 32. The compound, enantiomer, diastereomer or pharmaceutically accepted salt, hydrate, or solvate of Embodiment 31, wherein $R^1$ is isopropyl, tert-butyl,

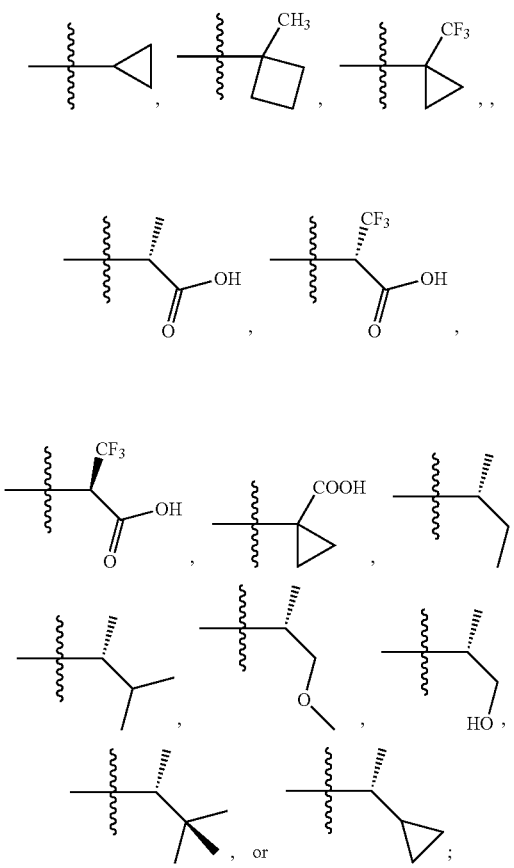

$R^2$ is H;
$R^3$ is

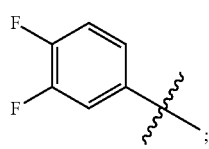

$R^5$, and $R^7$ are H; and
$R^8$ is H or F.

162

Embodiment 33. The compound, enantiomer, diastereomer or pharmaceutically accepted salt, hydrate, or solvate of Embodiment 1, the compound comprising a structure of any one of:

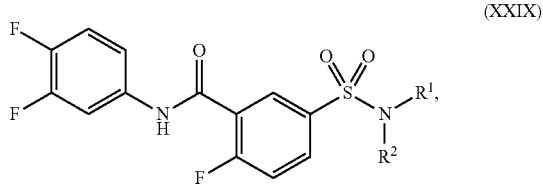
(XXIX)

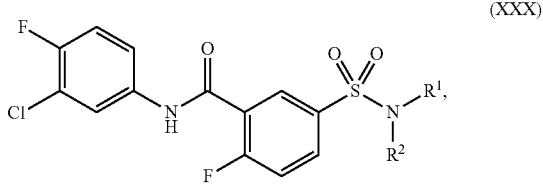
(XXX)

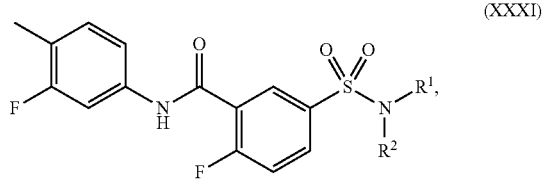
(XXXI)

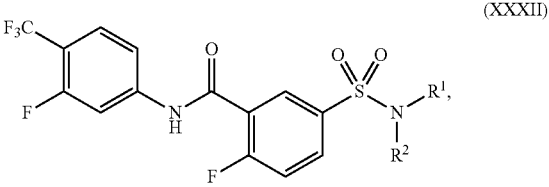
(XXXII)

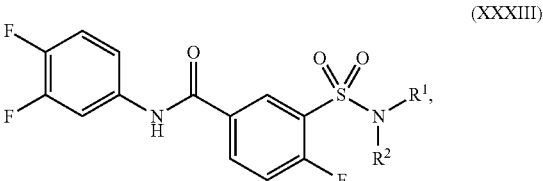
(XXXIII)

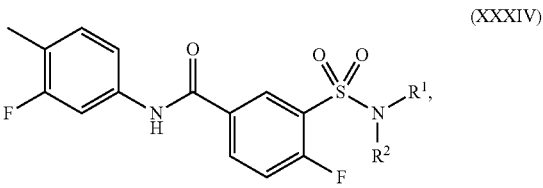
(XXXIV)

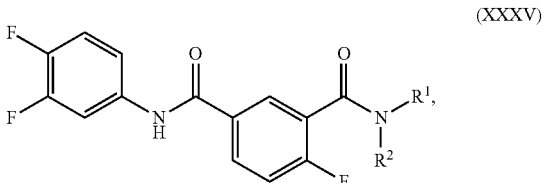
(XXXV)

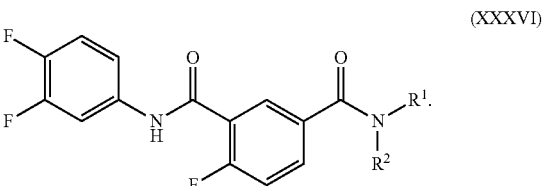
(XXXVI)

Embodiment 34. The compound, enantiomer, diastereomer or pharmaceutically accepted salt of Embodiment 1, the compound comprising a structure of Formula (XXII):

(XXII)

Embodiment 35. The compound, enantiomer, diastereomer or pharmaceutically accepted salt of Embodiment 1, the compound comprising a structure of Formula (XXIII):

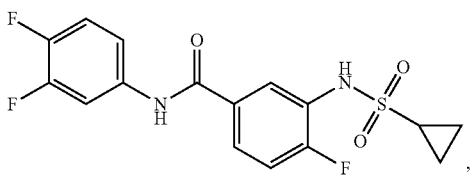

(XXIII)

Embodiment 36. The compound, enantiomer, diastereomer or pharmaceutically accepted salt of Embodiment 1, the compound comprising a structure of Formula (XXIV):

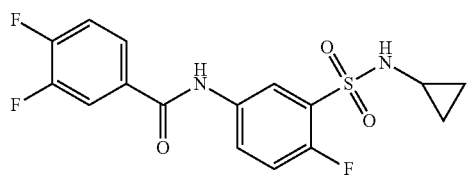

(XXIV)

Embodiment 37. The compound, enantiomer, diastereomer or pharmaceutically accepted salt of Embodiment 1, the compound comprising a structure of Formula (XXV):

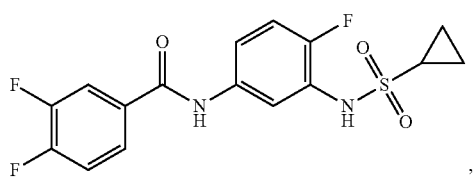

(XXV)

Embodiment 38. A compound comprising a structure of Formula (III) or Formula (VIII), or an enantiomer, diastereomer or pharmaceutically accepted salt thereof:

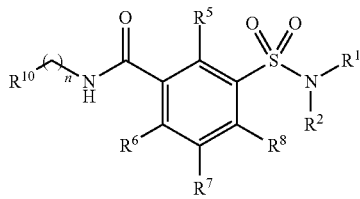

(III)

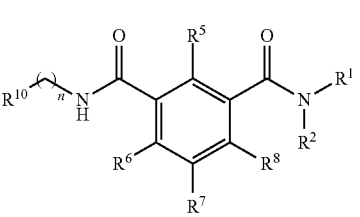

(VIII)

wherein:
$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted $C_{1-6}$ haloalkyl, optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;

$R^2$ is selected from a group consisting of hydrogen and optionally substituted $C_{1-6}$ linear alkyl; $R^2$ may also alternatively or additionally optionally include optionally substituted $C_{3-7}$ cycloalkyl or optionally substituted heterocyclic; or $R^1$ and $R^2$ are taken together with the atoms to which they are bound to form an optionally substituted heterocycle (including bicyclic or adamantyl structures) with 3 to 10 atoms; and $R^5$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^6$ may also alternatively or additionally optionally include cyano or $N(R^9)_2$;

$R^7$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^8$ may also alternatively or additionally optionally include cyano or $N(R^9)_2$; or $R^2$ and $R^8$ are taken together with the atoms to which they are bound to form an optionally substituted ring with 5 to 6 atoms; and $R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$ cycloalkyl, and optionally substituted $C_{1-6}$ haloalkyl; $R^9$ may also alternatively or additionally optionally include, independently at each occurrence, optionally substituted aryl, optionally substituted benzyl, optionally substituted heterocyclyl, or optionally substituted heteroaryl;

$R^{10}$ is selected from a group consisting of optionally substituted aryl and optionally substituted heteroaryl; and n is 0 or 1.

Embodiment 39. A compound comprising a structure of Formula (XI), or an enantiomer, diastereomer or pharmaceutically accepted salt thereof:

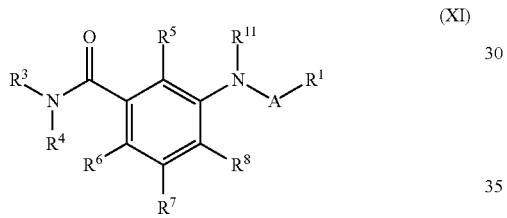

(XI)

wherein:
- $R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted $C_{1-6}$ haloalkyl, optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$ alkyl, optionally substituted heterocyclic, or optionally substituted heteroaryl;
- $R^3$ is selected from a group consisting of optionally substituted aryl, optionally substituted benzyl, optionally substituted alkylaryl, optionally substituted heteroaryl, optionally substituted alkylheteroaryl, and optionally substituted $C_{1-6}$ linear alkyl;
- $R^4$ is selected from a group consisting of hydrogen and optionally substituted $C_{1-6}$ linear alkyl;
- $R^5$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^5$ may also alternatively or additionally optionally include cyano or $N(R^9)_2$;
- $R^6$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^6$ may also alternatively or additionally optionally include cyano or $N(R^9)_2$; or
- $R^4$ and $R^6$ are taken together with the atoms to which they are bound to form an optionally substituted carbocyclic or heterocyclic ring with 5 to 6 atoms, optionally containing a carbonyl, optionally containing two carbonyls;
- $R^7$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, $OR^9$; $R^7$ may also alternatively or additionally optionally include cyano or $N(R^9)_2$;
- $R^8$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^8$ may also alternatively or additionally optionally include cyano or $N(R^9)_2$;
- $R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$ cycloalkyl, and optionally substituted $C_{1-6}$ haloalkyl; $R^9$ may also alternatively or additionally optionally include, independently at each occurrence, optionally substituted aryl, optionally substituted benzyl, optionally substituted heterocyclyl, or optionally substituted heteroaryl; and
- $R^{11}$ is selected from a group consisting of hydrogen, optionally substituted $C_{1-6}$ linear alkyl, optionally substituted $C_{1-6}$ branched alkyl, and optionally substituted $C_{3-7}$ cycloalkyl.

Embodiment 40. The compound, enantiomer, diastereomer or pharmaceutically accepted salt of Embodiment 39, wherein A is $SO_2$.

Embodiment 41. The compound, diastereomer or pharmaceutically accepted salt of Embodiment 39, the compound comprising a structure of Formula (XIII):

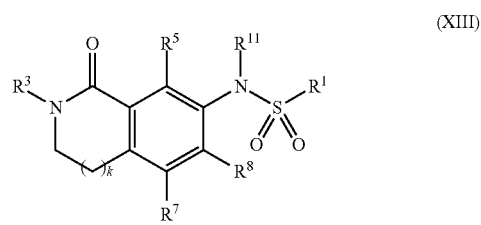

(XIII)

wherein k is 0 or 1.

Embodiment 42. The compound, enantiomer, diastereomer or pharmaceutically accepted salt of Embodiment 39, the compound comprising a structure of Formula (XIV),

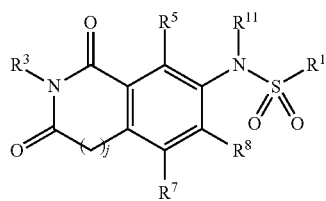

(XIV)

where j is 0 or 1.

Embodiment 43. The compound, enantiomer, diastereomer or pharmaceutically accepted salt of Embodiment 39, wherein A is carbonyl, CO.

Embodiment 44. The compound, enantiomer, diastereomer or pharmaceutically accepted salt of Embodiment 39, the compound comprising a structure of Formula (XVI):

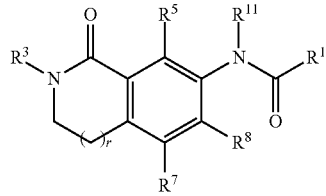

(XVI)

wherein r is 0 or 1.

Embodiment 45. The compound, enantiomer, diastereomer or pharmaceutically accepted salt of Embodiment 39, the compound comprising a structure of Formula (XVII),

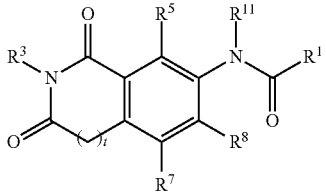

(XVII)

wherein t is 0 or 1.

Embodiment 46. The compound, enantiomer, diastereomer or pharmaceutically accepted salt of Embodiment 39, the compound comprising a structure of Formulae XXXXVII:

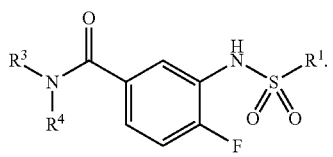

(XXXXVII)

Embodiment 47. The compound, enantiomer, diastereomer or pharmaceutically accepted salt of Embodiment 39, the compound comprising a structure of

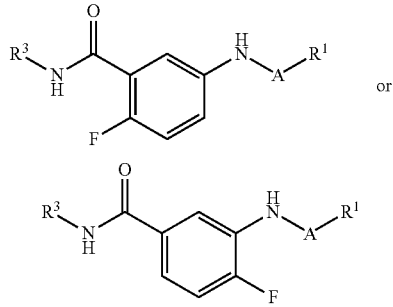

or

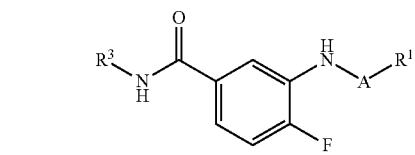

wherein $R^1$ is isopropyl, t-butyl,

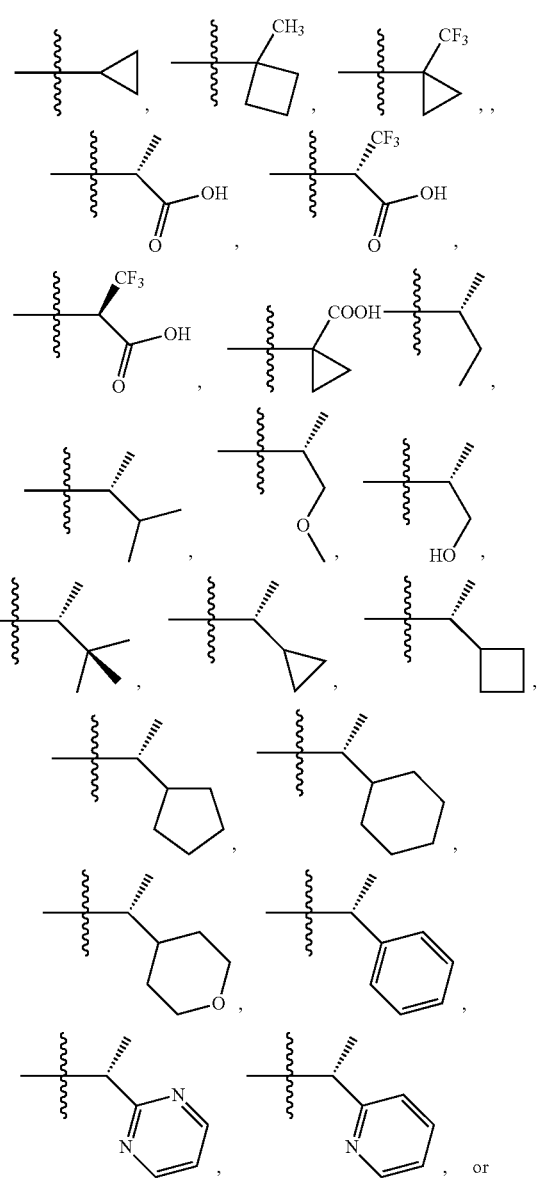

, or

-continued $R^3$ is

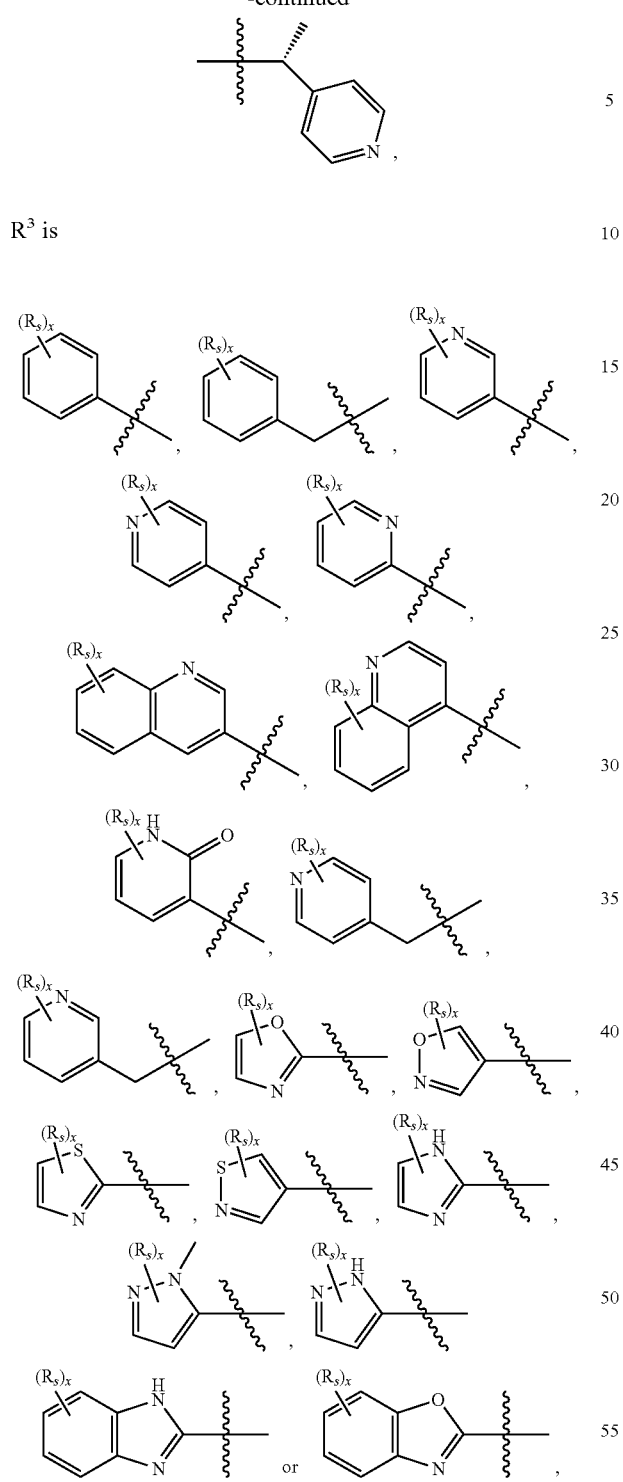

$R_S$ is independently at each occurrence bromo, chloro, fluoro, cyano, hydroxyl, optionally fluorinated $C_{1-6}$ alkyl (e.g., —$CH_3$, —$CH_2F$, —$CF_2H$, —$CF_3$), —O—($C_{1-6}$ alkyl), or when two are taken form a fused cyclic or heterocyclic moiety; and x is 0, 1, 2, or 3.

Embodiment 48. The compound, enantiomer, diastereomer or pharmaceutically accepted salt of Embodiment 47, wherein $R^1$ is

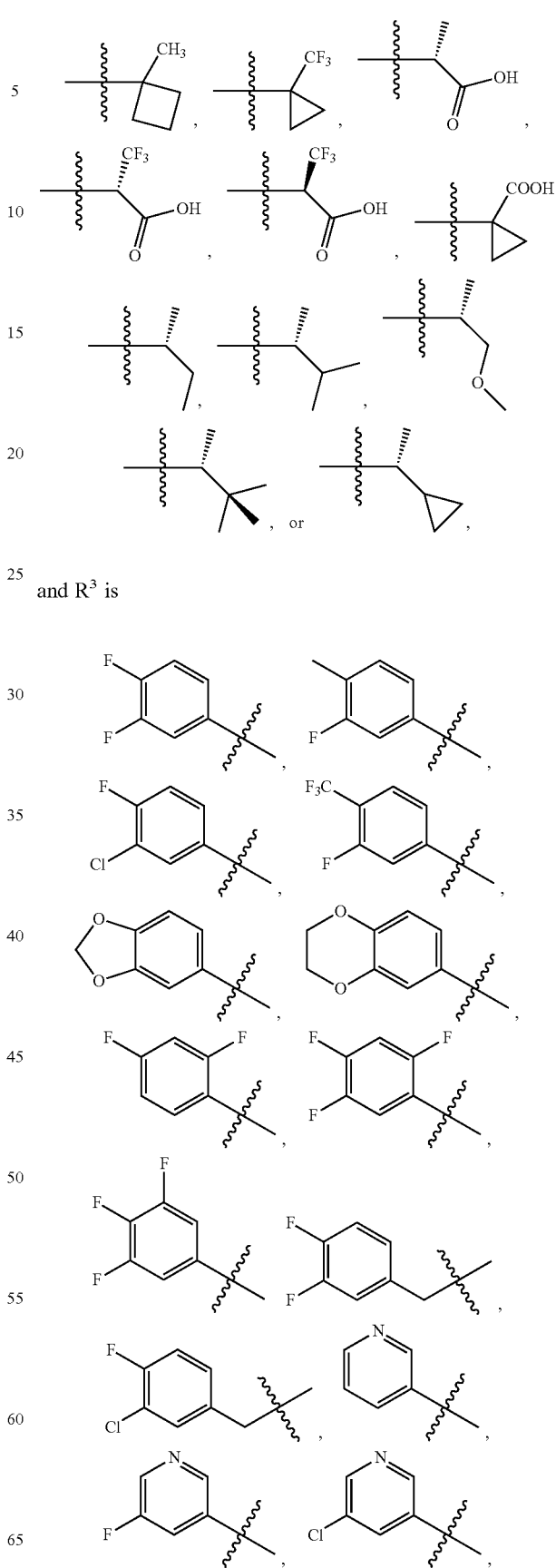

and $R^3$ is

-continued

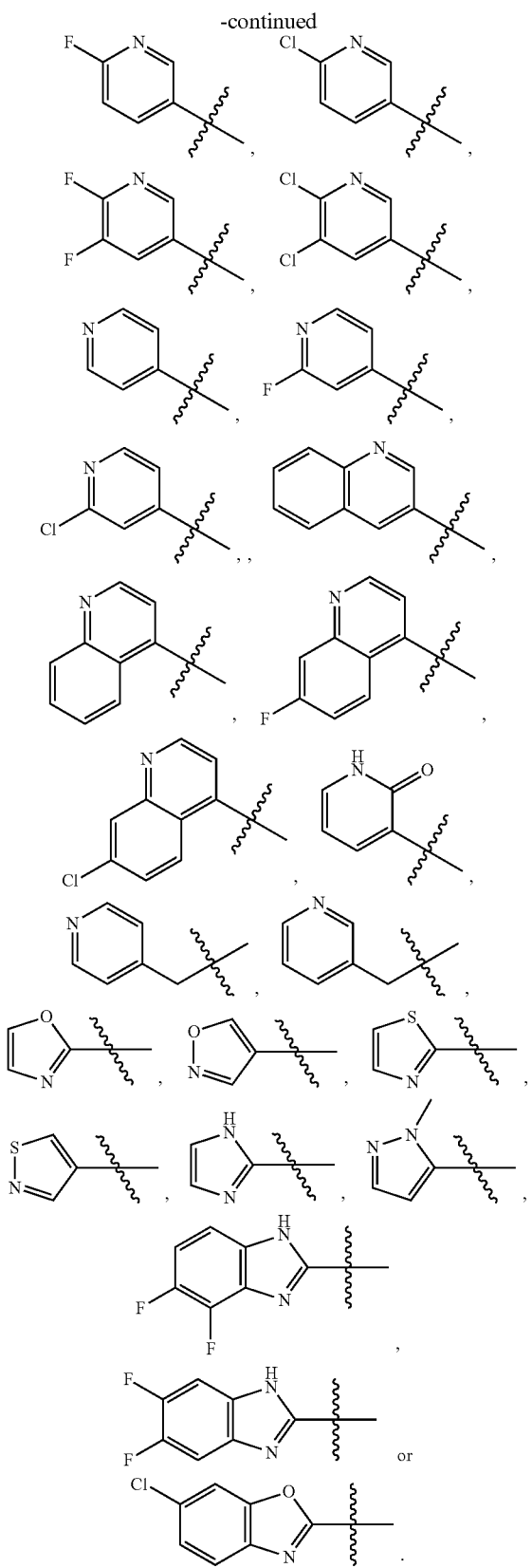

Embodiment 49. A compound comprising a structure of Formula (XVIII), or an enantiomer, diastereomer or pharmaceutically accepted salt thereof:

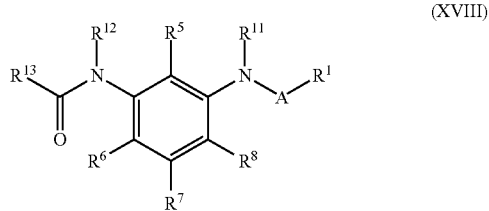

wherein:

A is selected from a group consisting of $SO_2$ and CO;

$R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted $C_{1-6}$ haloalkyl, optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;

$R^5$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^5$ may also alternatively or additionally optionally include cyano or $N(R^9)_2$;

$R^6$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^6$ may also alternatively or additionally optionally include cyano or $N(R^9)_2$;

$R^7$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^7$ may also alternatively or additionally optionally include cyano or $N(R^9)_2$;

$R^8$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^8$ may also alternatively or additionally optionally include cyano or $N(R^9)_2$; or $R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$ cycloalkyl, and optionally substituted $C_{1-6}$ haloalkyl; $R^9$ may also alternatively or additionally optionally include, independently at each occurrence, optionally substituted aryl, optionally substituted benzyl, optionally substituted heterocyclyl, or optionally substituted heteroaryl; and $R^{12}$ is selected from a group consisting of hydrogen, optionally substituted $C_{1-6}$ linear alkyl, optionally substituted $C_{1-6}$ branched alkyl, and optionally substituted $C_{3-7}$ cycloalkyl; and $R^{13}$ is selected from a group consisting of optionally substituted aryl, optionally substituted benzyl, optionally substituted alkylaryl, optionally substituted heteroaryl, and optionally substituted alkylhetero aryl.

Embodiment 50. The compound, enantiomer, diastereomer or pharmaceutically accepted salt of Embodiment 49, wherein A is $SO_2$.

Embodiment 51. The compound, enantiomer, diastereomer or pharmaceutically accepted salt of Embodiment 49, wherein A is carbonyl, CO.

Embodiment 52. A compound comprising a structure of Formula (XXI), or an enantiomer, diastereomer or pharmaceutically accepted salt thereof:

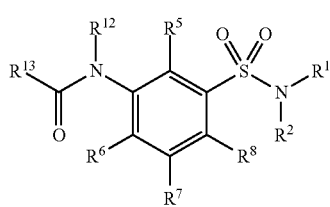

wherein:
- $R^1$ is selected from a group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted benzyl; $R^1$ may also alternatively or additionally optionally include optionally substituted $C_{1-6}$ haloalkyl, optionally substituted 3-7 membered cycloheteroalkyl, optionally substituted $C_{2-8}$ alkenyl, optionally substituted $C_{2-8}$ alkynyl, optionally substituted $C_{1-6}$ alkoxy, optionally substituted amine, optionally substituted amidine, optionally substituted carboxyamine, optionally substituted carboxy-$C_{1-6}$-alkoxide, —$SO_2$—$C_{1-6}$alkyl, optionally substituted heterocyclic, or optionally substituted heteroaryl;
- $R^2$ is selected from a group consisting of hydrogen and optionally substituted $C_{1-6}$ linear alkyl; $R^2$ may also alternatively or additionally optionally include optionally substituted $C_{3-7}$ cycloalkyl or optionally substituted heterocyclic; or
- $R^1$ and $R^2$ are taken together with the atoms to which they are bound to form an optionally substituted heterocycle (including bicyclic or adamantyl structures) with 3 to 10 atoms;
- $R^5$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^5$ may also alternatively or additionally optionally include cyano or $N(R^9)_2$;
- $R^6$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^6$ may also alternatively or additionally optionally include cyano or $N(R^9)_2$;
- $R^7$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^7$ may also alternatively or additionally optionally include cyano or $N(R^9)_2$;
- $R^8$ is selected from a group consisting of hydrogen, halogen, optionally substituted $C_{1-6}$ linear alkyl, optionally substituted $C_{1-6}$ branched alkyl, optionally substituted $C_{1-6}$ haloalkyl, and $OR^9$; $R^8$ may also alternatively or additionally optionally include cyano or $N(R^9)_2$; or
- $R^2$ and $R^8$ are taken together with the atoms to which they are bound to form an optionally substituted ring with 5 to 6 atoms;
- $R^9$ is independently at each occurrence selected from a group consisting of hydrogen, optionally substituted $C_{1-6}$ linear alkyl, optionally substituted $C_{1-6}$ branched alkyl, and optionally substituted $C_{3-7}$ cycloalkyl; $R^9$ may also alternatively or additionally optionally include, independently at each occurrence, optionally substituted aryl, optionally substituted benzyl, optionally substituted heterocyclyl, or optionally substituted heteroaryl;
- $R^{12}$ is selected from a group consisting of hydrogen, optionally substituted $C_{1-6}$ linear alkyl, optionally substituted $C_{1-6}$ branched alkyl, and optionally substituted $C_{3-7}$ cycloalkyl; and
- $R^{13}$ is selected from a group consisting of optionally substituted aryl, optionally substituted benzyl, optionally substituted alkylaryl, optionally substituted heteroaryl, and optionally substituted alkylheteroaryl.

Embodiment 53. The compound, enantiomer, diastereomer or pharmaceutically accepted salt of Embodiment 52, the compound comprising a structure of Formula XXXXVIII:

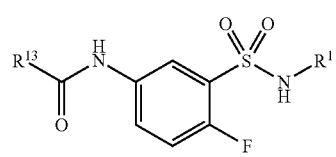

Embodiment 54. The compound, enantiomer, diastereomer or pharmaceutically accepted salt of Embodiment 53, the compound comprising a structure of

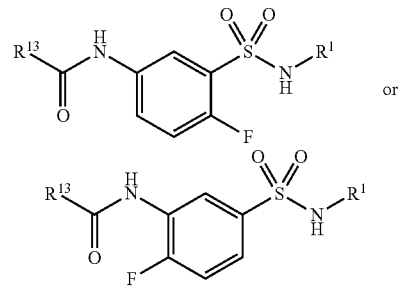 or wherein $R^1$ is isopropyl, t-butyl,

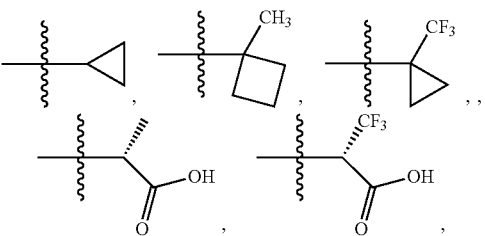

-continued

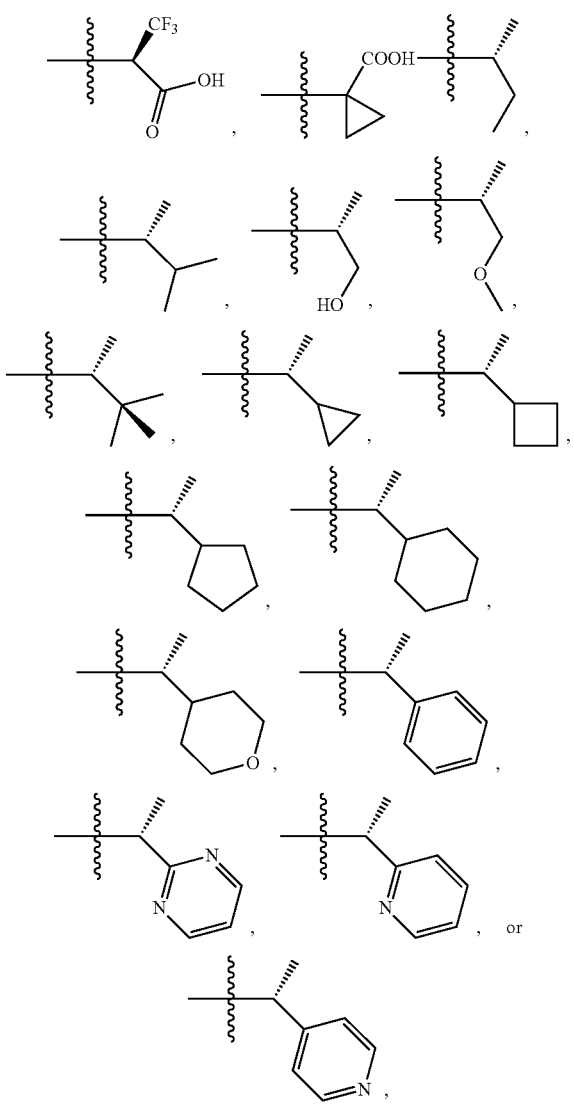

R[13] is

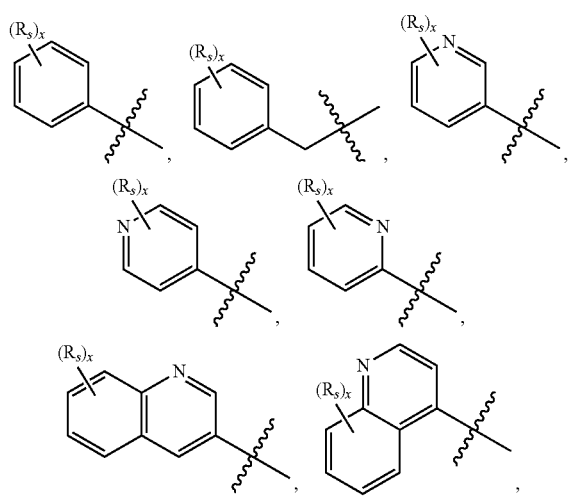

-continued

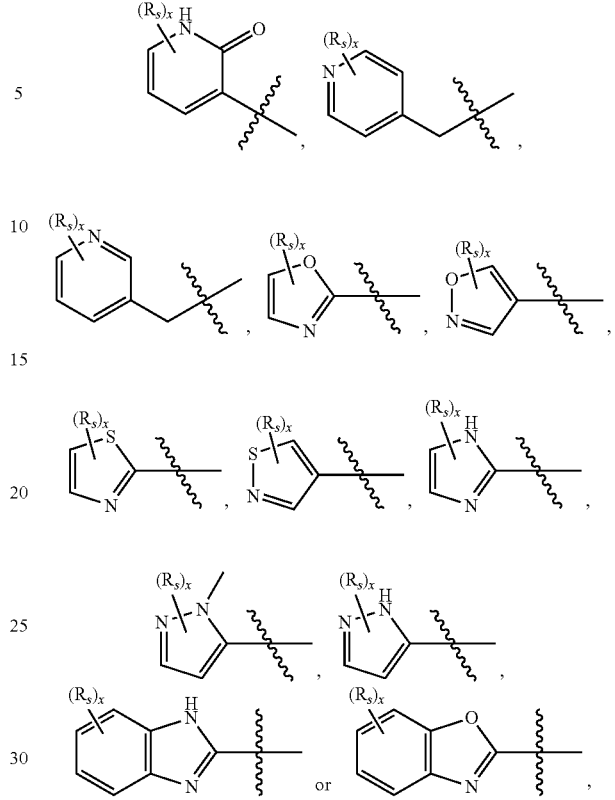

$R_S$ is independently at each occurrence bromo, chloro, fluoro, cyano, hydroxyl, optionally fluorinated $C_{1-6}$ alkyl (e.g., —$CH_3$, —$CH_2F$, —$CF_2H$, —$CF_3$), —O—($C_{1-6}$ alkyl), or when two are taken form a fused cyclic or heterocyclic moiety; and x is 0, 1, 2, or 3.

Embodiment 55. The compound, enantiomer, diastereomer or pharmaceutically accepted salt of Embodiment 54, wherein $R^1$ is

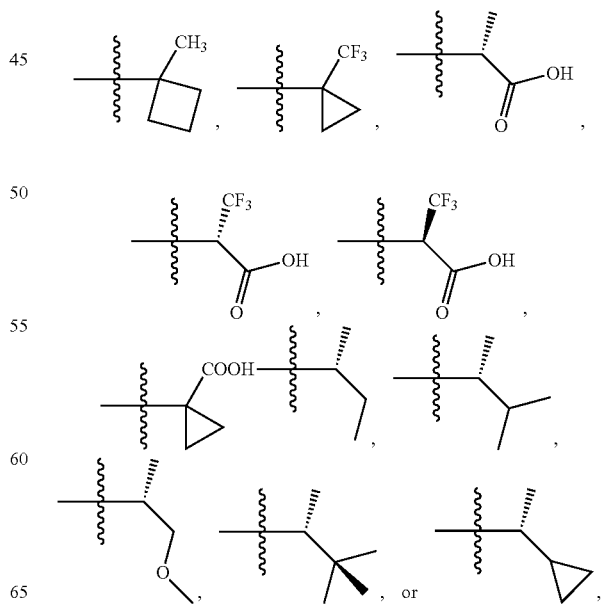

and R[13] is

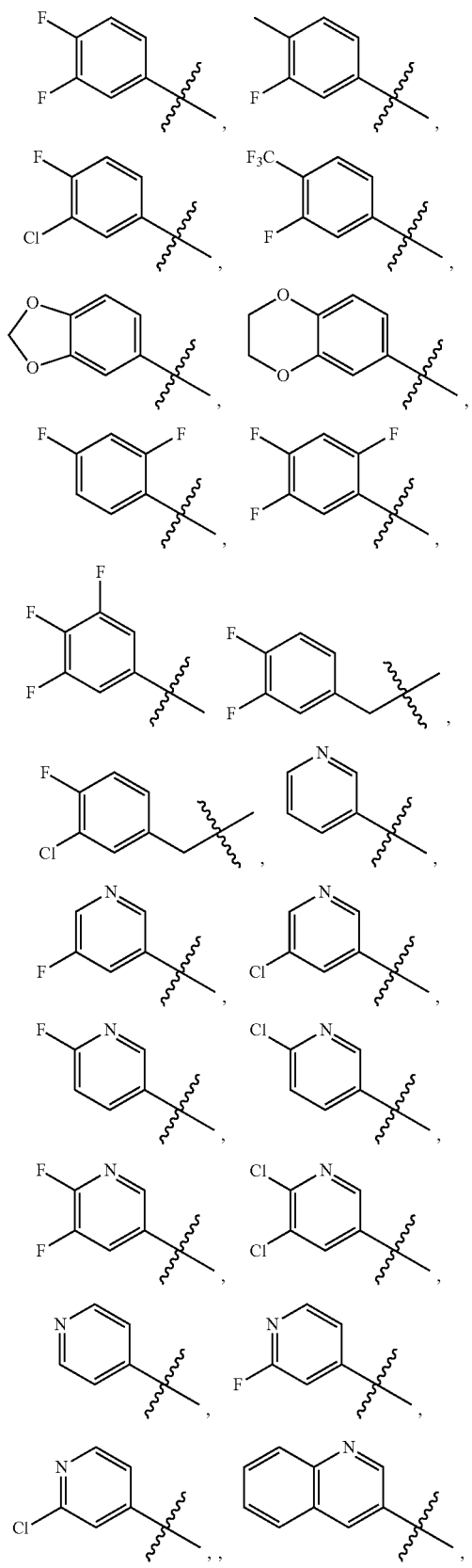

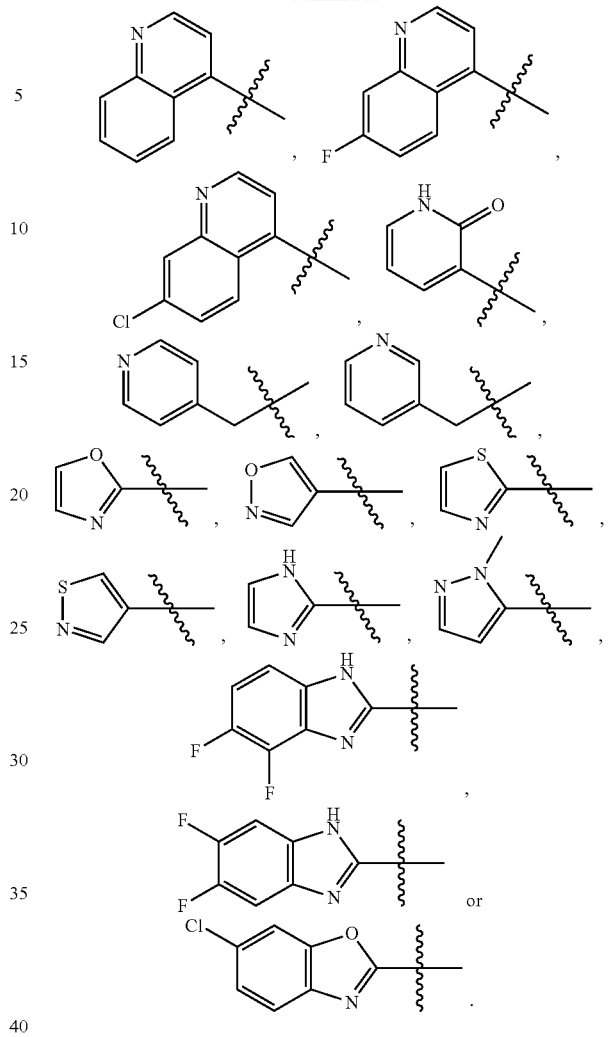

Embodiment 56. A pharmaceutical composition comprising a compound of any one of Embodiments 1 to 55, or any compound recited within this specification, and a pharmaceutically acceptable excipient.

Embodiment 57. A method of treating a disease that involves pregenomic RNA encapsidation, said method comprising administering to a patient in need of such treatment an effective amount of at least one compound of any one of Embodiments 1 to 55 or a composition of Embodiment 56.

Embodiment 58. The method of Embodiment 57, wherein the disease that involves pregenomic RNA encapsidation is a Hepatitis B virus infection.

Embodiment 59. A method of treating a Hepatitis B viral infection, said method comprising administering to a patient in need of such treatment an effective amount of at least one compound of any one of claim Embodiments 1 to55 or any individual compound recited in this specification or a composition of Embodiment 56.

Embodiment 60. The method of Embodiment 59, wherein the treatment controls or ameilorates a condition associated with liver disease, including cirrhosis and hepatocellular carcinoma.

Embodiment 61. A method of repressing viral replication, morphogenesis, or both replication and morphogenesis comprising administering to a patient in need thereof a compound, enantiomer, diastereomer or pharmaceutically accepted salt of any one of Embodiments 1 to 55 or a composition of Embodiment 56.

Embodiment 62. The method of any one of Embodiments 57 to 61, wherein the compound, or pharmaceutically acceptable salt is administered in combination with one or more additional therapeutic agents.

Embodiment 63. The method of Embodiment 62, wherein the additional therapeutic agent comprises an HBV polymerase inhibitor, interferon, viral entry inhibitor, viral maturation inhibitor, literature-described capsid assembly modulator, 5 reverse transcriptase inhibitor, a TLR-agonist, or an agents of distinct or unknown mechanism, or a combination thereof.

Embodiment 64. The method of Embodiment 62, wherein the additional therapeutic agent comprises an immune modulator or immune stimulator therapy, comprising a biological agent belonging to the interferon class, such as interferon alpha 2a or 2b or modified interferons such as pegylated interferon, alpha 2a, alpha 2b, lamda; or TLR modulators such as TLR-7 agonists or TLR-9 agonists, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HB V replication or persistence.

Embodiment 65. The method of Embodiment 62, wherein the reverse transcriptase inhibitor comprises at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

Embodiment 66. The method of Embodiment 62, wherein the the TLR-agonist comprises SM360320 (9-benzyl-8-hydroxy-2-(2-methoxyethoxy) adenine) or AZD 8848 (methyl[3-({[3-(6-amino-2-butoxy-8-oxo-7,8-dihydro-9H-purin-9-yl)propyl][3-(4-morpholinyl)propyl]amino}methyl) phenyl]acetate).

Embodiment 67. The method of any one of Embodiments 60 to 66, wherein the compound, or pharmaceutically acceptable salt thereof, and the additional therapeutic agent are co-formulated, co-administered, or both co-formulated and co-administered.

Embodiment 68. The method of any one of Embodiments 60 to 64, wherein the compound, or pharmaceutically acceptable salt thereof, and the additional therapeutic agent are separately formulated, separately administered, or both separately formulated and separately administered.

Embodiment 69. The method of any one of Embodiments 57 to 68, wherein administering the compound, or pharmaceutically acceptable salt of the present invention allows for administering of the additional therapeutic agent at a lower dose or frequency as compared to the administering of the at least one additional therapeutic agent alone that is required to achieve similar results in prophylactically treating an HBV infection in an individual in need thereof.

Embodiment 70. The method of any one of Embodiments 57 to 69, wherein, before administering the therapeutically effective amount of the compound, or pharmaceutically acceptable salt, the patient is known to be refractory to an HBV polymerase inhibitor, interferon, viral entry inhibitor, viral maturation inhibitor, distinct capsid assembly modulator, an antiviral compound of distinct or unknown mechanism, or a combination thereof.

Embodiment 71. The method of any one of Embodiments 57 to 70, wherein administering a compound, or pharmaceutically acceptable salt reduces viral load in the individual to a greater extent compared to the administering of a a HBV polymerase inhibitor, interferon, viral entry inhibitor, viral maturation inhibitor, distinct capsid assembly modulator, an antiviral compound of distinct or unknown mechanism, or a combination thereof.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

The examples below provide non-limiting methods for preparing representative compounds of the disclosure. The skilled practitioner will know how to substitute the appropriate reagents, starting materials and purification methods known to those skilled in the art, in order to prepare additional compounds of the present invention.

$^1$H NMR spectra were recorded on a 300 MHz INOVA VARIAN spectrometer. Chemical shifts values are given in ppm and referred as the internal standard to TMS (tetramethylsilane). The peak patterns are indicated as follows: b, broad; s, singlet; d, doublet; t, triplet; q, quadruplet; qint, quintet; m, multiplet; dd, doublet of doublets; and dt, doublet of triplets. The coupling constants (J) are reported in Hertz (Hz). Mass Spectra were obtained on a 1200 Aligent LC-MS spectrometer (ES-API, Positive). Silica gel column chromatography was performed over silica gel 100-200 mesh, and the eluent was a mixture of ethyl acetate and hexanes, or a mixture of methanol and dichloromethane. Analytical HPLC was run on the Agilent 1100 HPLC instrument, equipped with Agilent, ZORBAX SB-C18 column and UV detection at 210 nm.

Example 1

General Procedure A

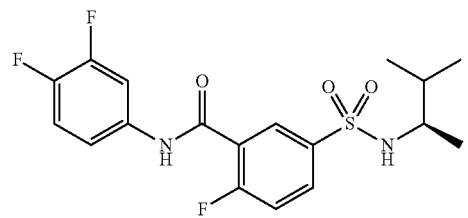

(R)-N-(3,4-Difluorophenyl)-2-fluoro-5-(N-(3-methylbutan-2-yl)sulfamoyl)benzamide: To a 0° C. solution of 5-chlorosulfonyl-2-fluorobenzoic acid (150 mg, 0.62 mmol) in THF (3 mL) was added NEt$_3$ (125 mg, 1.24 mmol) and (R)-(–)-2-amino-3-methylbutane (54 mg, 0.62 mmol). The reaction was warmed to 20° C., and was stirred for 20 minutes. The mixture was concentrated, and the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated. The material was used without further purification.

To the material from the previous step was added thionyl chloride (2 mL), and this mixture was heated at reflux for 2 hours. The mixture was concentrated, and the residue was treated with THF (1 mL). This solution was added to a 0° C. solution of NEt$_3$ (144 mg, 1.43 mmol) and 3,4-difluoroaniline (60 mg, 0.48 mmol) in THF (3 mL). The reaction was warmed to 20° C., and was stirred for 16 hours. The mixture was concentrated, and the residue was partitioned between EtOAc (20 mL) and 1 N HCl (5 mL). The organic layer was washed with 2 N HCl (10 mL), water (10 mL), dilute NaHCO$_3$ (10 mL), and brine (1 mL), dried (Na$_2$SO$_4$), and concentrated. The crude material was purified by silica column (20-50% EtOAc/Hexane) to give the desired product (44 mg, 18% over 3 steps) as an off-white solid. MS: M+H$^+$401. $^1$H NMR (300 MHz, MeOH-d$_4$): δ 8.23-8.20 (m, 1H), 8.07-8.04 (m, 1H), 7.85-7.77 (m, 1H), 7.47-7.35 (m, 2H), 7.26 (q, J=9.0 Hz, 1H), 3.15-3.12 (m, 1H), 1.65-1.59 (m, 1H), 0.90-0.82 (m, 6H).

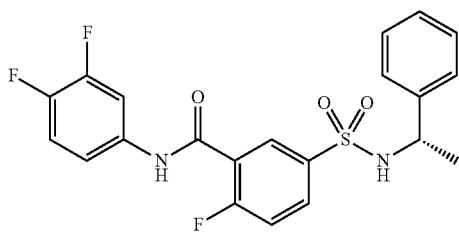 [SMILES: C[C@H](NS(=O)(=O)c1ccc(F)c(C(=O)Nc2ccc(F)c(F)c2)c1)c1ccccc1]

(S)-N-(3,4-Difluorophenyl)-2-fluoro-5-(N-(1-phenylethyl)sulfamoyl)benzamide: General procedure A was followed using (S)-(+)-1-methyl-benzylamine (75 mg, 0.62 mmol) to give the desired product (106 mg, 39% over 3 steps) as an off-white solid. MS: M+H$^+$435. $^1$H NMR (300 MHz, CDCl$_3$): δ 8.41 (dd, J=2.6, 7.6 Hz, 1H), 8.25 (d, J=14.0 Hz, 1H), 7.78-7.71 m, 2H), 7.20-7.05 (m, 9H), 5.11 (d, J=7.3 Hz, 1H), 4.56 (dq, J=6.7, 7.0 Hz, 1H), 1.47 (d, J=6.7 Hz, 3H).

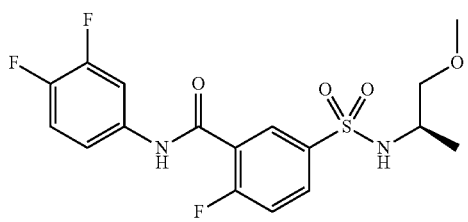 [SMILES: COC[C@@H](C)NS(=O)(=O)c1ccc(F)c(C(=O)Nc2ccc(F)c(F)c2)c1]

(R)-N-(3,4-Difluorophenyl)-2-fluoro-5-(N-(1-methoxypropan-2-yl)sulfamoyl)benzamide: General procedure A was followed using (R)-(−)-1-methoxy-2-aminopropane-.HCl (78 mg, 0.62 mmol) to give the desired product (60 mg, 24% over 3 steps) as an off-white solid. MS: M+H$^+$403. $^1$H NMR (300 MHz, CDCl$_3$): δ 8.63 (dd, J=2.4, 7.0 Hz, 1H), 8.42 (d, J=13.2 Hz, 1H), 8.07-8.02 (m, 1H), 7.80-7.73 (m, 1H), 7.36-7.7.11 (m, 3H), 5.08 (d, J=6.7 Hz, 1H), 3.54-3.50 (m, 1H), 3.29-3.21 (m, 5H), 1.13 (d, J=6.7 Hz, 1H).

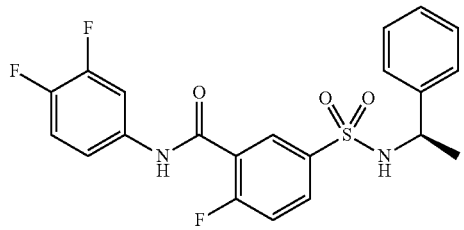 [SMILES: C[C@@H](NS(=O)(=O)c1ccc(F)c(C(=O)Nc2ccc(F)c(F)c2)c1)c1ccccc1]

(R)-N-(3,4-Difluorophenyl)-2-fluoro-5-(N-(1-phenylethyl)sulfamoyl)benzamide: General procedure A was followed using (R)-(−)-1-methyl-benzylamine (75 mg, 0.62 mmol) to give the desired product (136 mg, 51% over 3 steps) as an off-white solid. MS: M+H$^+$436. $^1$H NMR (300 MHz, CDCl$_3$): δ 8.41 (dd, J=2.6, 7.3 Hz, 1H), 8.27 (d, J=13.5 Hz, 1H), 7.79-7.72 (m, 2H), 7.9 (d, J=4.4 Hz, 1H), 7.26-7.03 (m, 8 H), 5.18 (d, J=7.0 Hz, 1H), 4.58 (dq, J=6.7, 7.0 Hz, 1H), 1.48 (d, J=7.0 Hz, 1H).

(S)-N-(3,4-Difluorophenyl)-2-fluoro-5-(N-(1-methoxypropan-2-yl)sulfamoyl)benzamide. General procedure A was followed using (S)-(−)-1-methoxy-2-aminopropane (55 mg, 0.62 mmol) to give the desired product (64 mg, 26% over 3 steps) as a white solid. MS: M+H$^+$403. $^1$H NMR (300 MHz, MeOH-d$_4$): δ 8.22 (dd, J=2.6, 6.5 Hz, 1H), 8.07-8.02 (m, 1H), 7.85-7.78 (m, 1H), 7.47-7.20 (m, 3H), 3.49-3.73 (m, 1H), 3.32-3.15 (m, 5H), 1.04 (d, J=6.7 Hz, 3H).

Example 2

General Procedure B 3-(3,4-Difluorophenylcarbamoyl)-4-fuorobenzene-1-sulfonyl chloride: A mixture of 5-chlorosulfonyl-2-fluorobenzoic acid (1.00 g, 4.19 mmol), thionyl chloride (3.5 mL), and 1,2-dichloroethane (3.5 mL) was heated at reflux for 1 h. The reaction was concentrated, then the residue was treated with toluene (5 mL), then the mixture was concentrated. The crude material was used without further purification.

To a solution of 3,4-difluoroaniline (0.55 g, 4.24 mmol) in toluene (10 mL) was added the material from the previous step. The reaction was stirred for 16 hours then was filtered.

The concentrated filtrate was purified by silica column (0-100% EtOAc/Hexane) to give the desired product (0.38 g, 27%) as a white solid. $^1$H NMR (300 MHz, DMSO-d$_6$): δ10.72 (s, 1H), 7.90-7.7.72 (m, 2H), 7.46-7.26 (m, 4H).

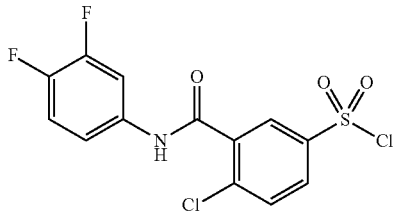 [SMILES: O=C(Nc1ccc(F)c(F)c1)c1cc(S(=O)(=O)Cl)ccc1Cl]

3-(3,4-Difluorophenyl-carbamoyl)-4-chlorobenzene-1-sulfonyl chloride:

General Procedure B was followed, using of 5-chlorosulfonyl-2-chlorobenzoic acid (0.50 g, 2.06 mmol) to give the desired product (0.29 g, 40% over 2 steps) as an off-white solid. $^1$H NMR (300 MHz, DMSO-d$_6$): δ 10.81 (s, 1H), 7.89-7.80 (m, 1H), 7.70-7.66 (m, 2H), 7.46 (d, J=17.3 Hz, 1H), 7.44-7.36 (m, 1H).

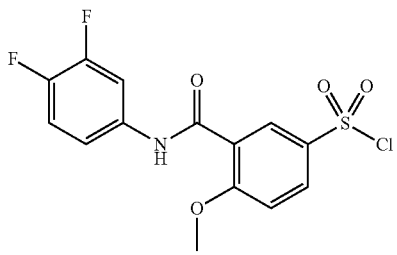 [SMILES: COc1ccc(S(=O)(=O)Cl)cc1C(=O)Nc1ccc(F)c(F)c1]

3-(3,4-Difluorophenyl-carbamoyl)-methoxybenzene-1-sulfonyl chloride. General Procedure B was followed, using of 5-chlorosulfonyl-2-methoxybenzoic acid (0.50 g, 2.00 mmol) to give the desired product (0.33 g, 45% over 2 steps) as an off-white solid. MS: M+H$^+$362. $^1$H NMR (300 MHz, DMSO-d$_6$): δ 10.33 (s, 1H), 7.94-7.78 (m, 2H), 7.69 (dd, J=2.2, 8.5 Hz, 1H), 7.50-7.34 (m, 2H), 7.10 (d, J=8.8 Hz, 1H), 3.87 (s, 3H).

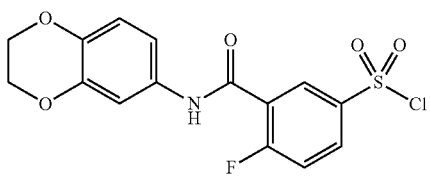 [SMILES: O=C(Nc1ccc2c(c1)OCCO2)c1cc(S(=O)(=O)Cl)ccc1F]

3-((2,3-Dihydrobenzo[b][1,4]dioxin-6-yl)carbamoyl)-4-fluorobenzene-1-sulfonyl chloride: In a similar procedure as General Procedure B, final compound was obtained as a white solid (0.95 g, 61%). MS (ES) m/z: 372.1 (M+H$^+$), calculated 372.00.

Example 3

General Procedure C

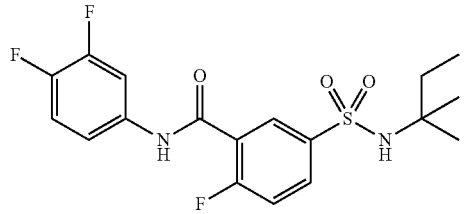 [SMILES: CCC(C)(C)NS(=O)(=O)c1ccc(F)c(C(=O)Nc2ccc(F)c(F)c2)c1]

N-(3,4-Difluorophenyl)-2-fluoro-5-(N-tert-pentylsulfamoyl)benzamide: To a 0° C. solution of 3-(3,4-difluorophenyl-carbamoyl)-4-fluorobenzene-1-sulfonyl chloride (30 mg, 0.086 mmol) in CH$_2$Cl$_2$ (1 mL) was added NEt$_3$ (17 mg, 0.17 mmol) and tert-amylamine (8 mg, 0.086 mmol). The reaction was warmed to 20° C., and was stirred for 1.5 hours. The mixture was concentrated, and the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated. The crude material was purified by silica column (10-50% EtOAc/Hexane) to give the desired product (26 mg, 76%) as a clear gum. MS: M+H$^+$403. $^1$H NMR (300 MHz, MeOH-d$_4$): δ 8.55 (dd, J=2.4, 6.5 Hz, 1H), 8.08-8.03 (m, 1H), 7.86-7.78 (m, 1H), 7.46-7.21 (m, 3H), 1.54 (q, J=7.6 Hz, 2H), 1.14 (s, 6H), 0.84 (t, J=7.3 Hz, 3H).

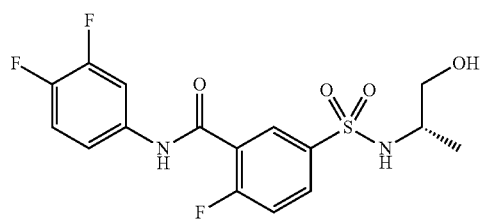 [SMILES: C[C@@H](CO)NS(=O)(=O)c1ccc(F)c(C(=O)Nc2ccc(F)c(F)c2)c1]

(S)-N-(3,4-Difluorophenyl)-2-fluoro-5-(N-(1-hydroxypropan-2-yl)sulfamoyl)benzamide: General Procedure C was followed, using 3-(3,4-difluorophenyl-carbamoyl)-4-fluorobenzene-1-sulfonyl chloride (25 mg, 0.072 mmol), NEt$_3$ (14 mg, 0.14 mmol), and (S)-2-amino-1-propanol (6 mg, 0.072 mmol) to give the desired product (20 mg, 72%) as a white solid. MS: M+H$^+$389. $^1$H NMR (300 MHz, MeOH-d$_4$): δ 8.22 (dd, J=2.4, 6.2 Hz, 1H), 8.09-8.04 (m, 1H), 7.86-7.80 (m, 1H), 7.48-7.21 (m, 3H), 3.44-3.31 (m, 3H), 1.02 (d, J=6.4 Hz, 3H).

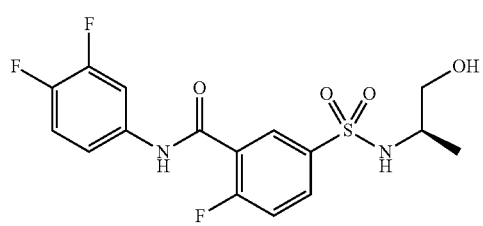 [SMILES: C[C@H](CO)NS(=O)(=O)c1ccc(F)c(C(=O)Nc2ccc(F)c(F)c2)c1]

(R)-N-(3,4-Difluorophenyl)-2-fluoro-5-(N-(1-hydroxypropan-2-yl)sulfamoyl)benzamide: General Procedure C was followed, using 3-(3,4-difluorophenyl-carbamoyl)-4-fluorobenzene-1-sulfonyl chloride (25 mg, 0.072 mmol), NEt₃ (14 mg, 0.14 mmol), and (R)-2-amino-1-propanol (6 mg, 0.072 mmol) to give the desired product (26 mg, 93%) as a clear gum. MS: M+H⁺389. ¹H NMR (300 MHz, MeOH-d₄): δ 8.22 (dd, J=2.4, 6.2 Hz, 1H), 8.09-8.04 (m, 1H), 7.86-7.78 (m, 1H), 7.49-7.21 (m, 3H), 3.44-3.29 (m, 3H), 1.02 (d, J=6.5 Hz, 3H).

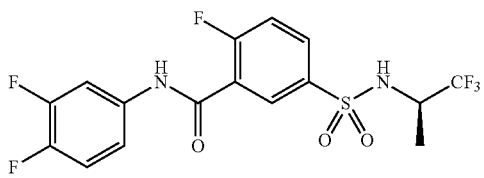 [SMILES: C[C@@H](NS(=O)(=O)c1ccc(F)c(C(=O)Nc2ccc(F)c(F)c2)c1)C(F)(F)F]

(R)-N-(3,4-difluorophenyl)-2-fluoro-5-(N-(1,1,1-trifluoropropan-2-yl)sulfamoyl)benzamide: In a similar procedure as General Procedure C, final compound was obtained in 13.4% yield. ¹H NMR (300 MHz, CDCl₃): δ 8.68 (dd, J=7.0, 2.6 Hz, 1H), 8.40 (bd, J=14.1 Hz, 1H), 8.05 (ddd, J=8.8, 4.7, 2.6 Hz, 1H), 7.36 (dd, J=11.4, 8.8 Hz, 1H), 7.26-7.10 (m, 2H), 5.24 (d, J=9.4 Hz, 1H), 4.12-3.98 (m, 1H), 1.37 (d, J=7.0 Hz, 3H); Calculated for C16H12F6N2O3S, 426.05; observed MS (ESI) (m/z) 427.2 (M+1)⁺.

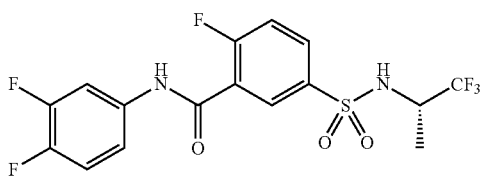 [SMILES: C[C@H](NS(=O)(=O)c1ccc(F)c(C(=O)Nc2ccc(F)c(F)c2)c1)C(F)(F)F]

(S)-N-(3,4-difluorophenyl)-2-fluoro-5-(N-(1,1,1-trifluoropropan-2-yl)sulfamoyl)benzamide: In a similar procedure as General Procedure C, final compound was obtained in 21% yield. ¹H NMR (300 MHz, CDCl₃): δ 8.68 (dd, J=7.0, 2.6 Hz, 1H), 8.40 (bd, J=14.1 Hz, 1H), 8.05 (ddd, J=8.8, 4.7, 2.6 Hz, 1H), 7.36 (dd, J=11.4, 8.8 Hz, 1H), 7.26-7.10 (m, 2H), 5.24 (d, J=9.4 Hz, 1H), 4.12-3.98 (m, 1H), 1.37 (d, J=7.0 Hz, 3H); Calculated for C16H12F6N2O3S, 426.05; observed MS (ESI) (m/z) 427.1 (M+1)⁺.

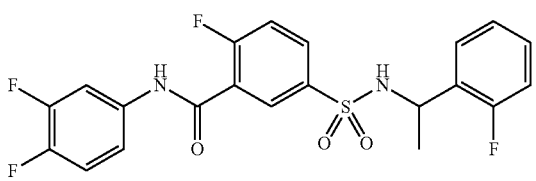 [SMILES: CC(NS(=O)(=O)c1ccc(F)c(C(=O)Nc2ccc(F)c(F)c2)c1)c1ccccc1F]

N-(3,4-difluorophenyl)-2-fluoro-5-(N-(1-(2-fluorophenyl)ethyl)sulfamoyl)benzamide: In a similar procedure as General Procedure C, final compound was obtained in 78% yield. ¹H NMR (300 MHz, CDCl₃): δ 8.40 (dd, J=7.0, 2.3 Hz, 1H), 8.22 (bd, J=14.1 Hz, 1H), 7.84-7.72 (m, 2H), 7.24-7.06 (m, 5H), 6.99-6.92 (m, 1H), 6.86-6.76 (m, 1H), 5.16 (d, J=8.5 Hz, 1H), 4.73 (dt, J=15.5, 7.0 Hz, 1H), 1.53 (d, J=7.0 Hz, 3H); Calculated for C21H16F4N2O3S, 452.08; observed MS (ESI) (m/z) 453.2 (M+1)⁺.

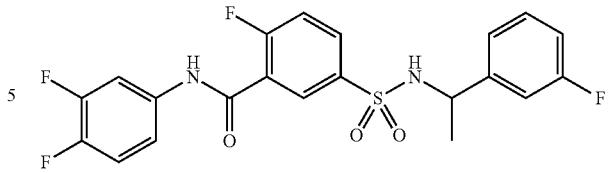

N-(3,4-difluorophenyl)-2-fluoro-5-(N-(1-(3-fluorophenyl)ethyl)sulfamoyl)benzamide: In a similar procedure as General Procedure C, final compound was obtained in 84% yield. ¹H NMR (300 MHz, CDCl₃): δ 8.46 (dd, J=7.0, 2.6 Hz, 1H), 8.28 (bd, J=14.1 Hz, 1H), 7.82-7.70 (m, 2H), 7.24-7.10 (m, 4H), 6.94-6.88 (m, 1H), 6.83 (ddt, J=8.5, 2.6, 0.9 Hz, 1H), 6.75 (td, J=9.7, 2.0 Hz, 1H), 5.10 (d, J=6.7 Hz, 1H), 4.64-4.52 (m, 1H), 1.46 (d, J=7.0 Hz, 3H); Calculated for C21H16F4N2O3S, 452.08; observed MS (ESI) (m/z) 453.2 (M+1)⁺.

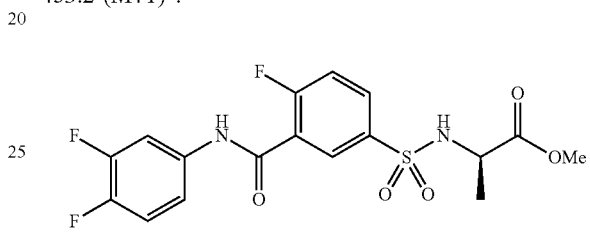

(R)-methyl-2-(3-((3,4-difluorophenyl)carbamoyl)-4-fluorophenylsulfonamido)propanoate: ¹H NMR (300 MHz, CDCl₃): δ 8.56 (dd, J=7.0, 2.6 Hz, 1H), 8.42 (bd, J=12.3 Hz, 1H), 8.01 (ddd, J=8.7, 4.5, 2.6 Hz, 1H), 7.76 (ddd, J=12.4, 7.0, 2.0 Hz, 1H), 7.32 (dd, J=11.1, 8.8 Hz, 1H), 7.26-7.10 (m, 2H), 5.57 (d, J=7.0 Hz, 1H), 4.16-4.02 (m, 1H), 3.61 (s, 3H), 1.42 (d, J=7.3 Hz, 3H); Calculated for C17H15F3N2O5S, 416.07; observed MS (ESI) (m/z) 417.2 (M+1)⁺.

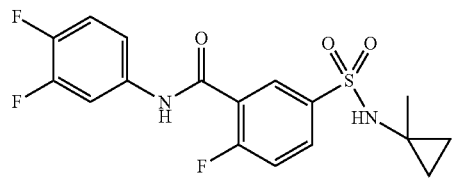 [SMILES: CC1(NS(=O)(=O)c2ccc(F)c(C(=O)Nc3ccc(F)c(F)c3)c2)CC1]

N-(3,4-difluorophenyl)-2-fluoro-5-(N-(1-methylcyclopropyl)sulfamoyl)benzamide: In a similar procedure as General Procedure C, final compound was obtained as a white solid (60 mg, 78%). ¹H NMR (300 MHz, CD₃OD): 8.21-8.18 (dd, J=6.4, 2.3 Hz, 1H), 8.07-8.01 (m, 1H), 7.86-7.79 (m, 1H), 7.49-7.37 (m, 2H), 7.31-7.22 (m, 1H), 1.17 (s, 3H), 0.74-0.70 (t, J=5.7 Hz, 2H), 0.48-0.46 (m, 2H); MS (ES) m/z: 385.2 (M+H⁺), calculated 385.08.

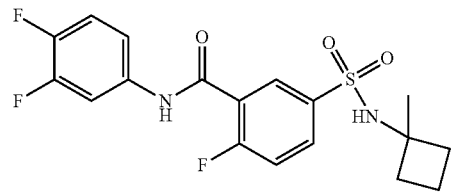 [SMILES: CC1(NS(=O)(=O)c2ccc(F)c(C(=O)Nc3ccc(F)c(F)c3)c2)CCC1]

N-(3,4-difluorophenyl)-2-fluoro-5-(N-(1-methylcyclobutyl)sulfamoyl)benzamide: In a similar procedure as General Procedure C, final compound was obtained as a white solid (123 mg, 88.5%). ¹H NMR (300 MHz, CD₃OD): 8.22-8.19 (dd, J=6.3, 2.3 Hz, 1H), 8.07-8.02 (m, 1H), 7.86-7.79 (m, 1H), 7.48-7.36 (m, 2H), 7.31-7.22 (m, 1H), 2.27-2.19 (m, 2H), 1.84-1.67 (m, 4H), 1.36 (s, 3H); MS (ES) m/z: 399.2 (M+H⁺), calculated 399.09.

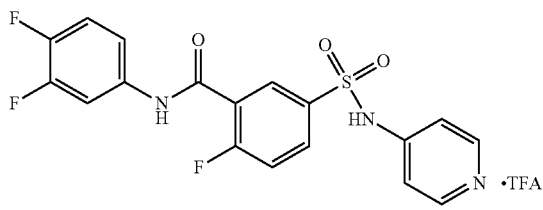 [SMILES: O=C(Nc1ccc(F)c(F)c1)c1cc(S(=O)(=O)Nc2ccncc2)ccc1F]

N-(3,4-difluorophenyl)-2-fluoro-5-(N-(pyridin-4-yl)sulfamoyl)benzamide: In a similar procedure as General Procedure C, final compound was obtained as a TFA salt beige solid (20 mg, 28%). ¹H NMR (300 MHz, CD₃OD): 8.38 (bs, 1H), 8.31-8.29 (m, 1H), 8.18-8.13 (m, 1H), 7.77-7.70 (m, 1H), 7.48-7.42 (m, 3H), 7.27-7.14 (m, 3H); MS (ES) m/z: 408.2 (M+H⁺), calculated 408.06.

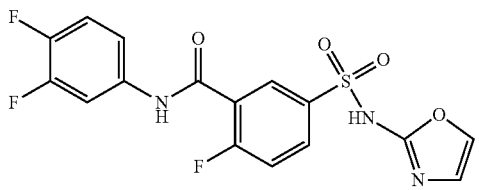 [SMILES: O=C(Nc1ccc(F)c(F)c1)c1cc(S(=O)(=O)Nc2ncco2)ccc1F]

N-(3,4-difluorophenyl)-2-fluoro-5-(N-(oxazol-2-yl)sulfamoyl)benzamide: In a similar procedure as General Procedure C, final compound was obtained as a beige TFA salt (7 mg, 12%). ¹H NMR (300 MHz, CD₃OD): 8.26-8.23 (m, 1H), 8.13-8.07 (m, 1H), 7.94 (s, 1H), 7.77-7.70 (m, 1H), 7.46-7.40 (m, 1H), 7.41-7.17 (m, 3H); MS (ES) m/z: 398.2 (M+H⁺), calculated 398.03.

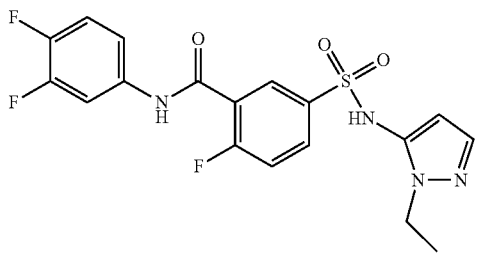 [SMILES: CCn1nccc1NS(=O)(=O)c1ccc(F)c(C(=O)Nc2ccc(F)c(F)c2)c1]

N-(3,4-difluorophenyl)-5-(N-(1-ethyl-1H-pyrazol-5-yl)sulfamoyl)-2-fluorobenzamide: In a similar procedure as General Procedure C, final compound was obtained as a beige solid (13.5 mg, 23%). ¹H NMR (300 MHz, CD₃OD): 8.15-8.13 (m, 1H), 7.96-7.93 (m, 1H), 7.86-7.79 (m, 1H), 7.47-7.24 (m, 5H), 3.20-3.17 (m, 2H), 1.34-1.29 (t, J=7.3 Hz, 3H); MS (ES) m/z: 425.2 (M+H⁺), calculated 425.08.

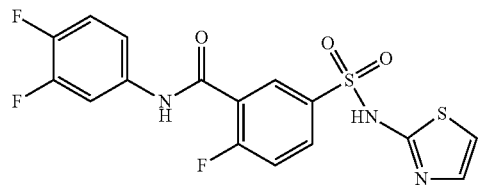 [SMILES: O=C(Nc1ccc(F)c(F)c1)c1cc(S(=O)(=O)Nc2nccs2)ccc1F]

N-(3,4-difluorophenyl)-2-fluoro-5-(N-(thiazol-2-yl)sulfamoyl)benzamide: In a similar procedure as General Procedure C, final compound was obtained as a beige solid (7 mg, 12%). ¹H NMR (300 MHz, CD₃OD): 8.15-8.12 (m, 1H), 8.10-7.93 (m, 1H), 7.76-7.70 (m, 1H), 7.34-7.23 (m, 2H), 7.22-7.16 (m, 1H), 7.03 (bs, 1H), 6.64 (bs, 1H); MS (ES) m/z: 414.1 (M+H⁺), calculated 414.01.

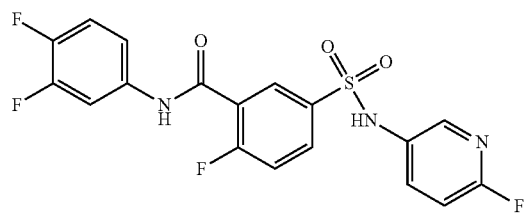 [SMILES: O=C(Nc1ccc(F)c(F)c1)c1cc(S(=O)(=O)Nc2ccc(F)nc2)ccc1F]

N-(3,4-difluorophenyl)-2-fluoro-5-(N-(6-fluoropyridin-3-yl)sulfamoyl)benzamide: In a similar procedure as General Procedure C, final compound was obtained as a beige solid (8.3 mg, 14%). ¹H NMR (300 MHz, CD3OD): 8.15-8.12 (m, 1H), 7.94-7.92 (m, 1H), 7.82-7.70 (m, 3H), 7.42-7.23 (m, 3H), 6.97-6.94 (m, 1H); MS (ES) m/z: 426.2 (M+H⁺), calculated 426.05.

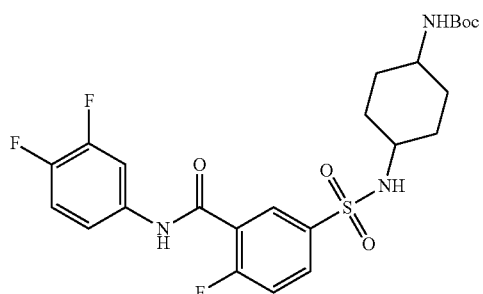

tert-Butyl(4-(3-((3,4-difluorophenyl)carbamoyl)-4-fluorophenylsulfonamido)cyclohexyl)carbamate: In a similar procedure as General Procedure C, final compound was obtained as a white solid (128 mg, 85%). ¹H NMR (300 MHz, d₆-DMSO): 10.82 (s, 1H), 8.10-8.08 (m, 1H), 8.04-7.99 (m, 1H), 7.88-7.82 (m, 1H), 7.70 (m, 1H), 7.62-7.57 (m, 1H), 7.49-7.42 (m, 2H), 6.73 (m, 1H), 3.22 (m, 1H), 3.00 (bs, 1H), 1.55-1.39 (m, 8H), 1.35 (s, 9H); MS (ES) m/z: 528.3 (M+H⁺), calculated 528.17.

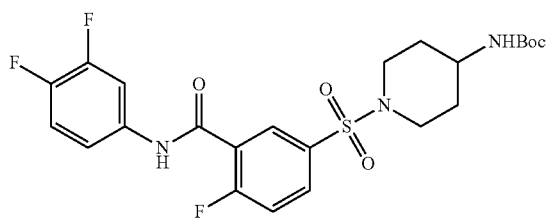 [SMILES: CC(C)(C)OC(=O)NC1CCN(S(=O)(=O)c2ccc(F)c(C(=O)Nc3ccc(F)c(F)c3)c2)CC1]

tert-Butyl(1-((3-((3,4-difluorophenyl)carbamoyl)-4-fluorophenyl)sulfonyl)piperidin-4-yl)carbamate: In a similar procedure as General Procedure C, final compound was obtained as a white solid (120 mg, 82%). ¹H NMR (300 MHz, d₄-MeOH): 8.11-8.00 (m, 1H), 8.09-7.95 (m, 1H), 7.86-7.79 (m, 1H), 7.54-7.40 (m, 1H), 7.40-7.31 (m, 1H), 7.28-7.22 (m, 1H), 3.69-3.65 (m, 2H), 2.57-2.50 (m. 2H), 1.93-1.89 (m, 2H), 1.57-1.49 (m, 3H), 1.41 (m, 9H); MS (ES) m/z: 536.3 (M+Na⁺), calculated 536.15.

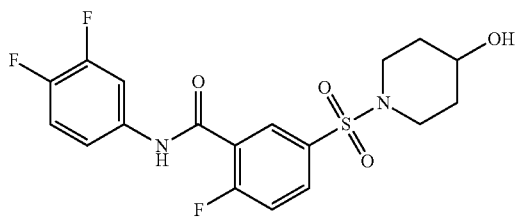 [SMILES: O=C(Nc1ccc(F)c(F)c1)c1cc(S(=O)(=O)N2CCC(O)CC2)ccc1F]

N-(3,4-Difluorophenyl)-2-fluoro-5-((4-hydroxypiperidin-1-yl)sulfonyl)benzamide: In a similar procedure as General Procedure C, final compound was obtained as a white solid (31 mg, 41%). ¹H NMR (300 MHz, d₄-MeOH): 8.12-8.09 (m, 1H), 8.01-7.95 (m, 1H), 7.86-7.78 (m, 1H), 7.54-7.48 (m, 1H), 7.40-7.37 (m, 1H), 7.31-7.22 (m, 1H), 3.69-3.63 (m, 1H), 3.41-3.30 (m, 2H), 2.89-2.82 (m, 2H), 1.92-1.86 (m, 2H), 1.64-1.54 (m, 2H); MS (ES) m/z: 415.2 (M+H⁺), calculated 415.09.

Example 4

General Procedure D

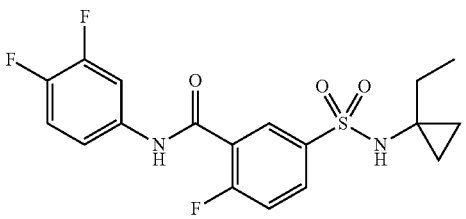 [SMILES: CCC1(NS(=O)(=O)c2ccc(F)c(C(=O)Nc3ccc(F)c(F)c3)c2)CC1]

N-(3,4-Difluorophenyl)-5-(N-(1-ethylcyclopropyl)sulfamoyl)-2-fluorobenzamide: To a 0° C. solution of 3-(3,4-difluorophenyl-carbamoyl)-4-fluorobenzene-1-sulfonyl chloride (30 mg, 0.086 mmol) in THF (1 mL) was added NEt₃ (17 mg, 0.17 mmol), and 1-ethylcycolproylamine.HCl (9 mg, 0.072 mmol). The reaction was warmed to 20° C., and was stirred for 1.5 hours. The mixture was concentrated, ande residue was partitioned between EtOAc (20 mL) and 1 N HCl (5 mL). The organic layer was washed with 2 N HCl (5 mL), water (5 mL), and brine (1 mL), dried (Na₂SO₄), and concentrated. The crude material was purified by silica column (10-50% EtOAc/Hexane) to give the desired product (13 mg, 45%) as a clear gum. MS: M+H⁺399. ¹H NMR (300 MHz, MeOH-d₄): δ 10.47 (s, 1H), 8.20 (dd, J=2.4, 6.5 Hz, 1H), 8.06-8.00 (m, 1H), 7.86-7.78 (m, 1H), 7.48-7.12 (m, 4H), 1.42 (q, J=7.6 Hz, 2H), 0.87 (t, J=7.3 Hz, 3H), 0.64 (dd, J=1.8, 5.3 Hz, 2H), 0.46 64 (dd, J=2.1, 5.0 Hz, 2H).

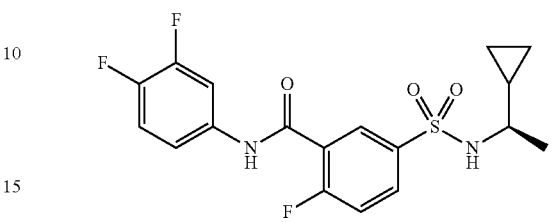

(R)-5-(N-(1-cyclopropylethyl)sulfamoyl)-N-(3,4-Difluorophenyl)-2-fluorobenzamide: General Procedure D was followed, using 3-(3,4-difluorophenyl-carbamoyl)-4-fluorobenzene-1-sulfonyl chloride (25 mg, 0.072 mmol), NEt₃ (14 mg, 0.14 mmol), and (R)-1-cyclopropylethylamine (9 mg, 0.11 mmol) to give the desired product (16 mg, 56%) as a white solid. MS: M+H⁺399. ¹H NMR (300 MHz, CDCl₃): δ 8.64 (dd, J=2.6, 7.0 Hz, 1H), 8.46 (d, J=13.2 Hz, 1H), 8.08-8.03, 1H), 7.80-7.73 (m, 1H), 7.36-7.11 (m, 3H), 5.03 (d, J=6.7 Hz, 1H), 2.75 (dt, J=1.8, 6.5, 1H), 1.17 (d, J=26.5 Hz, 3H), 0.82-0.74 (m, 1H), 0.50-0.43 (m, 1H), 0.38-0.32 (m, 1H), 0.18-0.04 (m, 2H).

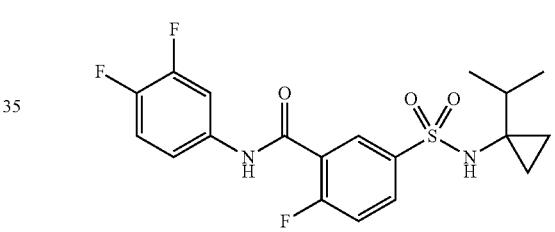

N-(3,4-Difluorophenyl)-2-fluoro-5-(N-(1-isopropylcyclopropyl)sulfamoyl)benzamide: General Procedure D was followed, using 3-(3,4-difluorophenyl-carbamoyl)-4-fluorobenzene-1-sulfonyl chloride (25 mg, 0.072 mmol), NEt₃ (28 mg, 0.28 mmol), and isopropylcyclopropylamine.HCl (15 mg, 0.11 mmol) to give the desired product (22 mg, 74%) as a white solid. MS: M+H⁺413. ¹H NMR (300 MHz, CDCl₃): δ 8.56 (dd, J=2.4, 6.7 Hz, 1H), 8.48 (d, J=12.9 Hz, 1H), 8.05-7.99 (m, 1H), 7.80-7.72 (m, 1H), 7.34-7.11 (m, 3H), 5.57 (s, 1H), 1.54 (qint, J=6.7 Hz, 1H), 0.87 (d, J=6.7 Hz, 6H), 0.69-0.58 (m, 4H).

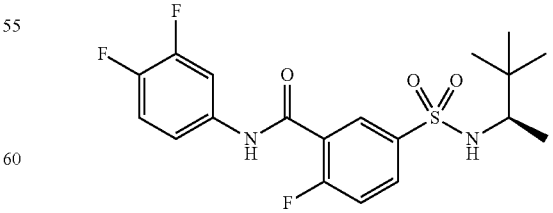

(R)-N-(3,4-Difluorophenyl)-5-(N-(3,3-dimethylbutan-2-yl)sulfamoyl)-2-fluorobenzamide: General Procedure D was followed, using 3-(3,4-difluorophenyl-carbamoyl)-4-fluorobenzene-1-sulfonyl chloride (25 mg, 0.072 mmol), NEt₃

(14 mg, 0.14 mmol), and (R)-(+3,3-dimethyl-2-aminopropane (11 mg, 0.11 mmol) to give the desired product (12 mg, 40%) as a white solid. MS: M+H+415. $^1$H NMR (300 MHz, MeOH-d$_4$): δ 8.21 (dd, J=2.4, 6.5 Hz, 1H), 8.08-8.03 (m, 1H), 7.86-7.79 (m, 1H), 7.49-7.21 (m, 3H), 3.07 (q, J=6.7 Hz, 1H), 0.87 (s, 9H), 0.81 (d, J=6.7 Hz, 3H).

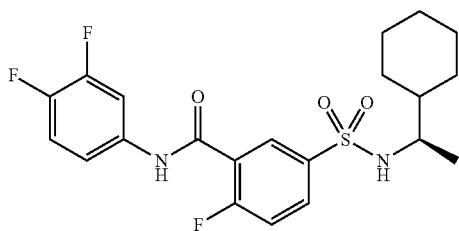 [SMILES: C[C@@H](NS(=O)(=O)c1ccc(F)c(C(=O)Nc2ccc(F)c(F)c2)c1)C1CCCCC1]

(R)-5-(N-(1-cyclohexylethyl)sulfamoyl)-N-(3,4-Difluorophenyl)-2-fluorobenzamide: General Procedure D was followed, using 3-(3,4-difluorophenyl-carbamoyl)-4-fluorobenzene-1-sulfonyl chloride (25 mg, 0.072 mmol), NEt$_3$ (14 mg, 0.14 mmol), and (R)-(−)-cyclohexylethylamine (14 mg, 0.11 mmol) to give the desired product (15 mg, 47%) as a white solid. MS: M+H+441. $^1$H NMR (300 MHz, CDCl$_3$): δ 8.63 (dd, J=2.4, 7.0 Hz, 1H), 8.45 (d, J=13.2 Hz, 1H), 8.06-8.01 (m, 1H), 7.80-7.73 (m, 1H), 7.36-7.11 (m, 3H), 4.73 (d, J=8.8 Hz, 1H), 3.25-3.18 (m, 1H), 1.72-1.53 (m, 4H), 1.31-1.01 (m, 5H), 0.98 (d, J=6.5 Hz, 3H), 0.96-0.80 (m, 1H).

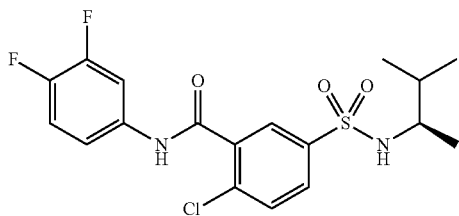 [SMILES: CC(C)[C@@H](C)NS(=O)(=O)c1ccc(Cl)c(C(=O)Nc2ccc(F)c(F)c2)c1]

(R)-2-chloro-N-(3,4-Difluorophenyl)-5-(N-(3-methylbutan-2-yl)sulfamoyl)benzamide: General Procedure D was followed, using 3-(3,4-difluorophenyl-carbamoyl)-4-chlorobenzene-1-sulfonyl chloride (25 mg, 0.068 mmol), NEt$_3$ (13 mg, 0.14 mmol), and (R)-(−)-2-amino-3-methylbutane (9 mg, 0.10 mmol) to give the desired product (23 mg, 81%) as an off-white solid. MS: M+H+417. $^1$H NMR (300 MHz, CDCl$_3$): δ 8.38 (s, 1H), 8.12 (d, J=2.1 Hz, 1H), 7.81-7.68 (m, 2H), 7.53 (d, J=8.5 Hz, 1H), 7.19-7.12 (m, 2H), 4.83 (d, J=8.8 Hz, 1H), 3.23-3.16 (m, 1H), 1.70-1.62 (m, 1H), 1.26 (d, J=7.0 Hz, 3H), 0.82 (d, J=6.7 Hz, 6H).

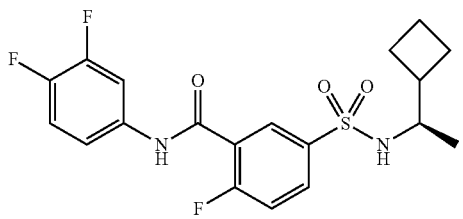 [SMILES: C[C@@H](NS(=O)(=O)c1ccc(F)c(C(=O)Nc2ccc(F)c(F)c2)c1)C1CCC1]

(R)-5-(N-(1-cyclobutylethyl)sulfamoyl)-N-(3,4-Difluorophenyl)-2-fluorobenzamide: General Procedure D was followed, using 3-(3,4-difluorophenyl-carbamoyl)-4-fluorobenzene-1-sulfonyl chloride (25 mg, 0.072 mmol), NEt$_3$ (28 mg, 0.28 mmol), and (R)-(−)-cyclobutylethylamine.HCl (15 mg, 0.11 mmol) to give the desired product (19 mg, 64%) as a white solid. MS: M+H+417. $^1$H NMR (300 MHz, CDCl$_3$): δ 8.64 (dd, J=2.4, 7.0 Hz, 1H), 8.44 (d, J=13.8 Hz, 1H), 8.08-8.03 (m, 1H), 7.80-7.73 (m, 1H), 7.37-7.11 (m, 3H), 4.69 (d, J=8.2 Hz, 1H), 3.29-3.22 (m, 1H), 2.19 (q, J=8.2 Hz, 1H), 1.94-1.60 (m, 5H), 0.96 (d, J=6.5 Hz, 1H), 0.88-0.83 (m, 1H).

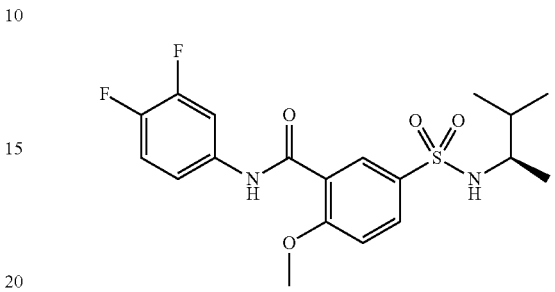

(R)-N-(3,4-Difluorophenyl)-2-methoxy-5-(N-(3-methylbutan-2-yl)sulfamoyl)benzamide: General Procedure D was followed, using 3-(3,4-difluorophenyl-carbamoyl)-methoxybenzene-1-sulfonyl chloride (25 mg, 0.069 mmol), NEt$_3$ (13 mg, 0.13 mmol), and (R)-(−)-2-amino-3-methylbutane (9 mg, 0.10 mmol) to give the desired product (12 mg, 42%) as a white solid. MS: M+H+413. $^1$H NMR (300 MHz, CDCl$_3$): 9.60 (s, 1H), 8.72 (d, J=2.6 Hz, 1H), 7.99 (dd, J=2.6, 8.8 Hz, 1H), 7.81-7.74 (m, 1H), 7.22-7.08 (m, 3H), 4.61 (d, J=8.5 Hz, 1H), 3.23-3.17 (m, 1H), 1.68-1.61 (m, 1H), 0.95 (d, J=6.7 Hz, 1H), 0.82 (d, J=7.0 Hz, 1H).

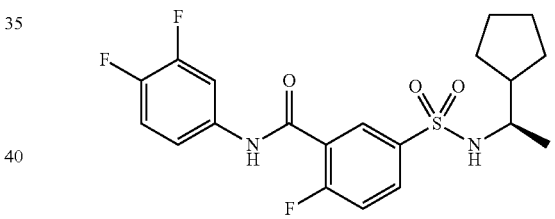

(R)-5-(N-(1-cyclopentylethyl)sulfamoyl)-N-(3,4-Difluorophenyl)-2-fluorobenzamide: General Procedure D was followed, using 3-(3,4-difluorophenyl-carbamoyl)-4-fluorobenzene-1-sulfonyl chloride (25 mg, 0.072 mmol), NEt$_3$ (28 mg, 0.28 mmol), and (R)-(−)-cyclopentylethylamine-.HCl (17 mg, 0.11 mmol) to give the desired product (24 mg, 78%) as a white solid. MS: M+H+427. $^1$H NMR (300 MHz, CDCl$_3$): 8.62 (dd, J=2.4, 7.0 Hz, 1H), 8.47 (d, J=13.2 Hz, 1H), 8.06-8.01 (m, 1H), 7.79-7.72 (m, 1H), 7.35-7.11 (m, 3H), 4.84 (d, J=8.5 Hz, 1H), 3.26-3.19 (m, 1H), 1.84-1.43 (m, 5H), 1.39-1.06 (m, 3H), 1.03 (d, J=6.5 Hz, 1H), 0.88-0.83 (m, 1H).

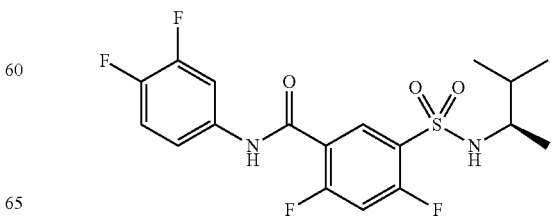

(R)-N-(3,4-Difluorophenyl)-2,4-difluoro-5-(N-(3-methylbutan-2-yl)sulfamoyl)benzamide: General Procedure D was followed, using 3-(3,4-difluorophenyl-carbamoyl)-2,4-difluorobenzene-1-sulfonyl chloride (25 mg, 0.068 mmol), NEt$_3$ (13 mg, 0.13 mmol), and (R)-(−)-2-amino-3-methylbutane (9 mg, 0.10 mmol) to give the desired product (10 mg, 35%) as a white solid. MS: M+H$^+$419. $^1$H NMR (300 MHz, CDCl$_3$): 8.68 (t, J=8.2 Hz, 1H), 8.28 (d, J=12.3 Hz, 1H), 7.78-7.71 (m, 1H), 7.25-7.07 (m, 3H), 7.70 (m, 1H), 3.33-3.26 (m, 1H), 1.73-1.64 (m, 1H), 1.02 (d, J=6.5 Hz, 1H), 0.86 (dd, J=1.8, 7.0 Hz, 1H).

5-(N-(2-adamantyl)sulfamoyl)-N-(3,4-Difluorophenyl)-2-fluorobenzamide: General Procedure D was followed, using 3-(3,4-difluorophenyl-carbamoyl)-4-fluorobenzene-1-sulfonyl chloride (30 mg, 0.086 mmol), NEt$_3$ (28 mg, 0.28 mmol), and 2-amino-adamantane.HCl (24 mg, 0.13 mmol) to give the desired product (31 mg, 78%) as a white solid. MS: M+H$^+$465. $^1$H NMR (300 MHz, CDCl$_3$): 8.66-8.63 (m, 1H), 8.44 (d, J=13.5 Hz, 1H), 8.08-8.03 (m, 1H), 7.79-7.72 (m, 1H), 7.36-7.11 (m, 3H), 5.23 (d, J=7.3 Hz, 1H), 3.44 (d, J=7.0 Hz, 1H), 1.80-1.16 (m, 14H).

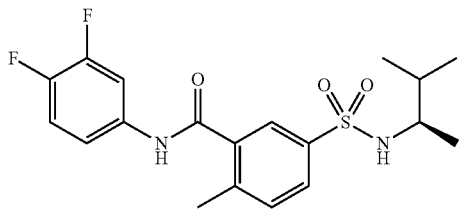 [SMILES: Cc1ccc(S(=O)(=O)N[C@H](C)C(C)C)cc1C(=O)Nc1ccc(F)c(F)c1]

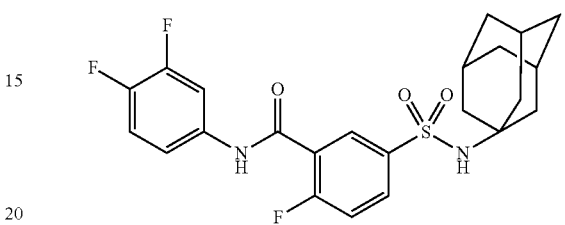

(R)-N-(3,4-Difluorophenyl)-2-methyl-5-(N-(3-methylbutan-2-yl)sulfamoyl)benzamide: General Procedure D was followed, using 3-(3,4-difluorophenyl-carbamoyl)-4-methylbenzene-1-sulfonyl chloride (25 mg, 0.068 mmol), NEt$_3$ (13 mg, 0.13 mmol), and (R)-(−)-2-amino-3-methylbutane (9 mg, 0.10 mmol) to give the desired product (10 mg, 35%) as a white solid. MS: M+H$^+$397. $^1$H NMR (300 MHz, CDCl$_3$): 8.23 (s, 1H), 7.93 (d, J=1.5 Hz, 1H), 7.74-7.70 (m, 2H), 7.35 (d, J=8.2 Hz, 1H), 7.26-7.12 (m, 2H), 4.59 ((d, J=8.5 Hz, 1H), 3.17-3.15 (m, 1H), 2.56 (s, 3H), 1.66-1.62 (m, 1H), 0.93 (d, J=6. Hz, 1H), 0.81 (d, J=6.7 Hz, 1H).

5-(N-(1-adamantyl)sulfamoyl)-N-(3,4-Difluorophenyl)-2-fluorobenzamide: General Procedure D was followed, using 3-(3,4-difluorophenyl-carbamoyl)-4-fluorobenzene-1-sulfonyl chloride (30 mg, 0.086 mmol), NEt$_3$ (17 mg, 0.17 mmol), and 1-amino-adamantane.HCl (20 mg, 0.13 mmol) to give the desired product (26 mg, 65%) as a white solid. MS: M+Na$^+$487. $^1$H NMR (300 MHz, DMSO-d$_6$): 10.81 (s, 1H), 8.11-8.09 (m, 1H), 8.05-8.00 (m, 1H), 7.90-7.83 (m, 1H), 7.70 (s, 1H), 7.60 (d, J=9.4 Hz, 1H), 7.47-7.42 (m, 2H), 1.97-1.92 (m, 3H), 1.69 (s, 6H), 1.55-1.45 (m, 6H).

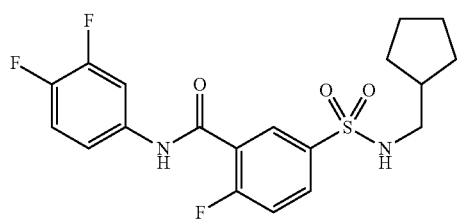 [SMILES: O=C(Nc1ccc(F)c(F)c1)c1cc(S(=O)(=O)NCC2CCCC2)ccc1F]

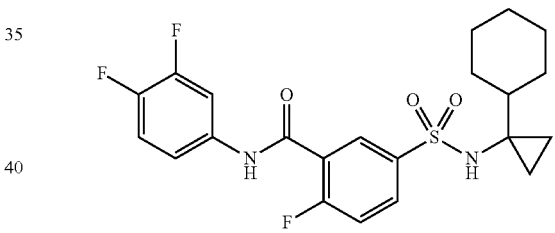

5-(N-(cyclopentylmethyl)sulfamoyl)-N-(3,4-Difluorophenyl)-2-fluorobenzamide: General Procedure D was followed, using 3-(3,4-difluorophenyl-carbamoyl)-4-fluorobenzene-1-sulfonyl chloride (25 mg, 0.072 mmol), NEt$_3$ (28 mg, 0.28 mmol), and C-cyclopentyl-methylamine (11 mg, 0.11 mmol) to give the desired product (14 mg, 47%) as a white solid. MS: M+H$^+$413. $^1$H NMR (300 MHz, DMSO-d$_6$): 10.82 (s, 1H), 8.06-7.96 (m, 2H), 7.90-7.76 (m, 2H), 7.61 (t, J=9.2 Hz, 1H), 7.50-7.42 (m, 2H), 2.67 (t, J=6.2 Hz, 2H), 1.98-1.86 (m, 1H), 1.64-1.43 (m, 6H), 1.14-1.08 (m, 2H).

5-(N-(1-cyclohexylcyclopropyl)sulfamoyl)-N-(3,4-Difluorophenyl)-2-fluorobenzamide: General Procedure D was followed, using 3-(3,4-difluorophenyl-carbamoyl)-4-fluorobenzene-1-sulfonyl chloride (30 mg, 0.086 mmol), NEt$_3$ (17 mg, 0.17 mmol), and (1-cyclohexylcyclopropyl)amine-.HCl (18 mg, 0.13 mmol) to give the desired product (11 mg, 28%) as a white solid. MS: M+H$^+$453. $^1$H NMR (300 MHz, CDCl$_3$): 8.61-8.58 (m, 1H), 8.38 (d, J=14.1 Hz, 1H), 8.06-8.01 (m, 1H), 7.80-7.74 (m, 1H), 7.35-7.12 (m, 4H), 5.20 (s, 1H), 1.70-1.58 (m, 3H), 1.43-0.93 (m, 8H), 0.64 (d, J=4.7 Hz, 4H).

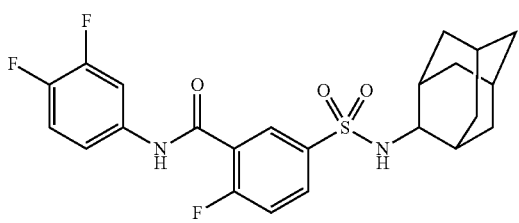 [SMILES: O=C(Nc1ccc(F)c(F)c1)c1cc(S(=O)(=O)NC2C3CC4CC(C3)CC2C4)ccc1F]

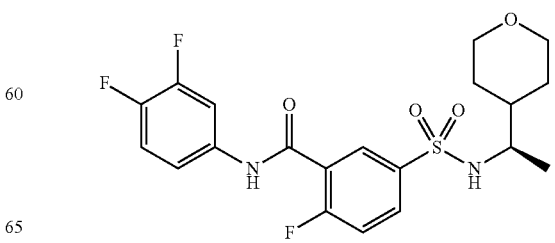

(R)-N-(3,4-Difluorophenyl)-2-fluoro-5-(N-(1-(tetrahydro-2H-pyran-4-yl)ethyl)sulfamoyl)benzamide: General Procedure D was followed, using 3-(3,4-difluorophenyl-carbamoyl)-4-fluorobenzene-1-sulfonyl chloride (50 mg, 0.14 mmol), NEt$_3$ (42 mg, 0.42 mmol), and (R)-1-(tetrahydro-2H-pyran-4-yl)ethanamine HCl (35 mg, 0.21 mmol) to give the desired product (36 mg, 58%) as a white solid. MS: M+H$^+$443. $^1$H NMR (300 MHz, DMSO-d$_6$): 10.81 (s, 1H), 8.08-8.05 (m, 1H), 8.02-7.96 (m, 1H), 7.90-7.82 (m, 1H), 7.65 (d, J=12.9 Hz, 1H), 7.60 (t, J=9.7 Hz, 1H), 7.47-7.39 (m, 2H), 3.83-3.78 (m, 2H), 3.20-2.99 (m, 3H), 1.53-1.38 (m, 3H), 1.25-0.97 (m, 3H), 0.80 (d, J=6.7 Hz, 1H).

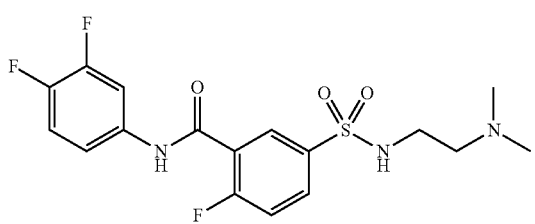 [SMILES: CN(C)CCNS(=O)(=O)c1ccc(F)c(C(=O)Nc2ccc(F)c(F)c2)c1]

N-(3,4-difluorophenyl)-5-(N-(2-(dimethylamino)ethyl)sulfamoyl)-2-fluorobenzamide: General Procedure D was followed, using 3-(3,4-difluorophenyl-carbamoyl)-4-fluorobenzene-1-sulfonyl chloride (50 mg, 0.14 mmol), NEt$_3$ (28 mg, 0.28 mmol), and N,N-dimethylethylenediamine (19 mg, 0.22 mmol) to give the desired product (46 mg, 82%) as a white solid. MS: M+H$^+$402.

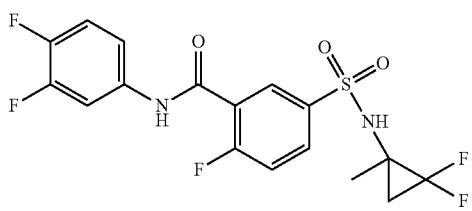 [SMILES: CC1(NS(=O)(=O)c2ccc(F)c(C(=O)Nc3ccc(F)c(F)c3)c2)CC1(F)F]

5-(N-(2,2-Difluoro-1-methylcyclopropyl)sulfamoyl)-N-(3,4-difluorophenyl)-2-fluorobenzamide: In a similar procedure as General Procedure D, final compound was obtained as a white solid (29.8 mg, 50%). $^1$H NMR (300 MHz, d$_4$-MeOH): 8.23-8.20 (m, 1H), 8.08-8.03 (m, 1H), 7.86-7.78 (m, 1H), 7.50-7.44 (t, J=9.2 Hz, 1H), 7.40-7.22 (m, 2H), 1.67-1.57 (m, 1H), 1.45-1.30 (m, 1H), 1.29 (s, 3H); MS (ES) m/z: 421.2 (M+H$^+$), calculated 421.06.

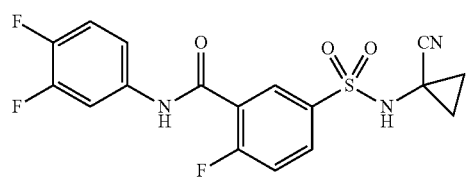 [SMILES: N#CC1(NS(=O)(=O)c2ccc(F)c(C(=O)Nc3ccc(F)c(F)c3)c2)CC1]

5-(N-(1-Cyanocyclopropyl)sulfamoyl)-N-(3,4-difluorophenyl)-2-fluorobenzamide: In a similar procedure as General Procedure D, final compound was obtained as a white solid (30.6 mg, 75%). $^1$H NMR (300 MHz, d$_4$-MeOH): 8.30-8.27 (m, 1H), 8.15-8.10 (m, 1H), 7.86-7.79 (m, 1H), 7.55-7.49 (m, 1H), 7.40-7.22 (m, 2H), 143 (s, 4H); MS (ES) m/z: 396.2 (M+H$^+$), calculated 396.06.

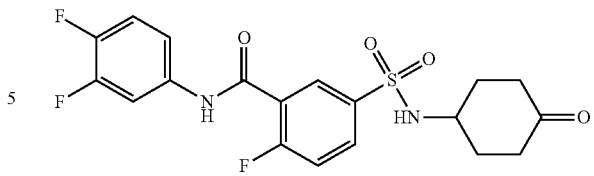

N-(3,4-Difluorophenyl)-2-fluoro-5-(N-(4-oxocyclohexyl)sulfamoyl)benzamide: In a similar procedure as General Procedure D, final compound was obtained as a white solid (45 mg, 46%). $^1$H NMR (300 MHz, d$_4$-MeOH): 8.27-8.19 (m, 1H), 8.13-8.03 (m, 1H), 7.85-7.79 (m, 1H), 7.52-7.37 (m, 2H), 7.31-7.22 (m, 1H), 3.61-3.53 (m, 1H), 2.01-1.97 (m, 2H), 1.81-1.76 (m, 3H), 1.68-1.62 (m, 1H), 1.49-1.45 (m, 2H); MS (ES) m/z: 427.2 (M+H$^+$), calculated 427.09.

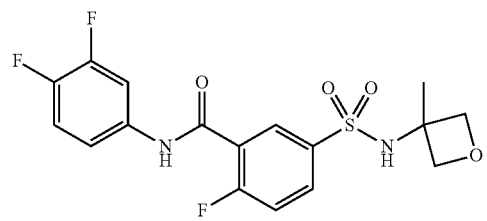 [SMILES: CC1(NS(=O)(=O)c2ccc(F)c(C(=O)Nc3ccc(F)c(F)c3)c2)COC1]

N-(3,4-Difluorophenyl)-2-fluoro-5-(N-(3-methyloxetan-3-yl)sulfamoyl)benzamide: General Procedure D was followed, using 3-(3,4-difluorophenyl-carbamoyl)-4-fluorobenzene-1-sulfonyl chloride (50 mg, 0.14 mmol), NEt$_3$ (28 mg, 0.28 mmol), and 3-amino-3-methyl-oxetane (19 mg, 0.22 mmol) to give the desired product (41 mg, 73%) as a white solid. MS: M+H$^+$401.

Example 5

General Procedure E

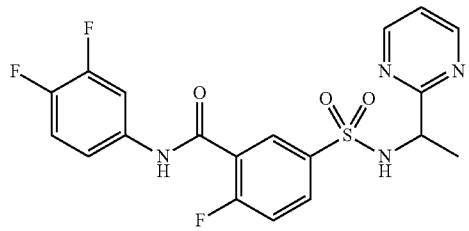

N-(3,4-Difluorophenyl)-2-fluoro-5-(N-(1-(pyrimidin-2-yl)ethyl)sulfamoyl)benzamide: To a 0° C. solution of 3-(3,4-difluorophenyl-carbamoyl)-4-fluorobenzene-1-sulfonyl chloride (25 mg, 0.072 mmol) in THF (1 mL) was added NEt$_3$ (14 mg, 0.14 mmol) and 1-pyrimidin-2yl-ethylamine HCl (18 mg, 0.11 mmol). The reaction was warmed to 20° C., and was stirred for 3 hours. The mixture was concentrated, then the residue was partitioned between EtOAc (20 mL) and dilute NaHCO$_3$ (5 mL). The organic layer was washed with water (5 mL), and brine (1 mL), dried (Na$_2$SO$_4$), and concentrated. The crude material was purified by silica column (20-100% EtOAc/Hexane) to give the desired product (11 mg, 35%) as an off-white solid. MS: M+H$^+$436. $^1$H NMR (300 MHz, CDCl$_3$): δ 8.59 (d, J=5.0

Hz, 1H), 8.46-8.40 (m, 1H), 7.97-7.92 (m, 1H), 7.79-7.72 (m, 1H), 7.26-7.11 (m, 4H), 6.32 (d, J=8.2 Hz, 1H), 4.68 (dq, J=1.2, 7.0 Hz, 1H), 1.54 (d, J=6.7 Hz, 1H).

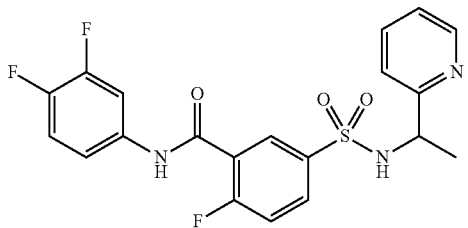 [SMILES: CC(NS(=O)(=O)c1ccc(F)c(C(=O)Nc2ccc(F)c(F)c2)c1)c1ccccn1]

N-(3,4-Difluorophenyl)-2-fluoro-5-(N-(1-(pyridin-2-yl)ethyl)sulfamoyl)benzamide: General Procedure E was followed, using 3-(3,4-difluorophenyl-carbamoyl)-4-fluorobenzene-1-sulfonyl chloride (25 mg, 0.072 mmol), NEt$_3$ (14 mg, 0.14 mmol), and 1-pyridin-2-yl-ethylamine (13 mg, 0.11 mmol) to give the desired product (24 mg, 77%) as a white solid. MS: M+H$^+$436. $^1$H NMR (300 MHz, DMSO-d$_6$): 10.72 (s, 1H), 8.44 (d, J=7.3 Hz, 1H), 8.35-8.33 (m, 1H), 7.92-7.80 (m, 3H), 7.66-7.60 (m, 1H), 7.50-7.42 (m, 3H), 7.27 (d, J=7.9 Hz, 1H), 7.17-7.12 (m, 2H), 4.44 (m, 1H), 1.27 (d, J=7.0 Hz, 1H).

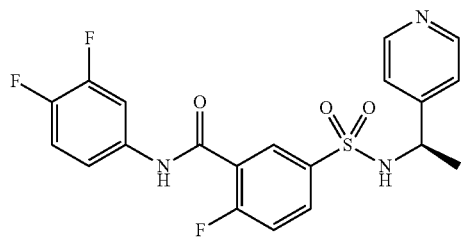 [SMILES: C[C@@H](NS(=O)(=O)c1ccc(F)c(C(=O)Nc2ccc(F)c(F)c2)c1)c1ccncc1]

(R)-N-(3,4-Difluorophenyl)-2-fluoro-5-(N-(1-(pyridin-4-yl)ethyl)sulfamoyl)benzamide: General Procedure E was followed, using 3-(3,4-difluorophenyl-carbamoyl)-4-fluorobenzene-1-sulfonyl chloride (25 mg, 0.072 mmol), NEt$_3$ (14 mg, 0.14 mmol), and (R)-1-pyridin-4-ylethanamine (13 mg, 0.11 mmol) to give the desired product (16 mg, 51%) as a white solid. MS: M+H$^+$436. $^1$H NMR (300 MHz, DMSO-d$_6$): 10.75 (s, 1H), 8.55 (d, J=7.9 Hz, 1H), 8.39 (dd, J=1.2, 4.4 Hz, 2H), 8.00-7.97 (m, 1H), 7.90-7.82 (m, 1H), 7.51-7.42 (m, 3H), 7.24 (dd, J=1.5, 4.7 Hz, 1H), 4.44-4.39 (m, 1H), 1.22 (d, J=7.0 Hz, 1H).

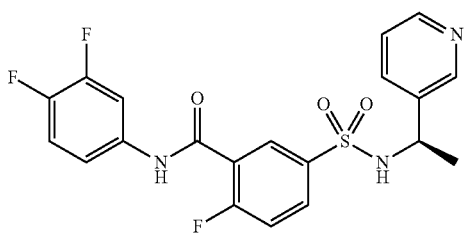 [SMILES: C[C@@H](NS(=O)(=O)c1ccc(F)c(C(=O)Nc2ccc(F)c(F)c2)c1)c1cccnc1]

(R)-N-(3,4-Difluorophenyl)-2-fluoro-5-(N-(1-(pyridin-3-yl)ethyl)sulfamoyl)benzamide General Procedure E was followed, using 3-(3,4-difluorophenyl-carbamoyl)-4-fluorobenzene-1-sulfonyl chloride (25 mg, 0.072 mmol), NEt$_3$ (42 mg, 0.42 mmol), and (1R)-pyridin-3-yl-ethylamine 2 HCl (21 mg, 0.11 mmol) to give the desired product (21 mg, 67%) as a white solid. MS: M+H$^+$436. $^1$H NMR (300 MHz, DMSO-d$_6$): 10.71 (s, 1H), 8.48 (d, J=7.9 Hz, 1H), 8.39-8.34 (m, 1H), 7.93-7.80 (m, 3H), 7.61-7.57 (m, 1H), 7.50-7.42 (m, 2H), 7.23-7.18 (m, 1H), 4.51-4.41 (m, 1H), 1.27 (d, J=7.0 Hz, 1H).

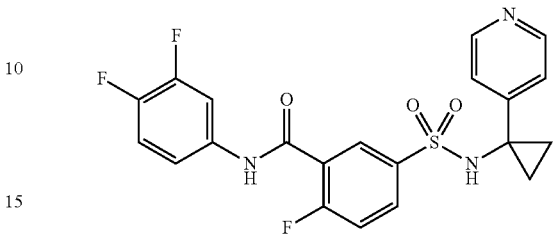

N-(3,4-difluorophenyl)-2-fluoro-5-(N-(1-(pyridin-4-yl)cyclopropyl)sulfamoyl)benzamide General Procedure E was followed, using 3-(3,4-difluorophenyl-carbamoyl)-4-fluorobenzene-1-sulfonyl chloride (50 mg, 0.14 mmol), NEt$_3$ (56 mg, 0.56 mmol), and 1-pyridin-4-yl-cyclopropylamine.2 HCl (44 mg, 0.22 mmol) to give the desired product (15 mg, 24%) as an off-white solid. MS: M+H$^+$448. $^1$H NMR (300 MHz, MeOH-d$_4$): 8.30 (bs, 2H), 8.07-8.04 (m, 1H), 7.89-7.78 (m, 2H), 7.39-7.22 (m, 5H), 1.40-1.36 (m, 2H), 1.33-1.21 (m, 2H).

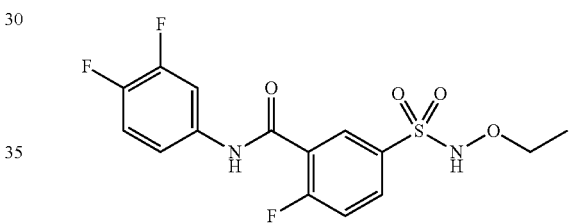

N-(3,4-difluorophenyl)-5-(N-ethoxysulfamoyl)-2-fluorobenzamide: General Procedure E was followed, using 3-(3,4-difluorophenyl-carbamoyl)-4-fluorobenzene-1-sulfonyl chloride (50 mg, 0.14 mmol), NEt$_3$ (42 mg, 0.42 mmol), and O-ethylhydroxylamine.HCl (21 mg, 0.22 mmol) to give the desired product (24 mg, 46%) as a white solid. MS: M+H$^+$375.

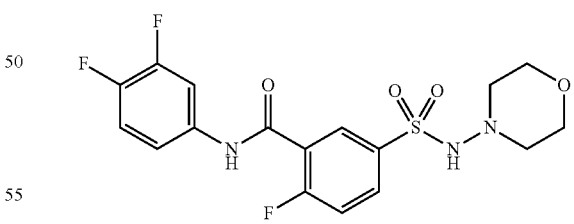

N-(3,4-difluorophenyl)-2-fluoro-5-(N-morpholinosulfamoyl)benzamide: General Procedure E was followed, using 3-(3,4-difluorophenyl-carbamoyl)-4-fluorobenzene-1-sulfonyl chloride (50 mg, 0.14 mmol), NEt$_3$ (28 mg, 0.28 mmol), and N-amino-morpholine (22 mg, 0.22 mmol) to give the desired product (28 mg, 48%) as a white solid. MS: M+H$^+$ 416. $^1$H NMR (300 MHz, MeOH-d$_4$): 8.28 (dd, J=2.4, 6.5 Hz, 1H), 8.15-8.09 (m, 1H), 7.86-7.79 (m, 1H), 7.48 (t, J=9.3 Hz, 1H), 7.40-7.37 (m, 1H), 7.26 (q, J=9.0 Hz, 1H), 3.60-3.57 (m, 2H), 2.60-2.58 (m, 2H).

Example 6

General Procedure F

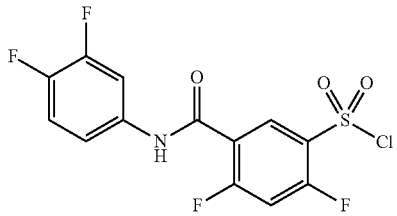 [SMILES: O=C(Nc1ccc(F)c(F)c1)c1cc(S(=O)(=O)Cl)c(F)cc1F]

3-(3,4-Difluorophenyl-carbamoyl)-2,4-difluorobenzene-1-sulfonyl chloride: A mixture of 5-chlorosulfonyl-2,4-difluorobenzoic acid (0.50 g, 1.96 mmol), thionyl chloride (2 mL), and 1,2-dichloroethane (1 mL) was heated at reflux for 3 h. The reaction was concentrated, then the residue was treated with toluene (5 mL), then the mixture was concentrated. The crude material was used with further purification.

To a 0° C. solution of 3,4-difluoroaniline (0.51 g, 3.92 mmol) in toluene (5 mL) was added a solution of the material from the previous step in toluene (1 mL). The reaction was stirred for 16 hours then was filtered. The residue was partitioned between $CH_2Cl_2$ (25 mL) and a mixture of ice and 2N HCl (10 mL). The aqueous layer was extracted with $CH_2Cl_2$ (2×25 mL). The combined organic layers were washed with brine (5 mL), dried ($Na_2SO_4$), and concentrated. The crude material was purified by silica column (10-50% EtOAc/Hexane) to give the desired product (0.53 g, 74%) as a white solid. MS: M+H$^+$368.

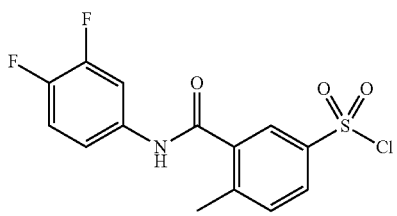 [SMILES: Cc1ccc(S(=O)(=O)Cl)cc1C(=O)Nc1ccc(F)c(F)c1]

3-(3,4-Difluorophenylcarbamoyl)-4-methylbenzene-1-sulfonyl chloride: General Procedure F was followed, using 5-chlorosulfonyl-2-methyllbenzoic acid (0.50 g, 2.13 mmol) to give the desired product (0.48 g, 65% over two steps) as a white solid. MS: M+H$^+$346.

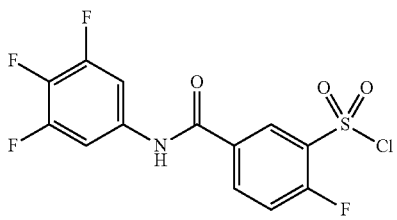 [SMILES: O=C(Nc1cc(F)c(F)c(F)c1)c1ccc(F)c(S(=O)(=O)Cl)c1]

2-Fluoro-5-(3,4,5-trifluorophenylcarbamoyl)-benzene-1-sulfonyl chloride: In a similar procedure to General Procedure F, the final compound was obtained as a white solid (0.85 g, 53%). MS (ES) m/z: 367.70 (M+H$^+$), calculated 367.97.

Example 7

General Procedure G

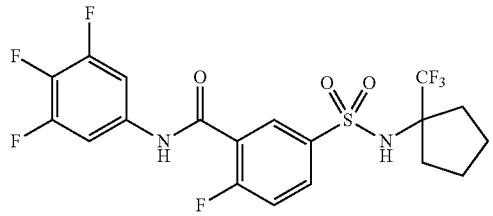 [SMILES: O=C(Nc1cc(F)c(F)c(F)c1)c1cc(S(=O)(=O)NC2(C(F)(F)F)CCCC2)ccc1F]

N-(3,4-Difluorophenyl)-2-fluoro-5-(N-(1-(trifluoromethyl)cyclopentylamine)sulfamoyl)benzamide: To a 0° C. solution of 3-(3,4-difluorophenyl-carbamoyl)-4-fluorobenzene-1-sulfonyl chloride (75 mg, 0.22 mmol) and DMAP (10 mg) in pyridine (0.2 mL) was added 1-trifluoromethyl-cyclopentane (67 mg, 0.44 mmol). The reaction was warmed to 20° C., and was stirred for 4 hours. The mixture was concentrated, and the residue was partitioned between EtOAc (20 mL) and 1 N HCl (5 mL). The organic layer was washed with 2 N HCl (5 mL), water (5 mL), and brine (1 mL), dried ($Na_2SO_4$), and concentrated. The crude material was purified by silica column (10-50% EtOAc/Hexane) to give the desired product (56 mg, 55%) as a white solid. MS: M+H$^+$467. $^1$H NMR (300 MHz, DMSO-d$_6$): 10.82 (s, 1H), 8.51 (s, 1H), 8.11-8.08 (m, 1H), 8.03-7.98 (m, 1H), 7.90-7.83 (m, 1H), 7.62 (d, J=9.1 Hz, 1H), 7.47-7.42 (m, 2H), 2.17-2.13 (m, 2H), 1.80-1.75 (m, 2H), 1.59 (bs, 4H), 1.31-1.29 (m, 2H).

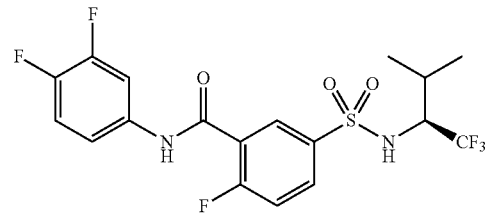 [SMILES: CC(C)[C@H](NS(=O)(=O)c1ccc(F)c(C(=O)Nc2ccc(F)c(F)c2)c1)C(F)(F)F]

(S)-N-(3,4-Difluorophenyl)-2-fluoro-5-(N-(1,1,1-trifluoro-3-methylbutan-2-yl)sulfamoyl)benzamide: General Procedure G was followed, using 3-(3,4-difluorophenyl-carbamoyl)-4-fluorobenzene-1-sulfonyl chloride (50 mg, 0.14 mmol), and (S)-1,1,1,-trifluoro-3-methyl-2-butylamine (40 mg, 0.28 mmol) to give the desired product (19 mg, 30%) as a white solid. MS: M+H$^+$455. $^1$H NMR (300 MHz, CDCl$_3$): 8.63-8.60 (m, 1H), 8.31 (d, J=14.4 Hz, 1H), 7.98-7.93 (m, 1H), 7.71-7.65 (m, 1H), 7.29-7.04 (m, 3H), 5.16 (d, J=10.3 Hz, 1H), 3.88-3.81 (m, 1H), 2.17-2.06 (m, 1H), 1.00 (d, J=6.7 Hz, 3H), 0.90 (d, J=6.7 Hz, 1H).

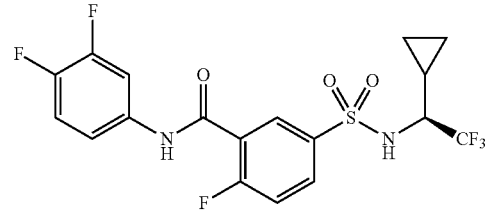 [SMILES: O=C(Nc1ccc(F)c(F)c1)c1cc(S(=O)(=O)N[C@@H](C2CC2)C(F)(F)F)ccc1F]

(S)-5-(N-(1-Cyclopropyl-2,2,2-trifluoroethyl)sulfamoyl)-N-(3,4-difluorophenyl)-2-fluorobenzamide. General Procedure G was followed, using 3-(3,4-difluorophenyl-carbamoyl)-4-fluorobenzene-1-sulfonyl chloride (50 mg, 0.14 mmol), and (S)-1-cyclopropyl-2,2,2-trifluoromethylethylamine.HCl (49 mg, 0.28 mmol) to give the desired product (25 mg, 40%) as a white solid. MS: M+H⁺453.

Example 8

General Procedure H

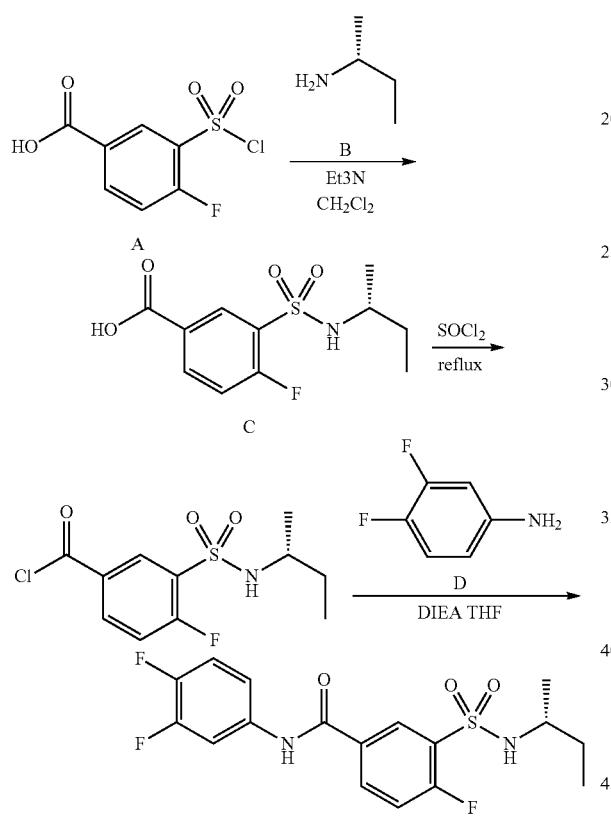

A (1.007 g, 0.0042 mol), B (0.3086 g, 0.0042 mol) and Et₃N (1.28 g, 0.01266 mol) in CH₂Cl₂ (20 mL) were stirred at room temperature overnight. The solvent was evaporated and the crude product was purified by column chromatography to give compound C (0.462 g, 40%). After drying overnight under vacuum, C (0.176 g, 0.64 mmol) in SOCl₂ was heated at 80° C. for 8 h. After which the reagent was evaporated, dried overnight. The residue was then dissolved in THF (5 mL), D (0.15 g, 1.16 mmol) was added followed by DIEA (0.5 mL) (where DIEA is N,N-diisopropylethylamine) The mixture was heated to 70° C. overnight. The solvent was evaporated, followed by EtOAc extraction. After purification by column chromatography on silica gel (EtOAc/hexane), 199 mg (80%) of final product was obtained. ¹H NMR (300 MHz, CDCl₃): δ 8.25 (dd, J=6.7, 2.4 Hz, 1H), 8.14 (m, 1H), 8.01 (m, 1H), 7.68 (m, 1H), 7.25 (m, 1H), 7.16 (m, 2H), 4.63 (d, J=8.2 Hz, 1H), 3.28 (m, 1H), 1.39 (m, 2H), 1.01 (d, J=6.7 Hz, 3H), 0.78 (t, J=7.3 Hz, 3H); MS (ES) m/z: 387.1 (M+H⁺), calculated 387.09.

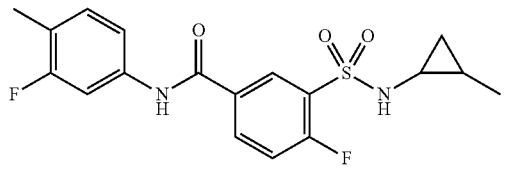

4-fluoro-N-(3-fluoro-4-methylphenyl)-3-(N-(2-methylcyclopropyl)sulfamoyl)benzamide: In a similar procedure as General Procedure H, final compound was obtained as a white solid (108 mg, 100%). ¹H NMR (300 MHz, CDCl₃): δ 8.28 (dd, J=6.4, 2.3 Hz, 1H), 8.15 (m, 1H), 8.10 (s, 1H), 7.46 (m, 1H), 7.24 (m, 1H), 7.16 (m, 2H), 5.21 (s, 1H), 2.19 (d, J=1.8 Hz, 3H), 1.89 (m, 1H), 0.95 (m, 1H), 0.87 (d, J=5.6 Hz, 3H), 0.74 (m, 1H), 0.35 (m, 1H); MS (ES) m/z: 381.1 (M+H⁺), calculated 381.10.

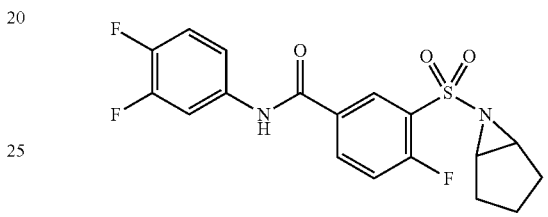

3-(6-azabicyclo[3.1.0]hexan-6-ylsulfonyl)-N-(3,4-difluorophenyl)-4-fluorobenzamide: In a similar procedure as General Procedure H, final compound was obtained as a white solid (37 mg, 13%). ¹H NMR (300 MHz, CDCl₃): δ 8.62 (dd, J=6.4, 2.5 Hz, 1H), 8.17 (m, 1H), 7.96 (s, 1H), 7.68 (m, 1H), 7.30 (t, J=9.0 Hz, 1H), 7.15 (m, 2H), 4.99 (m, 1H), 3.96 (m, 1H), 3.56 (m, 1H), 2.14 (m, 2H), 1.74 (m, 3H), 1.44 (m, 2H); MS (ES) m/z: 397.1 (M+H⁺), calculated 397.08.

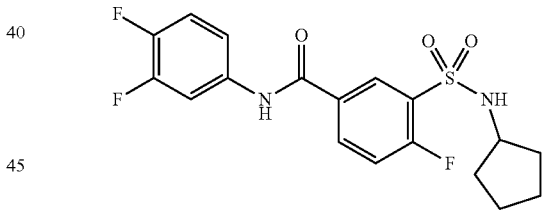

3-(N-cyclopentylsulfamoyl)-N-(3,4-difluorophenyl)-4-fluorobenzamide: In a similar procedure as General Procedure H, final compound was obtained as a white solid (168 mg, 40%). ¹H NMR (300 MHz, CDCl₃): δ 8.31 (dd, J=6.4, 2.4 Hz, 1H), 8.20 (m, 1H), 8.06 (s, 1H), 7.74 (m, 1H), 7.33 (t, J=9.0 Hz, 1H), 7.19 (m, 2H), 4.80 (d, J=7.6 Hz, 1H), 3.65 (m, 1H), 1.78 (m, 2H), 1.63 (m, 2H), 1.53 (m, 2H), 1.39 (m, 2H); MS (ES) m/z: 399.2 (M+H⁺), calculated 399.09.

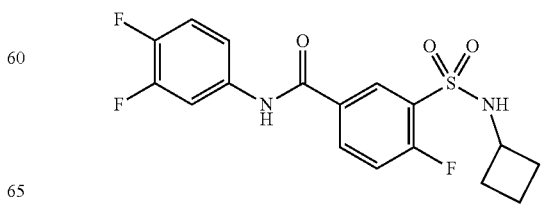

3-(N-cyclobutylsulfamoyl)-N-(3,4-difluorophenyl)-4-fluorobenzamide: In a similar procedure as General Procedure H, final compound was obtained as a white solid (328 mg, 78%). $^1$H NMR (300 MHz, CDCl$_3$): δ 8.24 (dd, J=6.7, 2.4 Hz, 1H), 8.14 (m, 2H), 7.68 (m, 1H), 7.22 (m, 1H), 7.17 (m, 2H), 5.05 (d, J=9.4 Hz, 1H), 3.79 (m, 1H), 2.06 (m, 2H), 1.79 (m, 2H), 1.67 (m, 1H); MS (ES) m/z: 385.1 (M+H$^+$), calculated 385.08.

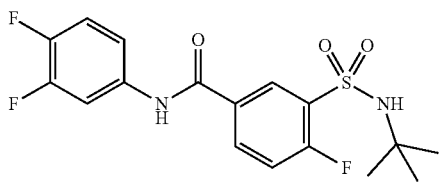 [SMILES: CC(C)(C)NS(=O)(=O)c1cc(C(=O)Nc2ccc(F)c(F)c2)ccc1F]

3-(N-(tert-butyl)sulfamoyl)-N-(3,4-difluorophenyl)-4-fluorobenzamide: In a similar procedure as General Procedure H, final compound was obtained as a white solid (261 mg, 37%). $^1$H NMR (300 MHz, CDCl$_3$): δ 8.25 (dd, J=6.5, 2.4 Hz, 1H), 8.12 (m, 1H), 7.97 (s, 1H), 7.68 (m, 1H), 7.21 (m, 1H), 7.17 (m, 1H), 4.83 (s, 1H), 1.19 (s, 9H); MS (ES) m/z: 387.1 (M+H$^+$), calculated 387.09.

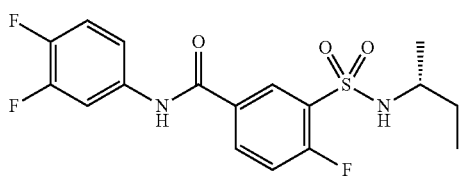 [SMILES: CC[C@@H](C)NS(=O)(=O)c1cc(C(=O)Nc2ccc(F)c(F)c2)ccc1F]

(R)-3-(N-(sec-butyl)sulfamoyl)-N-(3,4-difluorophenyl)-4-fluorobenzamide: In a similar procedure as General Procedure H, final compound was obtained as a white solid (199 mg, 80%). $^1$H NMR (300 MHz, CDCl$_3$): δ 8.25 (dd, J=6.7, 2.4 Hz, 1H), 8.14 (m, 1H), 8.01 (m, 1H), 7.68 (m, 1H), 7.25 (m, 1H), 7.16 (m, 2H), 4.63 (d, J=8.2 Hz, 1H), 3.28 (m, 1H), 1.39 (m, 2H), 1.01 (d, J=6.7 Hz, 3H), 0.78 (t, J=7.3 Hz, 3H); MS (ES) m/z: 387.1 (M+H$^+$), calculated 387.09.

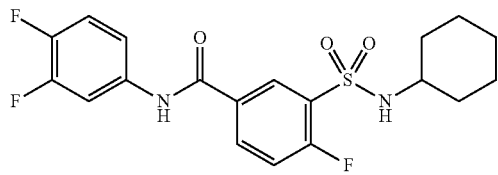 [SMILES: O=C(Nc1ccc(F)c(F)c1)c1ccc(F)c(S(=O)(=O)NC2CCCCC2)c1]

3-(N-cyclohexylsulfamoyl)-N-(3,4-difluorophenyl)-4-fluorobenzamide: In a similar procedure as General Procedure H, final compound was obtained as a white solid (106 mg, 43%). $^1$H NMR (300 MHz, CDCl$_3$): δ 8.26 (dd, J=6.6, 2.5 Hz, 1H), 8.14 (m, 2H), 7.69 (m, 1H), 7.22 (m, 1H), 7.14 (m, 2H), 4.76 (d, J=5.9 Hz, 1H), 3.18 (m, 1H), 1.65 (m, 2H), 1.58 (m, 2H), 1.48 (m, 2H), 1.17 (m, 4H); MS (ES) m/z: 413.2 (M+H$^+$), calculated 413.11.

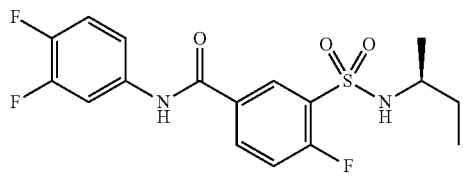 [SMILES: CC[C@H](C)NS(=O)(=O)c1cc(C(=O)Nc2ccc(F)c(F)c2)ccc1F]

(S)-3-(N-(sec-butyl)sulfamoyl)-N-(3,4-difluorophenyl)-4-fluorobenzamide: In a similar procedure as General Procedure H, final compound was obtained as a white solid (66 mg, 24%). $^1$H NMR (300 MHz, CDCl$_3$): δ 8.26 (dd, J=6.7, 2.3 Hz, 1H), 8.15 (m, 1H), 8.01 (m, 1H), 7.70 (m, 1H), 7.22 (m, 1H), 7.17 (m, 2H), 4.62 (d, J=7.2 Hz, 1H), 3.29 (m, 1H), 1.40 (m, 2H), 1.02 (d, J=6.7 Hz, 3H), 0.79 (t, J=7.3 Hz, 3H); MS (ES) m/z: 387.1 (M+H$^+$), calculated 387.09.

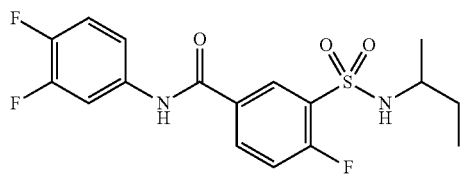 [SMILES: CCC(C)NS(=O)(=O)c1cc(C(=O)Nc2ccc(F)c(F)c2)ccc1F]

3-(N-(sec-butyl)sulfamoyl)-N-(3,4-difluorophenyl)-4-fluorobenzamide: In a similar procedure as General Procedure H, final compound was obtained as a white solid (120 mg, 43%). $^1$H NMR (300 MHz, CDCl$_3$): δ 8.25 (dd, J=6.5, 2.3 Hz, 1H), 8.14 (m, 1H), 7.90 (s, 1H), 7.68 (m, 1H), 7.20 (m, 1H), 7.17 (m, 2H), 4.57 (d, J=8.2 Hz, 1H), 3.28 (m, 1H), 1.39 (m, 2H), 1.02 (d, J=6.7 Hz, 3H), 0.79 (t, J=7.4 Hz, 3H); MS (ES) m/z: 387.1 (M+H$^+$), calculated 387.09.

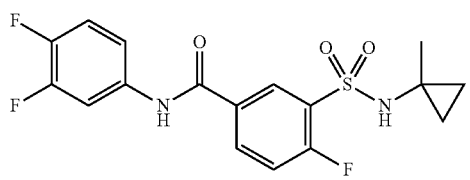 [SMILES: CC1(NS(=O)(=O)c2cc(C(=O)Nc3ccc(F)c(F)c3)ccc2F)CC1]

N-(3,4-difluorophenyl)-4-fluoro-3-(N-(1-methylcyclopropyl)sulfamoyl)benzamide: In a similar procedure as General Procedure H, final compound was obtained as a white solid (63 mg, 15%). $^1$H NMR (300 MHz, CDCl$_3$): δ 8.28 (dd, J=6.5, 2.5 Hz, 1H), 8.16 (m, 1H), 7.89 (s, 1H), 7.70 (m, 1H), 7.21 (m, 1H), 7.16 (m, 2H), 5.23 (d, J=2.3 Hz, 1H), 1.17 (m, 5H), 0.80 (m, 2H); MS (ES) m/z: 385.1 (M+H$^+$), calculated 385.08.

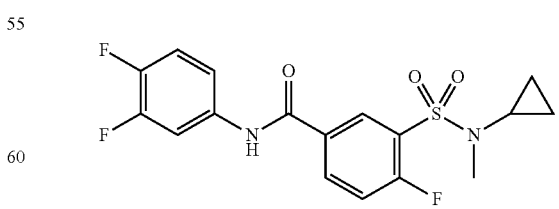

3-(N-cyclopropyl-N-methylsulfamoyl)-N-(3,4-difluorophenyl)-4-fluorobenzamide: In a similar procedure as General Procedure H, final compound was obtained as a white solid (158 mg, 83%). $^1$H NMR (300 MHz, CDCl$_3$): δ 8.24

(dd, J=6.2, 2.6 Hz, 1H), 8.13 (m, 1H), 8.01 (s, 1H), 7.69 (m, 1H), 7.21 (m, 1H), 7.17 (m, 2H), 2.85 (d, J=2.1 Hz, 3H), 2.06 (m, 1H), 0.77 (m, 2H), 0.67 (m, 2H); MS (ES) m/z: 385.1 (M+H⁺), calculated 385.08.

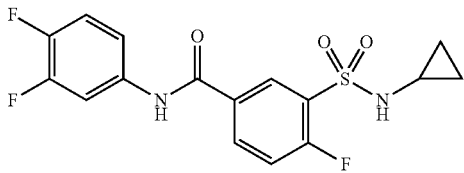 [SMILES: O=C(Nc1ccc(F)c(F)c1)c1ccc(F)c(S(=O)(=O)NC2CC2)c1]

3-(N-cyclopropylsulfamoyl)-N-(3,4-difluorophenyl)-4-fluorobenzamide: In a similar procedure as General Procedure H, final compound was obtained as a white solid (118 mg, 35%). ¹H NMR (300 MHz, CDCl₃): δ 8.30 (dd, J=6.4, 2.3 Hz, 1H), 8.19 (m, 1H), 7.98 (s, 1H), 7.70 (m, 1H), 7.31 (t, J=8.9 Hz 1H), 7.16 (m, 2H), 5.18 (s, 1H), 2.23 (m, 1H), 0.61 (m, 4H); MS (ES) m/z: 371.1 (M+H⁺), calculated 371.35.

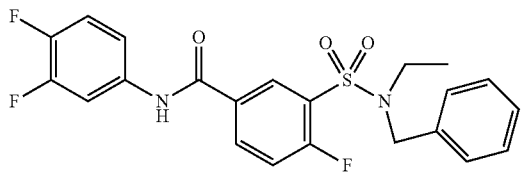 [SMILES: CCN(Cc1ccccc1)S(=O)(=O)c1cc(C(=O)Nc2ccc(F)c(F)c2)ccc1F]

3-(N-benzyl-N-ethylsulfamoyl)-N-(3,4-difluorophenyl)-4-fluorobenzamide: In a similar procedure as General Procedure H, final compound was obtained as a white solid (60 mg, 11%). ¹H NMR (300 MHz, CDCl₃): δ 8.21 (dd, J=6.2, 2.4 Hz, 1H), 8.11 (m, 1H), 7.94 (s, 1H), 7.69 (m, 1H), 7.25 (m, 1H), 7.18 (m, 7H), 4.45 (s, 2H), 3.26 (m, 2H), 0.91 (t, J=7.2 Hz, 3H); MS (ES) m/z: 449.2 (M+H⁺), calculated 449.11.

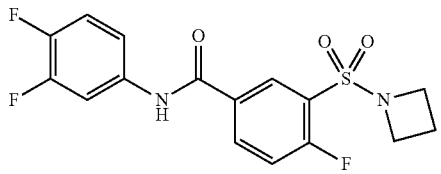 [SMILES: O=C(Nc1ccc(F)c(F)c1)c1ccc(F)c(S(=O)(=O)N2CCC2)c1]

3-(azetidin-1-ylsulfonyl)-N-(3,4-difluorophenyl)-4-fluorobenzamide: In a similar procedure as General Procedure H, final compound was obtained as a white solid (5 mg, 2%). ¹H NMR (300 MHz, CDCl₃): δ 8.25 (dd, J=6.2, 2.3 Hz, 1H), 8.16 (m, 2H), 7.68 (m, 1H), 7.21 (m, 1H), 7.15 (m, 2H), 3.54 (m, 4H), 2.08 (m, 2H); MS (ES) m/z: 371.1 (M+H⁺), calculated 371.06.

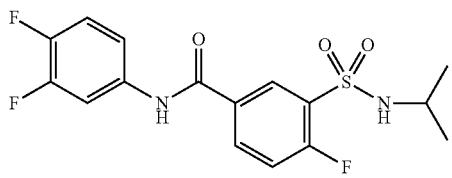 [SMILES: CC(C)NS(=O)(=O)c1cc(C(=O)Nc2ccc(F)c(F)c2)ccc1F]

N-(3,4-difluorophenyl)-4-fluoro-3-(N-isopropylsulfamoyl)benzamide: In a similar procedure as General Procedure H, final compound was obtained as a white solid (410 mg, 87%). ¹H NMR (300 MHz, CDCl₃): δ 8.26 (dd, J=6.4, 2.3 Hz, 1H), 8.14 (m, 1H), 8.02 (s, 1H), 7.68 (m, 1H), 7.25 (m, 1H), 7.15 (m, 2H), 4.64 (d, J=7.6 Hz, 1H), 3.50 (m, 1H), 1.07 (d, J=6.4 Hz, 2H); MS (ES) m/z: 373.1 (M+H⁺), calculated 373.08.

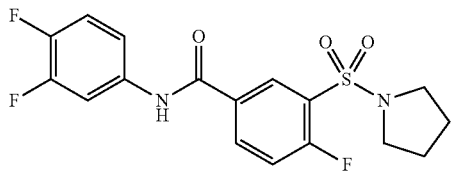 [SMILES: O=C(Nc1ccc(F)c(F)c1)c1ccc(F)c(S(=O)(=O)N2CCCC2)c1]

N-(3,4-difluorophenyl)-4-fluoro-3-(pyrrolidin-1-ylsulfonyl)benzamide: In a similar procedure as General Procedure H, final compound was obtained as a white solid (350 mg, 70%). ¹H NMR (300 MHz, CDCl₃): δ 8.25 (dd, J=6.2, 2.3 Hz, 1H), 8.11 (m, 2H), 7.69 (m, 1H), 7.22 (m, 1H), 7.11 (m, 2H), 3.32 (m, 4H), 1.80 (m, 4H); MS (ES) m/z: 385.1 (M+H⁺), calculated 385.08.

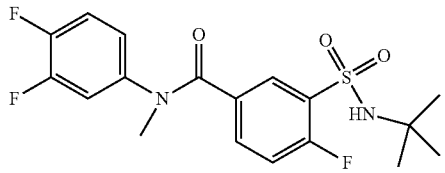 [SMILES: CN(C(=O)c1ccc(F)c(S(=O)(=O)NC(C)(C)C)c1)c1ccc(F)c(F)c1]

3-(N-(tert-butyl)sulfamoyl)-N-(3,4-difluorophenyl)-4-fluoro-N-methylbenzamide: In a similar procedure as General Procedure H, final compound was obtained as a beige solid (118 mg, 43.4%). ¹H NMR (300 MHz, CD3OD): 7.73-7.67 (m, 2H), 7.31-7.14 (m, 3H), 7.04-7.02 (m, 1H), 3.45 (s, 3H), 1.06 (s, 9H); MS (ES) m/z: 401.2 (M+H⁺), calculated 401.11.

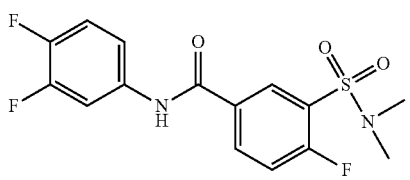 [SMILES: CN(C)S(=O)(=O)c1cc(C(=O)Nc2ccc(F)c(F)c2)ccc1F]

N-(3,4-difluorophenyl)-3-(N,N-dimethylsulfamoyl)-4-fluorobenzamide: In a similar procedure as General Procedure H, final compound was obtained as a white solid (128 mg, 44%). ¹H NMR (300 MHz, CD3OD): 8.13-8.10 (dd, J=6.1, 2.3 Hz, 1H), 8.02-7.97 (m, 1H), 7.86-7.79 (m, 1H), 7.55-7.49 (dd, J=10, 8.8 Hz, 1H), 7.41-7.36 (m, 1H), 7.31-7.22 (m, 1H), 2.73 (s, 6H); MS (ES) m/z: 359.1 (M+H⁺), calculated 359.06.

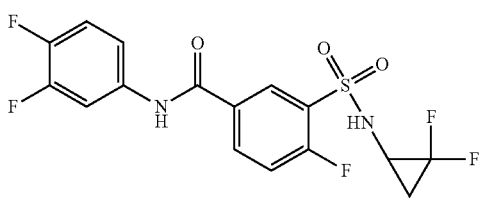 [SMILES: O=C(Nc1ccc(F)c(F)c1)c1ccc(F)c(S(=O)(=O)NC2CC2(F)F)c1]

3-(N-(2,2-Difluorocyclopropyl)sulfamoyl)-N-(3,4-difluorophenyl)-4-fluorobenzamide: In a similar procedure as General Procedure H, final compound was obtained as a white solid (3 mg, 3%). $^1$H NMR (300 MHz, CDCl$_3$): δ 8.32 (m, 1H), 8.20 (m, 1H), 7.98 (s, 1H), 7.70 (m, 1H), 7.30 (m, 1H), 7.16 (m, 2H), 5.18 (s, 1H), 2.06 (m, 1H), 0.77 (m, 1H), 0.68 (m, 1H); MS (ES) m/z: 407.1 (M+H$^+$), calculated 407.04.

Example 9

General Procedure I

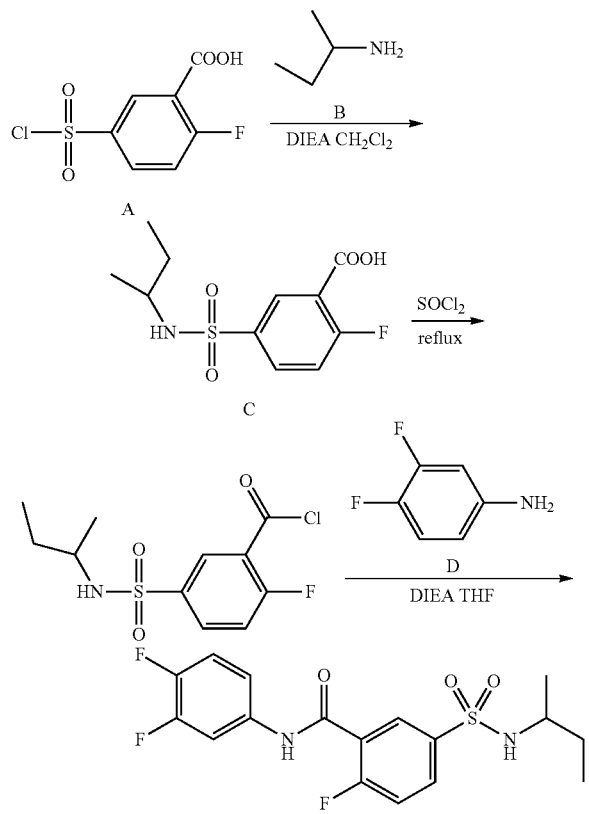

A (0.506 g, 0.0021 mol), B (0.155 g, 0.00212 mol) and DIEA (1.1 mL, 0.00636 mol) (where DIEA is N,N-diisopropylethylamine) in CH$_2$Cl$_2$ were stirred at room temperature overnight. The solvent was evaporated and the crude product was purified by column chromatography on silica gel to give compound C (0.56 g, 96%). After drying overnight under vacuum, C (0.56 g, 0.0020 mol) in SOCl$_2$ was heated at 80° C. for 8 h. After which the reagent was evaporated, dried under vacuum. The residue was then dissolved in THF (5 mL), D (0.26 g, 0.0020 mol) was added followed by DIEA (0.8 mL). The mixture was heated to 70° C. overnight. The solvent was evaporated, followed by EtOAc extraction. After purification by column chromatography on silica gel (EtOAc/hexane), 0.45 g (57%) of final product was obtained. $^1$H NMR (300 MHz, CDCl$_3$): δ 8.61 (dd, J=7.1, 2.5 Hz, 1H), 8.30 (d, J=14.1 Hz, 1H), 8.00 (m, 1H), 7.70 (m, 1H), 7.26 (m, 1H), 7.15 (m, 2H), 4.46 (d, J=8.2 Hz, 1H), 3.25 (m, 1H), 1.34 (m, 2H), 1.01 (d, J=6.4 Hz, 3H), 0.75 (t, J=7.3 Hz, 3H); MS (ES) m/z: 387.2 (M+H$^+$), calculated 387.09.

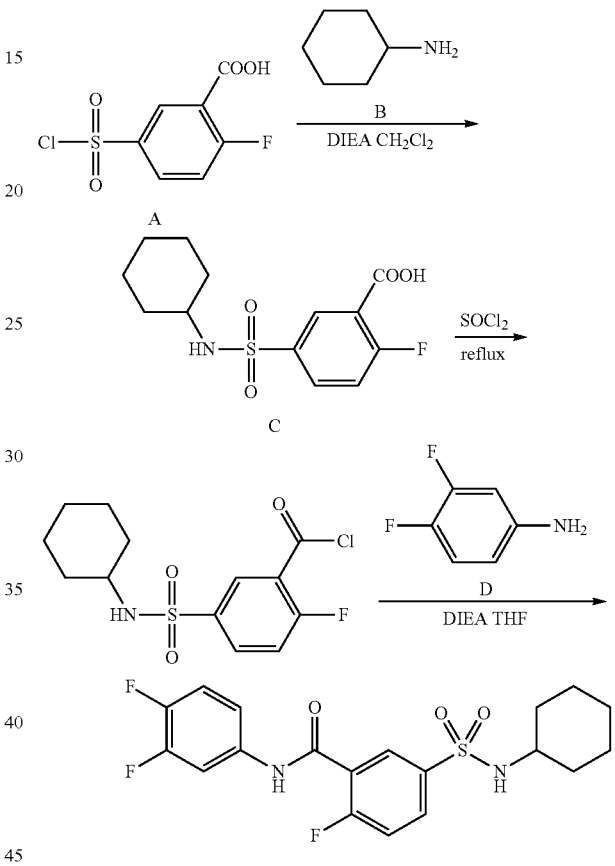

A (0.508 g, 0.0021 mol), B (0.211 g, 0.00212 mol) and DIEA (1.1 mL, 0.00636 mol) (where DIEA is N,N-diisopropylethylamine) in CH$_2$Cl$_2$ were stirred at room temperature overnight. The solvent was evaporated and the crude product was purified by column chromatography on silica gel to give compound C (0.6 g, 95%). After drying overnight under vacuum, C (0.22 g, 0.737 mmol) in SOCl$_2$ (5 mL) was heated at 80° C. for overnight. After which the reagent was evaporated, dried under vacuum. The residue was then dissolved in THF (5 mL), D (95 mg, 0.737 mmol) was added followed by DIEA (0.8 mL). The mixture was heated to 70° C. overnight. The solvent was evaporated, followed by EtOAc extraction. After purification by column chromatography on silica gel (EtOAc/hexane), 0.192 g (63%) of final product 18083 was obtained and submitted. $^1$H NMR (300 MHz, CDCl$_3$): δ 8.59 (dd, J=7.2, 2.4 Hz, 1H), 8.33 (d, J=13.4 Hz, 1H), 8.00 (m, 1H), 7.70 (m, 1H), 7.20 (m, 1H), 7.12 (m, 2H), 4.62 (d, J=7.9 Hz, 1H), 3.12 (m, 1H), 1.72 (m, 2H), 1.59 (m, 2H), 1.46 (m, 2H), 1.17 (m, 4H); MS (ES) m/z: 413.2 (M+H$^+$), calculated 413.11.

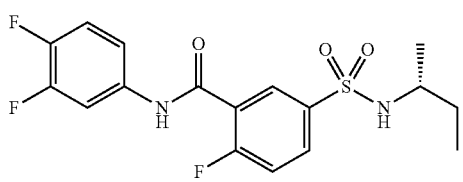

(R)-5-(N-(sec-butyl)sulfamoyl)-N-(3,4-difluorophenyl)-2-fluorobenzamide: In a similar procedure as General Procedure I, final compound was obtained as a white solid (137 mg, 75%). $^1$H NMR (300 MHz, CDCl$_3$): δ 8.60 (dd, J=7.1, 2.5 Hz, 1H), 8.32 (d, J=13.8 Hz, 1 H), 8.00 (m, 1H), 7.70 (m, 1H), 7.24 (m, 1H), 7.13 (m, 2H), 4.45 (d, J=8.2 Hz, 1H), 3.26 (m, 1H), 1.37 (m, 2H), 1.01 (d, J=6.4 Hz, 3H), 0.75 (t, J=7.4 Hz, 3H); MS (ES) m/z: 387.1 (M+H$^+$), calculated 387.09.

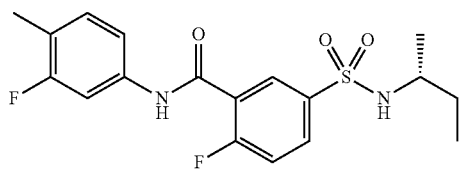 [SMILES: CC[C@@H](C)NS(=O)(=O)c1ccc(F)c(C(=O)Nc2ccc(C)c(F)c2)c1]

(R)-5-(N-(sec-butyl)sulfamoyl)-2-fluoro-N-(3-fluoro-4-methylphenyl)benzamide: In a similar procedure as General Procedure I, final compound was obtained as a white solid (117 mg, 65%). $^1$H NMR (300 MHz, CDCl$_3$): δ 8.60 (dd, J=7.0, 2.4 Hz, 1H), 8.29 (d, J=13.8 Hz, 1H), 7.99 (m, 1H), 7.47 (m, 1H), 7.25 (m, 1H), 7.09 (m, 2H), 4.46 (m, 1H), 3.25 (m, 1H), 2.20 (d, J=2.0 Hz, 3H), 1.36 (m, 2H), 1.00 (d, J=6.4 Hz, 3H), 0.75 (t, J=7.5 Hz, 3H); MS (ES) m/z: 383.2 (M+H$^+$), calculated 383.12.

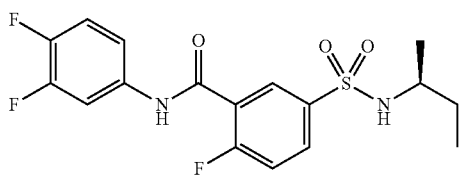 [SMILES: CC[C@H](C)NS(=O)(=O)c1ccc(F)c(C(=O)Nc2ccc(F)c(F)c2)c1]

(S)-5-(N-(sec-butyl)sulfamoyl)-N-(3,4-difluorophenyl)-2-fluorobenzamide: In a similar procedure as General Procedure I, final compound was obtained as a white solid (134 mg, 45%). $^1$H NMR (300 MHz, CDCl$_3$): δ 8.61 (dd, J=7.1, 2.5 Hz, 1H), 8.29 (d, J=14.9 Hz, 1H), 8.00 (m, 1H), 7.71 (m, 1H), 7.23 (m, 1H), 7.15 (m, 2H), 4.31 (d, J=8.2 Hz, 1H), 3.26 (m, 1H), 1.37 (m, 2H), 1.01 (d, J=6.4 Hz, 3H), 0.75 (t, J=7.4 Hz, 3H); MS (ES) m/z: 387.1 (M+H$^+$), calculated 387.09.

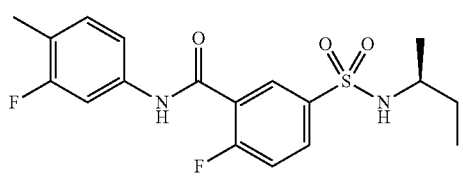 [SMILES: CC[C@H](C)NS(=O)(=O)c1ccc(F)c(C(=O)Nc2ccc(C)c(F)c2)c1]

(S)-5-(N-(sec-butyl)sulfamoyl)-2-fluoro-N-(3-fluoro-4-methylphenyl)benzamide: In a similar procedure as General Procedure I, final compound was obtained as a white solid (86 mg, 44%). $^1$H NMR (300 MHz, CDCl$_3$): δ 8.61 (dd, J=7.1, 2.5 Hz, 1H), 8.29 (d, J=14.4 Hz, 1H), 8.00 (m, 1H), 7.49 (m, 1H), 7.25 (m, 1H), 7.09 (m, 2H), 4.40 (m, 1H), 3.26 (m, 1H), 2.20 (d, J=2.0 Hz, 3H), 1.36 (m, 2H), 1.00 (d, J=6.4 Hz, 3H), 0.75 (t, J=7.5 Hz, 3H); MS (ES) m/z: 383.2 (M+H$^+$), calculated 383.12.

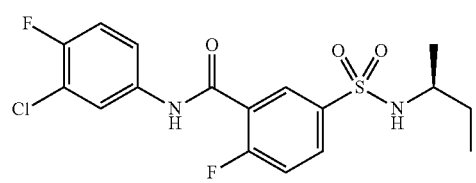 [SMILES: CC[C@H](C)NS(=O)(=O)c1ccc(F)c(C(=O)Nc2ccc(F)c(Cl)c2)c1]

(S)-5-(N-(sec-butyl)sulfamoyl)-N-(3-chloro-4-fluorophenyl)-2-fluorobenzamide: In a similar procedure as General Procedure I, final compound was obtained as a white solid (97 mg, 47%). $^1$H NMR (300 MHz, CDCl$_3$): δ 8.60 (dd, J=7.2, 2.5 Hz, 1H), 8.27 (d, J=14.1 Hz, 1H), 8.00 (m, 1H), 7.78 (dd, J=6.6, 2.8 Hz, 1H), 7.39 (m, 1H), 7.25 (m, 1H), 7.09 (t, J=8.7 Hz, 1H), 4.40 (d, J=8.2 Hz, 1H), 3.26 (m, 1H), 1.35 (m, 2H), 1.00 (d, J=6.7 Hz, 3H), 0.75 (t, J=7.5 Hz, 3H); MS (ES) m/z: 403.1 (M+H$^+$), calculated 403.06.

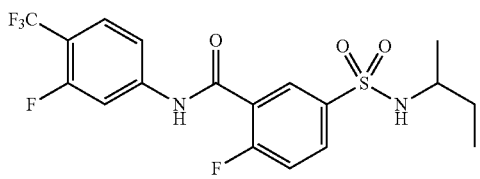 [SMILES: CCC(C)NS(=O)(=O)c1ccc(F)c(C(=O)Nc2ccc(C(F)(F)F)c(F)c2)c1]

5-(N-(sec-butyl)sulfamoyl)-2-fluoro-N-(3-fluoro-4-(trifluoromethyl)phenyl)benzamide: In a similar procedure as General Procedure I, final compound was obtained as a white solid (68 mg, 38%). $^1$H NMR (300 MHz, CDCl$_3$): δ 8.60 (dd, J=7.2, 2.4 Hz, 1H), 8.48 (d, J=14.4 Hz, 1H), 8.02 (m, 1H), 7.77 (d, J=11.7 Hz, 1H), 7.53 (t, J=8.2 Hz, 1H), 7.27 (m, 1H), 4.38 (d, J=8.2 Hz, 1H), 3.25 (m, 1H), 1.38 (m, 2H), 1.01 (m, 3H), 0.75 (t, J=7.5 Hz, 3H); MS (ES) m/z: 437.2 (M+H$^+$), calculated 437.09.

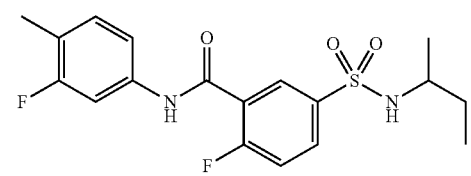 [SMILES: CCC(C)NS(=O)(=O)c1ccc(F)c(C(=O)Nc2ccc(C)c(F)c2)c1]

5-(N-(sec-butyl)sulfamoyl)-2-fluoro-N-(3-fluoro-4-methylphenyl)benzamide: In a similar procedure as General Procedure I, final compound was obtained as a white solid (113 mg, 72%). $^1$H NMR (300 MHz, CDCl$_3$): δ 8.60 (dd, J=7.0, 2.6 Hz, 1H), 8.29 (d, J=13.5 Hz, 1H), 7.99 (m, 1H), 7.47 (m, 1H), 7.25 (m, 1H), 7.09 (m, 2H), 4.46 (m, 1H), 3.25 (m, 1H), 2.20 (d, J=2.0 Hz, 3H), 1.36 (m, 2H), 1.00 (m, 3H), 0.75 (t, J=7.5 Hz, 3H); MS (ES) m/z: 383.2 (M+H$^+$), calculated 383.12.

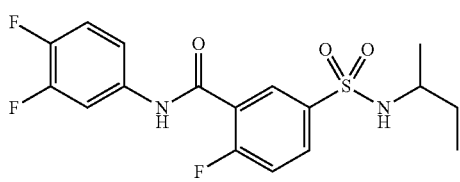 [SMILES: CCC(C)NS(=O)(=O)c1ccc(F)c(C(=O)Nc2ccc(F)c(F)c2)c1]

5-(N-(sec-butyl)sulfamoyl)-N-(3,4-difluorophenyl)-2-fluorobenzamide: In a similar procedure as General Procedure I, final compound was obtained as a white solid (101 mg, 63%). $^1$H NMR (300 MHz, CDCl$_3$): δ 8.61 (dd, J=7.1, 2.5 Hz, 1H), 8.30 (d, J=14.1 Hz, 1H), 8.00 (m, 1H), 7.70 (m, 1H), 7.26 (m, 1H), 7.15 (m, 2H), 4.46 (d, J=8.2 Hz, 1H), 3.25 (m, 1H), 1.34 (m, 2H), 1.01 (d, J=6.4 Hz, 3H), 0.75 (t, J=7.3 Hz, 3H); MS (ES) m/z: 387.2 (M+H$^+$), calculated 387.09.

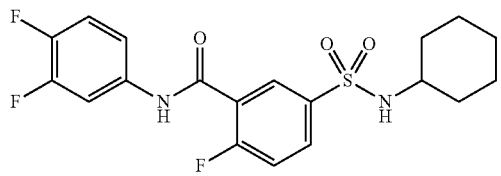 [SMILES: O=C(Nc1ccc(F)c(F)c1)c1cc(S(=O)(=O)NC2CCCCC2)ccc1F]

5-(N-cyclohexylsulfamoyl)-N-(3,4-difluorophenyl)-2-fluorobenzamide: In a similar procedure as General Procedure I, final compound was obtained as a white solid (238 mg, 46%). $^1$H NMR (300 MHz, CDCl$_3$): δ 8.59 (dd, J=7.2, 2.4 Hz, 1H), 8.33 (d, J=13.4 Hz, 1H), 8.00 (m, 1H), 7.70 (m, 1H), 7.20 (m, 1H), 7.12 (m, 2H), 4.62 (d, J=7.9 Hz, 1H), 3.12 (m, 1H), 1.72 (m, 2H), 1.59 (m, 2H), 1.46 (m, 2H), 1.17 (m, 4H); MS (ES) m/z: 413.2 (M+H$^+$), calculated 413.11.

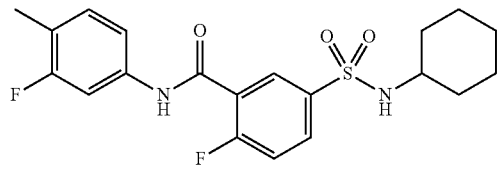 [SMILES: Cc1ccc(NC(=O)c2cc(S(=O)(=O)NC3CCCCC3)ccc2F)cc1F]

5-(N-cyclohexylsulfamoyl)-2-fluoro-N-(3-fluoro-4-methylphenyl)benzamide: In a similar procedure as General Procedure I, final compound was obtained as a white solid (131 mg, 34%). $^1$H NMR (300 MHz, CDCl$_3$): δ 8.59 (dd, J=7.2, 2.4 Hz, 1H), 8.33 (d, J=14.1 Hz, 1H), 8.00 (m, 1H), 7.48 (m, 1H), 7.25 (m, 1H), 7.11 (m, 2H), 4.59 (d, J=7.9 Hz, 1H), 3.12 (m, 1H), 2.20 (s, 3H), 1.72 (m, 2H), 1.59 (m, 2H), 1.46 (m, 2H), 1.15 (m, 4H); MS (ES) m/z: 409.2 (M+H$^+$), calculated 409.13.

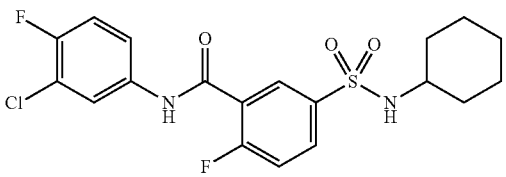 [SMILES: O=C(Nc1ccc(F)c(Cl)c1)c1cc(S(=O)(=O)NC2CCCCC2)ccc1F]

N-(3-chloro-4-fluorophenyl)-5-(N-cyclohexylsulfamoyl)-2-fluorobenzamide: In a similar procedure as General Procedure I, final compound was obtained as a white solid (139 mg, 35%). $^1$H NMR (300 MHz, CDCl$_3$): δ 8.59 (dd, J=7.1, 2.6 Hz, 1H), 8.33 (d, J=13.7 Hz, 1H), 8.00 (m, 1H), 7.78 (m, 1H), 7.39 (m, 1H), 7.26 (m, 1H), 7.18 (m, 1H), 4.67 (d, J=7.9 Hz, 1H), 3.12 (m, 1H), 1.71 (m, 2H), 1.59 (m, 2H), 1.46 (m, 2H), 1.12 (m, 4H); MS (ES) m/z: 429.1 (M+H$^+$), calculated 429.08.

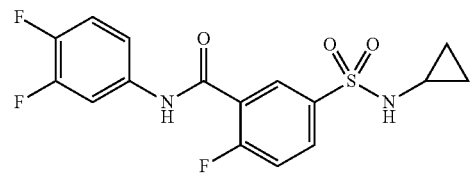 [SMILES: O=C(Nc1ccc(F)c(F)c1)c1cc(S(=O)(=O)NC2CC2)ccc1F]

5-(N-cyclopropylsulfamoyl)-N-(3,4-difluorophenyl)-2-fluorobenzamide: In a similar procedure as General Procedure I, final compound was obtained as a white solid (238 mg, 26%). $^1$H NMR (300 MHz, CDCl$_3$): δ 8.60 (dd, J=7.0, 2.4 Hz, 1H), 8.30 (d, J=13.7 Hz, 1H), 8.00 (m, 1H), 7.71 (m, 1H), 7.32 (m, 1H), 7.15 (m, 2H), 4.97 (s, 1H), 2.23 (m, 1H), 0.78 (m, 2H); MS (ES) m/z: 371.1 (M+H$^+$), calculated 371.06.

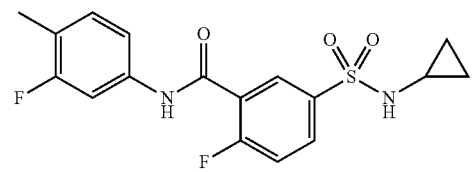 [SMILES: Cc1ccc(NC(=O)c2cc(S(=O)(=O)NC3CC3)ccc2F)cc1F]

5-(N-cyclopropylsulfamoyl)-2-fluoro-N-(3-fluoro-4-methylphenyl)benzamide: In a similar procedure as General Procedure I, final compound was obtained as a white solid (156 mg, 32%). $^1$H NMR (300 MHz, CDCl$_3$): δ 8.61 (dd, J=7.0, 2.6 Hz, 1H), 8.30 (d, J=13.8 Hz, 1H), 8.00 (m, 1H), 7.48 (m, 1H), 7.28 (m, 1H), 7.11 (m, 2H), 4.99 (s, 1H), 2.23 (m, 1H), 2.21 (s, 3H), 0.80 (m, 1H), 0.58 (m, 3H); MS (ES) m/z: 367.1 (M+H$^+$), calculated 367.08.

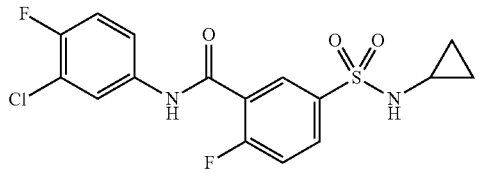 [SMILES: O=C(Nc1ccc(F)c(Cl)c1)c1cc(S(=O)(=O)NC2CC2)ccc1F]

N-(3-chloro-4-fluorophenyl)-5-(N-cyclopropylsulfamoyl)-2-fluorobenzamide: In a similar procedure as General Procedure I, final compound was obtained as a white solid (119 mg, 26%). $^1$H NMR (300 MHz, CDCl$_3$): δ 8.61 (dd, J=7.0, 2.5 Hz, 1H), 8.29 (d, J=13.7 Hz, 1H), 8.00 (m, 1H), 7.78 (m, 1H), 7.41 (m, 1H), 7.30 (m, 1H), 7.11 (m, 1H), 4.99 (s, 1H), 2.22 (m, 1H), 0.78 (m, 1H), 0.58 (m, 3H); MS (ES) m/z: 387.1 (M+H$^+$), calculated 387.03.

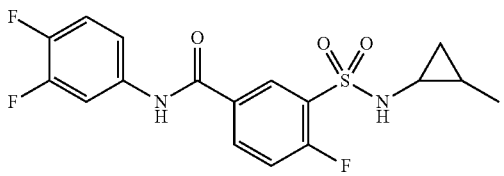 [SMILES: CC1CC1NS(=O)(=O)c1cc(C(=O)Nc2ccc(F)c(F)c2)ccc1F]

N-(3,4-difluorophenyl)-4-fluoro-3-(N-(2-methylcyclopropyl)sulfamoyl)benzamide: In a similar procedure as General Procedure I, final compound was obtained as a white solid (90 mg, 85%). $^1$H NMR (300 MHz, CDCl$_3$): δ 8.61 (dd, J=6.5, 2.3 Hz, 1H), 8.17 (m, 1H), 8.01 (s, 1H), 7.69 (m, 1H), 7.29 (m, 1H), 7.17 (m, 1H), 5.17 (s, 1H), 1.89 (m, 1H), 1.52 (d, J=9.0 Hz, 3H), 0.88 (m, 2H), 0.75 (m, 1H); MS (ES) m/z: 385.1 (M+H$^+$), calculated 385.08.

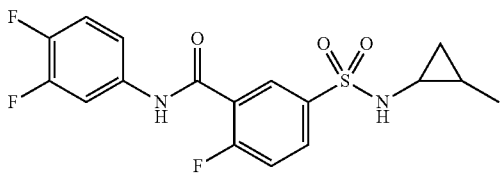 [SMILES: CC1CC1NS(=O)(=O)c1ccc(F)c(C(=O)Nc2ccc(F)c(F)c2)c1]

N-(3,4-difluorophenyl)-2-fluoro-5-(N-(2-methylcyclopropyl)sulfamoyl)benzamide: In a similar procedure as General Procedure I, final compound was obtained as a white solid (4 mg, 2%). $^1$H NMR (300 MHz, CDCl$_3$): δ 8.61 (dd, J=7.1, 2.5 Hz, 1H), 8.30 (d, J=13.5 Hz, 1H), 8.02 (m, 1H), 7.70 (m, 1H), 7.30 (m, 1H), 7.15 (m, 2H), 4.93 (s, 1H), 1.88 (m, 1H), 0.91 (m, 3H), 0.81 (m, 1H), 0.70 (m, 1H), 0.37 (m, 1H); MS (ES) m/z: 385.1 (M+H$^+$), calculated 385.08.

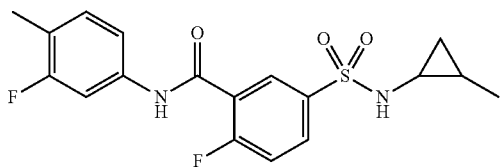

2-fluoro-N-(3-fluoro-4-methylphenyl)-5-(N-(2-methylcyclopropyl)sulfamoyl)benzamide: In a similar procedure as General Procedure I, final compound was obtained as a white solid (5 mg, 5%). $^1$H NMR (300 MHz, CDCl$_3$): δ 8.62 (dd, J=7.0, 2.6 Hz, 1H), 8.26 (d, J=14.1 Hz, 1H), 8.01 (m, 1H), 7.49 (d, J=12.0 Hz, 1H), 7.29 (dd, J=11.7, 8.2 Hz, 1H), 7.11 (m, 2H), 4.84 (s, 1H), 2.20 (d, J=2.2 Hz, 3H), 1.89 (m, 1H), 0.90 (m, 3H), 0.74 (m, 2H), 0.35 (m, 1H); MS (ES) m/z: 381.2 (M+H$^+$), calculated 381.10.

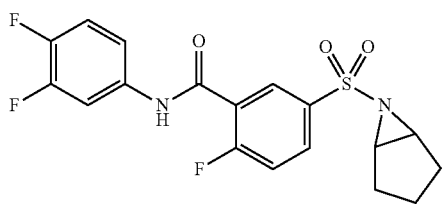 [SMILES: O=C(Nc1ccc(F)c(F)c1)c1cc(S(=O)(=O)N2C3CCCC32)ccc1F]

5-(6-azabicyclo[3.1.0]hexan-6-ylsulfonyl)-N-(3,4-difluorophenyl)-2-fluorobenzamide: In a similar procedure as General Procedure I, final compound was obtained as a white solid (27 mg, 12%). $^1$H NMR (300 MHz, CDCl$_3$): δ 8.62 (dd, J=7.0, 2.3 Hz, 1H), 8.29 (d, J=14.4 Hz, 1H), 8.04 (m, 1H), 7.69 (m, 1H), 7.30 (dd, J=11.4, 8.8 Hz, 1H), 7.16 (m, 2H), 4.78 (d, J=6.2 Hz, 1H), 3.94 (m, 1H), 3.54 (m, 1H), 2.15 (m, 2H), 1.78 (m, 2H), 1.66 (m, 1H), 1.41 (m, 2H); MS (ES) m/z: 397.2 (M+H$^+$), calculated 397.08.

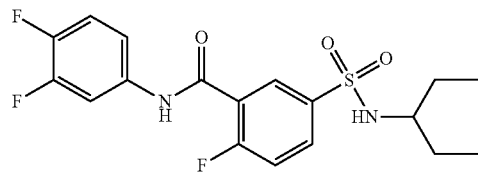 [SMILES: CCC(CC)NS(=O)(=O)c1ccc(F)c(C(=O)Nc2ccc(F)c(F)c2)c1]

N-(3,4-difluorophenyl)-2-fluoro-5-(N-(pentan-3-yl)sulfamoyl)benzamide: In a similar procedure as General Procedure I, final compound was obtained as a beige solid (239 mg, 74%). $^1$H NMR (300 MHz, CD$_3$OD): δ 8.22-8.19 (dd, J=6.4, 2.4 Hz, 1H), 8.07-8.02 (m, 1H), 7.86-7.79 (m, 1H), 7.48-7.36 (m, 2H), 7.31-7.21 (m, 1H), 3.11-3.06 (m, 1H), 1.51-1.42 (m, 2H), 1.40-1.28 (m, 2H), 0.79-0.74 (t, J=7.3 Hz, 6H); MS (ES) m/z: 401.2 (M+H$^+$), calculated 401.11.

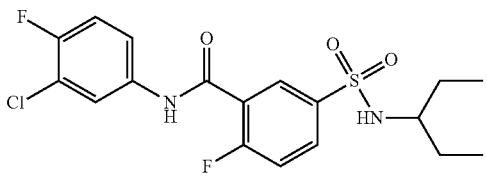 [SMILES: CCC(CC)NS(=O)(=O)c1ccc(F)c(C(=O)Nc2ccc(F)c(Cl)c2)c1]

N-(3-chloro-4-fluorophenyl)-2-fluoro-5-(N-(pentan-3-yl)sulfamoyl)benzamide: In a similar procedure as General Procedure I, final compound was obtained as a beige solid (244 mg, 72%). $^1$H NMR (300 MHz, CD$_3$OD): δ 8.23-8.20 (dd, J=6.4, 2.4 Hz, 1H), 8.07-8.02 (m, 1H), 7.98-7.94 (dd, J=6.6, 2.6 Hz, 1H), 7.61-7.56 (m, 1H), 7.48-7.42 (dd, J=9.9, 8.8 Hz, 1H), 7.28-7.22 (t, J=9.1 Hz, 1H), 3.11-3.06 (m, 1H), 1.51-1.40 (m, 2H), 1.38-1.28 (m, 2H), 0.79-0.74 (t, J=7.6 Hz, 6H); MS (ES) m/z: 417.1 (M+H$^+$), calculated 417.08.

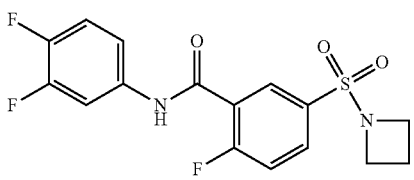 [SMILES: O=C(Nc1ccc(F)c(F)c1)c1cc(S(=O)(=O)N2CCC2)ccc1F]

5-(azetidin-1-ylsulfonyl)-N-(3,4-difluorophenyl)-2-fluorobenzamide: In a similar procedure as General Procedure I, final compound was obtained as a beige solid (34 mg, 12%). $^1$H NMR (300 MHz, CD$_3$OD): δ 8.56 (bs, 1H), 8.10-8.07 (dd, J=6.4, 2.4 Hz, 1H), 7.89-7.84 (m, 1H), 7.38-7.32 (dd, J=10, 8.6 Hz, 1H), 7.18-7.02 (m, 2H), 6.89-6.83 (m, 1H), 3.66-3.62 (t, J=6.5 Hz, 2H), 3.56-3.50 (m, 2H), 2.11-2.01 (m, 2H); MS (ES) m/z: 371.1 (M+H$^+$), calculated 371.06.

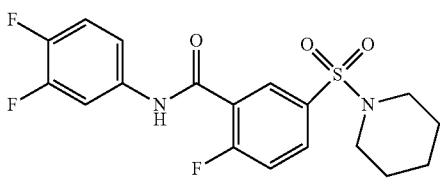 [SMILES: O=C(Nc1ccc(F)c(F)c1)c1cc(S(=O)(=O)N2CCCCC2)ccc1F]

N-(3,4-difluorophenyl)-2-fluoro-5-(piperidin-1-ylsulfonyl)benzamide: In a similar procedure as General Procedure I, final compound was obtained as a beige solid (74 mg, 26%). $^1$H NMR (300 MHz, CD$_3$OD): δ 8.10-8.07 (dd, J=6.4, 2.4 Hz, 1H), 7.99-7.94 (m, 1H), 7.85-7.79 (m, 1H), 7.54-7.47 (dd, J=9.6, 8.6 Hz, 1H), 7.40-7.36 (m, 1H), 7.31-7.22 (m, 1H), 3.04-3.01 (t, J=5.3 Hz, 4H), 1.68-1.61 (m, 4H), 1.50-1.44 (m, 2H); MS (ES) m/z: 399.2 (M+H$^+$), calculated 399.09.

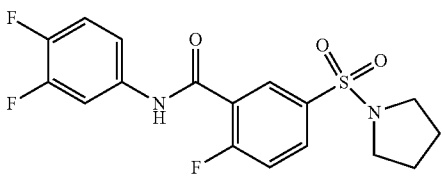 [SMILES: O=C(Nc1ccc(F)c(F)c1)c1cc(S(=O)(=O)N2CCCC2)ccc1F]

N-(3,4-difluorophenyl)-2-fluoro-5-(pyrrolidin-1-ylsulfonyl)benzamide: In a similar procedure as General Procedure I, final compound was obtained as a beige solid (164 mg, 58%). $^1$H NMR (300 MHz, CD$_3$OD): 8.17-8.14 (dd, J=6.4, 2.4 Hz, 1H), 8.07-8.02 (m, 1H), 7.86-7.79 (m, 1H), 7.54-7.47 (dd, J=9.8, 8.8 Hz, 1H), 7.40-7.37 (m, 1H), 7.31-7.22 (m, 1H), 3.29-3.25 (m, 4H), 1.81-1.76 (m, 4H); MS (ES) m/z: 385.1 (M+H$^+$), calculated 385.08.

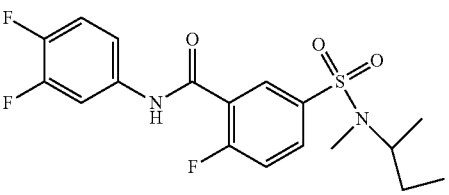 [SMILES: CCC(C)N(C)S(=O)(=O)c1ccc(F)c(C(=O)Nc2ccc(F)c(F)c2)c1]

5-(N-(sec-butyl)-N-methylsulfamoyl)-N-(3,4-difluorophenyl)-2-fluorobenzamide: In a similar procedure as General Procedure I, final compound was obtained as a beige solid (31 mg, 12%). $^1$H NMR (300 MHz, CD$_3$OD): 7.93-7.70 (m, 1H), 7.69-7.66 (m, 1H), 7.42-7.34 (m, 1H), 7.19-7.03 (m, 2H), 6.89-6.83 (m, 1H), 4.69-4.59 (m, 1H), 2.92 (s, 3H), 1.64-1.48 (m, 2H), 1.22-1.20 (d, J=6.7 Hz, 3H), 0.98-0.90 (m, 3H); MS (ES) m/z: 401.2 (M+H$^+$), calculated 401.11.

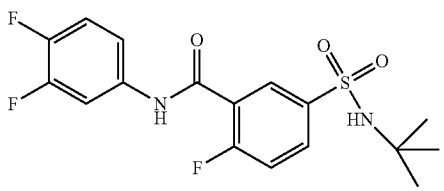 [SMILES: CC(C)(C)NS(=O)(=O)c1ccc(F)c(C(=O)Nc2ccc(F)c(F)c2)c1]

5-(N-(tert-butyl)sulfamoyl)-N-(3,4-difluorophenyl)-2-fluorobenzamide: In a similar procedure as General Procedure I, final compound was obtained as a white solid (171 mg, 52%). $^1$H NMR (300 MHz, CD$_3$OD): 8.23-8.20 (dd, J=6.5, 2.3 Hz, 1H), 8.09-8.03 (m, 1H), 7.86-7.79 (m, 1H), 7.47-7.36 (m, 2H), 7.31-7.21 (m, 1H), 1.21 (s, 9H); MS (ES) m/z: 387.2 (M+H$^+$), calculated 387.09.

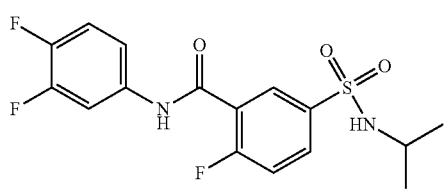 [SMILES: CC(C)NS(=O)(=O)c1ccc(F)c(C(=O)Nc2ccc(F)c(F)c2)c1]

N-(3,4-difluorophenyl)-2-fluoro-5-(N-isopropylsulfamoyl)benzamide: In a similar procedure as General Procedure I, final compound was obtained as a white solid (262 mg, 72%). $^1$H NMR (300 MHz, CD$_3$OD): 8.22-8.19 (dd, J=6.4, 2.3 Hz, 1H), 8.07-8.02 (m, 1H), 7.86-7.79 (m, 1H), 7.49-7.43 (dd, J=10.0, 8.8 Hz, 1H), 7.41-7.36 (m, 1H), 7.31-7.22 (m, 1H), 3.45-3.36 (m, 1H), 1.06-1.04 (d, J=6.4 Hz, 6H); MS (ES) m/z: 373.1 (M+H$^+$), calculated 373.08.

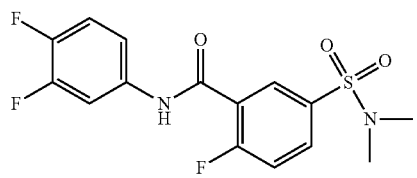 [SMILES: CN(C)S(=O)(=O)c1ccc(F)c(C(=O)Nc2ccc(F)c(F)c2)c1]

N-(3,4-difluorophenyl)-5-(N,N-dimethylsulfamoyl)-2-fluorobenzamide: In a similar procedure as General Procedure I, final compound was obtained as a white solid (196 mg, 66%). $^1$H NMR (300 MHz, CD$_3$OD): 8.13-8.10 (dd, J=6.4, 2.3 Hz, 1H), 8.02-7.97 (m, 1H), 7.87-7.80 (m, 1H), 7.79-7.49 (m, 1H), 7.41-7.36 (m, 1H), 7.31-7.22 (m, 1H), 2.73 (s, 6H); MS (ES) m/z: 359.1 (M+H$^+$), calculated 359.06.

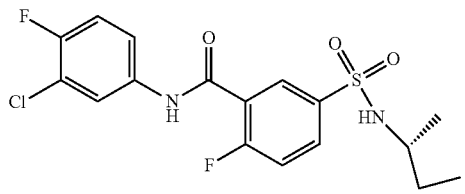 [SMILES: CC[C@@H](C)NS(=O)(=O)c1ccc(F)c(C(=O)Nc2ccc(F)c(Cl)c2)c1]

(R)-5-(N-(sec-butyl)sulfamoyl)-N-(3-chloro-4-fluorophenyl)-2-fluorobenzamide: In a similar procedure as General Procedure I, final compound was obtained as a white solid (59 mg, 24%). $^1$H NMR (300 MHz, CD$_3$OD): 8.23-8.20 (m, 1H), 8.07-8.04 (m, 1H), 7.98-7.94 (m, 1H), 7.58-7.57 (m, 1H), 7.49-7.43 (m, 1H), 7.28-7.22 (m, 1H), 3.24-3.20 (m, 1H), 1.43-1.38 (m, 2H), 1.00-0.98 (d, J=6.7 Hz, 3H), 0.84-0.79 (t, J=7.5 Hz, 3H); MS (ES) m/z: 403.1 (M+H$^+$), calculated 403.06.

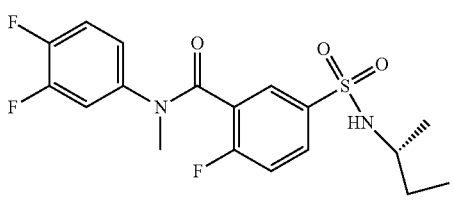 [SMILES: CC[C@@H](C)NS(=O)(=O)c1ccc(F)c(C(=O)N(C)c2ccc(F)c(F)c2)c1]

(R)-5-(N-(sec-butyl)sulfamoyl)-N-(3,4-difluorophenyl)-2-fluoro-N-methylbenzamide: In a similar procedure as General Procedure I, final compound was obtained as a white solid (67 mg, 24%). $^1$H NMR (300 MHz, CD$_3$OD): 7.84-7.82 (m, 2H), 7.32-7.06 (m, 4H), 3.46 (s, 3H), 3.01-2.95 (m, 1H), 1.36-1.29 (m, 2H), 0.88-0.86 (d, J=6.4 Hz, 3H), 0.77-0.72 (t, J=7.3 Hz, 3H); MS (ES) m/z: 401.2 (M+H$^+$), calculated 401.11.

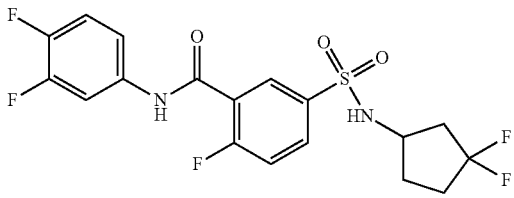 [SMILES: O=C(Nc1ccc(F)c(F)c1)c1cc(S(=O)(=O)NC2CCC(F)(F)C2)ccc1F]

5-(N-(3,3-difluorocyclopentyl)sulfamoyl)-N-(3,4-difluorophenyl)-2-fluorobenzamide: In a similar procedure as General Procedure I, final compound was obtained as a white solid (41 mg, 53%). $^1$H NMR (300 MHz, CD$_3$OD): 8.22-8.19 (m, 1H), 8.07-8.02 (m, 1H), 7.85-7.79 (m, 1H), 7.49-7.36 (m, 2H), 7.31-7.22 (m, 1H), 3.07-2.99 (m, 1H), 3.79-3.71 (m, 1H), 2.34-2.06 (m, 1H), 2.03-1.87 (m, 2H), 1.71-1.61 (m, 1H), 1.33-1.24 (m, 1H), 0.89-0.79 (m, 1H); MS (ES) m/z: 435.2 (M+H$^+$), calculated 435.07

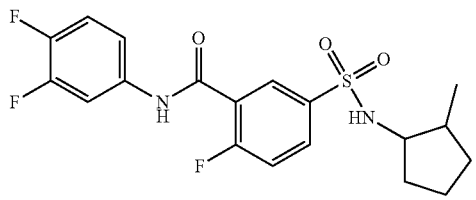 [SMILES: CC1CCCC1NS(=O)(=O)c1ccc(F)c(C(=O)Nc2ccc(F)c(F)c2)c1]

N-(3,4-difluorophenyl)-2-fluoro-5-(N-(2-methylcyclopentyl)sulfamoyl)benzamide: In a similar procedure as General Procedure I, final compound was obtained as a white solid (62 mg, 85%). $^1$H NMR (300 MHz, CD$_3$OD): 8.22-8.19 (m, 1H), 8.07-8.02 (m, 1H), 7.85-7.79 (m, 1H), 7.49-7.36 (m, 2H), 7.31-7.22 (m, 1H), 3.07-2.99 (m, 1H), 1.-3.71 (m, 1H), 2.34-2.06 (m, 1H), 2.03-1.87 (m, 2H), 1.71-1.61 (m, 1H), 1.33-1.24 (m, 1H), 0.89-0.79 (m, 1H); MS (ES) m/z: 435.2 (M+H$^+$), calculated 435.07.

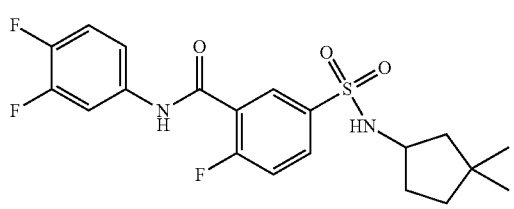 [SMILES: CC1(C)CCC(NS(=O)(=O)c2ccc(F)c(C(=O)Nc3ccc(F)c(F)c3)c2)C1]

N-(3,4-difluorophenyl)-5-(N-(3,3-dimethylcyclopentyl)sulfamoyl)-2-fluorobenzamide: In a similar procedure as General Procedure I, final compound was obtained as a white solid (54 mg, 89%). $^1$H NMR (300 MHz, CD$_3$OD): $^1$H NMR (300 MHz, CD$_3$OD): 8.21-8.18 (dd, J=6.4, 2.3 Hz, 1H), 8.07-8.01 (m, 1H), 7.86-7.79 (m, 1H), 7.46-7.37 (m, 2H), 7.31-7.22 (m, 1H), 3.72-3.54 (m, 1H), 2.01-1.84 (m, 1H), 1.64-1.53 (m, 1H), 1.50-1.40 (m, 2H), 1.37-1.15 (m, 2H), 1.01 (s, 3H), 0.91 (s, 3H); MS (ES) m/z: 427.2 (M+H$^+$), calculated 427.12.

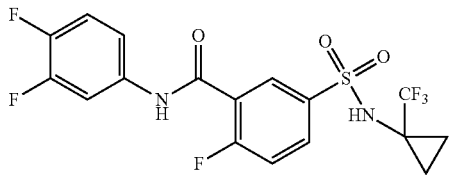 [SMILES: O=C(Nc1ccc(F)c(F)c1)c1cc(S(=O)(=O)NC2(C(F)(F)F)CC2)ccc1F]

N-(3,4-difluorophenyl)-2-fluoro-5-(N-(1-(trifluoromethyl)cyclopropyl)sulfamoyl)benzamide: In a similar procedure as General Procedure I, final compound was obtained as a white solid (22.3 mg, 18%). $^1$H NMR (300 MHz, CD$_3$OD): 8.20-8.18 (m, 1H), 8.10-8.04 (m, 1H), 7.90-7.79 (m, 1H), 7.49-7.37 (m, 2H), 7.31-7.21 (m, 1H), 1.21 (s, 4H); MS (ES) m/z: 439.2 (M+H$^+$), calculated 439.05.

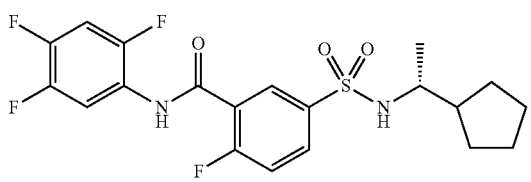 [SMILES: C[C@@H](NS(=O)(=O)c1ccc(F)c(C(=O)Nc2cc(F)c(F)cc2F)c1)C1CCCC1]

(R)-5-(N-(1-cyclopentylethyl)sulfamoyl)-2-fluoro-N-(2,4,5-trifluorophenyl)benzamide: In a similar procedure as General Procedure I, final compound was obtained as a white solid (8.3 mg, 14%). $^1$H NMR (300 MHz, CD$_3$OD): 8.31-8.28 (dd, J=6.4, 2.3 Hz, 1H), 8.13-8.04 (m, 2H), 7.50-7.43 (m, 1H), 7.37-7.28 (m, 1H), 3.18-3.13 (m, 1H), 1.85-1.74 (m, 1H), 1.68-1.51 (m, 6H), 1.20-1.15 (m, 2H), 0.96-0.94 (d, J=6.4 Hz, 3H); MS (ES) m/z: 445.2 (M+H$^+$), calculated 445.11.

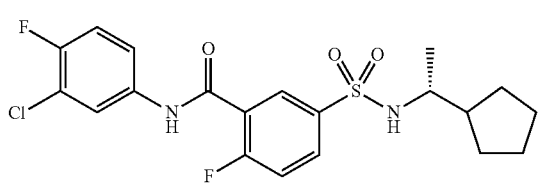

(R)-N-(3-chloro-4-fluorophenyl)-5-(N-(1-cyclopentylethyl)sulfamoyl)-2-fluorobenzamide: In a similar procedure as General Procedure I, final compound was obtained as a beige solid (18 mg, 10%). $^1$H NMR (300 MHz, CD$_3$OD): 8.22-8.19 (dd, J=6.4, 2.3 Hz, 1H), 8.07-8.02 (m, 1H), 7.97-7.94 (m, 1H), 7.61-7.56 (m, 1H), 7.48-7.42 (m, 1H), 7.28-7.25 (m, 1H), 3.18-3.13 (m, 1H), 1.82-1.74 (m, 1H), 1.67-1.51 (m, 6H), 1.29-1.12 (m, 2H), 0.96-0.94 (d, J=6.4 Hz, 3H); MS (ES) m/z: 443.2 (M+H$^+$), calculated 443.09.

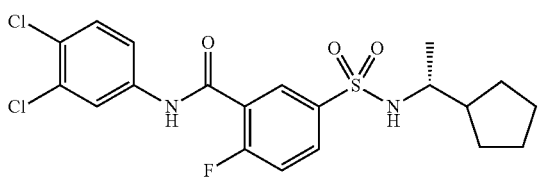 [SMILES: C[C@@H](NS(=O)(=O)c1ccc(F)c(C(=O)Nc2ccc(F)c(Cl)c2)c1)C1CCCC1]

(R)-5-(N-(1-cyclopentylethyl)sulfamoyl)-N-(3,4-dichlorophenyl)-2-fluorobenzamide: In a similar procedure as General Procedure I, final compound was obtained as a beige solid (49 mg, 25%). $^1$H NMR (300 MHz, CD$_3$OD): 8.22-8.19 (dd, J=6.4, 2.3 Hz, 1H), 8.06-8.02 (m, 2H), 7.61-7.57 (m, 1H), 7.52-7.42 (m, 2H), 3.17-3.13 (m, 1H), 1.84-1.47 (m, 7H), 1.28-1.11 (m, 2H), 0.96-0.94 (d, J=6.4 Hz, 3H); MS (ES) m/z: 459.2 (M+H$^+$), calculated 459.06.

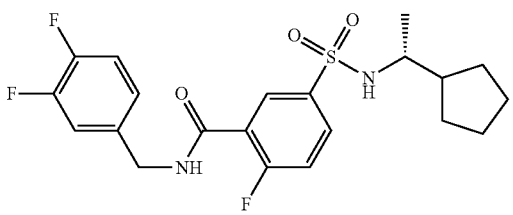 [SMILES: C[C@@H](NS(=O)(=O)c1ccc(F)c(C(=O)NCc2ccc(F)c(F)c2)c1)C1CCCC1]

(R)-5-(N-(1-cyclopentylethyl)sulfamoyl)-N-(3,4-difluorobenzyl)-2-fluorobenzamide: In a similar procedure as General Procedure I, final compound was obtained as a colorless oil (29.1 mg, 16%). $^1$H NMR (300 MHz, CD$_3$OD): 8.22-8.19 (dd, J=6.6, 2.6 Hz, 1H), 8.04-7.98 (m, 1H), 7.45-7.38 (m, 1H), 7.31-7.18 (m, 2H), 4.55 (s, 2H), 3.15-3.10 (m, 1H), 1.83-1.75 (m, 1H), 1.68-1.46 (m, 6H), 1.29-1.08 (m, 2H), 0.94-0.92 (d, J=6.4 Hz, 3H); MS (ES) m/z: 441.3 (M+H$^+$), calculated 441.14.

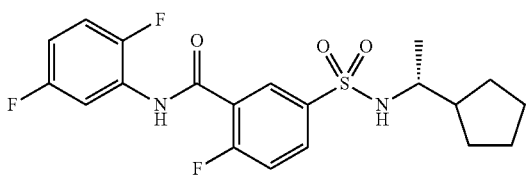 [SMILES: C[C@@H](NS(=O)(=O)c1ccc(F)c(C(=O)Nc2cc(F)ccc2F)c1)C1CCCC1]

(R)-5-(N-(1-cyclopentylethyl)sulfamoyl)-N-(2,5-difluorophenyl)-2-fluorobenzamide: In a similar procedure as General Procedure I, final compound was obtained as a white solid (47 mg, 32%). $^1$H NMR (300 MHz, CD$_3$OD): 8.32-8.30 (dd, J=6.4, 2.0 Hz, 1H), 8.09-8.00 (m, 2H), 7.50-7.44 (m, 1H), 7.27-7.19 (m, 1H), 7.00-6.92 (m, 1H), 3.20-3.11 (m, 1H), 1.85-1.75 (m, 1H), 1.68-1.51 (m, 6H), 1.29-1.14 (m, 2H), 0.97-0.95 (d, J=6.4 Hz, 3H); MS (ES) m/z: 427.2 (M+H$^+$), calculated 427.12.

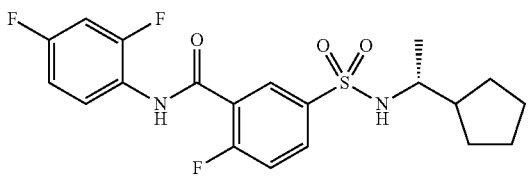 [SMILES: C[C@@H](NS(=O)(=O)c1ccc(F)c(C(=O)Nc2ccc(F)cc2F)c1)C1CCCC1]

(R)-5-(N-(1-cyclopentylethyl)sulfamoyl)-N-(2,4-difluorophenyl)-2-fluorobenzamide: In a similar procedure as General Procedure I, final compound was obtained as a white solid (54 mg, 29%). $^1$H NMR (300 MHz, CD$_3$OD): 8.30-8.27 (dd, J=6.4, 2.4 Hz, 1H), 8.09-8.03 (m, 1H), 7.92-7.87 (m, 1H), 7.50-7.44 (m, 1H), 7.14-7.00 (m, 2H), 3.20-3.13 (m, 1H), 1.85-1.74 (m, 1H), 1.68-1.51 (m, 6H), 1.29-1.12 (m, 2H), 0.97-0.94 (d, J=6.7 Hz, 3H); MS (ES) m/z: 427.3 (M+H$^+$), calculated 427.12.

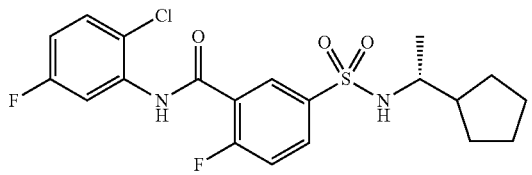 [SMILES: C[C@@H](NS(=O)(=O)c1ccc(F)c(C(=O)Nc2cc(F)ccc2Cl)c1)C1CCCC1]

(R)-N-(2-chloro-5-fluorophenyl)-5-(N-(1-cyclopentylethyl)sulfamoyl)-2-fluorobenzamide: In a similar procedure as General Procedure I, final compound was obtained as a white solid (24 mg, 13%). $^1$H NMR (300 MHz, CD$_3$OD): 8.46-8.43 (dd, J=6.7, 2.3 Hz, 1H), 8.12-8.07 (m, 2H), 7.55-7.47 (m, 2H), 7.04-6.97 (m, 1H), 3.18-3.14 (m, 1H), 1.86-1.77 (m, 1H), 1.68-1.51 (m, 6H), 1.28-1.11 (m, 2H), 0.97-0.95 (d, J=6.7 Hz, 3H); MS (ES) m/z: 443.2 (M+H$^+$), calculated 443.09.

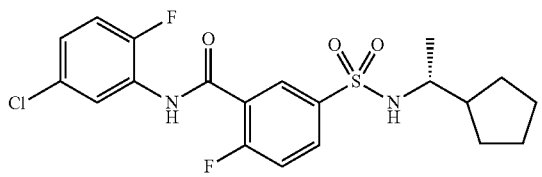 [SMILES: C[C@@H](NS(=O)(=O)c1ccc(F)c(C(=O)Nc2cc(Cl)ccc2F)c1)C1CCCC1]

(R)-N-(5-chloro-2-fluorophenyl)-5-(N-(1-cyclopentylethyl)sulfamoyl)-2-fluorobenzamide: In a similar procedure as General Procedure I, final compound was obtained as a white solid (30 mg, 16%). $^1$H NMR (300 MHz, CD$_3$OD): 8.32-8.29 (dd, J=6.5, 2.2 Hz, 1H), 8.19-8.17 (m, 1H), 8.09-8.04 (m, 1H), 7.50-7.44 (m, 1H), 7.24-7.21 (m, 2H), 3.20-3.11 (m, 1H), 1.85-1.75 (m, 1H), 1.72-1.51 (m, 6H), 1.28-1.12 (m, 2H), 0.97-0.95 (d, J=6.5 Hz, 3H); MS (ES) m/z: 443.2 (M+H$^+$), calculated 443.09.

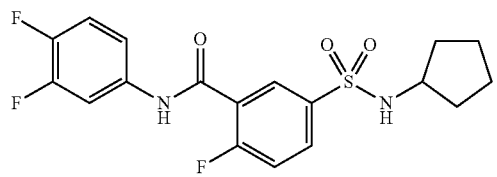 [SMILES: O=C(Nc1ccc(F)c(F)c1)c1cc(S(=O)(=O)NC2CCCC2)ccc1F]

5-(N-Cyclopentylsulfamoyl)-N-(3,4-difluorophenyl)-2-fluorobenzamide: In a similar procedure as General Procedure I, final compound was obtained as a white solid (300 mg, 45%). $^1$H NMR (300 MHz, CDCl$_3$): δ 8.67-8.65 (m, 1H), 8.64-8.37 (m, 1H), 8.10-8.04 (m, 1H), 7.80-7.73 (m, 1H), 7.26-7.12 (m, 3H), 4.72-4.13 (m, 1H), 3.69-3.62 (m, 1H), 1.88-1.78 (m, 2H), 1.69-1.26 (m, 6H); MS (ES) m/z: 399.1 (M+H$^+$), calculated 399.09.

221

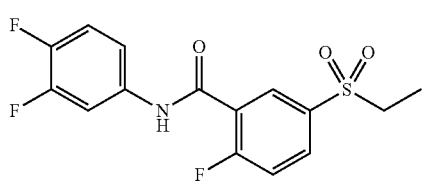 [SMILES: CCS(=O)(=O)c1ccc(F)c(C(=O)Nc2ccc(F)c(F)c2)c1]

N-(3,4-Difluorophenyl)-5-(ethylsulfonyl)-2-fluorobenzamide: In a similar procedure as General Procedure I, final compound was obtained as a white solid (155.5 mg, 96.4%). $^1$H NMR (300 MHz, $d_4$-MeOH): 8.27-8.24 (m, 1H), 8.14-8.09 (m, 1H), 7.86-7.79 (m, 1H), 7.57-7.51 (t, J=9.1 Hz, 1H), 7.40-7.22 (m, 2H), 3.30-3.24 (m, 2H), 1.28-1.23 (t, J=7.6 Hz, 3H); MS (ES) m/z: 344.2 (M+H$^+$), calculated 344.05.

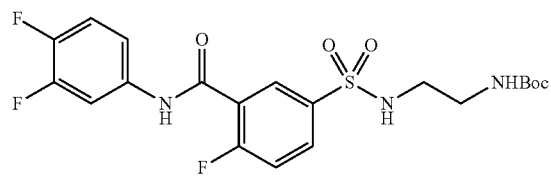 [SMILES: CC(C)(C)OC(=O)NCCNS(=O)(=O)c1ccc(F)c(C(=O)Nc2ccc(F)c(F)c2)c1]

tert-Butyl(2-(3-((3,4-difluorophenyl)carbamoyl)-4-fluorophenylsulfonamido)ethyl)carbamate: In a similar procedure as General Procedure I, final compound was obtained as a white solid (54.6 mg, 40%). $^1$H NMR (300 MHz, $d_4$-MeOH): 8.20-8.17 (m, 1H), 8.06-8.01 (m, 1H), 7.86-7.78 (m, 1H), 7.49-7.37 (m, 2H), 7.31-7.22 (m, 1H), 3.12-3.07 (m, 2H), 2.98-2.94 (t, J=6.3 Hz, 2H), 1.40 (s, 9H); MS (ES) m/z: 496.2 (M+Na$^+$), calculated 496.12.

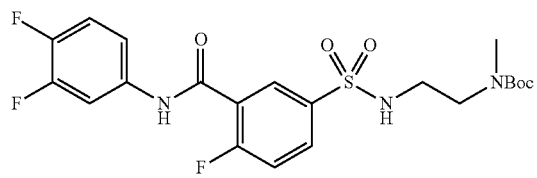 [SMILES: CN(CCNS(=O)(=O)c1ccc(F)c(C(=O)Nc2ccc(F)c(F)c2)c1)C(=O)OC(C)(C)C]

tert-Butyl(2-(3-((3,4-difluorophenyl)carbamoyl)-4-fluorophenylsulfonamido)ethyl)(methyl)carbamate: In a similar procedure as General Procedure I, final compound was obtained as a white solid (102 mg, 72%). $^1$H NMR (300 MHz, $d_4$-MeOH): 8.19-8.18 (m, 1H), 8.06-8.01 (m, 1H), 7.86-7.77 (m, 1H), 7.50-7.37 (m, 2H), 7.31-7.22 (m, 1H), 3.06-2.99 (m, 2H), 2.89-2.82 (m, 2H), 1.44 (s, 9H), 1.42 (s, 3H); MS (ES) m/z: 510.2 (M+Na$^+$), calculated 510.14.

222

Example 10

General Procedure J

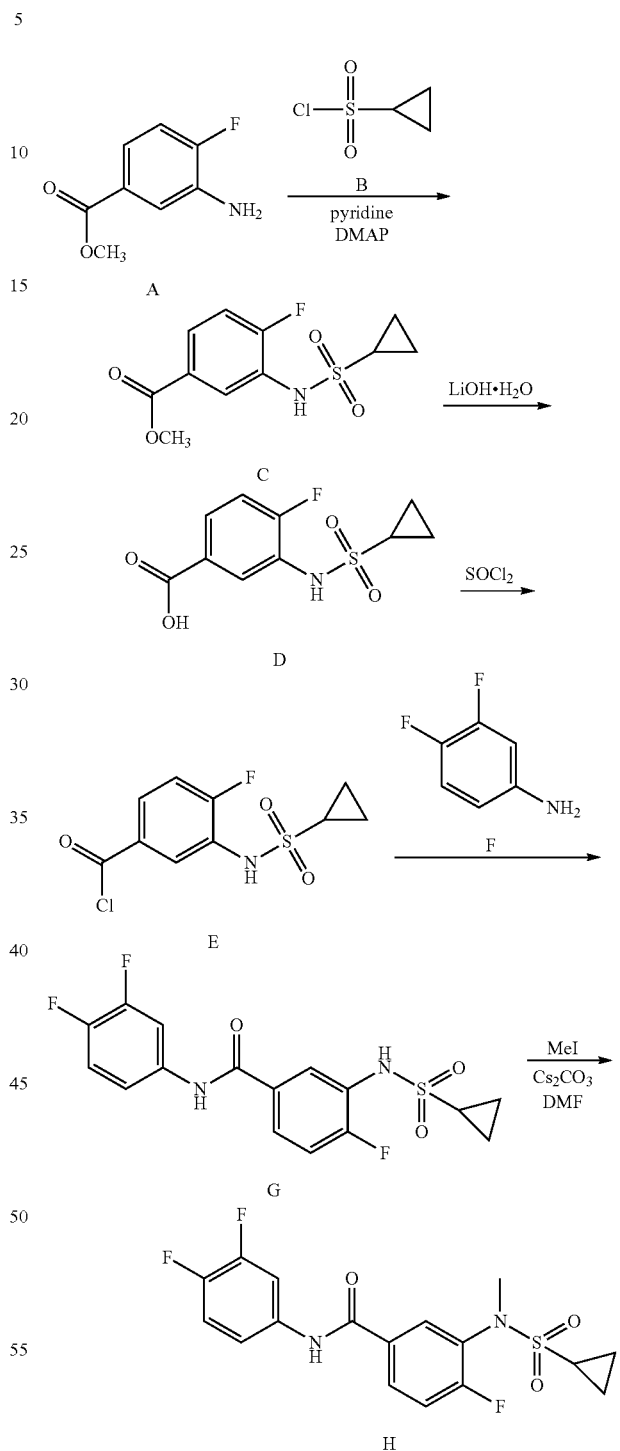

A (0.255 g, 1.51 mmol) was dissolved in pyridine, B (0.344 g, 1.88 mmol) and DMAP (92.2 mg, 0.755 mmol) were added and the mixture was stirred at 110° C. overnight. The solvent was evaporated and the crude product was extracted with CH$_2$Cl$_2$ and washed with 1N HCl, 2N H$_2$SO$_4$, followed by H$_2$O and brine, dried (Na$_2$SO$_4$) and concentrated to give the crude product C which was directly used for the next step. Product C was treated with LiOH.H₂O in Dioxane and H₂O overnight. The solvent was evaporated, adjusted pH with 1N HCl to slightly acidic, extracted with EtOAc, dried and concentrated to give product D. After dried overnight, D (0.37 g, 1.4 mmol) was reflux in SOCl₂ (5 mL) for 2 h, after evaporate excess SOCl₂, dried to give E (0.4188 g). The residue E was then dissolved in THF (5 mL), F (195 mg, 1.5 mmol) was added followed by DIEA (0.6 mL) (where DIEA is N,N-diisopropylethylamine). The mixture was stirred at room temperature overnight. The solvent was evaporated, followed by EtOAc extraction. After purified by isco (EtOAc/hexane), 0.337 g (63%) of final product G was obtained. Into G (20 mg, 0.054 mmol) in DMF (2 mL) was added MeI (1 eq) and Cs₂CO₃ (19.3 mg, 0.059 mmol). The mixture was stirred at room temperature overnight. The solvent was evaporated and prep-TLC to give the product H (18.3 mg, 88%).

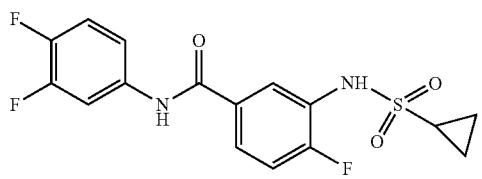 [SMILES: O=C(Nc1ccc(F)c(F)c1)c1ccc(F)c(NS(=O)(=O)C2CC2)c1]

3-(cyclopropanesulfonamido)-N-(3,4-difluorophenyl)-4-fluorobenzamide: In a similar procedure as General Procedure J, final compound was obtained as a white solid (336.7 mg, 63%). ¹H NMR (300 MHz, CD3OD): 8.11-8.09 (m, 1H), 7.83-7.80 (m, 2H), 7.40-7.20 (m, 3H), 2.70-2.60 (m, 1H), 1.03-0.98 (m, 4H); MS (ES) m/z: 371.2 (M+H⁺), calculated 371.06.

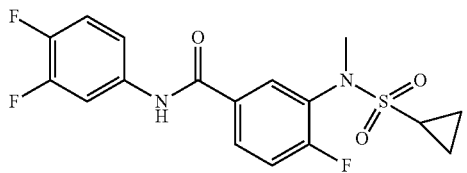 [SMILES: CN(c1cc(C(=O)Nc2ccc(F)c(F)c2)ccc1F)S(=O)(=O)C1CC1]

N-(3,4-difluorophenyl)-4-fluoro-3-(N-ethylcyclopropanesulfonamido)benzamide: In a similar procedure as General Procedure J, final compound was obtained as a white solid (18.3 mg, 88.4%). ¹H NMR (300 MHz, CD3OD): 8.11-8.07 (dd, J=7.3, 2.1 Hz, 1H), 8.02-7.97 (m, 1H), 7.85-7.77 (m, 1H), 7.43-7.34 (m, 2H), 7.29-7.20 (m, 1H), 3.36 (s, 3H), 2.76-2.69 (m, 1H), 1.10-1.01 (m, 4H); MS (ES) m/z: 385.2 (M+H⁺), calculated 385.08.

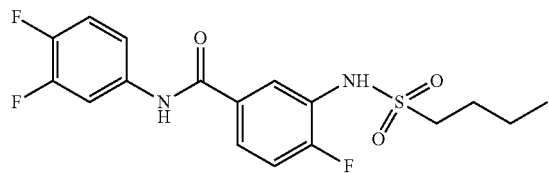 [SMILES: CCCCS(=O)(=O)Nc1cc(C(=O)Nc2ccc(F)c(F)c2)ccc1F]

3-(butylsulfonamido)-N-(3,4-difluorophenyl)-4-fluorobenzamide: In a similar procedure as General Procedure J, final compound was obtained as a white solid (94.8 mg, 79%). ¹H NMR (300 MHz, CD₃OD): 8.09-8.06 (dd, J=7.8, 2.2 Hz, 1H), 7.82-7.74 (m, 2H), 7.39-7.20 (m, 3H), 3.18- 3.13 (m, 2H), 1.86-1.76 (m, 2H), 1.49-1.42 (m, 2H), 0.96-0.91 (t, J=7.3 Hz, 3H); MS (ES) m/z: 387.2 (M+H⁺), calculated 387.09.

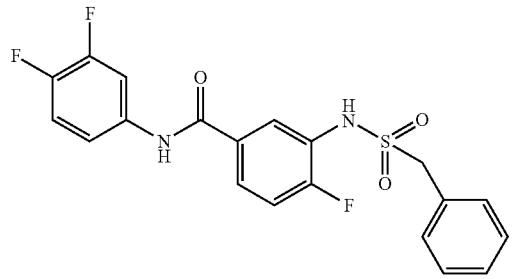 [SMILES: O=C(Nc1ccc(F)c(F)c1)c1ccc(F)c(NS(=O)(=O)Cc2ccccc2)c1]

N-(3,4-Difluorophenyl)-4-fluoro-3-(phenylmethylsulfonamido)benzamide: In a similar procedure as General Procedure J, final compound was obtained as a white solid (30.4 mg, 24%). ¹H NMR (300 MHz, d₄-MeOH): 7.93-7.90 (m, 1H), 7.83-7.75 (m, 1H), 7.71-7.65 (m, 1H), 7.42-7.35 (m, 3H), 7.32-7.20 (m, 5H), 4.51 (s, 2H); MS (ES) m/z: 421.2 (M+H⁺), calculated 421.08.

Example 11

General Procedure K

N¹-cyclopropyl-N³-(3,4-difluorophenyl)-4-fluoroisophthalamide: In a microwave vial (Biotage) was charged with N-(3,4-difluorophenyl)-2-fluoro-5-iodobenzamide (100.0 mg, 0.26 mmol), palladium acetate (8.9 mg, 0.013 mmol), sodium carbonate (82.7 mg, 0.78 mmol), Mo(CO)₆ (34.3 mg, 0.13 mmol) and water (1 mL). The mixture was sealed, evacuated, and refilled with Ar. cyclopropanamine (0.09 mL, 1.33 mmol) was added into the mixture, which was then heated at 100° C. in microwave reactor for 15 minutes. The mixture was diluted with ethyl acetate, washed with HCl (2N) twice, saturated NaHCO₃, and brine. The organic phase was concentrated, and the residue was purified on silica gel (24 g), eluted with a gradient of ethyl acetate and hexanes from 2:8 to 1:1 to give the compound as a light yellow solid (22.2 mg, 25%). ¹H NMR (300 MHz, CDCl₃-MeOD): δ 8.21 (dd, J=7.3, 2.3 Hz, 1H), 7.99 (ddd, J=8.5, 5.0, 2.3 Hz, 1H), 7.70 (ddd, J=12.0, 7.3, 2.3 Hz, 1H), 7.25-7.04 (m, 3H), 2.87-2.77 (m, 1H), 0.84-0.75 (m, 2H), 0.62-0.55 (m, 2H); Calculated for C₁₇H₁₃F₃N₂O₂, 334.09; observed MS (ESI) (m/z) 335.1 (M+1)⁺.

The following compounds can be prepared by following General Procedure K, the procedure for the synthesis of $N^1$-cyclopropyl-$N^3$-(3,4-difluorophenyl)-4-fluoroisophthalamide.

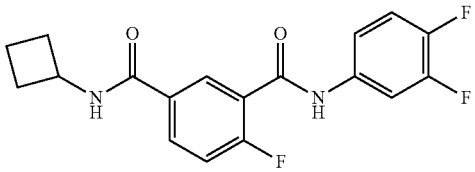 [SMILES: O=C(NC1CCC1)c1ccc(F)c(C(=O)Nc2ccc(F)c(F)c2)c1]

$N^1$-cyclobutyl-$N^3$-(3,4-difluorophenyl)-4-fluoroisophthalamide: yield: 38%; $^1$H NMR (300 MHz, CDCl$_3$-MeOD): δ 8.26 (dd, J=7.0, 2.3 Hz, 1H), 7.98 (ddd, J=8.5, 5.0, 2.3 Hz, 1H), 7.71 (ddd, J=12.0, 7.0, 2.3 Hz, 1H), 7.30-7.14 (m, 3H), 4.55-4.40 (m, 1H), 2.42-2.28 (m, 2H), 2.06-1.88 (m, 2H), 1.82-1.64 (m, 2H); Calculated for $C_{18}H_{15}F_3N_2O_2$, 348.11; MS (ESI) (m/z) observed 349.1 (M+1)$^+$.

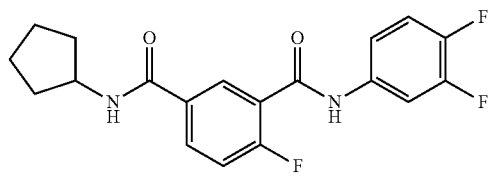 [SMILES: O=C(NC1CCCC1)c1ccc(F)c(C(=O)Nc2ccc(F)c(F)c2)c1]

$N^1$-cyclopentyl-$N^3$-(3,4-difluorophenyl)-4-fluoroisophthalamide: Yield, 27%; $^1$H NMR (300 MHz, CDCl$_3$-MeOD): δ 8.15 (dd, J=6.7, 2.3 Hz, 1H), 7.92 (ddd, J=8.8, 5.0, 2.3 Hz, 1H), 7.70 (ddd, J=12.3, 7.0, 2.3 Hz, 1H), 7.25-7.04 (m, 3H), 4.36-4.20 (m, 1H), 2.08-1.90 (m, 2H), 1.75-1.38 (m, 6H); Calculated for $C_{19}H_{17}F_3N_2O_2$, 362.12; observed MS (ESI) (m/z) 363.2 (M+1)$^+$.

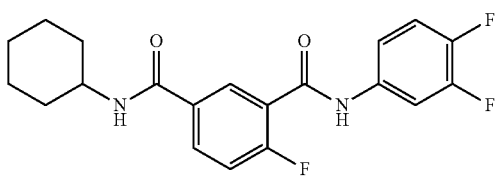 [SMILES: O=C(NC1CCCCC1)c1ccc(F)c(C(=O)Nc2ccc(F)c(F)c2)c1]

$N^1$-cyclohexyl-$N^3$-(3,4-difluorophenyl)-4-fluoroisophthalamide: Yield, 30%; $^1$H NMR (300 MHz, CDCl$_3$-MeOD): δ 8.22-8.15 (m, 1H), 7.98-7.90 (m, 1H), 7.75-7.65 (m, 1H), 7.24-7.04 (m, 3H), 3.92-3.76 (m, 1H), 2.00-1.00 (m, 10H); Calculated for $C_{20}H_{19}F_3N_2O_2$, 376.14; observed MS (ESI) (m/z) 377.2 (M+1)$^+$.

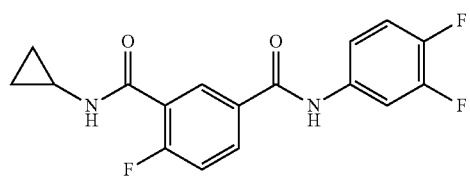 [SMILES: O=C(Nc1ccc(F)c(F)c1)c1ccc(F)c(C(=O)NC2CC2)c1]

$N^3$-cyclopropyl-$N^1$-(3,4-difluorophenyl)-4-fluoroisophthalamide: In a microwave vial (Biotage) was charged with 3-bromo-N-(3,4-difluorophenyl)-4-fluorobenzamide (86.0 mg, 0.26 mmol), palladium acetate (8.9 mg, 0.013 mmol), sodium carbonate (82.7 mg, 0.78 mmol), Xantphos (15.0 mg, 0.026 mmol), Mo(CO)$_6$ (34.3 mg, 0.13 mmol) and water (2 mL). The mixture was sealed, evacuated, and refilled with Ar. cyclopropanamine (0.09 mL, 1.33 mmol) was added into the mixture, which was then heated at 170° C. in microwave reactor for 15 minutes. The mixture was diluted with ethyl acetate, washed with HCl (2N) twice, saturated NaHCO$_3$, and brine. The organic phase was concentrated, and the residue was purified on silica gel (24 g), eluted with a gradient of ethyl acetate and hexanes from 1:9 to 3:7 to give the compound as a light yellow solid (26.0 mg, 30%). $^1$H NMR (300 MHz, CDCl$_3$-MeOD): δ 8.31 (dd, J=6.7, 2.3 Hz, 1H), 8.00 (ddd, J=8.5, 4.7, 2.3 Hz, 1H), 7.73-7.63 (m, 1H), 7.36-7.26 (m, 1H), 7.21-7.02 (m, 2H), 2.87-2.77 (m, 1H), 0.85-0.77 (m, 2H), 0.62-0.55 (m, 2H); Calculated for $C_{17}H_{13}F_3N_2O_2$, 334.09; observed MS (ESI) (m/z) 335.2 (M+1)$^+$.

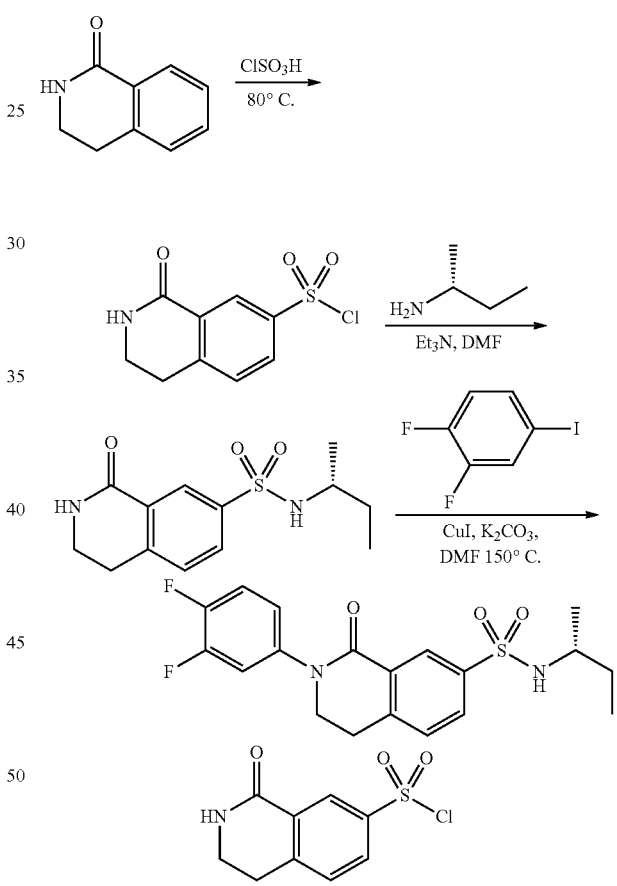

1-oxo-1,2,3,4-tetrahydroisoquinoline-7-sulfonyl chloride: 3,4-dihydroisoquinolin-1(2H)-one (300 mg, 2.0 mmol) was dissolved in sulfurochloridic acid (3 mL). The solution was heated at 80° C. for 4 hrs and cooled to room temperature. The mixture was poured onto ice in a separatory funnel and extracted with methylene chloride (10 mL×3). The combined organic phase was washed with water, brine, and dried over Na$_2$SO$_4$. Concentration provided a white solid, which was used directly in the next step. Calculated for $C_9H_8ClNO_3S$, 244.99; observed MS (ESI) (m/z) 246.0 (M+1)$^+$.

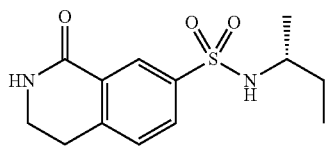 [SMILES: CC[C@@H](C)NS(=O)(=O)c1ccc2c(c1)C(=O)NCC2]

(R)-N-(sec-butyl)-1-oxo-1,2,3,4-tetrahydroisoquinoline-7-sulfonamide: The white solid obtained above was dissolved in DMF (2 mL) and added to a stirred solution of (R)-butan-2-amine (0.41 mL, 4.0 mmol) and triethyl amine (1.1 mL, 8 mmol) in DMF (3 mL) at rt. After 30 min at this temperature, the mixture was diluted with ethyl acetate, washed with HCl (2N, 5 mL×2), saturated NaHCO$_3$, brine, and concentrated. The residue was purified on silica gel (40 g) with a gradient of ethyl acetate:hexanes from 1:1 to 1:0 gave the desired product as a white solid (300 mg, 52% for two steps). $^1$H NMR (300 MHz, DMSO): δ 8.26 (d, J=2.0 Hz, 1H), 8.16 (bs, 1H, CONH), 7.86 (dd, J=7.9, 2.0 Hz, 1H), 7.60 (d, J=7.9 Hz, 1H, SO2NH), 7.52 (d, J=8.0 Hz, 1H), 3.40 (td, J=6.4, 2.9 Hz, 2H), 3.10-2.95 (m, 3H), 1.30 (dt, J=14.1, 7.6 Hz, 2H), 0.87 (d, J=6.7 Hz, 3H), 0.71 (t, J=7.3 Hz, 3H); Calculated for $C_{13}H_{18}N_2O_3S$, 282.1; observed MS (ESI) (m/z) 283.2 (M+1)$^+$.

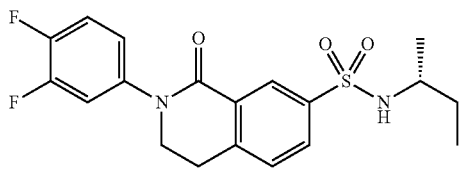 [SMILES: CC[C@@H](C)NS(=O)(=O)c1ccc2c(c1)C(=O)N(c1ccc(F)c(F)c1)CC2]

(R)-N-(sec-butyl)-2-(3,4-difluorophenyl)-1-oxo-1,2,3,4-tetrahydroisoquinoline-7-sulfonamide: To a pressure tube was charged with (R)-N-(sec-butyl)-1-oxo-1,2,3,4-tetrahydroisoquinoline-7-sulfonamide (135 mg, 0.48 mmol), 1,2-difluoro-4-iodobenzene (230 mg, 0.96 mmol), potassium carbonate (78 mg, 0.56 mmol), CuI (9.5 mg, 0.05 mmol), and DMF (5 mL). The mixture was degassed with vaccum and refilled with He, and then heated at 150° C. for 5 days. The mixture was diluted with ethyl acetate, washed with ammona (10%) and brine, and concentrated. The residue was purified on silica gel (24 g) with a gradient of ethyl acetate:hexanes from 1:9 to 1:1 gave the desired product as a light yellow solid (82.4 mg, 44%). $^1$H NMR (300 MHz, MeOD): δ 8.46 (d, J=1.8 Hz, 1H), 7.95 (dd, J=7.9, 2.0 Hz, 1H), 7.51 (d, J=8.2 Hz, 1H), 7.47-7.19 (m, 3H), 4.02 (t, J=6.4 Hz, 2H), 3.26 (t, J=6.4 Hz, 2H), 3.24-3.10 (m, 1H), 1.373 (td, J=14.4, 7.0 Hz, 2H), 0.95 (d, J=6.4 Hz, 3H), 0.78 (t, J=7.3 Hz, 3H); Calculated for $C_{19}H_{20}F_2N_2O_3S$, 394.1; observed MS (ESI) (m/z) 395.2 (M+1)$^+$.

Example 12

General Procedure L

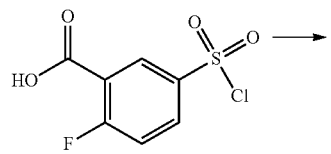

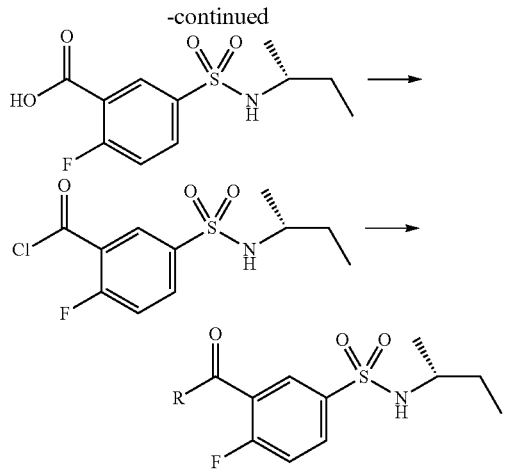

(R)-5-(N-(sec-butyl)sulfamoyl)-2-fluorobenzoic acid, 5-(chlorosulfonyl)-2-fluorobenzoic acid (239 mg) was dissolved in $CH_2Cl_2$ (20 ml), the reaction mixture was cooled to 0° C. Then Et$_3$N (405 mg) was added, after 15 minutes stirring, (R)-butan-2-amine (73 mg) was added. The resultant mixture was stirred for 3 hours until the reaction was complete. The solvent was stripped off and the crude product was used without further purification.

(R)-5-(N-(sec-butyl)sulfamoyl)-2-fluorobenzoyl chloride, (R)-5-(N-(sec-butyl)sulfamoyl)-2-fluorobenzoic acid (300 mg) was added into SOCl$_2$ (15 ml), the reaction mixture was heated to 75° C. and stirred for 1 hour until the reaction is complete. The solvent was stripped off and product, (R)-5-(N-(sec-butyl)sulfamoyl)-2-fluorobenzoyl chloride was used for the next step without purification.

(R)-5-(N-(sec-butyl)sulfamoyl-2-fluoro-N—R-benzamide: (R)-5-(N-(sec-butyl)sulfamoyl)-2-fluorobenzoyl chloride (400 mg) was dissolved in THF (20 ml), then Et$_3$N (405 mg) and RNH$_2$ (224 mg) were added. The reaction mixture was heated to 85° C. and stirred for 5 hours until the reaction is complete. The solvent of the reaction mixture was stripped off and the resultant crude product was purified by silica column (EtOAc/petroleum ether=1:3) to get the product, (R)-5-(N-(sec-butyl)sulfamoyl-2-fluoro-N—R-benzamide. The compounds were confirmed by LC-MS.

The following 16 compounds were synthesized using above general procedure:

Compound A

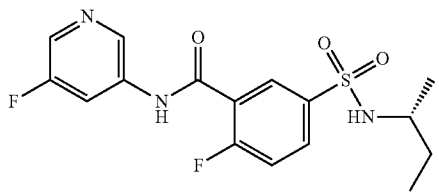

Compound B

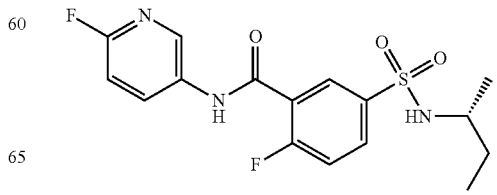

Compound C
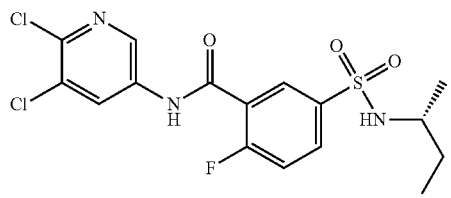
Compound J
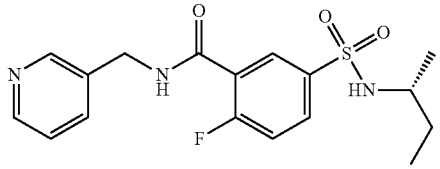
Compound D
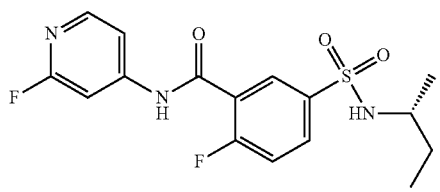
Compound K
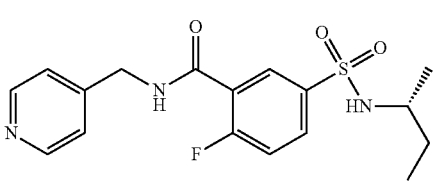
Compound E
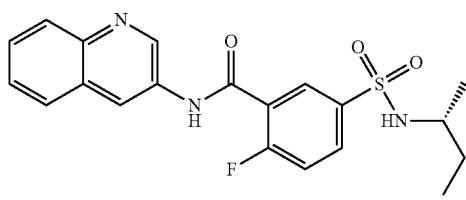
Compound L
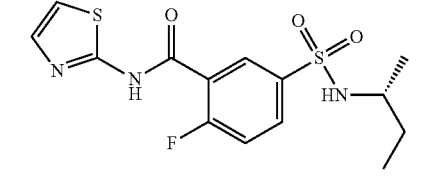
Compound F
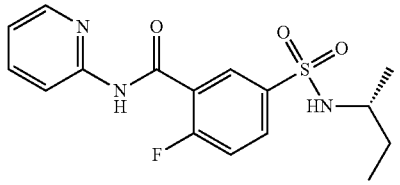
Compound M
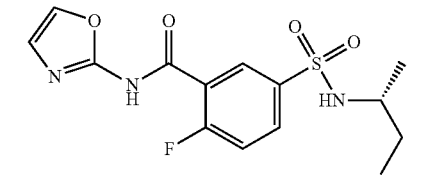
Compound G
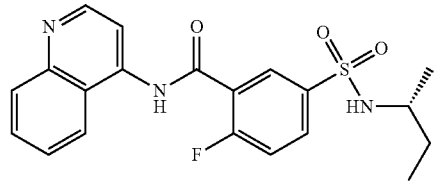
Compound N
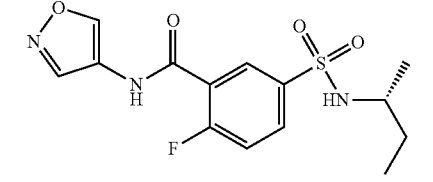
Compound H
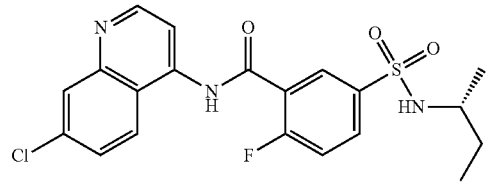
Compound O
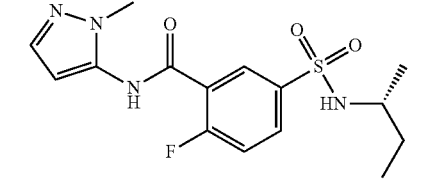
Compound I
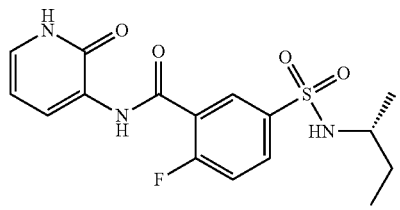
Compound P
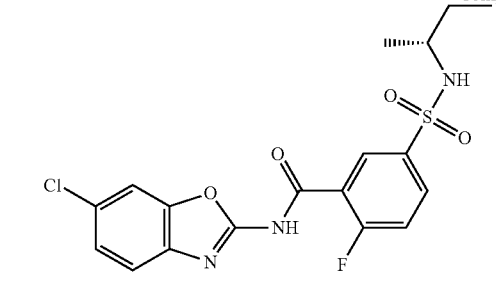

(R)-5-(N-(sec-butyl)sulfamoyl)-2-fluoro-N-(5-fluoro-pyridin-3-yl)benzamide (compound A), 40 mg as off-white solid, HPLC purity: 90%. MS Calcd.: 369.1; MS Found: 370.0 [M+H]+.

(R)-5-(N-(sec-butyl)sulfamoyl)-2-fluoro-N-(6-fluoro-pyridin-3-yl)benzamide (compound B), 50 mg as off-white solid, HPLC purity: 90%. MS Calcd.: 369.1; MS Found: 370.0 [M+H]+.

(R)-5-(N-(sec-butyl)sulfamoyl)-N-(5,6-dichloropyridin-3-yl)-2-fluorobenzamide (compound C), 20 mg as off-white solid, HPLC purity: 90%.

(R)-5-(N-(sec-butyl)sulfamoyl)-2-fluoro-N-(2-fluoro-pyridin-4-yl)benzamide (compound D), 14 mg as off-white solid, HPLC purity: 90%. MS Calcd.: 369.1; MS Found: 370.0 [M+H]+.

(R)-5-(N-(sec-butyl)sulfamoyl)-2-fluoro-N-(quinolin-3-yl)benzamide (compound E), 50 mg as off-white solid, HPLC purity: 90%.

(R)-5-(N-(sec-butyl)sulfamoyl)-2-fluoro-N-(pyridin-2-yl)benzamide (compound F), 60 mg as off-white solid, HPLC purity: 90%.

(R)-5-(N-(sec-butyl)sulfamoyl)-2-fluoro-N-(quinolin-4-yl)benzamide (compound G), 55 mg as off-white solid, HPLC purity: 90%. MS Calcd.: 401.4; MS Found: 402.4 [M+H]+.

(R)-5-(N-(sec-butyl)sulfamoyl)-N-(7-chloroquinolin-4-yl)-2-fluorobenzamide (compound H), 40 mg as off-white solid, HPLC purity: 90%.

(R)-5-(N-(sec-butyl)sulfamoyl)-2-fluoro-N-(2-oxo-1,2-dihydropyridin-3-yl)benzamide (compound I), 40 mg as off-white solid, HPLC purity: 90%.

(R)-5-(N-(sec-butyl)sulfamoyl)-2-fluoro-N-(pyridin-3-ylmethyl)benzamide (compound J), 50 mg as off-white solid, HPLC purity: 90%.

(R)-5-(N-(sec-butyl)sulfamoyl)-2-fluoro-N-(pyridin-4-ylmethyl)benzamide (compound K), 40 mg as off-white solid, HPLC purity: 90%. MS Calcd.: 365.4; MS Found: 366.4 [M+H]+.

(R)-5-(N-(sec-butyl)sulfamoyl)-2-fluoro-N-(thiazol-2-yl)benzamide (compound L), 40 mg as off-white solid, HPLC purity: 90%.

(R)-5-(N-(sec-butyl)sulfamoyl)-2-fluoro-N-(oxazol-2-yl)benzamide (compound M), 22 mg as off-white solid, HPLC purity: 90%.

(R)-5-(N-(sec-butyl)sulfamoyl)-2-fluoro-N-(isoxazol-4-yl)benzamide (compound N), 22 mg as off-white solid, HPLC purity: 90%.

(R)-5-(N-(sec-butyl)sulfamoyl)-2-fluoro-N-(1-methyl-1H-pyrazol-5-yl)benzamide (compound O), 40 mg as off-white solid, HPLC purity: 90%.

(R)-5-(N-(sec-butyl)sulfamoyl)-N-(6-chlorobenzo[d]oxazol-2-yl)-2-fluorobenzamide (compound P), 15 mg as off-white solid, HPLC purity: 90%.

Example 13

General Procedure M

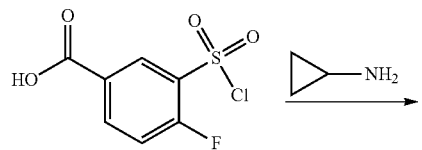

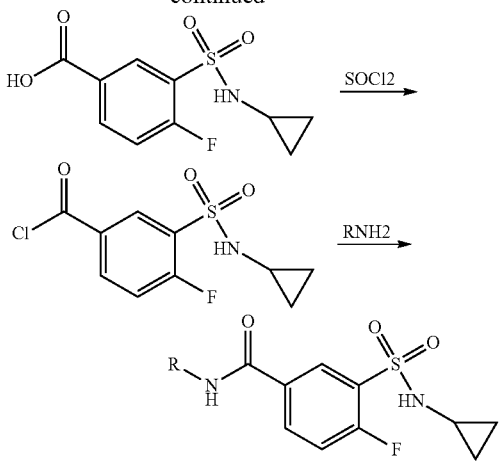

3-(N-cyclopropylsulfamoyl)-4-fluorobenzoic acid, 5-(chlorosulfonyl)-2-fluorobenzoic acid (239 mg) was dissolved in CH$_2$Cl$_2$ (20 mL), the reaction mixture was cooled to 0° C. Then Et$_3$N (405 mg) was added, after 15 minutes stirring, cyclopropanamine (57.1 mg) was added. The resultant mixture was stirred for 3 hours until the reaction was complete. The solvent was stripped off and the crude product 3-(N-cyclopropylsulfamoyl)-4-fluorobenzoic acid was obtained as white solid. It was used without further purification.

3-(N-cyclopropylsulfamoyl)-4-fluorobenzoyl chloride, 3-(N-cyclopropylsulfamoyl)-4-fluorobenzoic acid (300 mg) was added into SOCl$_2$ (15 ml), the reaction mixture was heated to 75° C. and stirred for 1 hour until the reaction is complete. The solvent was stripped off and product, 3-(N-cyclopropylsulfamoyl)-4-fluorobenzoyl chloride as off white solid was used for the next step without purification.

3-(N-cyclopropylsulfamoyl)-4-fluoro-N—R-benzamide, 3-(N-cyclopropylsulfamoyl)-4-fluorobenzoyl chloride (400 mg) was dissolved in THF (20 ml), then Et$_3$N (405 mg) and RNH$_2$ (112 mg) were added. The reaction mixture was heated to 85° C. and stirred for 5 hours until the reaction is complete. The solvent of the reaction mixture was stripped off and the resultant crude product was purified by silica column (EtOAc/petroleum ether=1:3) to get the product, 3-(N-cyclopropylsulfamoyl)-4-fluoro-N—R-benzamide.

The compounds were confirmed by LC-MS and $^1$H-NMR.

The following 16 compounds were synthesized using above general procedure:

Compound AA

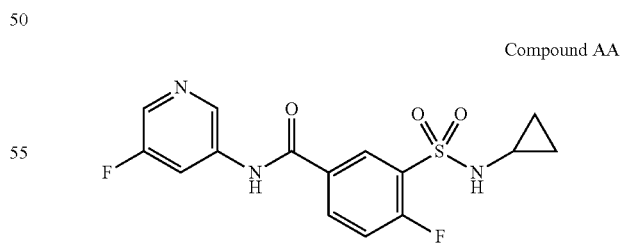

Compound BB

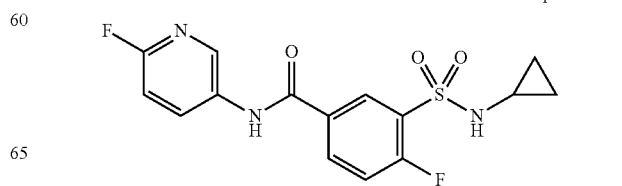

Compound CC
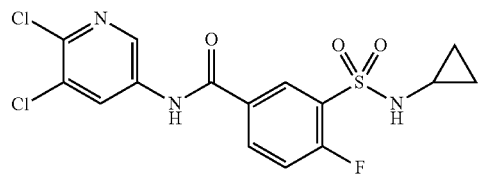

Compound DD
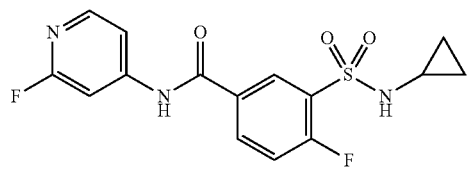

Compound EE

Compound FF
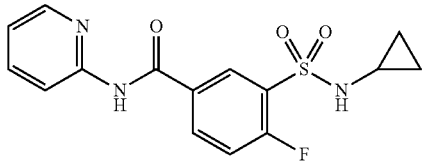

Compound GG
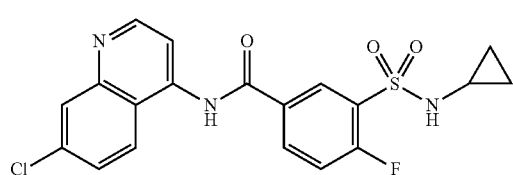

Compound HH
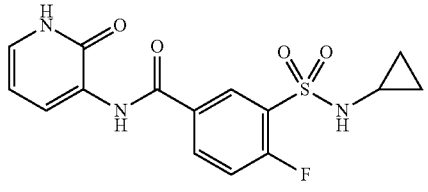

Compound II
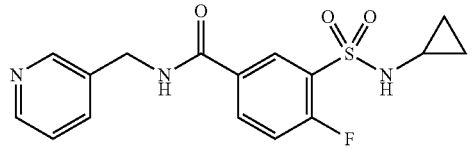

Compound JJ
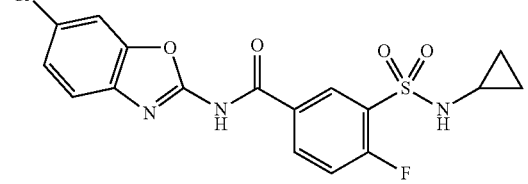

Compound KK
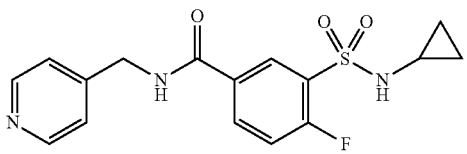

Compound LL
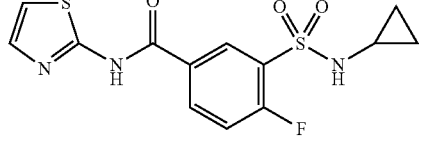

Compound MM
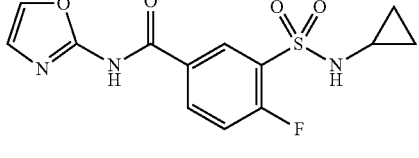

Compound NN
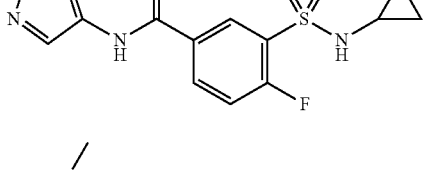

Compound OO
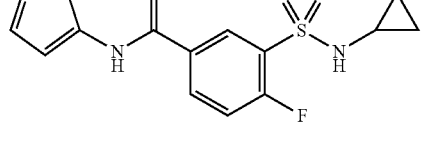

Compound PP 3-(N-cyclopropylsulfamoyl)-4-fluoro-N-(5-fluoropyridin-3-yl)benzamide (Compound AA), 100 mg as white solid, MS: M+H$^+$354.

3-(N-cyclopropylsulfamoyl)-4-fluoro-N-(6-fluoropyridin-3-yl)benzamide (Compound BB), 100 mg as off-white solid, M+H$^+$354.

3-(N-cyclopropylsulfamoyl)-N-(5,6-dichloropyridin-3-yl)-4-fluorobenzamide (Compound CC), 100 mg as off-white solid, M+H$^+$404.

3-(N-cyclopropylsulfamoyl)-4-fluoro-N-(2-fluoropyridin-4-yl)benzamide (Compound DD), 60 mg as off-white solid, M+H$^+$354.

3-(N-cyclopropylsulfamoyl)-4-fluoro-N-(quinolin-3-yl)benzamide (Compound EE), 110 mg as off-white solid, M+H$^+$386. $^1$HNMR (CDCl$_3$, Bruker Avance 400 MHz) δ: 0.41-0.48 (2H, m), 0.51-0.56 (2H, m), 2.25-2.32 (1H, m), 7.59-7.64 (1H, m), 7.68-7.72 (2H, m), 8.01 (1H, d, J=5.6 Hz), 8.39-8.42 (2H, m), 8.91 (1H, d, J=3.6 Hz), 8.83 (1H, s), 9.16 (1H, s), 10.99 (1H, brs).

3-(N-cyclopropylsulfamoyl)-4-fluoro-N-(pyridin-2-yl)benzamide (Compound FF), 100 mg as off-white solid, M+H$^+$336.

3-(N-cyclopropylsulfamoyl)-4-fluoro-N-(quinolin-4-yl)benzamide (Compound GG), 100 mg as off-white solid, M+H$^+$386. $^1$HNMR (CDCl$_3$, BrukerAvance 400 MHz) δ: 0.41-0.48 (2H, m), 0.51-0.60 (2H, m), 2.25-2.32 (1H, m), 7.63-7.67 (1H, m), 7.71 (1H, t, J=6.4 Hz), 7.81 (1H, t, J=5.2 Hz), 7.89 (1H, d, J=3.2 Hz), 8.06 (1H, d, J=2.4 Hz), 8.25 (1H, d, J=5.2 Hz) 8.42-8.48 (2H, m), 8.51 (1H, d, J=4.4 Hz), 8.91 (1H, d, J=3.6 Hz), 10.95 (1H, brs).

N-(7-chloroquinolin-4-yl)-3-(N-cyclopropylsulfamoyl)-4-fluorobenzamide (Compound HH), 120 mg as off-white solid, M+H$^+$420. $^1$HNMR (CDCl$_3$, Bruker Avance 400 MHz) δ: 0.35-0.41 (2H, m), 0.44-0.51 (2H, m), 2.25-2.30 (1H, m), 7.67-7.73 (2H, m), 7.91-7.93 (1H, m), 8.11 (1H, d, J=1.2 Hz), 8.28-8.32 (1H, m), 8.42-8.47 (2H, m), 8.48-8.50 (1H, m), 8.93-8.96 (1H, m), 11.00 (1H, brs).

3-(N-cyclopropylsulfamoyl)-4-fluoro-N-(2-oxo-1,2-dihydropyridin-3-yl)benzamide (Compound II), 120 mg as off-white solid, M+H$^+$352.

3-(N-cyclopropylsulfamoyl)-4-fluoro-N-(pyridin-3-ylmethyl)benzamide (Compound JJ), 60 mg as off-white solid, M+H$^+$350.

3-(N-cyclopropylsulfamoyl)-4-fluoro-N-(pyridin-4-ylmethyl)benzamide (Compound KK), 100 mg as off-white solid, M+H$^+$350, $^1$HNMR (CDCl$_3$, BrukerAvance 400 MHz) δ: 0.35-0.41 (2H, m), 0.44-0.51 (2H, m), 2.25-2.30 (1H, m), 4.51 (2H, d, J=3.6 Hz), 7.32 (2H, d, J=3.6 Hz), 7.61 (1H, t, J=6.0 Hz), 8.26 (1H, brs), 8.37-8.40 (2H, m), 8.49-8.53 (2H, m), 9.44 (1H, t, J=4.0 Hz).

3-(N-cyclopropylsulfamoyl)-4-fluoro-N-(thiazol-2-yl)benzamide (Compound LL), 90 mg as off-white solid, M+H$^+$342.

3-(N-cyclopropylsulfamoyl)-4-fluoro-N-(oxazol-2-yl)benzamide (Compound MM), 15 mg as off-white solid, M+H$^+$326.

3-(N-cyclopropylsulfamoyl)-4-fluoro-N-(isoxazol-4-yl)benzamide (Compound NN), 10 mg as off-white solid, M+H$^+$326.

3-(N-cyclopropylsulfamoyl)-4-fluoro-N-(1-methyl-1H-pyrazol-5-yl)benzamide (Compound OO), 110 mg as off-white solid, M+H$^+$339.

N-(6-chlorobenzo[d]oxazol-2-yl)-3-(N-cyclopropylsulfamoyl)-4-fluorobenzamide (Compound PP), 40 mg as off-white solid, M+H$^+$410.

Example 14

General Procedure N

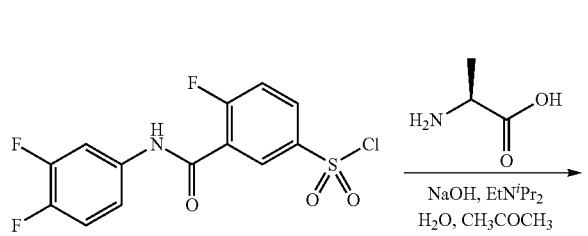

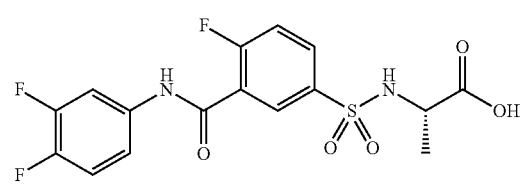

(S)-2-(3-((3,4-difluorophenyl)carbamoyl)-4-fluorophenylsulfonamido)propanoic acid: To a vial (2 ml) was charged with L-alanine (25.5 mg, 0.28 mmol), NaOH (2M, 0.15 ml, 0.28 mmol). The mixture was cooled to 0° C., and treated with sulfonyl chloride (100 mg, 0.28 mmol), followed by EtN$^i$Pr$_2$ (0.055 ml, 0.31 mmol) and acetone (0.15 ml) to get a clear solution. The mixture was stirred at 0° C. for 15 minutes and then at rt for 6 hours. Volatiles were removed in vacco, the residue was diluted with water (1 ml), basicified with NaOH (2 M, 0.15 ml), extracted with diethyl ether. The aqueous phase was acidified with concentrated HCl to PH 1 and extracted with ethyl acetate. The organic phase was washed with brine and concentrated. The residue was dissolved in acetonitrile and purified on preparative HPLC with a gradient of acetonitrile in water from 20% to 100% in 15 minutes. A white solid was obtained after lyophilization (45 mg, 39%). $^1$H NMR (300 MHz, CDCl$_3$): δ 8.62 (dd, J=6.7, 2.0 Hz, 1H), 8.40 (bd, J=13.2 Hz, 1H), 8.10-8.00 (m, 1H), 7.77-7.66 (m, 1H), 7.33 (dd, J=10.8, 8.5 Hz, 1H), 7.26-7.10 (m, 2H), 5.63 (bd, J=8.2 Hz, 1H), 4.16-4.04 (m, 1H), 1.46 (d, J=7.3 Hz, 3H); Calculated for C$_{16}$H$_{13}$F$_3$N$_2$O$_5$S, 402.05; observed MS (ESI) (m/z) 403.2 (M+1)$^+$.

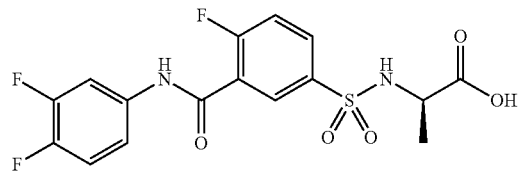 [SMILES: C[C@@H](NS(=O)(=O)c1ccc(F)c(C(=O)Nc2ccc(F)c(F)c2)c1)C(=O)O]

(R)-2-(3-((3,4-difluorophenyl)carbamoyl)-4-fluorophenylsulfonamido)propanoic acid: Was prepared by a procedure analogous to that described for General Procedure N. $^1$H NMR (300 MHz, MeOD): δ 8.20 (dd, J=6.4, 2.3 Hz, 1H), 8.04 (ddd, J=8.5, 4.7, 2.6 Hz, 1H), 7.81 (ddd, J=13.0, 7.3, 2.3 Hz, 1H), 7.48-7.34 (m, 2H), 7.32-7.18 (m, 1H), 3.98 (q, J=7.3 Hz, 1H), 1.34 (d, J=7.0 Hz, 3H); Calculated for C$_{16}$H$_{13}$F$_3$N$_2$O$_5$S, 402.05; observed MS (ESI) (m/z) 403.2 (M+1)$^+$.

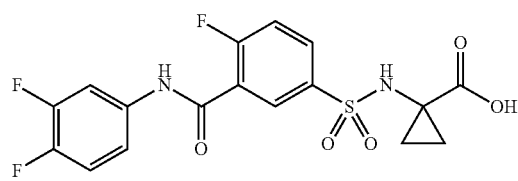 [SMILES: O=C(Nc1ccc(F)c(F)c1)c1cc(S(=O)(=O)NC2(C(=O)O)CC2)ccc1F]

1-(3-((3,4-difluorophenyl)carbamoyl)-4-fluorophenylsulfonamido)cyclopropanecarboxylic acid: Was prepared by a procedure analogous to that described for General Procedure N. $^1$H NMR (300 MHz, MeOD): δ 8.20 (dd, J=6.4, 2.3 Hz, 1H), 8.04 (ddd, J=8.5, 4.7, 2.6 Hz, 1H), 7.82 (ddd, J=12.7, 7.6, 2.6 Hz, 1H), 7.48-7.34 (m, 2H), 7.32-7.20 (m, 1H), 1.44-1.37 (m, 2H), 1.35-1.29 (m, 2H); Calculated for C$_{17}$H$_{13}$F$_3$N$_2$O$_5$S, 414.05; observed MS (ESI) (m/z) 415.1 (M+1)$^+$.

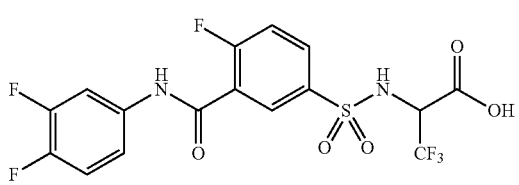 [SMILES: O=C(Nc1ccc(F)c(F)c1)c1cc(S(=O)(=O)NC(C(=O)O)C(F)(F)F)ccc1F]

2-(3-((3,4-difluorophenyl)carbamoyl)-4-fluorophenylsulfonamido)-3,3,3-trifluoropropanoic acid: Was prepared by a procedure analogous to that described for General Procedure N. ¹H NMR (300 MHz, MeOD): δ 8.25 (dd, J=6.4, 2.6 Hz, 1H), 8.08 (ddd, J=8.8, 4.7, 2.3 Hz, 1H), 7.82 (ddd, J=12.7, 7.3, 2.6 Hz, 1H), 7.49-7.37 (m, 2H), 7.32-7.20 (m, 1H), 4.79 (q, J+7.9 Hz, 1H); Calculated for $C_{16}H_{10}F_6N_2O_5S$, 456.02; observed MS (ESI) (m/z) 457.2 (M+1)⁺.

Example 15

General Procedure O

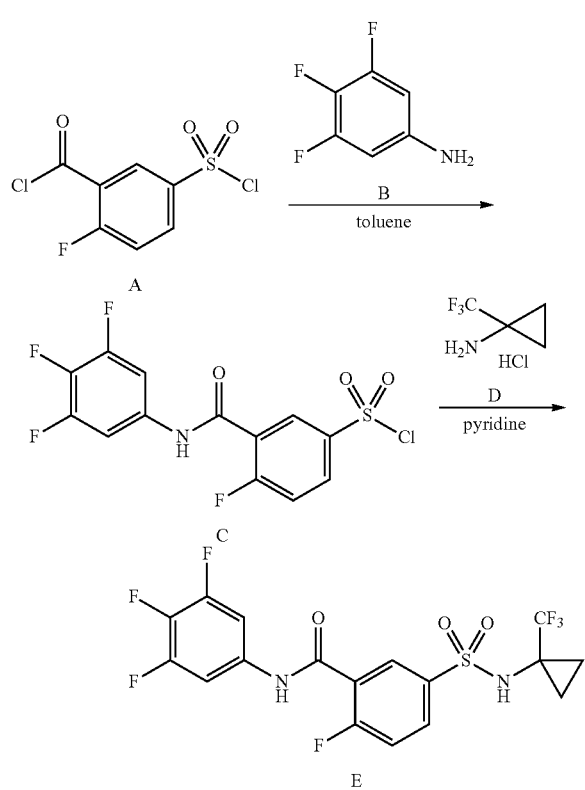

N-(3,4,5-Trifluorophenyl)-2-fluoro-5-(N-(1-(trifluoromethyl)cyclopropyl)sulfamoyl)benzamide: To a 0° C. solution of 3,4,5-trifluoroaniline (0.618 g, 0.0042 mol) in toluene (5 mL) was added dropwise a solution of 5-chlorosulfonyl-2-fluorobenzoyl chloride (1.08 g, 0.0042 mol) (prepared as in the first step of General Procedure B) in 5 mL of toluene. The mixture was stirred at room temperature overnight. The solvent was evaporated and the crude product was purified by column chromatography (EtOAc/hexane) to give compound 3-(3,4,5-trifluorophenylcarbamoyl)-4-fluorobenzene-1-sulfonyl chloride (1.14 g, 74%). After drying overnight under vacuum, a mixture of 3-(3,4,5-trifluorophenylcarbamoyl)-4-fluorobenzene-1-sulfonyl chloride (59 mg, 0.16 mmol), and 1-trifluoromethyl-cyclopropylamine.HCl (39 mg, 0.24 mmol) in pyridine (0.2 mL) was stirred at room temperature overnight. After which the reagent was evaporated, the residue was dissolved in EtOAc, washed with 1N HCl and then brine, dried and purified by chromatography (EtOAc/hexane) to give the desire product (58.2 mg, 80%) as a white solid. ¹H NMR (300 MHz, d₄-MeOH): 8.20-8.18 (m, 1H), 8.06-8.01 (m, 1H), 7.58-7.43 (m, 3H), 1.22 (m, 4H); MS (ES) m/z: 457.2 (M+H⁺), calculated 457.04.

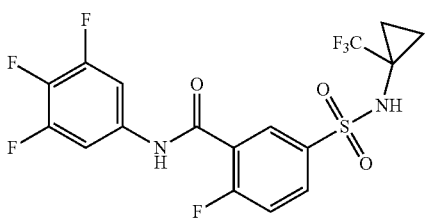 [SMILES: O=C(Nc1cc(F)c(F)c(F)c1)c1cc(S(=O)(=O)NC2(C(F)(F)F)CC2)ccc1F]

2-Fluoro-5-(N-(1-(trifluoromethyl)cyclopropyl)sulfamoyl)-N-(3,4,5-trifluorophenyl)benzamide: In a similar procedure as General Procedure O, final compound was obtained as a white solid (58.2 mg, 80%). ¹H NMR (300 MHz, d₄-MeOH): 8.20-8.18 (m, 1H), 8.06-8.01 (m, 1H), 7.58-7.43 (m, 3H), 1.22 (m, 4H); MS (ES) m/z: 457.2 (M+H⁺), calculated 457.04.

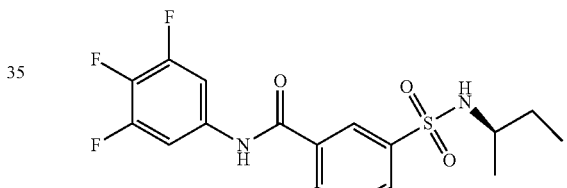

(R)-5-(N-(Sec-butyl)sulfamoyl)-2-fluoro-N-(3,4,5-trifluorophenyl)benzamide: In a similar procedure as General Procedure O, final compound was obtained as a white solid (29 mg, 42%). ¹H NMR (300 MHz, d₄-MeOH): 8.22-8.19 (m, 1H), 8.08-8.03 (m, 1H), 7.58-7.43 (m, 3H), 3.24-3.18 (m, 1H), 1.42-1.35 (m, 2H), 1.01-0.98 (d, J=6.7 Hz, 3H), 0.83-0.78 (t, J=7.3 Hz, 3H); MS (ES) m/z: 405.2 (M+H⁺), calculated 405.08.

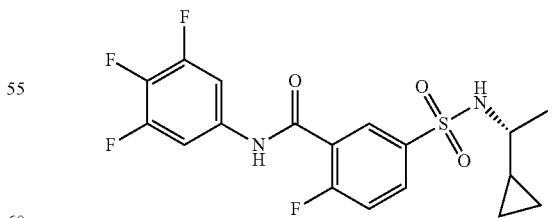

(R)-5-(N-(1-Cyclopropylethyl)sulfamoyl)-2-fluoro-N-(3,4,5-trifluorophenyl)benzamide: In a similar procedure as General Procedure O, final compound was obtained as a white solid (23.1 mg, 36%). ¹H NMR (300 MHz, d₄-MeOH): 8.24-8.21 (m, 1H), 8.09-8.05 (m, 1H), 7.59-7.44 (m, 3H), 2.71-2.66 (m, 1H), 1.14-1.12 (d, J=6.7 Hz, 3H), 0.82-0.76 (m, 1H), 0.48-0.40 (m, 1H), 0.35-0.29 (m, 1H), 0.19-0.14 (m, 1H), 0.06-0.03 (m, 1H); MS (ES) m/z: 417.2 (M+H⁺), calculated 417.08.

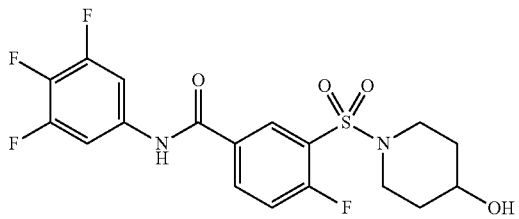 [SMILES: O=C(Nc1cc(F)c(F)c(F)c1)c1ccc(F)c(S(=O)(=O)N2CCC(O)CC2)c1]

4-Fluoro-3-((4-hydroxypiperidin-1-yl)sulfonyl)-N-(3,4,5-trifluorophenyl)benzamide: In a similar procedure as General Procedure O, final compound was obtained as a white solid (53 mg, 77%). ¹H NMR (300 MHz, d₄-MeOH): 8.42-8.39 (m, 1H), 8.27-8.22 (m, 1H), 7.62-7.47 (m, 3H), 3.75-3.70 (m, 1H), 3.54-3.52 (m, 2H), 3.08-3.01 (m, 2H), 1.92-1.86 (m, 2H), 1.62-1.52 (m, 2H); MS (ES) m/z: 433.2 (M+H⁺), calculated 433.08.

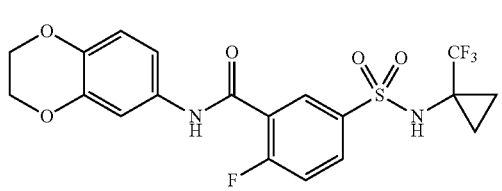 [SMILES: O=C(Nc1ccc2c(c1)OCCO2)c1cc(S(=O)(=O)NC2(C(F)(F)F)CC2)ccc1F]

N-(2,3-Dihydrobenzo[b][1,4]dioxin-6-yl)-2-fluoro-5-(N-(1-(trifluoromethyl)cyclopropyl) sulfamoyl)benzamide: In a similar procedure as General Procedure O, final compound was obtained as a white solid (73 mg, 69.2%). ¹H NMR (300 MHz, d₄-MeOH): 8.19-8.16 (m, 1H), 8.03-7.99 (m, 1H), 7.47-7.41 (t, J=9.2 Hz, 1H), 7.30 (s, 1H), 7.07-7.04 (m, 1H), 6.83-6.80 (d, J=8.7 Hz, 1H), 4.24 (s, 4H), 1.24 (s, 4H); MS (ES) m/z: 461.2 (M+H⁺), calculated 461.07.

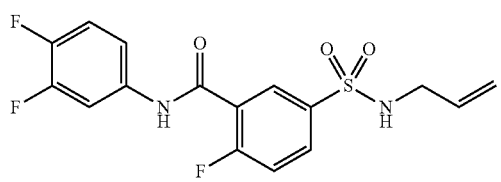 [SMILES: C=CCNS(=O)(=O)c1ccc(F)c(C(=O)Nc2ccc(F)c(F)c2)c1]

5-(N-Allylsulfamoyl)-N-(3,4-difluorophenyl)-2-fluorobenzamide: In a similar procedure as General Procedure O, final compound was obtained as a white solid (6.4 mg, 12%). ¹H NMR (300 MHz, d₄-MeOH): 8.20-8.17 (m, 1H), 8.06-8.01 (m, 1H), 7.86-7.78 (m, 1H), 7.49-7.36 (m, 2H), 7.31-7.22 (m, 1H), 5.80-5.67 (m, 1H), 5.21-5.14 (m, 1H), 5.08-5.03 (m, 1H), 4.87-4.84 (m, 2H); MS (ES) m/z: 371.2 (M+H⁺), calculated 371.06.

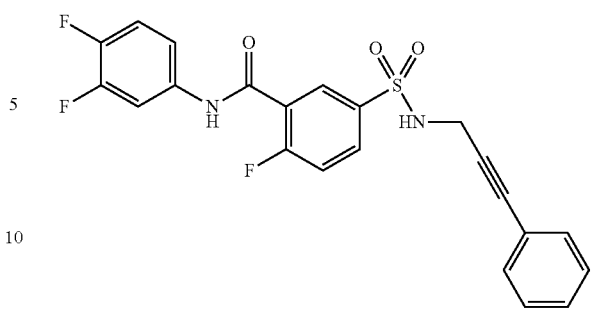

N-(3,4-Difluorophenyl)-2-fluoro-5-(N-(3-phenylprop-2-yn-1-yl)sulfamoyl)benzamide: In a similar procedure as General Procedure O, final compound was obtained as a white solid (58.8 mg, 65.2%). ¹H NMR (300 MHz, d₄-MeOH): 8.33-8.30 (m, 1H), 8.12-8.07 (m, 1H), 7.81-7.75 (m, 1H), 7.41-7.19 (m, 8H), 4.07 (s, 2H); MS (ES) m/z: 445.2 (M+H⁺), calculated 445.08.

Example 16

General Procedure P

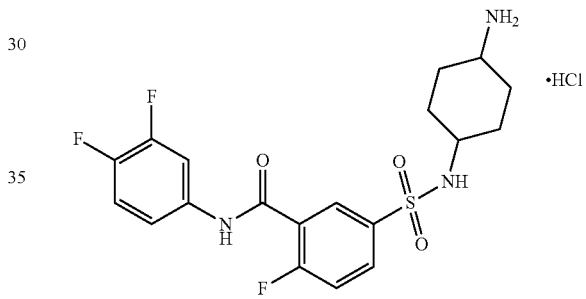

5-(N-(4-Aminocyclohexyl)sulfamoyl)-N-(3,4-difluorophenyl)-2-fluorobenzamide hydrochloride: tert-Butyl(4-(3-((3,4-difluorophenyl)carbamoyl)-4-fluorophenylsulfonamido)cyclohexyl)carbamate (25 mg, 0.047 mmol) was treated with 4N HCl in dioxane (0.5 mL). The mixture was stirred at room temperature overnight. The white solid was filtered and washed with ether gave the desired product as an HCl salt (25 mg, 100%). ¹H NMR (300 MHz, CD3OD): 8.24-8.21 (m, 1H), 8.10-8.05 (m, 1H), 7.87-7.79 (m, 1H), 7.51-7.48 (m, 1H), 7.45-7.35 (m, 1H), 7.31-7.22 (m, 1H), 3.28-3.25 (m, 1H), 3.15-3.09 (m, 1H), 1.87-1.56 (m, 8H); MS (ES) m/z: 428.2 (M+H⁺), calculated 428.12.

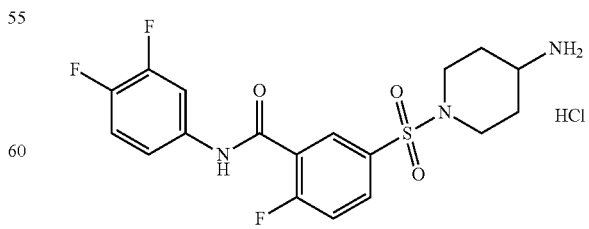

5-((4-Aminopiperidin-1-yl)sulfonyl)-N-(3,4-difluorophenyl)-2-fluorobenzamide hydrochloride: In a similar procedure as General Procedure P, the final product was obtained as an HCl salt (49 mg, 100%). $^1$H NMR (300 MHz, d$_4$-MeOH): 8.14-8.11 (m, 1H), 8.03-7.98 (m, 1H), 7.87-7.79 (m, 1H), 7.56-7.50 (m, 1H), 7.40-7.36 (m, 1H), 7.32-7.23 (m, 1H), 3.92-3.88 (m, 2H), 3.15-3.07 (m, 1H), 2.56-2.47 (m, 2H), 2.08-2.05 (m, 2H), 1.73-1.63 (m, 2H); MS (ES) m/z: 414.2 (M+H$^+$), calculated 414.10.

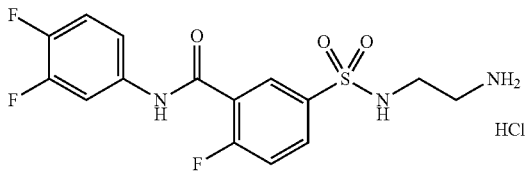 [SMILES: NCCNS(=O)(=O)c1ccc(F)c(C(=O)Nc2ccc(F)c(F)c2)c1 ; Cl]

5-(N-(2-Aminoethyl)sulfamoyl)-N-(3,4-difluorophenyl)-2-fluorobenzamide hydrochloride: In a similar procedure as General Procedure P, the final product was obtained as an HCl salt (8.3 mg, 37%). $^1$H NMR (300 MHz, d$_4$-MeOH): 8.24-8.22 (m, 1H), 8.10-8.05 (m, 1H), 7.87-7.79 (m, 1H), 7.55-7.49 (m, 1H), 7.40-7.36 (m, 1H), 7.32-7.23 (m, 1H), 3.16-3.05 (m, 4H); MS (ES) m/z: 374.2 (M+H$^+$), calculated 374.07.

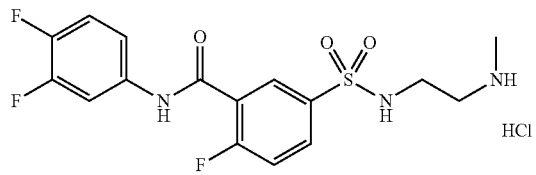 [SMILES: CNCCNS(=O)(=O)c1ccc(F)c(C(=O)Nc2ccc(F)c(F)c2)c1 ; Cl]

N-(3,4-Difluorophenyl)-2-fluoro-5-(N-(2-(methylamino)ethyl)sulfamoyl)benzamide hydrochloride: In a similar procedure as General Procedure P, the final product was obtained as an HCl salt (20 mg, 56%). MS (ES) m/z: 388.2 (M+H$^+$), calculated 388.09.

Example 17

Other Syntheses

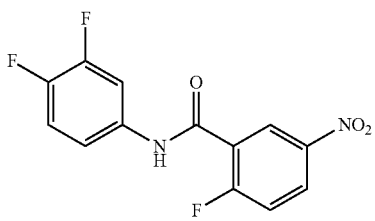 [SMILES: O=C(Nc1ccc(F)c(F)c1)c1cc([N+](=O)[O-])ccc1F]

N-(3,4-Difluorophenyl)-2-fluoro-5-nitrobenzamide: To a solution of 3,4-difluoroaniline (0.64 g, 4.92 mmol) and NEt$_3$ (0.82 g, 8.22 mmol) in CH$_2$Cl$_2$ (18 mL) was added dropwise a solution of 2-fluoro-5-nitro-benzoyl chloride (1.00 g, 4.92 mmol) in CH$_2$Cl$_2$ (18 mL). The reaction was stirred for 14 days, then was concentrated. The residue was partitioned between EtOAc (50 mL) and dilute NaHCO$_3$ (20 mL). The organic layer was washed with and d5 mL), dilute NaHCO$_3$ (10 mL), water (10 mL), 2 N HCl (2×15 mL), and brine (5 mL), dried (Na$_2$SO$_4$), and concentrated. The crude material was purified by silica column (10-20% EtOAc/Hexane) to give the desired product (0.91 g, 62%) as a pale yellow solid. MS: M+H$^+$273. $^1$H NMR (300 MHz, CDCl$_3$): 8.62 (dd, J=2.9, 6.7 Hz, 1H), 8.46-841 (m, 1H), 8.35 (d, J=14.1 Hz, 1H), 7.80-7.73 (m, 1H), 7.41 (dd, J=1.5, 9.1 Hz, 1H), 7.26-7.14 (m, 3H).

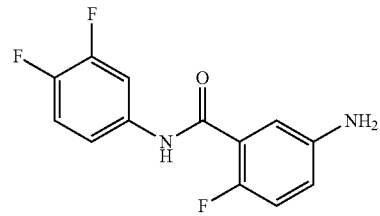 [SMILES: Nc1ccc(F)c(C(=O)Nc2ccc(F)c(F)c2)c1]

5-amino-N-(3,4-Difluorophenyl)-2-fluorobenzamide: A mixture of N-(3,4-difluorophenyl)-2-fluoro-5-nitrobenzene (0.50 g, 1.69 mmol) and 10% Pd/C (30 mg) in methanol (8 mL) was evacuated and then purged with hydrogen three times. The reaction was stirred under a hydrogen atmosphere for 16 hours. The reaction was filtered through Celite, and the filtrate was concentrated to give the desired product (0.43 g, 96%) as a pale yellow solid. MS: M+H$^+$267. $^1$H NMR (300 MHz, DMSO-d$_6$): 10.46 (s, 1H), 7.89-7.82 (m, 1H), 7.47-7.35 (m, 2H), 6.98 (dd, J=1.2, 8.8 Hz, 1H), 6.77-6.65 (m, 2H), 5.20 (s, 2H).

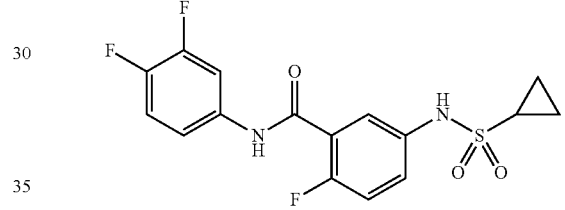

5-(cyclopropanesulfonamido)-N-(3,4-Difluorophenyl)-2-fluorobenzamide: To a 0° C. solution of 5-amino-(N-3,4-difluorophenyl)-2-fluorobenzamide (40 mg, 0.15 mmol) in THF (1 mL) was added and NEt$_3$ (30 mg, 0.30 mmol) and cyclopropyl-sulfonyl chloride (24 mg, 0.17 mmol). The reaction was warmed to 20° C., and was stirred for 3 hours. The reaction was cooled to 0° C. and further NEt$_3$ (19 mg, 0.19 mmol) in THF (1 mL) was added cyclopropyl-sulfonyl chloride (24 mg, 0.17 mmol) were added. The reaction was warmed to 20° C., and was stirred for 60 hours. The mixture was concentrated, then the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated. The crude material was purified by silica column (10-50% EtOAc/Hexane) to give the desired product (44 mg, 79%) as an off-white solid. MS: M+H$^+$371. $^1$H NMR (300 MHz, DMSO-d$_6$): 10.64 (s, 1H), 9.9 (s, 1H), 7.90-7.81 (m, 1H), 7.47-7.41 (m, 5H), 2.66-2.60 (m, 1H), 1.00-0.91 (m, 4H).

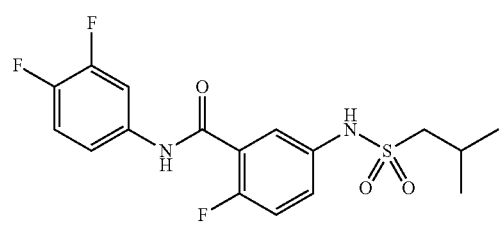 [SMILES: CC(C)CS(=O)(=O)Nc1ccc(F)c(C(=O)Nc2ccc(F)c(F)c2)c1]

N-(3,4-Difluorophenyl)-2-fluoro-5-(2-methylpropylsulfonamido)benzamide: A mixture of 5-amino-(N-3,4-difluorophenyl)-2-fluorobenzamide (25 mg, 0.094 mmol) and DMAP (10 mg) in pyridine (1 mL) was treated with isobutane-sulfonyl chloride (16 mg, 0.11 mmol). The reaction was heated at 110° C. for 16 hours. Further DMAP (10 mg) and isobutane-sulfonyl chloride (32 mg, 0.22 mmol) were added, and the reaction was heated at 110° C. for 3 hours. The mixture was concentrated, then the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated. The crude material was purified by silica column (10-50% EtOAc/Hexane) to give the desired product (15 mg, 41%) as an off-white solid. MS: M+H$^+$387. $^1$H NMR (300 MHz, DMSO-d$_6$): 10.64 (s, 1H), 9.97 (s, 1H), 7.89-7.82 (m, 1H), 7.45-7.34 (m, 5H), 2.99 (d, J=6.5 Hz, 1H), 2.16-2.07 (m, 1H), 0.98 (d, J=6.7 Hz, 1H).

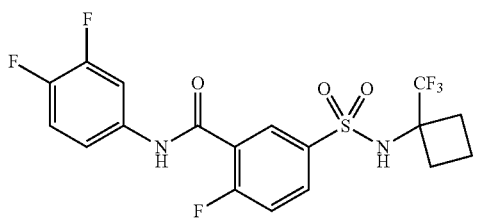 [SMILES: O=C(Nc1ccc(F)c(F)c1)c1cc(S(=O)(=O)NC2(C(F)(F)F)CCC2)ccc1F]

N-(3,4-Difluorophenyl)-2-fluoro-5-(N-(1-(trifluoromethyl)cyclobutyl)sulfamoyl)benzamide: A mixture of 3-(3,4-difluorophenyl-carbamoyl)-4-fluorobenzene-1-sulfonyl chloride (30 mg, 0.086 mmol) and DMAP (10 mg) in pyridine (1 mL) was treated with 1-trifluoromethyl-cyclobutane (36 mg, 0.26 mmol). The reaction was heated at 95° C. for 4 hours. The mixture was concentrated, then the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated. The crude material was purified by silica column (10-50% EtOAc/Hexane) to give the desired product (2 mg, 5%) as a clear gum. MS: M+H$^+$453. $^1$H NMR (300 MHz, DMSO-d$_6$): 8.22-8.20 (m, 1H), 8.10-8.06 (m, 1H), 7.82-7.76 (m, 1H), 7.49 (d, J=9.4 Hz, 1H), 7.32-7.23 (m, 3H), 2.47-2.41 (m, 4H), 1.92-1.83 (m, 2H).

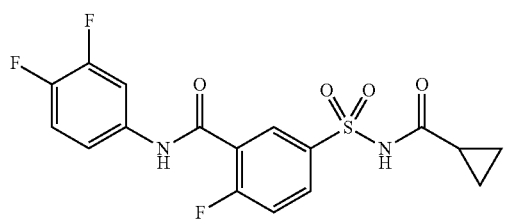 [SMILES: O=C(Nc1ccc(F)c(F)c1)c1cc(S(=O)(=O)NC(=O)C2CC2)ccc1F]

5-(N-(Cyclopropanecarbonyl)sulfamoyl)-N-(3,4-difluorophenyl)-2-fluorobenzamide: To a 0° C. solution of cyclopropanecarboxamide (29 mg, 0.28 mmol) in THF (1 mL) was added a 60% dispersion of NaH in mineral oil (11 mg, 0.28 mmol). The reaction was warmed to 20° C., and was stirred for 30 minutes. The mixture was cooled to 0° C., then 3-(3,4-difluorophenylcarbamoyl)-4-fluorobenzene-1-sulfonyl chloride (50 mg, 0.14 mmol) was added. The reaction was warmed to 20° C., and was stirred for 16 hours. The mixture was concentrated, then the residue was partitioned between EtOAc (20 mL) and dilute NaHCO$_3$ (5 mL). The organic layer was washed with water (5 mL), and brine (1 mL), dried (Na$_2$SO$_4$), and concentrated. The crude material was purified by silica column (20-100% EtOAc/Hexane), followed by prep-TLC (70% EtOAc/Hexane) to give the desired product (3 mg, 5%) as a clear gum. MS: M+H$^+$399.

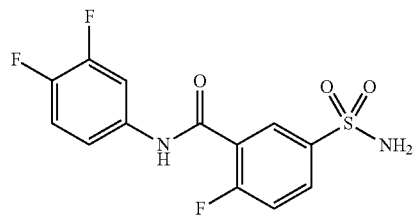 [SMILES: NS(=O)(=O)c1ccc(F)c(C(=O)Nc2ccc(F)c(F)c2)c1]

N-(3,4-Difluorophenyl)-2-fluoro-5-sulfamoylbenzamide. To a solution of 3-(3,4-difluorophenylcarbamoyl)-4-fluorobenzene-1-sulfonyl chloride (0.50 g, 1.43 mmol) in THF (4 mL) was added dropwise 28-30% ammonia in water (1 mL). The reaction was stirred for 60 hours. The mixture was concentrated, then the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated. The crude material was purified by silica column (20-100% EtOAc/Hexane) to give the desired product (410 mg, 87%) as a white solid. MS: M+H$^+$331.

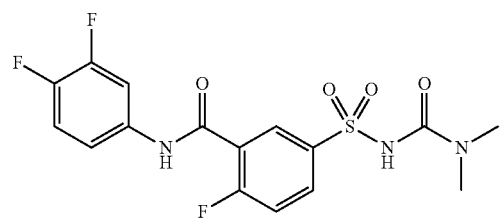 [SMILES: CN(C)C(=O)NS(=O)(=O)c1ccc(F)c(C(=O)Nc2ccc(F)c(F)c2)c1]

N-(3,4-Difluorophenyl)-5-(N-(dimethylcarbamoyl)sulfamoyl)-2-fluorobenzamide. A mixture of N-(3,4-difluorophenyl)-2-fluoro-5-sulfamoylbenzamide (50 mg, 0.15 mmol) and DMAP (10 mg) in pyridine (0.1 mL) was treated with dimethyl carbamoyl chloride (48 mg, 0.45 mmol). The reaction was heated at 90° C. for 2 hours. The mixture was concentrated, then the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated. The crude material was purified by silica column (1-10% MeOH/CH$_2$Cl$_2$) to give the desired product (12 mg, 20%) as a white solid. MS: M+H$^+$402.

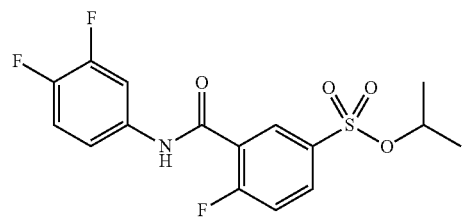 [SMILES: CC(C)OS(=O)(=O)c1ccc(F)c(C(=O)Nc2ccc(F)c(F)c2)c1]

Isopropyl 3-((3,4-difluorophenyl)carbamoyl)-4-fluorobenzenesulfonate. To a 0° C. solution of isopropanol (0.1 mL) and pyridine (0.1 mL) was added portionwise of 3-(3,4-difluorophenylcarbamoyl)-4-fluorobenzene-1-sulfonyl chloride (50 mg, 0.14 mmol). The reaction was warmed to 20° C., and was stirred for 16 hours. The mixture was concentrated, then the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated to give the desired product (22 mg, 42%) as a white solid. MS: M+H$^+$374.

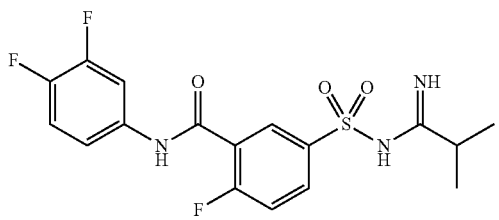 [SMILES: CC(C)C(=N)NS(=O)(=O)c1ccc(F)c(C(=O)Nc2ccc(F)c(F)c2)c1]

N-(3,4-Difluorophenyl)-2-fluoro-5-(N-(1-imino-2-methylpropyl)sulfamoyl)benzamide. To a mixture of 2-methylpropanimidamide.HCl (35 mg, 0.28 mmol) in THF (0.2 mL) was added a 10 N solution of NaOH (4 drops), followed by a solution of 3-(3,4-difluorophenylcarbamoyl)-4-fluorobenzene-1-sulfonyl chloride (50 mg, 0.14 mmol) in THF (0.2 mL). The reaction was stirred for 16 hours. The mixture was concentrated, then the residue was partitioned between EtOAc (20 mL) and dilute NaHCO$_3$ (5 mL). The organic layer was washed with water (5 mL), and brine (1 mL), dried (Na$_2$SO$_4$), and concentrated. The crude material was purified by preparative-HPLC to give the desired product (2 mg, 5%) as an off-white solid. MS: M+H$^+$400.

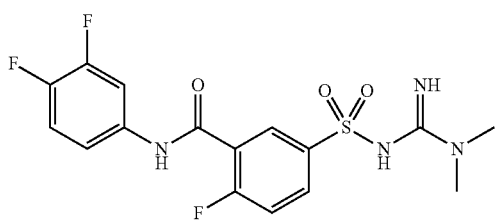

N-(3,4-Difluorophenyl)-5-(N—(N,N-dimethylcarbamimidoyl)sulfamoyl)-2-fluorobenzamide. A mixture of 1,1-dimethylguanidine sulfate (76 mg, 0.28 mmol) and 10 N aqueous NaOH solution (9 drops) was heated at 40° C. for 10 minutes. To this mixture was added THF (0.3 mL), and the mixture was cooled to 0° C. To the cooled solution was added 3-(3,4-difluorophenylcarbamoyl)-4-fluorobenzene-1-sulfonyl chloride (50 mg, 0.14 mmol). The reaction was warmed to 20° C., and was stirred for 16 hours. The mixture was concentrated, then the residue was partitioned between EtOAc (20 mL) and dilute NaHCO$_3$ (5 mL). The organic layer was washed with water (5 mL), and brine (1 mL), dried (Na$_2$SO$_4$), and concentrated to give the desired product (33 mg, 59%) as a pale yellow solid. MS: M+H$^+$401.

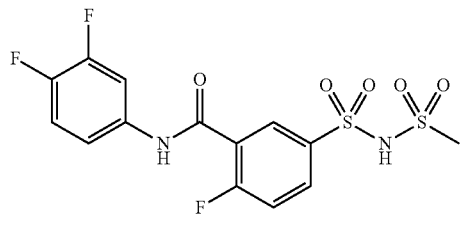 [SMILES: CS(=O)(=O)NS(=O)(=O)c1ccc(F)c(C(=O)Nc2ccc(F)c(F)c2)c1]

N-(3,4-difluorophenyl)-2-fluoro-5-(N-(methylsulfonyl)sulfamoyl)benzamide: To a solution of methanesulfonamide (38 mg, 0.14 mmol) and NEt$_3$ (40 mg, 40 mmol) in acetonitrile (1 mL) was added 3-(3,4-difluorophenyl-carbamoyl)-4-fluorobenzene-1-sulfonyl chloride (50 mg, 0.14 mmol). The reaction was heated at reflux for 2 hours. The mixture was concentrated, then the residue was partitioned between EtOAc (20 mL) and 1 N HCl (5 mL). The organic layer was washed with 2 N HCl (5 mL), water (5 mL), and brine (1 mL), dried (Na$_2$SO$_4$), and concentrated to give the desired product (33 mg, 60%) as a pale brown solid. MS: M+H$^+$409.

Synthesis of 3-(cyclopropanesulfonamido)-N-(3,4-difluorophenyl)-4-fluorobenzamide

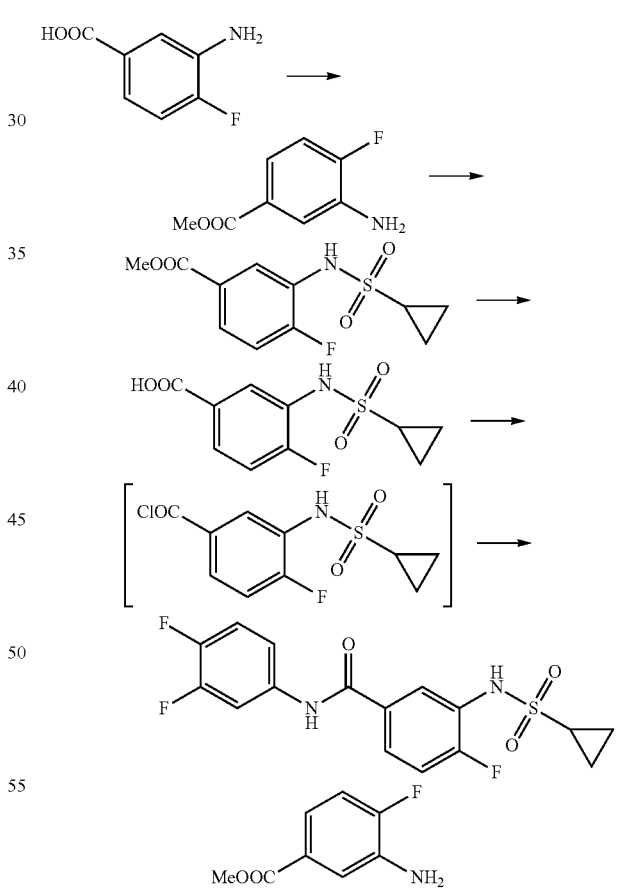

Methyl 3-amino-4-fluorobenzoate: 3-amino-4-fluorobenzoic acid (0.5 g) was dissolved in methanol (10 ml), then concentrated sulfuric acid (1 ml) was added. The reaction solution was heated to reflux until the reaction is complete. Then the reaction mixture was cooled down and poured into water, the pH of the resultant solution was adjusted to 8 by 2N NaOH solution. The product was extracted to EtOAc layer and the solvent was stripped off. 290 mg of methyl 3-amino-4-fluorobenzoate was obtained.

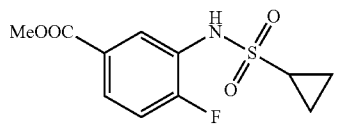 [SMILES: COC(=O)c1ccc(F)c(NS(=O)(=O)C2CC2)c1]

Methyl 3-(cyclopropanesulfonamido)-4-fluorobenzoate: Methyl 3-amino-4-fluorobenzoate (275 mg) and DMAP (100 mg) were dissolved in pyridine (10 ml). Then cyclopropanesulfonyl chloride (330 mg) was added into the solution. The reaction mixture was heated to 110° C. and stirred for 12 hours until the reaction is complete. The solvent was stripped off, the solid was dissolved in $CH_2Cl_2$ (50 ml) followed by 1N HCl solution (50 ml). The bottom aqueous layer was split off and the organic layer was washed with water and dried by anhydrous $Na_2SO_4$. The $CH_2Cl_2$ was stripped off and 270 mg of methyl 3-(cyclopropanesulfonamido)-4-fluorobenzoate was used for the next step directly.

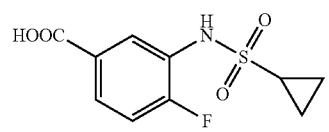 [SMILES: O=C(O)c1ccc(F)c(NS(=O)(=O)C2CC2)c1]

3-(Cyclopropanesulfonamido)-4-fluorobenzoic acid: Crude methyl 3-(cyclopropanesulfonamido)-4-fluorobenzoate (270 mg) was dissolved in MeOH (15 ml) and 10% LiOH solution (15 ml) was added. The reaction mixture was stirred at ambient temperature overnight until the reaction is complete. The solvent was stripped off and the pH of the resultant aqueous solution was adjusted to 1.0 by 1N HCl solution. The product was extracted with EtOAc and the EtOAc layer was dried with anhydrous $Na_2SO_4$. The solvent was stripped off and the resultant 3-(cyclopropanesulfonamido)-4-fluorobenzoic acid (250 mg) was used directly for the next step.

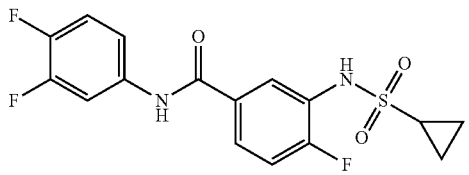 [SMILES: O=C(Nc1ccc(F)c(F)c1)c1ccc(F)c(NS(=O)(=O)C2CC2)c1]

3-(cyclopropanesulfonamido)-N-(3,4-difluorophenyl)-4-fluorobenzamide: 3-(cyclopropanesulfonamido)-4-fluorobenzoic acid (250 mg) was dissolved in $SOCl_2$ (5 ml) and the solution was heated to reflux and kept for 1 hours until the reaction is complete. The solvent was stripped off, then $CH_2Cl_2$ (10 ml) was added in. The resultant solution was cooled to 0° C., then $Et_3N$ (1 ml) and 3,4-difluoroaniline (0.25 g) were added. The resultant solution was stirred at ambient temperature overnight until the reaction is complete. The reaction mixture was poured into water (10 ml) and the bottom aqueous layer was split off. The organic layer was washed with 1N HCl solution, followed by brine solution and then dried with anhydrous $Na_2SO_4$. The solvent was stripped off and the crude product was purified by silica column twice. 35 mg of 3-(cyclopropanesulfonamido)-N-(3,4-difluorophenyl)-4-fluorobenzamide was obtained. HPLC purity: 96%. LC-MS: Calcd: 370.3; Measured: [M+1] =371.3.

Synthesis of N-(3-(N-cyclopropylsulfamoyl)-4-fluorophenyl)-3,4-difluorobenzamide:

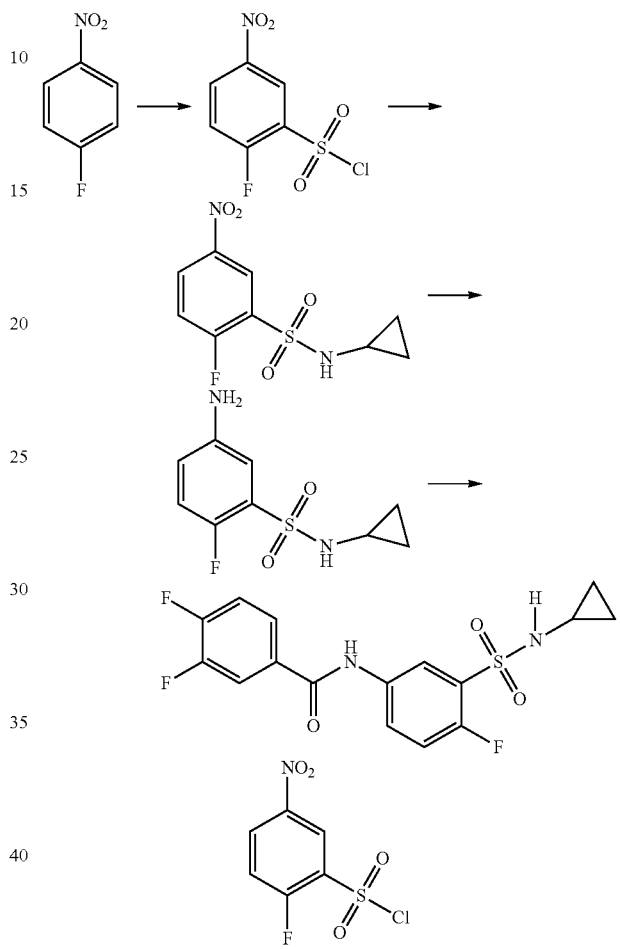

2-Fluoro-5-nitrobenzene-1-sulfonyl chloride: 1-fluoro-4-nitrobenzene (20 g) was dissolved in chlorosulfonic acid (35 ml), the reaction mixture was heated to 115° C. and stirred for 9 h until the reaction is complete. Then the reaction was cooled to ambient temperature and poured into ice water (300 g), the compound was extracted into EtOAc. The aqueous layer was split off. The EtOAc layer was washed by water, then brine solution and dried with anhydrous Na2SO4. The solvent was stripped off the crude product was purified by silica column (petroleum ether/EtOAc=10:1). 15 g of 2-fluoro-5-nitrobenzene-1-sulfonyl chloride was obtained.

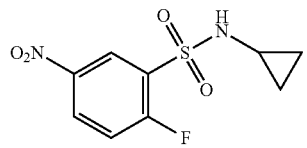 [SMILES: O=[N+]([O-])c1ccc(F)c(S(=O)(=O)NC2CC2)c1]

N-cyclopropyl-2-fluoro-5-nitrobenzenesulfonamide: To the mixture of cyclopropylamine (7.92 g) and N,N-Diisopropylethylamine (11 g) and CH₂Cl₂ (60 ml) at 0° C., the solution of 2-fluoro-5-nitrobenzene-1-sulfonyl chloride (7.2 g) dissolved in CH₂Cl₂ (50 ml) was added in dropwise, the reaction mixture was stirred for 2 hours at 0° C. until the reaction is complete. The solvent was stripped off and the crude product was dissolved in CH₂Cl₂ and washed by water twice. The crude product was purified by silica column (Petroleum ether/EtOAc=3:1) and 4.3 g of N-cyclopropyl-2-fluoro-5-nitrobenzenesulfonamide was obtained, yield: 67%.

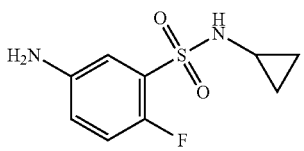

5-Amino-N-cyclopropyl-2-fluorobenzenesulfonamide: N-cyclopropyl-2-fluoro-5-nitrobenzenesulfonamide (2.2 g) was dissolved in 1,4-dioxane (44 ml), then 6N HCl (4.4 ml) and SnCl₂ (7.7 g) were added into the reaction mixture. The resultant mixture was stirred for 2 h at ambient temperature untile the reaction is complete. The reaction mixture was poured into the mixture of EtOAc (100 ml) and watero (50 ml) and the pH of the resultant mixture was adjusted to 11 by 2N NaOH. The bottom aqueous layer was split off and the organic layer was washed with water and dried with anhydrous Na₂SO₄. The solvent was stripped off by rotovap and 2 g of 5-amino-N-cyclopropyl-2-fluorobenzenesulfonamide was obtained as brown oil.

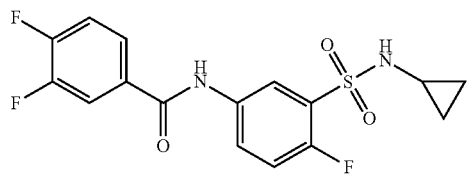 [SMILES: O=C(Nc1ccc(F)c(S(=O)(=O)NC2CC2)c1)c1ccc(F)c(F)c1]

N-(3-(N-cyclopropylsulfamoyl)-4-fluorophenyl)-3,4-difluorobenzamide: To the mixture of 5-amino-N-cyclopropyl-2-fluorobenzenesulfonamide (2 g), CH₂Cl₂ (50 ml) and Et₃N (1.8 g), 3,4-Difluorobenzoyl chloride (1.5 g) was added dropwise. The resultant reaction mixture was stirred at ambient temperature for 2 hours until the reaction is complete. The product was filtered and washed with CH₂Cl₂ twice and dried in a vacuum oven at 50° C. 1.3 g as a white solid. Yield 62%. HPLC purity: 96%. LC-MS, Calcd: 370.0, Measured: [M+1]=371.0. ¹HNMR (DMSO-d₆, Bruker Avance 400 MHz) δ: 0.42 (2H, m), 0.49 (2H, m), 2.25-2.36 (1H, m), 7.45-7.48 (1H, t), 7.62-7.67 (1H, dd), 7.89 (1H, brs), 8.05-8.11 (2H, m), 8.20-8.32 (2H, m), 10.62 (1H, s).

Synthesis of N-(3-(cyclopropanesulfonamido)-4-fluorophenyl)-3,4-difluorobenzamide:

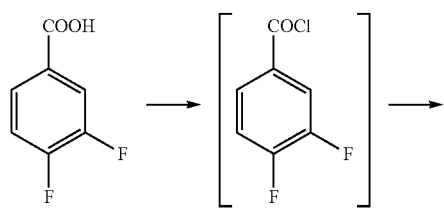

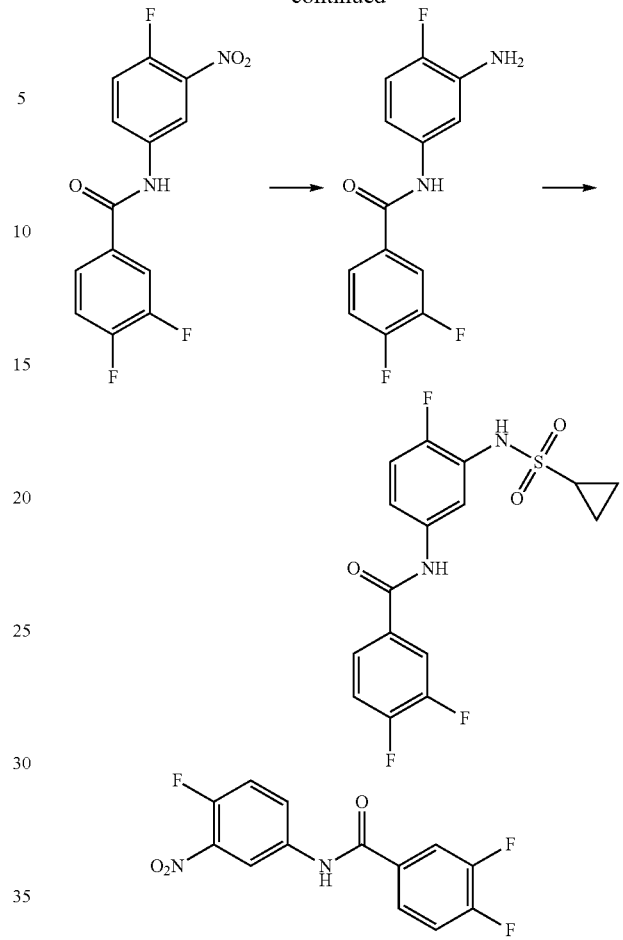

3,4-Difluoro-N-(4-fluoro-3-nitrophenyl)benzamide: 3,4-difluorobenzoic acid (1 g) was dissolved CH₂Cl₂ (10 ml). To the solution, oxalyl chloride (1 ml) was added. The reaction mixture was stirred at ambient temperature for 30 minutes until the reaction is complete. The solvent was stripped off and CH₂Cl₂ (20 ml) was added, the resultant solution was cooled to −5° C. and then Et₃N (2 ml) was added, followed by addition of 3-nitro-4-fluoroaniline (1 g). The reaction mixture was stirred at ambient temperature for 30 minutes until the reaction is complete. The solvent was stripped off and 3 g of 3,4-difluoro-N-(4-fluoro-3-nitrophenyl)benzamide was obtained as solid.

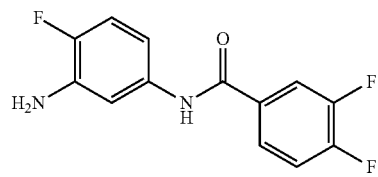 [SMILES: Nc1cc(NC(=O)c2ccc(F)c(F)c2)ccc1F]

N-(3-amino-4-fluorophenyl)-3,4-difluorobenzamide: 3,4-difluoro-N-(4-fluoro-3-nitrophenyl)benzamide (2 g) was dissolved in 1,4-dioxane (40 ml), then 6N HCl (6 ml) and SnCl₂ (8 g) were added. The reaction mixture was stirred at ambient temperature for 4 hours until the reaction is complete. The reaction mixture was poured into 1N NaOH solution and extracted with EtOAc twice. The organic layer was washed with brine solution and the solvent was stripped off by rotovap and 1.24 g of N-(3-amino-4-fluorophenyl)-3,4-difluorobenzamide was obtained as oil. The crude product was used without further purification.

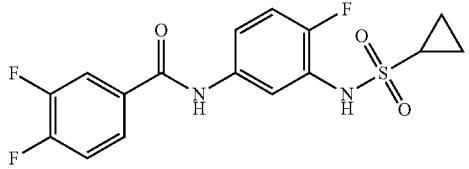 [SMILES: O=C(Nc1ccc(F)c(NS(=O)(=O)C2CC2)c1)c1ccc(F)c(F)c1]

N-(3-(cyclopropanesulfonamido)-4-fluorophenyl)-3,4-difluorobenzamide: N-(3-amino-4-fluorophenyl)-3,4-difluorobenzamide (12.4 g) was dissolved in pyridine (15 ml), then DMAP (100 mg) and cyclopropanesulfonyl chloride (0.65 g) were added. The reaction mixture was stirred at ambient temperature overnight until the reaction is complete. The reaction mixture was poured into water (100 ml) and extracted with EtOAc twice. The organic layer was washed with water and dried with anhydrous $Na_2SO_4$. The solvent was stripped off by rotovap and the solid product was purified by slurried in MTBE (20 ml). 800 mg of N-(3-(cyclopropanesulfonamido)-4-fluorophenyl)-3,4-difluorobenzamide was obtained as off white solid. $^1H$ NMR (300 MHz, $CDCl_3$): δ 7.8-7.10 (m, 6H), 6.6 (bs, 1H), 2.58 (m, 1H), 1.21 (m, 2 H), 1.0 (m, 2 H). MS (ESI) (m/z) observed (M+1)=371. HPLC purity: 98%. LC-MS: Calcd: 370.0; Measured: [M+1]=371.0.

PROCEDURES

The following procedures can be utilized in evaluating and selecting compounds as inhibitors of HBV infection.

The HBV replication inhibitors of the present invention are capable of treating and preventing diseases associated with HBV infection. The results presented in Tables 21 to 39 demonstrated that compounds of the present invention inhibit HBV replication in an immortalized murine hepatocyte (AML12)-derived stable cell line (AML12HBV10) that supports robust HBV replication in a tetracycline inducible manner without measurable cytotoxicity up to 50 µM by using the standard MTT assay (Promega).

The antiviral efficacy of the compounds of the disclosure, as presented in Tables 21 through 39 were determined in AML12HBV10 cells. AML12HBV10 is an immortalized murine hepatocyte (AML12)-derived stable cell line that supports robust HBV replication in a tetracycline inducible manner (Xu et al.). The cells were seeded into 96 well plates at a density of $2\times10^4$ cells per well and cultured in DMEM/F12 media with 10% fetal bovine serum in the absence of tetracycline to allow pgRNA transcription and HBV DNA replication. One day after seeding, cells were left untreated or treated with a serial dilution of testing compounds, ranging from 50 µM to 0.39 µM, for 48 hours. Cells were then lysed by adding into each well of 100 µl lysis buffer containing 10 mM Tris-HCl (pH 7.6), 1 mM EDTA, 100 mM NaCl and 1% NP-40 and incubated at 37° C. for 30 minutes. Half amount (50 µl) of cell lysate from each well was combined with equal volume of denaturing solution containing 0.5N NaOH and 1.5M NaCl. After 5 minute incubation, 100 µl of neutralization solution (1M Tris-HCl, pH 7.4, 1.5M NaCl) was added into each well. The denatured cell lysates (totally 200 µl) were applied onto Nylon membrane using 96-well dot-blot manifold (Biorad). HBV DNA in the cell lysates were determined by dot-blot hybridization with alpha-$^{32}P$-UTP-labelled riboprobe specific for HBV minus strand DNA. The antiviral efficacy of a compound of the disclosure was expressed as the concentration that reduces the amount of HBV DNA by 50% ($EC_{50}$).

Determination of cytotoxicity of compounds of the disclosure in AML12HBV10 cells: To determine the cytotoxicity of the compounds, AML12HBV10 cells were seeded into 96-well plates at a density of $2\times10^4$ cells per well and cultured in DMEM/F12 media with 10% fetal bovine serum in the absence of tetracycline to allow pgRNA transcription and HBV DNA replication. One day after seeding, cells were left untreated or treated with a serial dilution of testing compounds, ranging from 50 µM to 0.39 µM, for 48 hours. The cell viability was measured by a MTT assay, following procedure provided by the manufacturer (Promega). The cytotoxicity of a compound was expressed as the concentration of compound that reduces the viability of the cells by 50% ($CC_{50}$).

Determination of antiviral activity of compounds of the disclosure, as presented in Tables 21 through 39, in human hepatoma-derived cell lines: To further confirm the antiviral activity of the compounds of the disclosure against HBV in human hepatocyte-derived cells, HepDES 19 cells, a human hepatoma cell line supporting HBV replication in a tetracycline inducible manner (Guo et al., 2007), seeded into 12-well plates at a density of $5\times10^5$ cells per well and cultured in DMEM/F12 media with 10% fetal bovine serum and 1 µg/ml tetracycline. Two days after seeding, the cells were mock-treated or treated with a serial dilution of compounds of the disclosure, ranging from 10 µM to 0.018 µM, for 6 days in the absence of tetracycline. Upon the completion of treatment, cells were lysed by adding into each well of the 12-well plates 0.5 ml of lysis buffer containing 10 mM Tris-HCl (pH 8.0), 1 mM EDTA, 1% NP40 and 2% sucrose and incubating at 37° C. for 10 minutes. Cell debris and nuclei were removed by centrifugation and the supernatant was mixed with 130 µl of 35% polyethylene glycol (PEG) 8000 containing 1.5 M NaCl. After 1 hour incubation in ice, viral nucleocapsids were pelleted by centrifugation at 6,000×g for 5 min at 4° C., followed by 1 hour digestion at 37° C. in 400 µl of digestion buffer containing 0.5 mg/ml pronase (Calbiochem), 0.5% SDS, 150 mM NaCl, 25 mM Tris-HCl (pH 8.0) and 10 mM EDTA. The digestion mixture was extracted twice with phenol and DNA was precipitated with ethanol, dissolved in TE buffer (10 mM Tris-HC 1, pH 8.0; 0.1 mM EDTA). One half of the DNA sample from each well was resolved by electrophoresis into a 1.5% agarose gel. The gel was then subjected to denaturation in a solution containing 0.5 M NaOH and 1.5 M NaCl, followed by neutralization in a buffer containing 1 M Tris-HCl (pH7.4) and 1.5 M NaCl. DNA was then blotted onto Hybond-XL membrane (GE Health care) in 20×SSC buffer. The amounts of cytoplasmic HBV core-associated HBV DNA were determined by Southern blot hybridization and the antiviral efficacy of a compound was expressed as its concentration that reduce the amount of HBV DNA by 50% ($EC_{50}$) or 90% ($EC_{90}$).

Determination of cytotoxicity of compounds of the disclosure in human hepatoma-derived cell lines, HepDES 19 cells were seeded into 96-well plates at a density of $6\times10^4$ cells per well and cultured in DMEM/F12 media with 10% fetal bovine serum in the absence of tetracycline. One day after seeding, cells were left untreated or treated with a serial dilution of testing compounds, ranging from 50 µM to 0.39 µM, for 6 days. The cell viability was measured by a MTT assay, following procedure provided by the manufacturer (Promega). The cytotoxicity of a compound was expressed as the concentration of compound that reduces the viability of the cells by 50% ($CC_{50}$).

TABLE 21

Antiviral activity of exemplary compounds in AML12HBV10 and HepDES19 cells. In the Table, $EC_{50}$ key: 0 = >10 µM; 1 = 5-10 µM; 2 = 1-5 µM; 3 = <1 µM.

(I)

| $R^x$ | AML12HBV10 $EC_{50}$ | HepDES19 $EC_{50}$ |
|---|---|---|
| cycloheptylamino | 2 | 3 |
| cyclohexylamino | 2 | 3 |
| 2-chlorobenzylamino | 2 | 3 |
| cyclopentylamino | 3 | 3 |
| sec-butylamino | 3 | 3 |
| azepan-1-yl | 3 | 3 |
| cyclopropylamino | 1 | — |
| 2-methylcyclopropylamino | 2 | — |
| (S)-sec-butylamino | 3 | 3 |

TABLE 21-continued

Antiviral activity of exemplary compounds in AML12HBV10 and HepDES19 cells. In the Table, $EC_{50}$ key: 0 = >10 µM; 1 = 5-10 µM; 2 = 1-5 µM; 3 = <1 µM.

(I)

| $R^x$ | AML12HBV10 $EC_{50}$ | HepDES19 $EC_{50}$ |
|---|---|---|
| (R)-sec-butylamino | 3 | 3 |
| sec-butylamino | 3 | — |
| cyclohexylamino | 3 | 3 |
| azabicyclo | 1 | — |
| 3-pentylamino | 3 | 3 |
| azetidin-1-yl | 0 | — |
| pyrrolidin-1-yl | 2 | — |
| piperidin-1-yl | 1 | — |
| N-methyl-sec-butylamino | 0 | — |
| tert-butylamino | 3 | 2 |

TABLE 21-continued

Antiviral activity of exemplary compounds in AML12HBV10 and HepDES19 cells. In the Table, EC$_{50}$ key: 0 = >10 μM; 1 = 5-10 μM; 2= 1-5 μM; 3 = <1 μM.

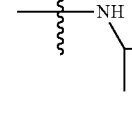
(I)

| R$^x$ | AML12HBV10 EC$_{50}$ | HepDES19 EC$_{50}$ |
|---|---|---|
| isopropyl-NH | 3 | — |
| dimethylamino | 2 | — |
| (S)-2-hydroxy-1-methylethylamino | 1 | — |
| (R)-2-hydroxy-1-methylethylamino | 3 | 3 |
| (S)-3-methyl-2-butylamino | 3 | 3 |
| (R)-3-methyl-2-butylamino | 2 | 2 |
| (S)-1-methoxy-2-propylamino | 3 | 3 |
| (R)-1-methoxy-2-propylamino | 2 | — |
| (S)-1-phenylethylamino | 3 | 3 |
| (R)-1-phenylethylamino | 2 | — |
| tert-amylamino | 3 | 3 |
| 1-ethylcyclopropylamino | 3 | 3 |
| 3,3-difluorocyclopentylamino | 3 | — |
| 2-methylcyclopentylamino | 3 | — |
| 3,3-dimethylcyclopentylamino | 3 | — |
| 1-ethylcyclopropylamino | 3 | 3 |
| 1-isopropylcyclopropylamino | 3 | — |

TABLE 21-continued
Antiviral activity of exemplary compounds in AML12HBV10 and HepDES19 cells. In the Table, EC$_{50}$ key: 0 = >10 μM; 1 = 5-10 μM; 2= 1-5 μM; 3 = <1 μM.
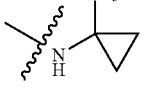
(I)
| R$^x$ | AML12HBV10 EC$_{50}$ | HepDES19 EC$_{50}$ |
|---|---|---|
| 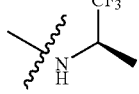 | 3 | 3 |
| 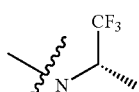 | 3 | — |
| 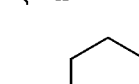 | 3 | — |
| 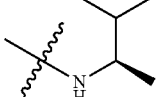 | 3 | — |
| 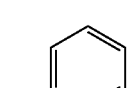 | 3 | — |
| 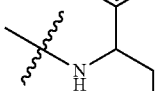 | 3 | — |
| 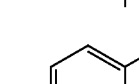 | 3 | — |
| 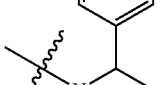 | 3 | 3 |
| R$^x$ | AML12HBV10 EC$_{50}$ | HepDES19 EC$_{50}$ |
| 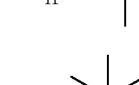 | 3 | 3 |
| 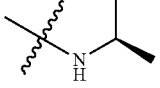 | 3 | 3 |
|  | 3 | 3 |
|  | 3 | 3 |
|  | 3 | — |
|  | 2 | — |
| 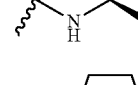 | 3 | 3 |

TABLE 21-continued
Antiviral activity of exemplary compounds in AML12HBV10 and HepDES19 cells. In the Table, EC$_{50}$ key: 0 = >10 µM; 1 = 5-10 µM; 2= 1-5 µM; 3 = <1 µM.
(I)
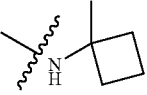
| R$^x$ | AML12HBV10 EC$_{50}$ | HepDES19 EC$_{50}$ |
|---|---|---|
| 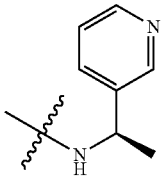 [SMILES: *N[C@H](C)c1cccnc1] | 3 | 3 |
| 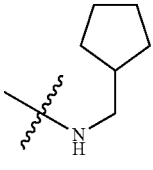 [SMILES: *NCC1CCCC1] | 3 | 3 |
| 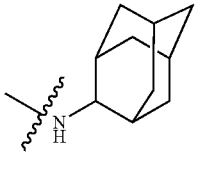 | 3 | 3 |
| 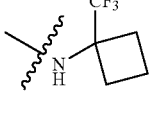 | 3 | 2 |
| 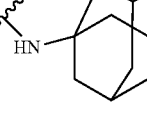 | 3 | 3 |
| 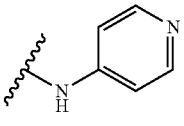 [SMILES: *Nc1ccncc1] | 2 | — |
| 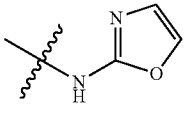 [SMILES: *Nc1ncco1] | 0 | — |
| 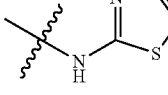 | 0 | — |
| 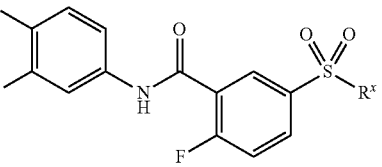 | 0 | — |
| 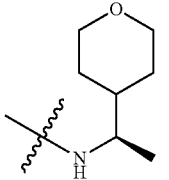 [SMILES: *N[C@H](C)C1CCOCC1] | 1 | — |
| 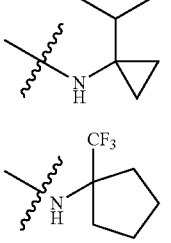 | 3 | 3 |
| 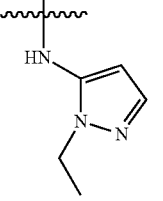 | 3 | — |
| 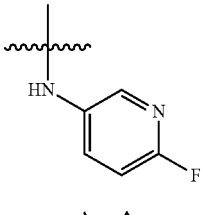 | 0 | — |
| 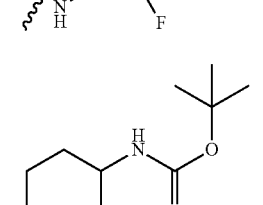 | 0 | — |
|  | 2 | — |
| (tert-butyl carbamate cyclohexyl) | 3 | — |

TABLE 21-continued

Antiviral activity of exemplary compounds in AML12HBV10 and HepDES19 cells. In the Table, EC$_{50}$ key: 0 = >10 μM; 1 = 5-10 μM; 2= 1-5 μM; 3 = <1 μM.

(I)

| R$^x$ | AML12HBV10 EC$_{50}$ | HepDES19 EC$_{50}$ |
|---|---|---|
| 4-aminocyclohexyl-NH- | 0 | — |
| 4-(Boc-amino)piperidin-1-yl | 0 | — |
| 4-aminopiperidin-1-yl | 0 | — |
| 1-(pyridin-4-yl)cyclopropyl-NH- | 3 | — |
| ethoxy-NH- | 2 | — |
| morpholin-4-yl-NH- | 0 | — |
| cyclopropanecarbonyl-NH- | 0 | — |
| NH$_2$ | 2 | — |
| (S)-1-cyclopropyl-2,2,2-trifluoroethyl-NH- | 3 | — |
| N,N-dimethylurea | 0 | — |
| N,N-dimethylguanidine | 0 | — |
| isopropoxy | 0 | — |
| 4-hydroxypiperidin-1-yl | 0 | — |

TABLE 22

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(II)

| R$^x$ | AML12HBV10 EC$_{50}$ | HepDES19 EC$_{50}$ |
|---|---|---|
| 2-Cl, 5-F phenyl | 0 | — |
| 2-F, 4-F phenyl | 1 | — |
| 2-F, 5-F phenyl | 2 | — |
| 2-F, 4-F, 5-F phenyl | 2 | — |
| 3-Cl, 4-Cl phenyl | 2 | — |
| 2-F, 5-Cl phenyl | 1 | — |
| 3-Cl, 4-F phenyl | 3 | — |
| 3-F, 4-F benzyl | 0 | — |

TABLE 23

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(IV)

| R | AML12HBV10 EC$_{50}$ | HepDES19 EC$_{50}$ |
|---|---|---|
| 1-CF$_3$-cyclopropyl-NH | 3 | — |
| (S)-sec-butyl-NH | 3 | — |
| (cyclopropyl)(methyl)CH-NH | 3 | — |

TABLE 24

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(V)

| R$^x$ | AML12HBV10 EC$_{50}$ | HepDES19 EC$_{50}$ |
|---|---|---|
| sec-butyl-NH | 2 | 2 |
| cyclohexyl-NH | 2 | — |
| cyclopropyl-NH | 1 | — |

TABLE 24-continued

Antiviral activity of exemplary compounds in AML12HBV10 and HepDES19 cells. In the Table, EC$_{50}$ key: 0 = >10 µM; 1 = 5-10 µM; 2 = 1-5 µM; 3 = <1 µM.

(V)

| R$^x$ | AML12HBV10 EC$_{50}$ | HepDES19 EC$_{50}$ |
|---|---|---|
| –NH–CH(Et)(Et) | 3 | 3 |
| –NH–CH(Me)(Et) (stereo) | 3 | — |

TABLE 25

Antiviral activity of exemplary compounds in AML12HBV10 and HepDES19 cells. In the Table, EC$_{50}$ key: 0 = >10 µM; 1 = 5-10 µM; 2 = 1-5 µM; 3 = <1 µM.

(VI)

| R$^x$ | AML12HBV10 EC$_{50}$ | HepDES19 EC$_{50}$ |
|---|---|---|
| –NH–CH(Me)(Et) (stereo) | 1 | — |
| –NH–CH(Me)(Et) (stereo) | 0 | — |
| –NH–CH(Me)(Et) | 0 | — |
| –NH–cyclohexyl | 0 | — |
| –NH–cyclopropyl | 0 | — |

TABLE 25-continued

Antiviral activity of exemplary compounds in AML12HBV10 and HepDES19 cells. In the Table, EC$_{50}$ key: 0 = >10 µM; 1 = 5-10 µM; 2 = 1-5 µM; 3 = <1 µM.

(VI)

| R$^x$ | AML12HBV10 EC$_{50}$ | HepDES19 EC$_{50}$ |
|---|---|---|
| –NH–cyclopropyl | 0 | — |

TABLE 26

Antiviral activity of exemplary compounds in AML12HBV10 and HepDES19 cells. In the Table, EC$_{50}$ key: 0 = >10 µM; 1 = 5-10 µM; 2 = 1-5 µM; 3 = <1 µM.

(VII)

| R$^x$ | AML12HBV10 EC$_{50}$ | HepDES19 EC$_{50}$ |
|---|---|---|
| –NH–CH(Me)(Et) | 0 | — |

TABLE 27

Antiviral activity of exemplary compounds in AML12HBV10 and HepDES19 cells. In the Table, EC$_{50}$ key: 0 = >10 µM; 1 = 5-10 µM; 2 = 1-5 µM; 3 = <1 µM.

(VIII)

| R$^x$ | AML12HBV10 EC$_{50}$ | HepDES19 EC$_{50}$ |
|---|---|---|
| –N(pyrrolidinyl) | 3 | 2 |

TABLE 27-continued

Antiviral activity of exemplary compounds in AML12HBV10 and HepDES19 cells. In the Table, EC$_{50}$ key: 0 = >10 µM; 1 = 5-10 µM; 2 = 1-5 µM; 3 = <1 µM.

(VIII)

| R$^x$ | AML12HBV10 EC$_{50}$ | HepDES19 EC$_{50}$ |
|---|---|---|
| NH-iPr | 3 | 2 |
| NH-tBu | 3 | 2 |
| N-azetidinyl | 3 | 3 |
| NH-cyclopropyl | 3 | 3 |
| N(Et)(CH$_2$Ph) | 2 | 3 |
| NH-(methylcyclopropyl) | 3 | — |
| NH-cyclohexyl | 2 | — |
| NH-cyclopentyl | 3 | — |
| NH-cyclobutyl | 3 | — |
| NH-(S)-sec-butyl | 3 | 3 |
| NH-(R)-sec-butyl | 2 | — |
| N-(bicyclo[3.1.0]) | 0 | — |
| NH-(1-methylcyclopropyl) | 3 | — |
| N(Me)(cyclopropyl) | 3 | 2 |
| NH-sec-butyl | 2 | — |
| NH-(2,2-difluorocyclopropyl) | 0 | — |
| N(Me)$_2$ | 2 | — |

TABLE 28

Antiviral activity of exemplary compounds in AML12HBV10 and HepDES19 cells. In the Table, EC$_{50}$ key: 0 = >10 µM; 1 = 5-10 µM; 2 = 1-5 µM; 3 = <1 µM.

(IX)

| | AML12HBV10 | HepDES19 |

TABLE 28-continued

| R^x | EC_{50} | EC_{50} |
|---|---|---|
| *cyclopropyl-methyl-NH-* | 0 | — |

TABLE 29

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(X)

| R^x | AML12HBV10 EC_{50} | HepDES19 EC_{50} |
|---|---|---|
| *N-cyclopropyl* | 2 | — |

TABLE 30

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XI)

| R^x | AML12HBV10 EC_{50} | HepDES19 EC_{50} |
|---|---|---|
| *N-cyclohexyl* | 2 | — |
| *N-cyclopentyl* | 0 | — |
| *N-cyclobutyl* | 0 | — |
| *N-cyclopropyl* | 0 | — |

TABLE 31

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XII)

| Rx | AML12HBV10 EC_{50} | HepDES19 EC_{50} |
|---|---|---|
| 6-fluoropyridin-3-yl-NH- | 2 | — |
| 5-fluoropyridin-3-yl-NH- | 2 | — |
| 2,3-dichloropyridin-5-yl-NH- | 0 | — |
| quinolin-3-yl-NH- | 0 | — |
| 2-oxopyridin-3-yl-NH- | 0 | — |
| pyridin-2-yl-NH- | 0 | — |
| 2-fluoropyridin-4-yl-NH- | 0 | — |
| quinolin-4-yl-NH- | 0 | — |
| pyridin-3-ylmethyl-NH- | 0 | — |

TABLE 31-continued

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XII)

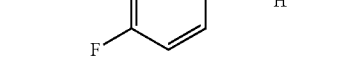

| Rx | AML12HBV10 EC$_{50}$ | HepDES19 EC$_{50}$ |
|---|---|---|
|  | 0 | — |
|  | 0 | — |
|  | 0 | — |
|  | 0 | — |
|  | 0 | — |
| 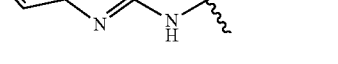 | 0 | — |
|  | 0 | — |

TABLE 32

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XIII)

| Rx | AML12HBV10 EC$_{50}$ | HepDES19 EC$_{50}$ |
|---|---|---|
| (3-fluoropyridin-5-yl)amino | 0 | — |
| (2-oxo-1,2-dihydropyridin-3-yl)amino | 0 | — |
| (quinolin-3-yl)amino | 0 | — |
| (quinolin-4-yl)amino | 0 | — |
| (thiazol-2-yl)amino | 0 | — |
| (oxazol-2-yl)amino | 0 | — |
| (isoxazol-4-yl)amino | 0 | — |
| (1-methyl-1H-pyrazol-5-yl)amino | 0 | — |
| (6-chlorobenzo[d]oxazol-2-yl)amino | 0 | — |

TABLE 32-continued

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

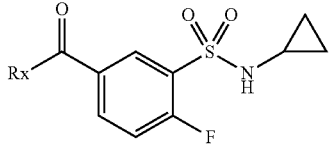

(XIII)

| Rx | AML12HBV10 EC$_{50}$ | HepDES19 EC$_{50}$ |
|---|---|---|
| 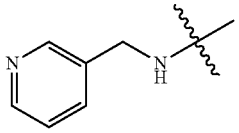 [SMILES: *NCc1cccnc1] | 0 | — |
| 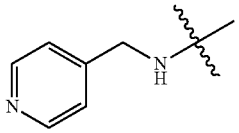 [SMILES: *NCc1ccncc1] | 0 | — |
| 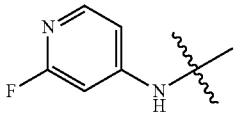 [SMILES: *Nc1ccnc(F)c1] | 0 | — |
| 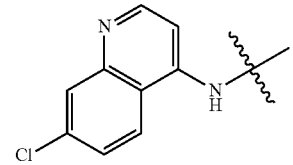 [SMILES: *Nc1ccnc2cc(Cl)ccc12] | 0 | — |
| 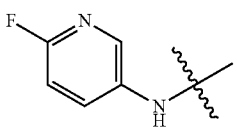 [SMILES: *Nc1ccc(F)nc1] | 0 | — |
| 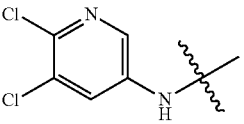 [SMILES: *Nc1cnc(Cl)c(Cl)c1] | 0 | — |

TABLE 33

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM

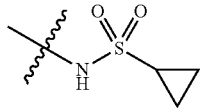 [SMILES: *NS(=O)(=O)C1CC1]

(XIV)

| A | B | C | D | AML12HBV10 EC$_{50}$ | HepDES19 EC$_{50}$ |
|---|---|---|---|---|---|
| H | Cl | H | H | 3 | — |
| H | OMe | H | H | 3 | 3 |
| H | F | H | F | 2 | — |
| H | Me | H | H | 3 | 3 |

TABLE 34

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XV)

| X | n | AML12HBV10 EC$_{50}$ | HepDES19 EC$_{50}$ |
|---|---|---|---|
| CH2 | 1 | 0 | — |

TABLE 35

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XVI)

| Rx | AML12HBV10 EC50 | HepDES19 EC50 |
|---|---|---|
| —NO$_2$ | 1 | — |
| —NH$_2$ | 1 | — |
| (cyclopropylsulfonamide group) | 2 | 0 |

TABLE 35-continued

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XVI)

| Rx | AML12HBV10 EC50 | HepDES19 EC50 |
|---|---|---|
| (isobutyl sulfonamide group) | 2 | — |

TABLE 36

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM (XVII)

| Rx | AML12HBV10 EC50 | HepDES19 EC50 |
|---|---|---|
| —NO$_2$ | 0 | — |
| —NH$_2$ | 0 | — |
| (cyclopropyl sulfonamide NH) | 3 | 2 |
| (N-methyl cyclopropyl sulfonamide) | 0 | 0 |
| (n-butyl sulfonamide) | 0 | 0 |
| (benzyl sulfonamide) | 0 | 0 |

TABLE 37

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XVIII)

| Rx | AML12HBV10 EC50 | HepDES19 EC50 |
|---|---|---|
| (cyclopropyl) | 0 | — |

TABLE 38

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XIX)

| Rx | Ry | AML12HBV10 EC50 | HepDES19 EC50 |
|---|---|---|---|
| (cyclopropyl) | (3,4-difluorophenyl) | 0 | — |

TABLE 39

Antiviral activity of exemplary compounds in AML12HBV10 and HepDES19 cells. In the Table, EC$_{50}$ key: 0 = >10 μM; 1 = 5-10 μM; 2 = 1-5 μM; 3 = <1 μM.

(XX)

| R$^x$ | A | B | AML12HBV10 EC50 | HepDES19 EC50 |
|---|---|---|---|---|
| (sec-butyl NH) | F | H | 2 | — |

TABLE 39-continued

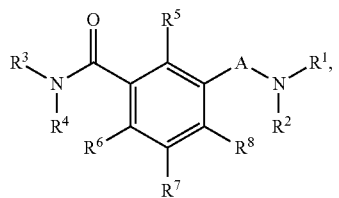

| | H | F | 0 | — |

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A compound of Formula (I), or an enantiomer, diastereomer, pharmaceutically accepted salt, or solvate thereof:

(I)

wherein in (I):

A is selected from the group consisting of $SO_2$ and CO;

$R^1$ is selected from the group consisting of optionally substituted $C_{1-6}$ linear alkyl, optionally substituted $C_{1-6}$ branched alkyl, optionally substituted $C_{3-7}$ cycloalkyl, optionally substituted benzyl, optionally substituted 3-7 membered cycloheteroalkyl, optionally substituted $C_{2-8}$ alkenyl, optionally substituted $C_{2-8}$ alkynyl, and optionally substituted heterocyclic;

$R^2$ is selected from the group consisting of hydrogen, optionally substituted $C_{1-6}$ linear alkyl, optionally substituted $C_{3-7}$ cycloalkyl, and optionally substituted heterocyclic;

$R^3$ is selected from the group consisting of optionally substituted aryl and optionally substituted heteroaryl;

$R^4$ is selected from the group consisting of hydrogen and optionally substituted $C_{1-6}$ linear alkyl;

$R^5$ is selected from the group consisting of hydrogen, halogen, optionally substituted $C_{1-6}$ linear alkyl, optionally substituted $C_{1-6}$ branched alkyl, optionally substituted $C_{1-6}$ haloalkyl, $OR^9$, cyano, and $N(R^9)_2$;

$R^6$ and $R^8$ are selected independently at each occurrence from the group consisting of fluoro, $C_{1-3}$ alkyl, and $C_{1-3}$ alkoxy;

$R^7$ is selected from the group consisting of hydrogen, halogen, optionally substituted $C_{1-6}$ linear alkyl, optionally substituted $C_{1-6}$ branched alkyl, $OR^9$, cyano, and $N(R^9)_2$;

$R^9$ is independently at each occurrence selected from the group consisting of hydrogen, optionally substituted $C_{1-6}$ linear alkyl, optionally substituted $C_{1-6}$ branched alkyl, optionally substituted $C_{3-7}$ cycloalkyl, optionally substituted benzyl, and optionally substituted heterocyclyl;

wherein a substituted group is substituted with at least one selected from the group consisting of $C_{1-6}$ alkyl, $C_{1-6}$ haloalkyl, $C_{2-8}$ alkenyl, $C_{2-8}$ alkynyl, $C_{3-6}$ cycloalkyl, —F, —Cl, —Br, —I, —CN —$NO_2$, —$OR^{41}$, —$SR^{14}$, —$N(R^{14})_2$, —$NR^{14}C(O)R^{14}$, —$SO_2\,R^{14}$, —$SO_2\,OR^{14}$ —$SO_2N(R^{14})_2$, —$C(O)R^{14}$, —$C(O)OR^{14}$ —$C(O)N(R^{14})_2$, aryl, heterocyclyl, or heteroaryl, wherein each occurrence of $R^{14}$ is independently selected from the group consisting of hydrogen, $C_{1-6}$ alkyl, $C_{1-6}$ haloalkyl, $C_{2-8}$ alkenyl, $C_{2-8}$ alkynyl, and $C_{3-6}$ cycloalkyl, or two $R^{14}$ units taken together with the atom(s) to which they are bound form an optionally substituted carbocyclyl or heterocyclyl group, wherein the carbocyclyl or heterocyclyl group has 3 to 7 ring atoms, wherein the heteroaryl is selected from the group consisting of diazolyl, imidazolyl, imidazolyl, triazinyl, thiazolyl, isothiazolyl, oxazolyl, isoxazolinyl, furanyl, thiophenyl, pyrimidinyl, pyridinyl, tetrazolyl, benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H -purinyl, 5H-pyrrolo[3,2-d]pyrimidinyl, 7H-pyrrolo[2,3-d]pyrimidinyl, pyrido[2,3-(ijpyrimidinyl, 2-phenylbenzo[d] thiazolyl, 1H-indolyl, 4,5,6,7-tetrahydro-1-H-indolyl, quinoxalinyl, quinazolinyl, quinolinyl, and isoquinolinyl;

provided that, when A is $SO_2$, then the compound is not selected from any of groups (a) through (c):

(a) $R^3$ is optionally substituted phenyl and $R^1$ or $R^2$, either individually or when taken together, contain a hydroxyl group; or (b) $R^3$ is optionally substituted phenyl, and $N(R^1)(R^2)$ is selected from the group consisting of

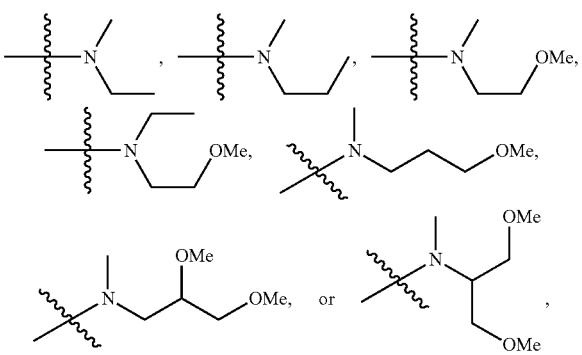

or (c) $R^3$ is optionally substituted phenyl and $N(R^1)(R^2)$ is selected from the group consisting of:

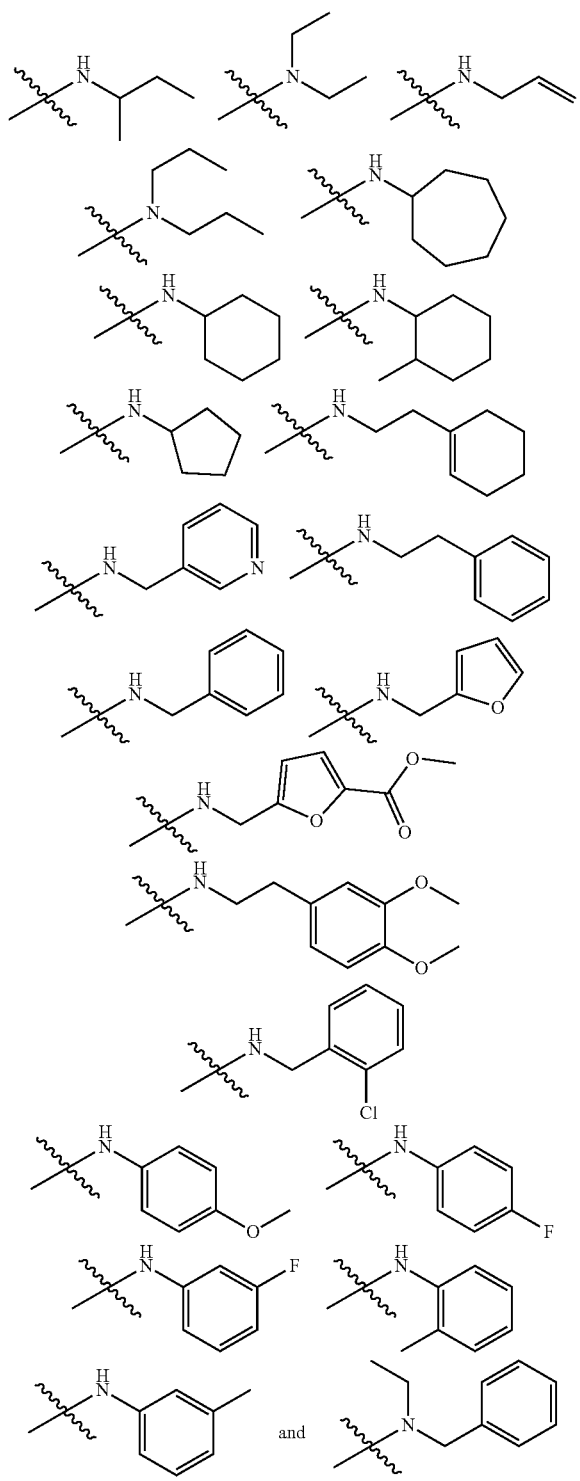

and

2. The compound of claim 1, wherein $R^3$ is selected from a group consisting of optionally substituted phenyl, optionally substituted benzoisoxazolyl, optionally substituted benzooxazolyl, optionally substituted furyl, optionally substituted imidazolyl, optionally substituted indoyl, optionally substituted isoxazolyl, optionally substituted isothiazolyl, optionally substituted oxazolyl, optionally substituted pyrazolyl, optionally substituted pyridin-2-on-yl, optionally substituted pyridyl, optionally substituted pyrrolyl, optionally substituted quinolinyl, optionally substituted thiazolyl, and optionally substituted thienyl.

3. The compound of claim 2, wherein $R^3$ is

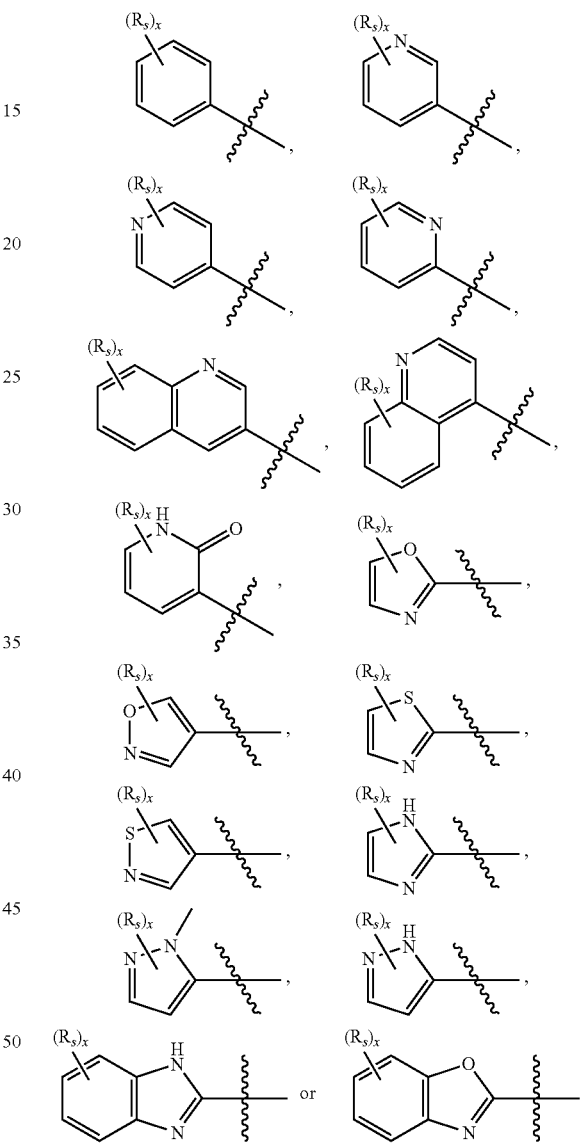

wherein $R_s$ is independently at each occurrence selected from the group consisting of bromo, chloro, fluoro, cyano, hydroxyl, optionally fluorinated $C_{1-6}$ alkyl, and —O—$(C_{1-6}$ alkyl), or when two are taken form a fused cyclic or heterocyclic moiety;

x is 0, 1, 2, or 3; and $R^4$ is hydrogen.

4. The compound of claim 2, wherein the optional substitution of $R^3$ comprises at least one halo or $C_{1-6}$ alkyl.

5. The compound of claim 1, wherein $R^3$ is

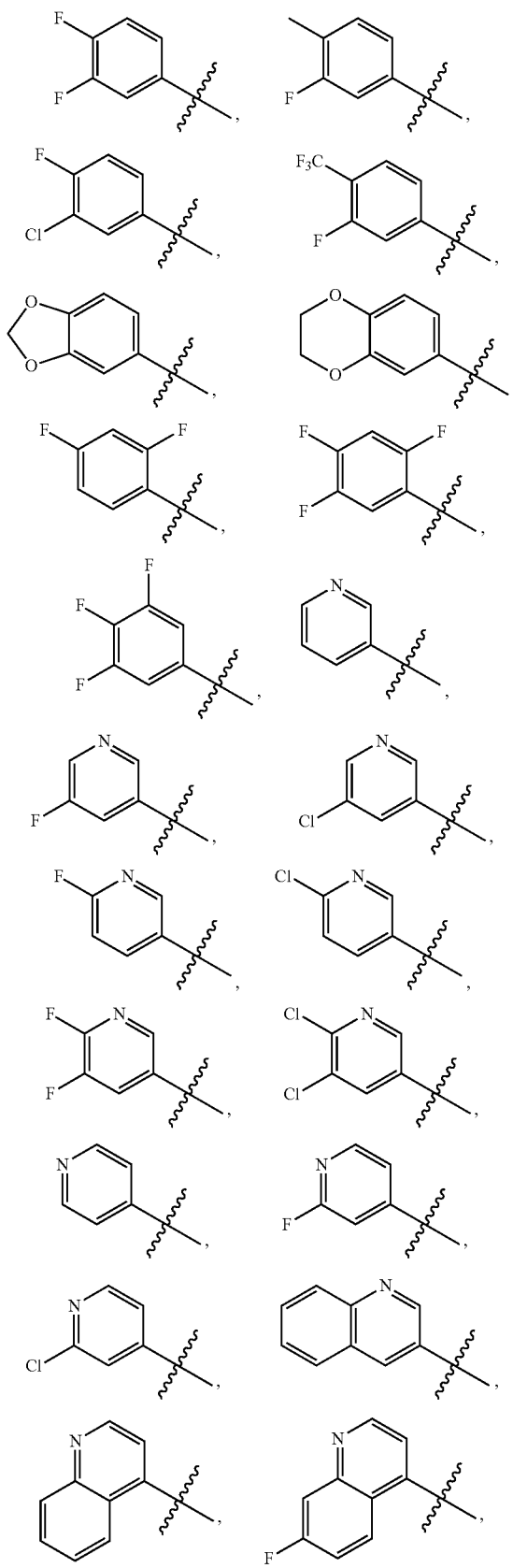

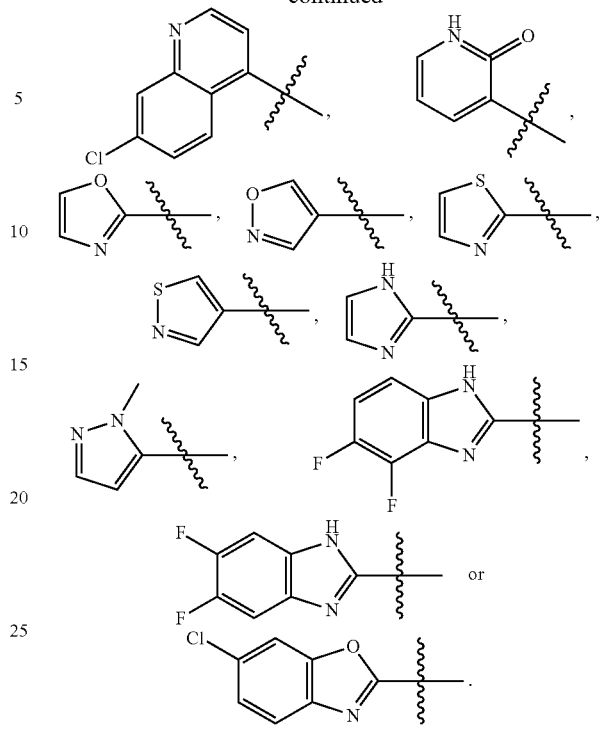

6. The compound of claim 1, wherein $R^5$ and $R^7$ are independently at each occurrence H or F.

7. The compound of claim 1, wherein $R^3$ is

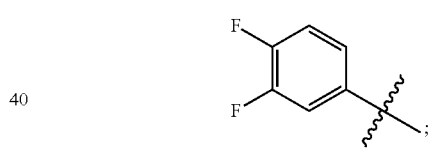

and
$R^4$ is hydrogen.

8. The compound of claim 1, wherein
$R^5$ and $R^7$ are each H; and
$R^6$ is fluoro or methoxy.

9. The compound of claim 1, wherein,
$R^1$ is methyl, ethyl, n-propyl, isopropyl, n-butyl, sec-butyl, tert-butyl, optionally substituted benzyl, optionally substituted methylpyridyl,

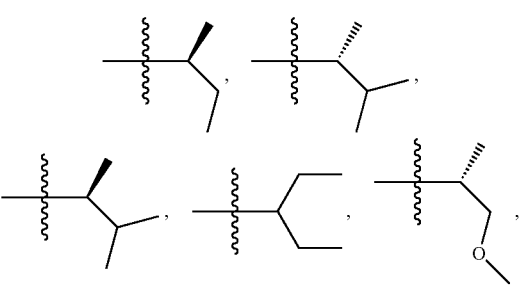

283
-continued
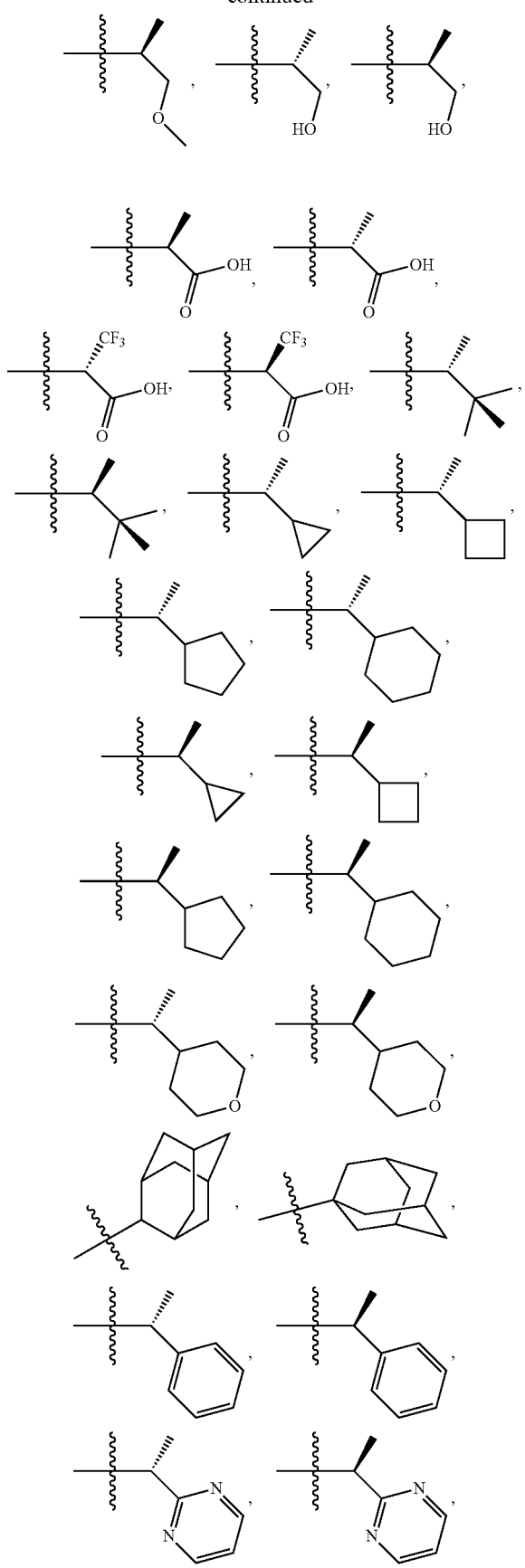
284
-continued
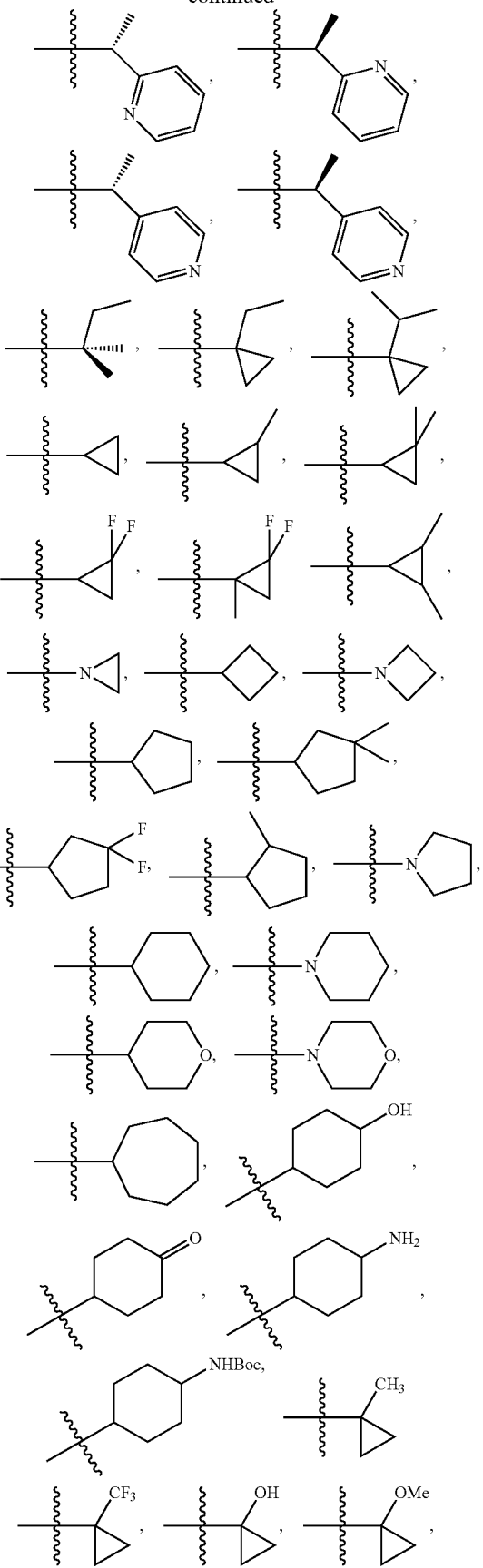

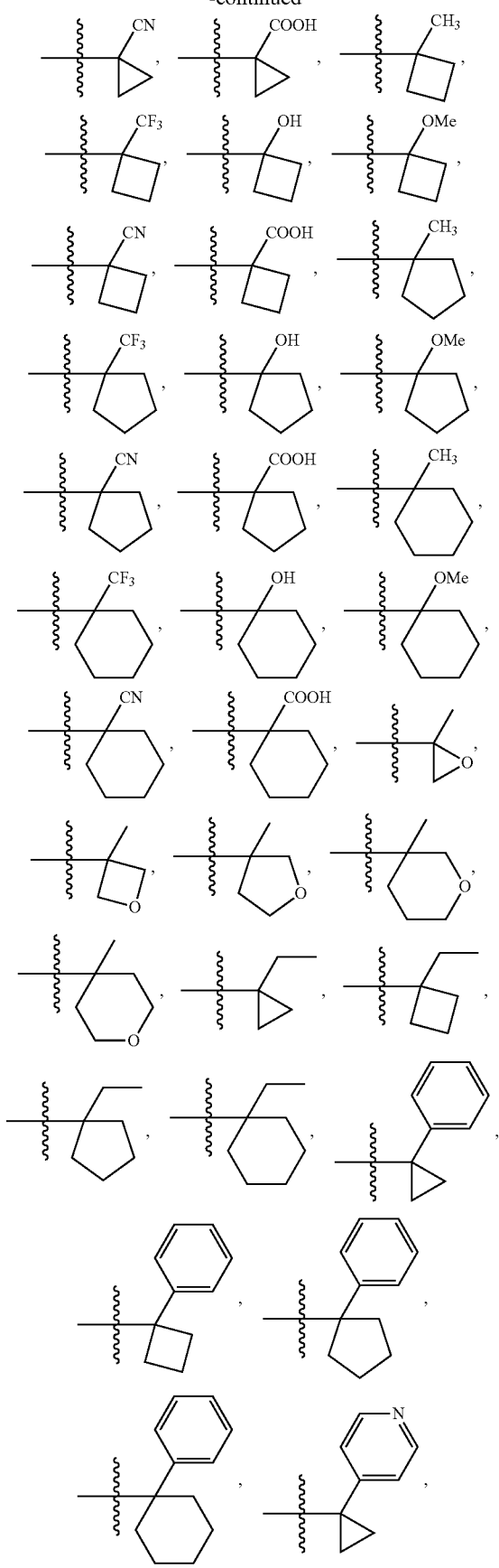
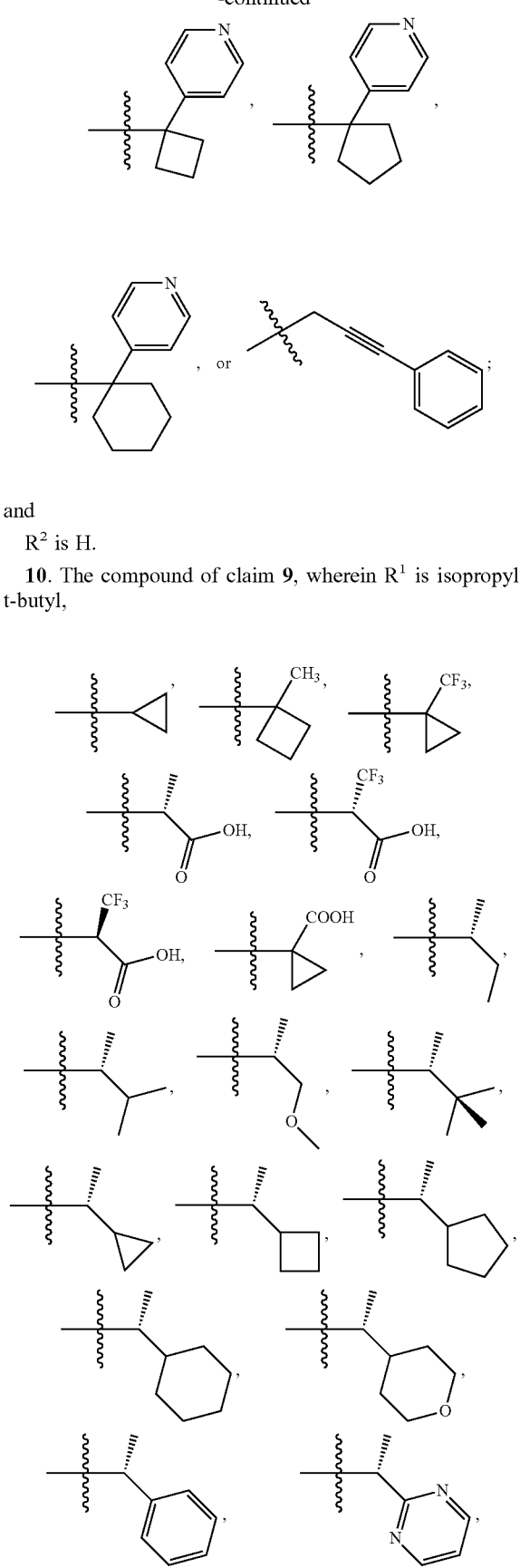
and
R² is H.
10. The compound of claim 9, wherein R¹ is isopropyl, t-butyl,

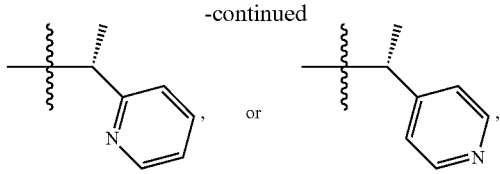

and
R² is H.

11. The compound of claim 1, with the proviso that the —N(R¹)(R²) moiety does not contain hydroxyl.

12. The compound of claim 1, with the proviso that R¹ is not cyclopentane.

13. The compound of claim 1, wherein

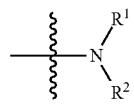

is

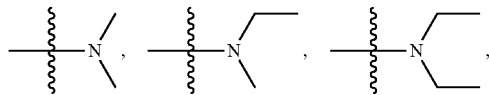

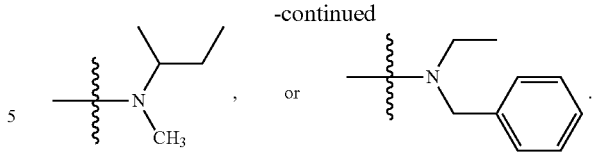

14. A pharmaceutical composition comprising a compound of claim 1 and a pharmaceutically acceptable excipient.

15. A method of inhibiting pregenomic RNA encapsidation in a patient in need thereof, said method comprising administering to the patient an effective amount of at least one compound of claim 1.

16. The method of claim 15, wherein the pregenomic RNA is from a Hepatitis B virus.

17. A method of treating a Hepatitis B viral infection in a patient in need thereof, said method comprising administering to the patient an effective amount of at least one compound of claim 1.

18. The method of claim 17, wherein the treatment controls or ameliorates a condition associated with liver disease.

19. A method of repressing at least one process selected from the group consisting of viral replication and morphogenesis in a patient in need thereof, said method comprising administering to the patient an effective amount of a compound of claim 1.

\* \* \* \* \*

UNITED STATES PATENT AND TRADEMARK OFFICE
CERTIFICATE OF CORRECTION

PATENT NO.       : 9,938,236 B2
APPLICATION NO.  : 14/759385
DATED            : April 10, 2018
INVENTOR(S)      : Xiaodong Xu et al.

Page 1 of 1

It is certified that error appears in the above-identified patent and that said Letters Patent is hereby corrected as shown below:

In the Claims

In Column 278, Line 40, Claim 1 "pyrido[2,3-(ijpyrimidinyl, 2-phenylbenzo[d]" should read as follows:
-- pyrido[2,3-*d*]pyrimidinyl, 2-phenylbenzo[d] --.

Signed and Sealed this
Thirteenth Day of November, 2018

Andrei Iancu
*Director of the United States Patent and Trademark Office*